(12) United States Patent
Hartnett

(10) Patent No.: US 10,214,741 B2
(45) Date of Patent: Feb. 26, 2019

(54) METHODS AND COMPOSITIONS FOR INHIBITING RETINOPATHY OF PREMATURITY

(71) Applicant: University of Utah Research Foundation, Salt Lake City, UT (US)

(72) Inventor: Mary Elizabeth Hartnett, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

(21) Appl. No.: 15/118,667

(22) PCT Filed: Feb. 13, 2015

(86) PCT No.: PCT/US2015/015886
§ 371 (c)(1),
(2) Date: Aug. 12, 2016

(87) PCT Pub. No.: WO2015/123561
PCT Pub. Date: Aug. 20, 2015

(65) Prior Publication Data
US 2017/0051280 A1 Feb. 23, 2017

Related U.S. Application Data

(60) Provisional application No. 62/008,148, filed on Jun. 5, 2014, provisional application No. 61/940,130, filed on Feb. 14, 2014.

(51) Int. Cl.
*C12N 15/11* (2006.01)
*C12N 15/113* (2010.01)
*C12N 7/00* (2006.01)

(52) U.S. Cl.
CPC .............. *C12N 15/113* (2013.01); *C12N 7/00* (2013.01); *C12N 15/1136* (2013.01); *C12N 15/1138* (2013.01); *C12N 2310/141* (2013.01); *C12N 2310/3519* (2013.01); *C12N 2320/32* (2013.01); *C12N 2330/51* (2013.01); *C12N 2740/15031* (2013.01); *C12N 2740/15043* (2013.01); *C12N 2740/15045* (2013.01)

(58) Field of Classification Search
None
See application file for complete search history.

(56) References Cited

U.S. PATENT DOCUMENTS

| | | |
|---|---|---|
| 4,684,611 A | 8/1987 | Schilperoort et al. |
| 4,868,116 A | 9/1989 | Morgan et al. |
| 4,897,355 A | 1/1990 | Eppstein et al. |
| 4,952,500 A | 8/1990 | Finnerty et al. |
| 4,980,286 A | 12/1990 | Morgan et al. |
| 5,302,523 A | 4/1994 | Coffee et al. |
| 5,322,783 A | 6/1994 | Tomes et al. |
| 5,384,253 A | 1/1995 | Krzyzek et al. |
| 5,464,765 A | 11/1995 | Coffee et al. |
| 5,538,877 A | 7/1996 | Lundquist et al. |
| 5,538,880 A | 7/1996 | Lundquist et al. |
| 5,550,318 A | 8/1996 | Adams et al. |
| 5,563,055 A | 10/1996 | Townsend et al. |
| 5,580,859 A | 12/1996 | Felgner et al. |
| 5,589,466 A | 12/1996 | Felgner et al. |
| 5,591,616 A | 1/1997 | Hiei et al. |
| 5,610,042 A | 3/1997 | Chang et al. |
| 5,656,610 A | 8/1997 | Shuler et al. |
| 5,702,932 A | 12/1997 | Hoy et al. |
| 5,736,524 A | 4/1998 | Content et al. |
| 5,780,448 A | 7/1998 | Davis |
| 5,789,215 A | 8/1998 | Berns et al. |
| 5,945,100 A | 8/1999 | Fick |
| 5,981,274 A | 11/1999 | Tyrrell et al. |
| 5,994,624 A | 11/1999 | Trolinder et al. |
| 2005/0196781 A1* | 9/2005 | Robin ............... C07H 21/02 435/6.11 |
| 2008/0199426 A1* | 8/2008 | Sukhatme ........... A61K 31/711 514/1.1 |
| 2012/0272346 A1 | 10/2012 | Stillman et al. |

FOREIGN PATENT DOCUMENTS

| | | |
|---|---|---|
| EP | 15749581.3 | 2/2015 |
| WO | WO-89/07136 A2 | 8/1989 |
| WO | WO-90/02806 A1 | 3/1990 |

(Continued)

OTHER PUBLICATIONS

Schmeckpeper et al, Lentiviral tracking of vascular differentiation in bone marrow progenitor cells, 2009, Differentiation, 78: 169-176.*
Al-Shabrawey, M. et al. (2013) Targeting Neovascularization in Ischemic Retinopathy: Recent Advances. Expert Rev Opthalmol. 8(3):267-86.
Arcasoy et al. (2008) The non-haematopoietic biological effects of erythropoietin, Br J Haematol, 141(1):14-31.
Berkner et al., (1987) Abundant Expression of Polyomavirus Middle T Antigen andDihydrofolate Reductase in an Adenovirus Recombinant, J. Virology 61(4):1213-1220.

(Continued)

*Primary Examiner* — Ekaterina Poliakova-Georgantas
(74) *Attorney, Agent, or Firm* — Ballard Spahr LLP

(57) ABSTRACT

Disclosed are vectors and compositions comprising a pol II promoter and an shRNA wherein the shRNA has a sense RNA strand and an antisense RNA strand, wherein the sense and the antisense RNA strands form an RNA duplex, and wherein the sense RNA strand comprises a nucleotide sequence identical to a target sequence in STAT3, VEGFR, or EPOR. Also disclosed are methods of treating retinopathy of prematurity (ROP), methods of inhibiting expression of STAT3, VEGFR, and EPOR, and methods of regulating signaling events associated with intravitreal neovascularization (IVNV).

10 Claims, 72 Drawing Sheets
Specification includes a Sequence Listing.

(56) References Cited

FOREIGN PATENT DOCUMENTS

| WO | WO-94/09699 A1 | 5/1994 |
|---|---|---|
| WO | WO-95/06128 A2 | 3/1995 |
| WO | WO-2010/045526 A1 | 4/2010 |
| WO | WO-2010/111712 A2 | 9/2010 |
| WO | PCT/US2015/015886 | 2/2015 |

OTHER PUBLICATIONS

Bout, (1994) Lung Gene Therapy: In Vivo Adenovirus-Mediated Gene Transfer to Rhesus Monkey Airway Epithelium, Human Gene Therapy 5(1): 3-10.
Brigham et al. (1989) Expression of a Prokaryotic Gene in Cultured Lung Endothelial Cells after Lipofection with a Plasmid Vector, Am. J. Resp. Cell. Mol. Biol. 1:95-100.
Brown and Burlingham, (1973) Penetration of host cell membranes by adenovirus 2, J.Virology 12:386-396.
Caillaud, (1993)Adenoviral Vector as a Gene Delivery System into Cultured Rat Neuronal and Glial Cells,Eur. J. Neuroscience 5:1287-1291.
Chardonnet and Dales, (1970) Early Events in the Interaction of Adenoviruses with HeLa Cells, Virology 40:462-477.
Davidson et al., (1987) Overproduction of polyomavirus middle T antigen in mammalian cells through the use of an adenovirus vector, J. Virology 61(4):1226-1239.
Felgner et al.(1987) Lipofection: a highly efficient, lipid-mediated DNA-transfection procedure, Proc. Natl. Acad. Sci USA 84:7413-7417.
Gomez-Foix, (1992) Adenovirus-mediated transfer of the muscle glycogen phosphorylase gene into hepatocytes confers altered regulation of glycogen metabolism, J. Biol. Chem. 267:25129-25134.
Guzman (1993) Efficient Gene Transfer Into Myocardium by Direct Injection of Adenovirus Vectors, Circulation Research 73(6) :1201-1207.
Hay-Ahmad et al. (1986)Development of a helper-independent human adenovirus vector and its use in the transfer of the herpes simplex virus thymidine kinase gene, J. Virology 57:267-274.
Jiang, Y. et al. (2014) Targeting Müller Cell-Derived $VEGF_{164}$ to Reduce Intravitreal Neovascularization in the Rat Model of Retinopathy of Prematurity. Invest Opthalmol Vis Sci. 55(2):824-31.
Kirshenbaum (1993) Highly efficient gene transfer into adult Ventricular Myocytes by recombinant adenovirus, J. Clin. Invest. 92:381-387.
La Salle (1993) An adenovirus vector for gene transfer into neurons and glia in the brain, Science 259:988-990.
Massie et al. (1986) Construction of a Helper-Free Recombinant Adenovirus That Expresses Polyomavirus Large T Antigen, Mol. Cell. Biol. 6(8):2872-2883.
Morsy (1993) Efficient adenoviral-mediated ornithine transcarbamylase expression in Deficient mouse and human hepatocytes, J. Clin. Invest. 92:1580-1586.
Moullier (1993) Correction of lysosomal storage in the liver and spleen of MPS VII mice by implantation of genetically modified skin fibroblasts, Nature Genetics 4:154-159.
Mulligan (1993) The Basic Science of Gene Therapy, Science 260:926-932.
Ragot (1993) Replication-defective recombinant adenovirus expressing the Epstein-Barr virus (EBV) envelope glycoprotein gp340/220 induces protective immunity against EBV-induced lymphomas in the cottontop tamarin. J. Gen. Virology 74:501-507.
Ram et al. (1993) In Situ Retroviral-mediated Gene Transfer for the Treatment of Brain Tumors in Rats, Cancer Res. 53:83-88.
Rich (1993) Development and Analysis of Recombinant Adenoviruses for Gene Therapy of Cystic Fibrosis, Human Gene Therapy 4:461-476.
Roessler (1993) Adenoviral-mediated gene transfer to rabbit synovium in vivo, J. Clin. Invest. 92:1085-1092.
Seth, et al. (1984) Evidence that the penton base of adenovirus is involved in potentiation of toxicity of Pseudomonas exotoxin conjugated to epidermal growth factor, Mol. Cell. Biol., 4:1528-1533.
Seth, et al. (1984) Role of a low-pH environment in adenovirus enhancement of the toxicity of a Pseudomonas exotoxin-epidermal growth factor conjugate.J. Virol. 51:650-655.
Svensson and Persson (1985) Role of vesicles during adenovirus 2 internalization into HeLa cells, J. Virology 55:442-449.
Varga et al. (1991) Infectious entry pathway of adenovirus type 2, J. Virology 65(11): 6061-6070.
Verma, I.M. (1985) Retroviral vectors for gene transfer. Amer Soc Microbiol. 229-232.
Wang et al. (2012) VEGF-mediated STAT3 activation inhibits retinal vascularization by down-regulating local erythropoietin expression. Am J Pathol. 180(3): 1243-53.
Wang et al. (2013) Short hairpin RNA-mediated knockdown of VEGFA in Muller cells reduces intravitreal neovascularization in a rat model of retinopathy of prematurity. Am J Pathol, 183(3): 964-74.
Wickham et al. (1993) Integrins $\alpha v \beta 3$ and $\alpha v \beta 5$ promote adenovirus internalization but not virus attachment, Cell 73:309-319.
Wolff, J. A. (1991) Human dystrophin expression in mdx mice after intramuscular injection of DNA constructs, Nature, 352: 815-818.
Wolff, J. A., et al., (1990) Direct Gene Transfer into Mouse Muscle in Vivo, Science, 247: 1465-1468.
Yang, G. (2009) Lentivirus-Mediated shRNA Interference Targeting STAT3 Inhibits Human Pancreatic Cancer Cell Invasion. World J Gastroenterol. 15(30):3757-66.
Yang, Z. et al. (2014) VEGFA Activates Erythropoietin Receptor and Enhances VEGFR2-Mediated Pathological Angiogenesis. Amer J Pathol. 184(4):1230-9.
Zabner (1993) Adenovirus-mediated gene transfer transiently corrects the chloride transport defect in nasal epithelia of patients with cystic fibrosis, Cell 75(2): 207-216.
Zabner (1994) Safety and efficacy of repetitive adenovirus-mediated transfer of CFTR cDNA to airway epithelia of primates and cotton rats, Nature Genetics 6:75-83.
Zhang (1993) Generation and identification of recombinant adenovirus by liposome-mediated transfection and PCR analysis. BioTechniques 15:868-872.
Zhang, Y. et al. (2013) Lung endothelial HO-1 targeting in vivo using lentiviral miRNA regulates apoptosis and autophagy during oxidant injury. FASEB J., 27(10): 4041-58.
Zhang, L. et al. (2008) Effects of Plasmid-Based Stat3-Specific Short Hairpin RNA and GRIM-19 on PC-3M Tumor Cell Growth. Clin Cancer Res. 14(2):559-68.
International Search Report and Written Opinion dated Aug. 13, 2015 by the International Searching Authority for Application No. PCT/US2015/015886 on Feb. 13, 2015 and published as WO/2015/123561 on Aug. 20, 2015 (Inventor—Hartnett; Applicant—University of Utah Res. Found.; (17 Pages).
International Preliminary Report on Patentability dated Aug. 16, 2016 by the International Searching Authority for Application No. PCT/US2015/015886 on Feb. 13, 2015 and published as WO/2015/123561 on Aug. 20, 2015 (Inventor—Hartnett; Applicant—University of Utah Res. Found.; (11 Pages).
Supplementary Partial European Search Report dated Sep. 5, 2017 by the European Patent Office for Patent Application No. 15749581.3, which was filed on Feb. 13, 2015 and published as EP 3105332 on Dec. 21, 2016 (Inventor—Hartnett; Applicant—Univ. of Utah Res. Found.; (5 pages).
European Search Report dated Dec. 8, 2017 by the European Patent Office for EP Patent Application No. 1574581.3, which was filed on Feb. 13, 2015 and published as EP 3105332 on Dec. 21, 2016 (Applicant—University of Utah Research Foundation) (15 pages).
U.S. Appl. No. 61/940,130, filed Feb. 14, 2014, Harnett (Univ. of Utah Res. Found.).
U.S. Appl. No. 62/008,148, filed Jun. 5, 2014, Harnett (Univ. of Utah Res. Found.).

* cited by examiner

A

B

A

B

D

E

A

B

A

Old one

B

Replaced with
VE-cad(CDH5)
promoter

A

B

B

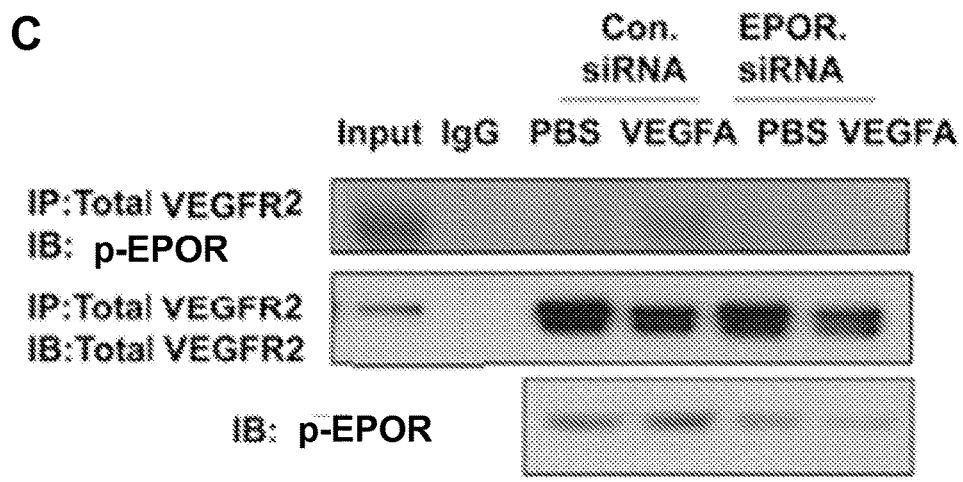
FIG. 37C
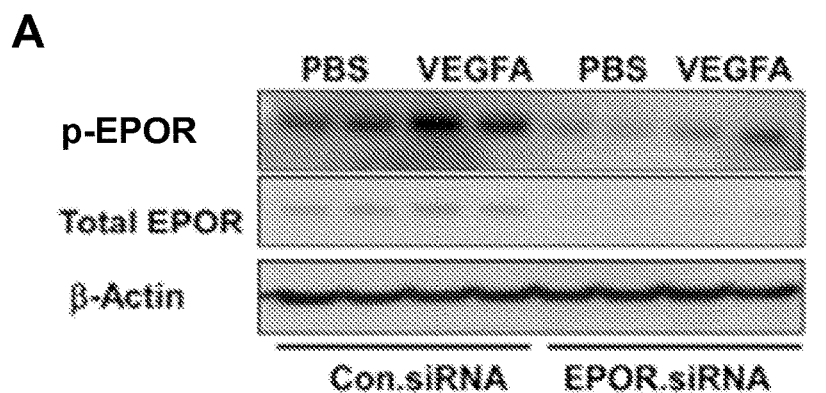
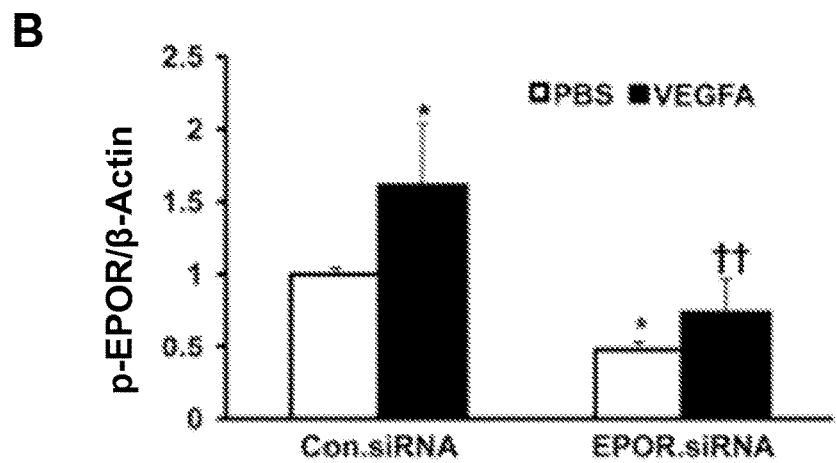
FIG. 38A, FIG. 38B

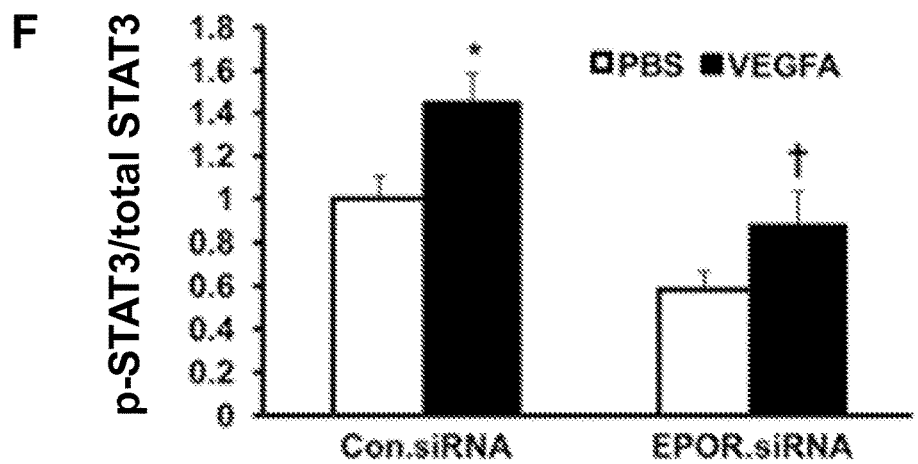
FIG. 38F
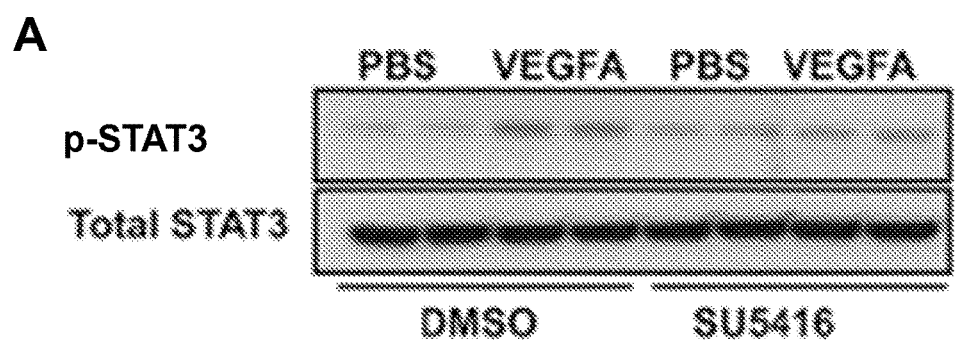
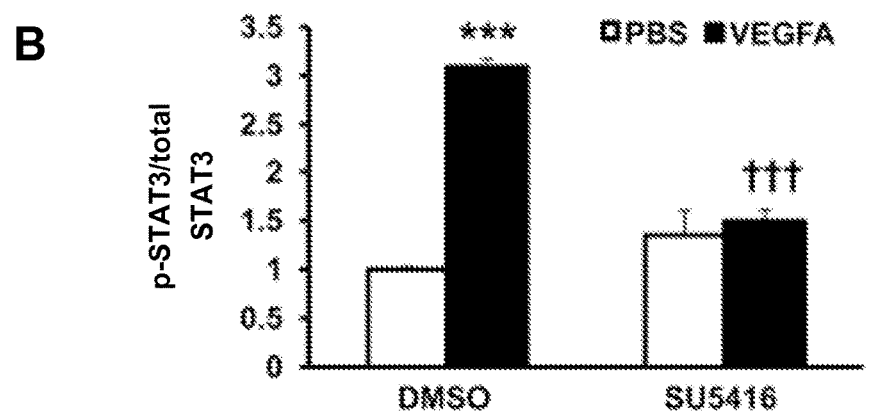
FIG. 39A, FIG. 39B

Table 1. shRNA sequences

| Target | Oligonucleotide |
| --- | --- |
| EPOR.shRNA#1 (pos 604) | TGCTGTTGACAGTGAGCGAACTGAGTGTGTCCTGA GCAACTAGTGAAGCCACAGATGTAGTTGCTCAGGAC ACACTCAGTGTGCCTACTGCCTCGGA |
| EPOR.shRNA #2 (pos 763) | TGCTGTTGACAGTGAGCGATCTCTCATTCTCGTCCTC ATCTAGTGAAGCCACAGATGTAGATGAGGACGAGAA TGAGAGACTGCCTACTGCCTCGGA |
| EPOR.shRNA #3 (pos 1313) Picked | TGCTGTTGACAGTGAGCGAGGGCACTGCCTCCTGA GCTACTAGTGAAGCCACAGATGTAGTAGCTCAGGAG GCAGTGCCCGTGCCTACTGCCTCGGA |
| VEGFR2.shRNA #1 (pos 335) Picked | TGCTGTTGACAGTGAGCGAATCGTTTATGTCTATGTT CAATAGTGAAGCCACAGATGTATTGAACATAGACAT AAACGATGTGCCTACTGCCTCGGA |
| VEGFR2.shRNA #2 (pos 1105) | TGCTGTTGACAGTGAGCGAACCCATTGAGTCCAATT ACACTAGTGAAGCCACAGATGTAGTGTAATTGGACT CAATGGGTCTGCCTACTGCCTCGGA |
| VEGFR2.shRNA #3 (pos 1232) | TGCTGTTGACAGTGAGCGAATGGTCTCTCTGGTTGT GAATTAGTGAAGCCACAGATGTAATTCACAACCAGA GAGACCATGTGCCTACTGCCTCGGA |
| STAT3.shRNA #1 (pos 551) | TGCTGTTGACAGTGAGCGAATGCAGGATCTGAATGG AAACTAGTGAAGCCACAGATGTAGTTTCCATTCAGA TCCTGCATGTGCCTACTGCCTCGGA |
| STAT3.shRNA #2 (pos 923) Picked | TGCTGTTGACAGTGAGCGAATCGTGGATCTGTTCAGA AACTAGTGAAGCCACAGATGTAGTTTCTGAACAGATC CACGATCTGCCTACTGCCTCGGA |
| STAT3.shRNA #3 (pos 1133) | TGCTGTTGACAGTGAGCGAAGAGGGTCTCGGAAAT TTAACTAGTGAAGCCACAGATGTAGTTAAATTTCCG AGACCCTCTGTGCCTACTGCCTCGGA |
| Luc.shRNA | TGCTGTTGACAGTGAGCGAAATGTTTACTACACTCG GATATAGTGAAGCCACAGATGTATATCCGAGTGTAGT AAACATTCTGCCTACTGCCTCGGA |

FIG. 48

SEQUENCE LISTING

```
<160> NUMBER OF SEQ ID NOS: 55

<210> SEQ ID NO 1
<211> LENGTH: 97
<212> TYPE: DNA
```

<213> ORGANISM: Artificial Sequence
<220> FEATURE:
<223> OTHER INFORMATION: synthetic construct; shRNA

<400> SEQUENCE: 1

```
tgctgttgac agtgagcgaa tgcaggatct gaatggaaac tagtgaagcc acagatgtag    60
tttccattca gatcctgcat gtgcctactg cctcgga                              97
```

<210> SEQ ID NO 2
<211> LENGTH: 97
<212> TYPE: DNA
<213> ORGANISM: Artificial Sequence
<220> FEATURE:
<223> OTHER INFORMATION: synthetic construct; shRNA

<400> SEQUENCE: 2

```
tgctgttgac agtgagcgaa tcgtggatct gttcagaaac tagtgaagcc acagatgtag    60
tttctgaaca gatccacgat ctgcctactg cctcgga                              97
```

<210> SEQ ID NO 3
<211> LENGTH: 97
<212> TYPE: DNA
<213> ORGANISM: Artificial Sequence
<220> FEATURE:
<223> OTHER INFORMATION: synthetic construct; shRNA

<400> SEQUENCE: 3

```
tgctgttgac agtgagcgaa gagggtctcg gaaatttaac tagtgaagcc acagatgtag    60
ttaaatttcc gagaccctct gtgcctactg cctcgga                              97
```

<210> SEQ ID NO 4
<211> LENGTH: 97
<212> TYPE: DNA
<213> ORGANISM: Artificial Sequence
<220> FEATURE:
<223> OTHER INFORMATION: synthetic construct; shRNA

<400> SEQUENCE: 4

```
tgctgttgac agtgagcgaa tcgtttatgt ctatgttcaa tagtgaagcc acagatgtat    60
tgaacataga cataaacgat gtgcctactg cctcgga                              97
```

<210> SEQ ID NO 5
<211> LENGTH: 97
<212> TYPE: DNA
<213> ORGANISM: Artificial Sequence
<220> FEATURE:
<223> OTHER INFORMATION: synthetic construct; shRNA

<400> SEQUENCE: 5

```
tgctgttgac agtgagcgaa cccattgagt ccaattacac tagtgaagcc acagatgtag    60
tgtaattgga ctcaatgggt ctgcctactg cctcgga                              97
```

<210> SEQ ID NO 6
<211> LENGTH: 97
<212> TYPE: DNA
<213> ORGANISM: Artificial Sequence
<220> FEATURE:
<223> OTHER INFORMATION: synthetic construct; shRNA

<400> SEQUENCE: 6

```
tgctgttgac agtgagcgaa tggtctctct ggttgtgaat tagtgaagcc acagatgtaa    60
ttcacaacca gagagaccat gtgcctactg cctcgga                              97
```

```
<210> SEQ ID NO 7
<211> LENGTH: 97
<212> TYPE: DNA
<213> ORGANISM: Artificial Sequence
<220> FEATURE:
<223> OTHER INFORMATION: synthetic construct; shRNA

<400> SEQUENCE: 7
tgctgttgac agtgagcgaa ctgagtgtgt cctgagcaac tagtgaagcc acagatgtag     60
ttgctcagga cacactcagt gtgcctactg cctcgga                              97

<210> SEQ ID NO 8
<211> LENGTH: 97
<212> TYPE: DNA
<213> ORGANISM: Artificial Sequence
<220> FEATURE:
<223> OTHER INFORMATION: synthetic construct; shRNA

<400> SEQUENCE: 8
tgctgttgac agtgagcgat ctctcattct cgtcctcatc tagtgaagcc acagatgtag     60
atgaggacga gaatgagaga ctgcctactg cctcgga                              97

<210> SEQ ID NO 9
<211> LENGTH: 97
<212> TYPE: DNA
<213> ORGANISM: Artificial Sequence
<220> FEATURE:
<223> OTHER INFORMATION: synthetic construct; shRNA

<400> SEQUENCE: 9
tgctgttgac agtgagcgag ggcactgcct cctgagctac tagtgaagcc acagatgtag     60
tagctcagga ggcagtgccc gtgcctactg cctcgga                              97

<210> SEQ ID NO 10
<211> LENGTH: 22
<212> TYPE: DNA
<213> ORGANISM: Artificial Sequence
<220> FEATURE:
<223> OTHER INFORMATION: synthetic construct; STAT3 target sequence

<400> SEQUENCE: 10
gtttcataat ctcctgggag ag                                              22

<210> SEQ ID NO 11
<211> LENGTH: 22
<212> TYPE: DNA
<213> ORGANISM: Artificial Sequence
<220> FEATURE:
<223> OTHER INFORMATION: synthetic construct; STAT3 target sequence

<400> SEQUENCE: 11
ggtagagaat ctccaggatg ac                                              22

<210> SEQ ID NO 12
<211> LENGTH: 22
<212> TYPE: DNA
<213> ORGANISM: Artificial Sequence
<220> FEATURE:
<223> OTHER INFORMATION: synthetic construct; STAT3 target sequence

<400> SEQUENCE: 12
aatcgtggag ctgtttagaa ac                                              22
```

```
<210> SEQ ID NO 13
<211> LENGTH: 97
<212> TYPE: DNA
<213> ORGANISM: Artificial Sequence
<220> FEATURE:
<223> OTHER INFORMATION: synthetic construct; shRNA

<400> SEQUENCE: 13
tgctgttgac agtgagcgat tcataatct cctgggagag tagtgaagcc acagatgtac      60
tctcccagga gattatgaaa ctgcctactg cctcgga                              97

<210> SEQ ID NO 14
<211> LENGTH: 97
<212> TYPE: DNA
<213> ORGANISM: Artificial Sequence
<220> FEATURE:
<223> OTHER INFORMATION: synthetic construct; shRNA

<400> SEQUENCE: 14
tgctgttgac agtgagcgag tagagaatct ccaggatgac tagtgaagcc acagatgtag      60
tcatcctgga gattctctac ctgcctactg cctcgga                              97

<210> SEQ ID NO 15
<211> LENGTH: 97
<212> TYPE: DNA
<213> ORGANISM: Artificial Sequence
<220> FEATURE:
<223> OTHER INFORMATION: synthetic construct; shRNA

<400> SEQUENCE: 15
tgctgttgac agtgagcgca tcgtggagct gtttagaaac tagtgaagcc acagatgtag      60
tttctaaaca gctccacgat ttgcctactg cctcgga                              97

<210> SEQ ID NO 16
<211> LENGTH: 22
<212> TYPE: DNA
<213> ORGANISM: Artificial Sequence
<220> FEATURE:
<223> OTHER INFORMATION: synthetic construct; VEGFR target sequence

<400> SEQUENCE: 16
cttggagcat ctcatctgtt ac                                              22

<210> SEQ ID NO 17
<211> LENGTH: 22
<212> TYPE: DNA
<213> ORGANISM: Artificial Sequence
<220> FEATURE:
<223> OTHER INFORMATION: synthetic construct; VEGFR target sequence

<400> SEQUENCE: 17
atgccaccat gttctctaat ag                                              22

<210> SEQ ID NO 18
<211> LENGTH: 22
<212> TYPE: DNA
<213> ORGANISM: Artificial Sequence
<220> FEATURE:
<223> OTHER INFORMATION: synthetic construct; VEGFR target sequence

<400> SEQUENCE: 18
ctgagtccgt ctcatggaat tg                                              22
```

```
<210> SEQ ID NO 19
<211> LENGTH: 97
<212> TYPE: DNA
<213> ORGANISM: Artificial Sequence
<220> FEATURE:
<223> OTHER INFORMATION: synthetic construct; shRNA

<400> SEQUENCE: 19
tgctgttgac agtgagcgat tggagcatct catctgttac tagtgaagcc acagatgtag      60
taacagatga gatgctccaa gtgcctactg cctcgga                              97

<210> SEQ ID NO 20
<211> LENGTH: 97
<212> TYPE: DNA
<213> ORGANISM: Artificial Sequence
<220> FEATURE:
<223> OTHER INFORMATION: synthetic construct; shRNA

<400> SEQUENCE: 20
tgctgttgac agtgagcgct gccaccatgt tctctaatag tagtgaagcc acagatgtac      60
tattagagaa catggtggca ttgcctactg cctcgga                              97

<210> SEQ ID NO 21
<211> LENGTH: 97
<212> TYPE: DNA
<213> ORGANISM: Artificial Sequence
<220> FEATURE:
<223> OTHER INFORMATION: synthetic construct; shRNA

<400> SEQUENCE: 21
tgctgttgac agtgagcgat gagtccgtct catggaattg tagtgaagcc acagatgtac      60
aattccatga gacggactca gtgcctactg cctcgga                              97

<210> SEQ ID NO 22
<211> LENGTH: 22
<212> TYPE: DNA
<213> ORGANISM: Artificial Sequence
<220> FEATURE:
<223> OTHER INFORMATION: synthetic construct; EPOR target sequence

<400> SEQUENCE: 22
caccgagtgt gtgctgagca ac                                              22

<210> SEQ ID NO 23
<211> LENGTH: 22
<212> TYPE: DNA
<213> ORGANISM: Artificial Sequence
<220> FEATURE:
<223> OTHER INFORMATION: synthetic construct; EPOR target sequence

<400> SEQUENCE: 23
ttccctggaa gtcctctcag ag                                              22

<210> SEQ ID NO 24
<211> LENGTH: 22
<212> TYPE: DNA
<213> ORGANISM: Artificial Sequence
<220> FEATURE:
<223> OTHER INFORMATION: synthetic construct; EPOR target sequence

<400> SEQUENCE: 24
ccgccgggct ctgaagcaga ag                                              22

<210> SEQ ID NO 25
```

```
<211> LENGTH: 97
<212> TYPE: DNA
<213> ORGANISM: Artificial Sequence
<220> FEATURE:
<223> OTHER INFORMATION: synthetic construct; shRNA

<400> SEQUENCE: 25
tgctgttgac agtgagcgaa ccgagtgtgt gctgagcaac tagtgaagcc acagatgtag     60
ttgctcagca cacactcggt gtgcctactg cctcgga                              97

<210> SEQ ID NO 26
<211> LENGTH: 97
<212> TYPE: DNA
<213> ORGANISM: Artificial Sequence
<220> FEATURE:
<223> OTHER INFORMATION: synthetic construct; shRNA

<400> SEQUENCE: 26
tgctgttgac agtgagcgct ccctggaagt cctctcagag tagtgaagcc acagatgtac     60
tctgagagga cttccaggga atgcctactg cctcgga                              97

<210> SEQ ID NO 27
<211> LENGTH: 97
<212> TYPE: DNA
<213> ORGANISM: Artificial Sequence
<220> FEATURE:
<223> OTHER INFORMATION: synthetic construct; shRNA

<400> SEQUENCE: 27
tgctgttgac agtgagcgac gccgggctct gaagcagaag tagtgaagcc acagatgtac     60
ttctgcttca gagcccggcg gtgcctactg cctcgga                              97

<210> SEQ ID NO 28
<211> LENGTH: 22
<212> TYPE: DNA
<213> ORGANISM: Artificial Sequence
<220> FEATURE:
<223> OTHER INFORMATION: synthetic construct; STAT3 target sequence

<400> SEQUENCE: 28
catgcaggat ctgaatggaa ac                                              22

<210> SEQ ID NO 29
<211> LENGTH: 22
<212> TYPE: DNA
<213> ORGANISM: Artificial Sequence
<220> FEATURE:
<223> OTHER INFORMATION: synthetic construct; STAT3 target sequence

<400> SEQUENCE: 29
gatcgtggat ctgttcagaa ac                                              22

<210> SEQ ID NO 30
<211> LENGTH: 22
<212> TYPE: DNA
<213> ORGANISM: Artificial Sequence
<220> FEATURE:
<223> OTHER INFORMATION: synthetic construct; STAT3 target sequence

<400> SEQUENCE: 30
cagagggtct cggaaattta ac                                              22

<210> SEQ ID NO 31
<211> LENGTH: 22
```

```
<212> TYPE: DNA
<213> ORGANISM: Artificial Sequence
<220> FEATURE:
<223> OTHER INFORMATION: synthetic construct; STAT3 target sequence

<400> SEQUENCE: 31
aatgcaggat ctgaatggaa ac                                              22

<210> SEQ ID NO 32
<211> LENGTH: 22
<212> TYPE: DNA
<213> ORGANISM: Artificial Sequence
<220> FEATURE:
<223> OTHER INFORMATION: synthetic construct; STAT3 target sequence

<400> SEQUENCE: 32
aatcgtggat ctgttcagaa ac                                              22

<210> SEQ ID NO 33
<211> LENGTH: 22
<212> TYPE: DNA
<213> ORGANISM: Artificial Sequence
<220> FEATURE:
<223> OTHER INFORMATION: synthetic construct; STAT3 target sequence

<400> SEQUENCE: 33
aagagggtct cggaaattta ac                                              22

<210> SEQ ID NO 34
<211> LENGTH: 22
<212> TYPE: DNA
<213> ORGANISM: Artificial Sequence
<220> FEATURE:
<223> OTHER INFORMATION: synthetic construct; STAT3 target sequence

<400> SEQUENCE: 34
atttcataat ctcctgggag ag                                              22

<210> SEQ ID NO 35
<211> LENGTH: 22
<212> TYPE: DNA
<213> ORGANISM: Artificial Sequence
<220> FEATURE:
<223> OTHER INFORMATION: synthetic construct; STAT3 target sequence

<400> SEQUENCE: 35
agtagagaat ctccaggatg ac                                              22

<210> SEQ ID NO 36
<211> LENGTH: 22
<212> TYPE: DNA
<213> ORGANISM: Artificial Sequence
<220> FEATURE:
<223> OTHER INFORMATION: synthetic construct; STAT3 target sequence

<400> SEQUENCE: 36
catcgtggag ctgtttagaa ac                                              22

<210> SEQ ID NO 37
<211> LENGTH: 22
<212> TYPE: DNA
<213> ORGANISM: Artificial Sequence
<220> FEATURE:
<223> OTHER INFORMATION: synthetic construct; VEGFR2 target sequence

<400> SEQUENCE: 37
```
catcgtttat gtctatgttc aa                                              22

<210> SEQ ID NO 38
<211> LENGTH: 22
<212> TYPE: DNA
<213> ORGANISM: Artificial Sequence
<220> FEATURE:
<223> OTHER INFORMATION: synthetic construct; VEGFR target sequence

<400> SEQUENCE: 38
gacccattga gtccaattac ac                                              22

<210> SEQ ID NO 39
<211> LENGTH: 22
<212> TYPE: DNA
<213> ORGANISM: Artificial Sequence
<220> FEATURE:
<223> OTHER INFORMATION: synthetic construct; VEGFR target sequence

<400> SEQUENCE: 39
catggtctct ctggttgtga at                                              22

<210> SEQ ID NO 40
<211> LENGTH: 22
<212> TYPE: DNA
<213> ORGANISM: Artificial Sequence
<220> FEATURE:
<223> OTHER INFORMATION: synthetic construct; VEGFR target sequence

<400> SEQUENCE: 40
aatcgtttat gtctatgttc aa                                              22

<210> SEQ ID NO 41
<211> LENGTH: 22
<212> TYPE: DNA
<213> ORGANISM: Artificial Sequence
<220> FEATURE:
<223> OTHER INFORMATION: synthetic construct; VEGFR target sequence

<400> SEQUENCE: 41
aacccattga gtccaattac ac                                              22

<210> SEQ ID NO 42
<211> LENGTH: 22
<212> TYPE: DNA
<213> ORGANISM: Artificial Sequence
<220> FEATURE:
<223> OTHER INFORMATION: synthetic construct; VEGFR target sequence

<400> SEQUENCE: 42
aatggtctct ctggttgtga at                                              22

<210> SEQ ID NO 43
<211> LENGTH: 22
<212> TYPE: DNA
<213> ORGANISM: Artificial Sequence
<220> FEATURE:
<223> OTHER INFORMATION: synthetic construct; VEGFR target sequence

<400> SEQUENCE: 43
attggagcat ctcatctgtt ac                                              22

<210> SEQ ID NO 44
<211> LENGTH: 22
<212> TYPE: DNA
<213> ORGANISM: Artificial Sequence

```
<220> FEATURE:
<223> OTHER INFORMATION: synthetic construct; VEGFR target sequence

<400> SEQUENCE: 44
ctgccaccat gttctctaat ag                                           22

<210> SEQ ID NO 45
<211> LENGTH: 22
<212> TYPE: DNA
<213> ORGANISM: Artificial Sequence
<220> FEATURE:
<223> OTHER INFORMATION: synthetic construct; VEGFR target sequence

<400> SEQUENCE: 45
atgagtccgt ctcatggaat tg                                           22

<210> SEQ ID NO 46
<211> LENGTH: 22
<212> TYPE: DNA
<213> ORGANISM: Artificial Sequence
<220> FEATURE:
<223> OTHER INFORMATION: synthetic construct; EPOR target sequence

<400> SEQUENCE: 46
cactgagtgt gtcctgagca ac                                           22

<210> SEQ ID NO 47
<211> LENGTH: 22
<212> TYPE: DNA
<213> ORGANISM: Artificial Sequence
<220> FEATURE:
<223> OTHER INFORMATION: synthetic construct; EPOR target sequence

<400> SEQUENCE: 47
gtctctcatt ctcgtcctca tc                                           22

<210> SEQ ID NO 48
<211> LENGTH: 22
<212> TYPE: DNA
<213> ORGANISM: Artificial Sequence
<220> FEATURE:
<223> OTHER INFORMATION: synthetic construct; EPOR target sequence

<400> SEQUENCE: 48
cgggcactgc ctcctgagct ac                                           22

<210> SEQ ID NO 49
<211> LENGTH: 22
<212> TYPE: DNA
<213> ORGANISM: Artificial Sequence
<220> FEATURE:
<223> OTHER INFORMATION: synthetic construct; EPOR target sequence

<400> SEQUENCE: 49
aactgagtgt gtcctgagca ac                                           22

<210> SEQ ID NO 50
<211> LENGTH: 22
<212> TYPE: DNA
<213> ORGANISM: Artificial Sequence
<220> FEATURE:
<223> OTHER INFORMATION: synthetic construct; EPOR target sequence

<400> SEQUENCE: 50
atctctcatt ctcgtcctca tc                                           22
```

```
<210> SEQ ID NO 51
<211> LENGTH: 22
<212> TYPE: DNA
<213> ORGANISM: Artificial Sequence
<220> FEATURE:
<223> OTHER INFORMATION: synthetic construct; EPOR target sequence

<400> SEQUENCE: 51
agggcactgc ctcctgagct ac                                              22

<210> SEQ ID NO 52
<211> LENGTH: 22
<212> TYPE: DNA
<213> ORGANISM: Artificial Sequence
<220> FEATURE:
<223> OTHER INFORMATION: synthetic construct; EPOR target sequence

<400> SEQUENCE: 52
aaccgagtgt gtgctgagca ac                                              22

<210> SEQ ID NO 53
<211> LENGTH: 22
<212> TYPE: DNA
<213> ORGANISM: Artificial Sequence
<220> FEATURE:
<223> OTHER INFORMATION: synthetic construct; EPOR target sequence

<400> SEQUENCE: 53
ctccctggaa gtcctctcag ag                                              22

<210> SEQ ID NO 54
<211> LENGTH: 22
<212> TYPE: DNA
<213> ORGANISM: Artificial Sequence
<220> FEATURE:
<223> OTHER INFORMATION: synthetic construct; EPOR target sequence

<400> SEQUENCE: 54
acgccgggct ctgaagcaga ag                                              22

<210> SEQ ID NO 55
<211> LENGTH: 97
<212> TYPE: DNA
<213> ORGANISM: Artificial Sequence
<220> FEATURE:
<223> OTHER INFORMATION: synthetic construct, luciferase shRNA

<400> SEQUENCE: 55
tgctgttgac agtgagcgaa atgtttacta cactcggata tagtgaagcc acagatgtat     60
atccgagtgt agtaaacatt ctgcctactg cctcgga                              97
```

METHODS AND COMPOSITIONS FOR INHIBITING RETINOPATHY OF PREMATURITY

CROSS-REFERENCE TO RELATED APPLICATIONS

This application claims benefit of and priority under 35 U.S.C. § 371 of PCT/US2015/015886, filed Feb. 13, 2015, which claims the benefit under 35 U.S.C. § 119(e) of U.S. Provisional Application No. 61/940,130, filed Feb. 14, 2014, and U.S. Provisional Application No. 62/008,148, filed Jun. 5, 2014, which are incorporated herein by reference in their entirety.

STATEMENT REGARDING FEDERALLY SPONSORED RESEARCH

This invention was made with government support under Grant Numbers EY015130 and EY017011 awarded by the National Institutes of Health. The government has certain rights in the invention.

REFERENCE TO THE SEQUENCE LISTING

The Sequence Listing submitted Jan. 17, 2018 as a text file named "21101_0294U3 _updated_Sequence_Listing.txt," created on Jan. 8,2018, and having a size of 13,404 bytes is hereby incorporated by reference pursuant to 37 C.F.R. § 1.52(e)(5).

BACKGROUND

Retinopathy of prematurity (ROP) is a leading cause of childhood blindness worldwide and is increasing as emerging countries develop technology to save preterm infants but lack resources to provide optimal care. In the U.S.,~14% of childhood blindness is attributed to ROP and in some developing nations, estimates are>20%. ROP is characterized by two phases based on clinical observations and animal models. In Phase I ROP, mainly peripheral avascular retina occurs from a delay in physiologic retinal vascular development (PRVD) and, in places with insufficient resources to regulate oxygen, hyperoxia-induced vaso-attenuation. In Phase II ROP, hypoxia-induced intravitreal neovascularization (IVNV) occurs. Treatments of IVNV in human severe ROP include laser ablation of peripheral avascular retina, which destroys developing retina, or intravitreal anti-VEGF agents, which can lead to persistent avascular retina, recurrent IVNV, and even blindness from retinal detachment. Intravitreal anti-VEGF agents reduce serum VEGF levels for weeks in human preterm infants and inhibit postnatal growth in pups in a rat model of ROP raising additional safety concerns. Some experimental methods to promote PRVD (e.g. insulin-like growth factor-1 or erythropoietin [EPO]) can worsen Phase II IVNV, whereas agents to inhibit IVNV (e.g. anti-VEGF) can cause persistent avascular retina, a stimulus for later IVNV. Therefore, the strategy for ROP in these fragile preterm infants is to understand mechanisms that allow for targeting specific cells and regulating signaling events involved in IVNV without interfering with PRVD.

BRIEF SUMMARY

Disclosed are methods of treating proliferative retinopathies associated with intravitreal neovascularization comprising, administering to a subject a composition comprising a vector, wherein the vector comprises a polymerase II (pol II) promoter and a first shRNA, wherein the shRNA is embedded in a microRNA construct, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition is administered via subretinal injection. For the disclosed methods, proliferative retinopathies associated with intravitreal neovascularization, include, but are not limited to retinopathy of prematurity (ROP), proliferative diabetic retinopathy and neovascularization associated with vein occlusions.

Disclosed are methods of treating proliferative retinopathies associated with intravitreal neovascularization comprising administering to a subject a composition comprising a vector, wherein the vector comprises a polymerase II (pol II) promoter and a first shRNA, wherein the shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition is administered via subretinal injection, wherein the sense RNA strand comprises a nucleotide sequence identical to a target sequence in STAT3. The nucleotide sequence identical to a target sequence in STAT3 consists of SEQ ID NO:28, SEQ ID NO:29, SEQ ID NO:30, SEQ ID NO:10, SEQ ID NO:11, SEQ ID NO:12, SEQ ID NO:31, SEQ ID NO:32, SEQ ID NO:33, SEQ ID NO:34, SEQ ID NO:35, or SEQ ID NO:36.

Disclosed are methods of treating proliferative retinopathies associated with intravitreal neovascularization comprising administering to a subject a composition comprising a vector, wherein the vector comprises a polymerase II (pol II) promoter and a first shRNA, wherein the shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition can be administered via subretinal injection, wherein the sense RNA strand comprises a nucleotide sequence identical to a target sequence in VEGFR. The VEGFR can be VEGFR2. The nucleotide sequence identical to a target sequence in VEGFR can consist of SEQ ID NO:37, SEQ ID NO:38, SEQ ID NO:39, SEQ ID NO:16, SEQ ID NO:17, SEQ ID NO:18, SEQ ID NO:40, SEQ ID NO:41, SEQ ID NO:42, SEQ ID NO:43, SEQ ID NO:44, or SEQ ID NO 45.

Disclosed are methods of treating proliferative retinopathies associated with intravitreal neovascularization comprising administering to a subject a composition comprising a vector, wherein the vector comprises a polymerase II (pol II) promoter and a first shRNA, wherein the shRNA is embedded in microRNA, and wherein the first shRNA has a sense RNA strand and an antisense RNA strand, wherein the sense and the antisense RNA strands form an RNA duplex, wherein the sense RNA strand comprise a nucleotide sequence identical to a target sequence in STAT3, VEGFR2, or EPOR mRNA, and wherein the composition can be administered via subretinal injection, wherein the sense RNA strand comprises a nucleotide sequence identical to a target sequence in EPOR. The nucleotide sequence identical to a target sequence in EPOR consists of SEQ ID NO:46, SEQ ID NO:47, SEQ ID NO:48, SEQ ID NO:22, SEQ ID NO:23, SEQ ID NO:24, SEQ ID NO:49, SEQ ID NO:50, SEQ ID NO:51, SEQ ID NO:52, SEQ ID NO:53, or SEQ ID NO:54.

Disclosed are methods of treating proliferative retinopathies associated with intravitreal neovascularization comprising administering to a subject a composition comprising a vector, wherein the vector comprises a polymerase II (pol II) promoter and a first shRNA, wherein the shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition can be administered via subretinal injection, wherein the vector is a viral vector. The viral vector can be a retroviral vector. The retroviral vector can be a lentiviral vector.

Disclosed are methods of treating proliferative retinopathies associated with intravitreal neovascularization comprising administering to a subject a composition comprising a vector, wherein the vector comprises a polymerase II (pol II) promoter and a first shRNA, wherein the shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition can be administered via subretinal injection further comprising administering a second shRNA.

Disclosed are methods of treating proliferative retinopathies associated with intravitreal neovascularization comprising administering to a subject a composition comprising a vector, wherein the vector comprises a polymerase II (pol II) promoter and a first shRNA, wherein the shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition can be administered via subretinal injection, wherein the method further comprises administering a second shRNA, wherein the second shRNA has a sense RNA strand and an antisense RNA strand, wherein the sense and the antisense RNA strands form an RNA duplex, and wherein the sense RNA strand comprises a nucleotide sequence identical to a target sequence in STAT3, VEGFR, EPOR, or VEGFA mRNA, and wherein the second shRNA is different than the first shRNA.

Disclosed are methods of treating proliferative retinopathies associated with intravitreal neovascularization comprising administering to a subject a composition comprising a vector, wherein the vector comprises a polymerase II (pol II) promoter and a first shRNA, wherein the shRNA is embedded in microRNA, and wherein the first shRNA can have a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition can be administered via subretinal injection, wherein the method further comprises administering a second shRNA, wherein the second shRNA is in the same vector as the first shRNA.

Disclosed are methods of treating proliferative retinopathies associated with intravitreal neovascularization comprising administering to a subject a composition comprising a vector, wherein the vector comprises a polymerase II (pol II) promoter and a first shRNA, wherein the shRNA is embedded in microRNA, and wherein the first shRNA can have a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition can be administered via subretinal injection, wherein the method further comprises administering a second shRNA, wherein the second shRNA is in a different vector than the first shRNA.

Disclosed are methods of treating proliferative retinopathies associated with intravitreal neovascularization comprising administering to a subject a composition comprising a vector, wherein the vector comprises a polymerase II (pol II) promoter and a first shRNA, wherein the shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition can be administered via subretinal injection, wherein the method further comprises administering a second shRNA, wherein the second shRNA is administered in a separate composition from the first shRNA.

Disclosed are methods of treating proliferative retinopathies associated with intravitreal neovascularization comprising administering to a subject a composition comprising a vector, wherein the vector comprises a polymerase II (pol II) promoter and a first shRNA, wherein the shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition is administered via subretinal injection, wherein the pol II promoter is an endothelial cell-specific promoter. The endothelial cell-specific promoter can be a VE-cad promoter.

Disclosed are methods of treating ROP comprising administering to a subject a composition comprising a vector, wherein the vector comprises a polymerase II (pol II) promoter and a first shRNA, wherein the shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition is administered via subretinal injection, wherein the IVNV phase of ROP is inhibited without interfering with physiologic retinal vascular development (PRVD).

Disclosed are methods of treating ROP comprising administering to a subject a composition comprising a vector, wherein the vector comprises a polymerase II (pol II) promoter and a first shRNA, wherein the shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition is administered via subretinal injection, wherein the subject has been previously diagnosed with ROP.

Disclosed are methods of inhibiting expression of STAT3 comprising administering to a subject a composition comprising a vector, wherein the vector comprises a pol II promoter and a first shRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3 mRNA, and wherein the composition is administered via subretinal injection.

Disclosed are methods of inhibiting expression of STAT3 comprising administering to a subject a composition comprising a vector, wherein the vector comprises a pol II promoter and a first shRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3 mRNA, and wherein the composition is administered via subretinal injection, wherein the nucleotide sequence identical to a target sequence in STAT3 mRNA consists of SEQ ID NO:28, SEQ ID NO:29, SEQ ID NO:30, SEQ ID NO:10, SEQ ID NO:11, SEQ ID NO:12, SEQ ID NO:31, SEQ ID NO:32, SEQ ID NO:33, SEQ ID NO:34, SEQ ID NO:35, or SEQ ID NO:36.

Disclosed are methods of inhibiting expression of EPOR comprising administering to a subject a composition comprising a vector, wherein the vector comprises a pol II promoter and a first shRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in EPOR mRNA, and wherein the composition is administered via subretinal injection.

Disclosed are methods of inhibiting expression of EPOR comprising administering to a subject a composition comprising a vector, wherein the vector comprises a pol II promoter and a first shRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in EPOR mRNA, and wherein the composition is administered via subretinal injection, wherein the nucleotide sequence identical to a target sequence in EPOR consists of SEQ ID NO:46, SEQ ID NO:47, SEQ ID NO:48, SEQ ID NO:22, SEQ ID NO:23, SEQ ID NO:24, SEQ ID NO:49, SEQ ID NO:50, SEQ ID NO:51, SEQ ID NO:52, SEQ ID NO:53, or SEQ ID NO:54.

Disclosed are methods of inhibiting expression of VEGFR comprising administering to a subject a composition comprising a vector, wherein the vector comprises a pol II promoter and a first shRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in VEGFR mRNA, and wherein the composition is administered via subretinal injection.

Disclosed are methods of inhibiting expression of VEGFR comprising administering to a subject a composition comprising a vector, wherein the vector comprises a pol II promoter and a first shRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in VEGFR mRNA, and wherein the composition is administered via subretinal injection, wherein the nucleotide sequence identical to a target sequence in VEGFR consists of SEQ ID NO:37, SEQ ID NO:38, SEQ ID NO:39, SEQ ID NO:16, SEQ ID NO:17, SEQ ID NO:18, SEQ ID NO:40, SEQ ID NO:41, SEQ ID NO:42, SEQ ID NO:43, SEQ ID NO:44, or SEQ ID NO 45.

Disclosed are methods of inhibiting expression of STAT3, EPOR, or VEGFR, comprising administering to a subject a composition comprising a vector, wherein the vector comprises a pol II promoter and a first shRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, EPOR, or VEGFR mRNA, and wherein the composition is administered via subretinal injection, wherein the shRNA is embedded in microRNA.

Disclosed are methods of inhibiting expression of STAT3, EPOR, or VEGFR, comprising administering to a subject a composition comprising a vector, wherein the vector comprises a pol II promoter and a first shRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, EPOR, or VEGFR mRNA, and wherein the composition is administered via subretinal injection, wherein the shRNA is embedded in microRNA, wherein the vector is a viral vector. The viral vector can be a retroviral vector. The retroviral vector can be a lentiviral vector.

Disclosed are methods of inhibiting expression of STAT3, EPOR, or VEGFR, comprising administering to a subject a composition comprising a vector, wherein the vector comprises a pol II promoter and a first shRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, EPOR, or VEGFR mRNA, and wherein the composition is administered via subretinal injection, wherein the shRNA is embedded in microRNA, wherein the pol II promoter is an endothelial cell-specific promoter. The endothelial cell-specific promoter can be a VE-cad promoter.

Disclosed are methods of regulating signaling events associated with IVNV comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR, or EPOR mRNA, and wherein the composition is administered via subretinal injection.

Disclosed are methods of regulating signaling events associated with IVNV comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR, or EPOR mRNA, and wherein the composition is administered via subretinal injection, wherein the sense RNA strand comprises a nucleotide sequence identical to a target sequence in STAT3.

Disclosed are methods of regulating signaling events associated with IVNV comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR, or EPOR mRNA, and wherein the composition is administered via subretinal injection, wherein the sense RNA strand comprises a nucleotide sequence identical to a target sequence in STAT3, wherein the nucleotide sequence identical to a target sequence in STAT3 consists of SEQ ID NO:28, SEQ ID NO:29, SEQ ID NO:30, SEQ ID NO:10, SEQ ID NO:11, SEQ ID NO:12, SEQ ID NO:31, SEQ ID NO:32, SEQ ID NO:33, SEQ ID NO:34, SEQ ID NO:35, or SEQ ID NO:36.

Disclosed are methods of regulating signaling events associated with IVNV comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR, or EPOR mRNA, and wherein the composition is administered via subretinal injection, wherein the sense RNA strand comprises a nucleotide sequence identical to a target sequence in VEGFR. The VEGFR can be VEGFR2.

Disclosed are methods of regulating signaling events associated with IVNV comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR, or EPOR mRNA, and wherein the composition is administered via subretinal injection, wherein the sense RNA strand comprises a nucleotide sequence identical to a target sequence in VEGFR, wherein the VEGFR is VEGFR2, wherein the nucleotide sequence identical to a target sequence in VEGFR consists of SEQ ID NO:37, SEQ ID NO:38, SEQ ID NO:39, SEQ ID NO:16, SEQ ID NO:17, SEQ ID NO:18, SEQ ID NO:40, SEQ ID NO:41, SEQ ID NO:42, SEQ ID NO:43, SEQ ID NO:44, or SEQ ID NO 45.

Disclosed are methods of regulating signaling events associated with IVNV comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR, or EPOR mRNA, and wherein the composition is administered via subretinal injection, wherein the sense RNA strand comprises a nucleotide sequence identical to a target sequence in EPOR.

Disclosed are methods of regulating signaling events associated with IVNV comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR, or EPOR mRNA, and wherein the composition is administered via subretinal injection, wherein the sense RNA strand comprises a nucleotide sequence identical to a target sequence in EPOR, wherein the nucleotide sequence identical to a target sequence in EPOR consists of SEQ ID NO:46, SEQ ID NO:47, SEQ ID NO:48, SEQ ID NO:22, SEQ ID NO:23, SEQ ID NO:24, SEQ ID NO:49, SEQ ID NO:50, SEQ ID NO:51, SEQ ID NO:52, SEQ ID NO:53, or SEQ ID NO:54.

Disclosed are methods of regulating signaling events associated with IVNV comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR, or EPOR mRNA, and wherein the composition is administered via subretinal injection, wherein the vector is a viral vector. The viral vector can be a retroviral vector. The retroviral vector can be a lentiviral vector.

Disclosed are methods of regulating signaling events associated with IVNV comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR, or EPOR mRNA, and wherein the composition is administered via subretinal injection further comprising administering a second shRNA.

Disclosed are methods of regulating signaling events associated with IVNV comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR, or EPOR mRNA, and wherein the composition is administered via subretinal injection further comprising administering a second shRNA, wherein the second shRNA has a sense RNA strand and an antisense RNA strand, wherein the sense and the antisense RNA strands form an RNA duplex, and wherein the sense RNA strand comprises a nucleotide sequence identical to a target sequence in STAT3, VEGFR, or EPOR mRNA, and wherein the second shRNA is different than the first shRNA.

Disclosed are methods of regulating signaling events associated with IVNV comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR, or EPOR mRNA, and wherein the composition is administered via subretinal injection further comprising administering a second shRNA, wherein the second shRNA has a sense RNA strand and an antisense RNA strand, wherein the sense and the antisense RNA strands form an RNA duplex, and wherein the sense RNA strand comprises a nucleotide sequence identical to a target sequence in STAT3, VEGFR, or EPOR mRNA, and wherein the second shRNA is different than the first shRNA, wherein the second shRNA is in the same vector as the first shRNA.

Disclosed are methods of regulating signaling events associated with IVNV comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR, or EPOR mRNA, and wherein the composition is administered via subretinal injection further comprising administering a second shRNA, wherein the second shRNA has a sense RNA strand and an antisense RNA strand, wherein the sense and the antisense RNA strands form an RNA duplex, and wherein the sense RNA strand comprises a nucleotide sequence identical to a target sequence in STAT3, VEGFR, or EPOR mRNA, and wherein the second shRNA is different than the first shRNA, wherein the second shRNA is in a different vector than the first shRNA.

Disclosed are methods of regulating signaling events associated with IVNV comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR, or EPOR mRNA, and wherein the composition is administered via subretinal injection further comprising administering a second shRNA, wherein the second shRNA has a sense RNA strand and an antisense RNA strand, wherein the sense and the antisense RNA strands form an RNA duplex, and wherein the sense RNA strand comprises a nucleotide sequence identical to a target sequence in STAT3, VEGFR, or EPOR mRNA, and wherein the second shRNA is different than the first shRNA, wherein the second shRNA is administered in a separate composition from the first shRNA.

Disclosed are methods of regulating signaling events associated with IVNV comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR, or EPOR mRNA, and wherein the composition is administered via subretinal injection, wherein the pol II promoter is an endothelial cell-specific promoter. The endothelial cell-specific promoter can be a VE-cad promoter.

Disclosed are vectors comprising a pol II promoter and an shRNA, wherein the shRNA has a sense RNA strand and an antisense RNA strand, wherein the sense and the antisense RNA strands form an RNA duplex, and wherein the sense RNA strand comprises a nucleotide sequence identical to a target sequence in STAT3, VEGFR, or EPOR mRNA.

Disclosed are vectors comprising a pol II promoter and an shRNA, wherein the shRNA has a sense RNA strand and an antisense RNA strand, wherein the sense and the antisense RNA strands form an RNA duplex, and wherein the sense RNA strand comprises a nucleotide sequence identical to a target sequence in STAT3, VEGFR, or EPOR mRNA, wherein the sense RNA strand comprises a nucleotide sequence identical to a target sequence in STAT3.

Disclosed are vectors comprising a pol II promoter and an shRNA, wherein the shRNA has a sense RNA strand and an antisense RNA strand, wherein the sense and the antisense RNA strands form an RNA duplex, and wherein the sense RNA strand comprises a nucleotide sequence identical to a target sequence in STAT3, VEGFR, or EPOR mRNA, wherein the sense RNA strand comprises a nucleotide sequence identical to a target sequence in VEGFR.

Disclosed are vectors comprising a pol II promoter and an shRNA, wherein the shRNA has a sense RNA strand and an antisense RNA strand, wherein the sense and the antisense RNA strands form an RNA duplex, and wherein the sense RNA strand comprises a nucleotide sequence identical to a target sequence in STAT3, VEGFR, or EPOR mRNA, wherein the sense RNA strand comprises a nucleotide sequence identical to a target sequence in EPOR.

Disclosed are vectors comprising a pol II promoter and an shRNA wherein the shRNA has a sense RNA strand and an antisense RNA strand, wherein the sense and the antisense RNA strands form an RNA duplex, and wherein the sense RNA strand comprises a nucleotide sequence identical to a target sequence in STAT3 consisting of SEQ ID NO:1, SEQ ID NO:2, or SEQ ID NO:3.

Disclosed are vectors comprising a pol II promoter and an shRNA wherein the shRNA has a sense RNA strand and an antisense RNA strand, wherein the sense and the antisense RNA strands form an RNA duplex, and wherein the sense RNA strand comprises a nucleotide sequence identical to a target sequence in VEGFR consisting of SEQ ID NO:4, SEQ ID NO:5, or SEQ ID NO:6.

Disclosed are vectors comprising a pol II promoter and an shRNA wherein the shRNA has a sense RNA strand and an antisense RNA strand, wherein the sense and the antisense RNA strands form an RNA duplex, and wherein the sense RNA strand comprises a nucleotide sequence identical to a target sequence in EPOR consisting of SEQ ID NO:7, SEQ ID NO:8, or SEQ ID NO:9.

Disclosed are any of the above vectors, wherein the pol II promoter is an endothelial cell-specific promoter. The endothelial cell-specific promoter can be a VE-cad promoter Disclosed are any of the above vectors, wherein the vector is a viral vector. The viral vector can be a retroviral vector. The retroviral vector can be a lentiviral vector.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIGS. 37A, 37B, and 37C show that VEGFA-activated EPOR interacts with p-VEGFR2 in hRMVECs. A: Western blots of phosphorylated and total VEGFR2 and EPOR in hRMVECs treated with PBS or VEGFA in the presence of DMSO control or SU5416. B and C: Coimmunoprecipitation of p-EPOR and VEGFR2 in hRMVECs treated with PBS or VEGFA in the presence of DMSO control or SU5416 (B) or in hRMVECs transfected with Con.siRNA or EPOR.siRNA (C). Gels are representative of three or more independent experiments. n=6. IB, immunoblot (Western blot); IP, immunoprecipitation.

FIGS. 38A, 38B, 38C, 38D, 38E, and 38F show that the knockdown of EPOR reduces VEGFA-induced p-VEGFR2 and inhibits VEGFA-induced p-EPOR and p-STAT3 in hRMVECs. Representative Western blots, with quantification of densitometry, for p-EPOR (A and B), p-VEGFR2 (C and D), and p-STAT3 (E and F) in hRMVECs transfected with Con.siRNA or EPOR.siRNA and treated with PBS or VEGFA. Data are expressed as means±SD, representative of three or more independent experiments. n=6. *P<0.05, **P<0.01 versus PBS of Con.siRNA. †P<0.05, ††P<0.01 versus VEGFA of Con.siRNA. ‡P<0.05 versus PBS of EPOR. siRNA.

FIGS. 39A, 39B, 39C, 39D, 39E, and 39F show that STAT3 is the downstream target of activated VEGFR2 and EPOR, and activation of STAT3 mediates VEGFA-induced EC proliferation. A and B: Representative Western blots (A) and quantification (B) of p-STAT3 and total STAT3 in hRMVECs treated with PBS or VEGFA in the presence of control DMSO or SU5416. Quantification of densitometry of p-STAT3 is normalized to total STAT3. C-E: Representative Western blots (C) with quantification (D and E) of p-VEGFR2, p-EPOR, total VEGFR2, and total STAT3 in hRMVECs transfected with Con.siRNA, VEGFR2.siRNA, or STAT3.siRNA and treated with PBS or with 20 ng/mL VEGFA for 30 minutes. Quantification of densitometry of p-VEGFR2 is normalized to total VEGFR2 (D) and that of p-EPOR is normalized to β-actin (E). F: Cell proliferation assay in hRMVECs treated with PBS or VEGFA in the presence of DMSO or AG490 Data are expressed as means±SD, representative of three or more independent experiments. n=6. ***P<0.001 versus PBS of DMSO control (B and F). †††P<0.001 versus VEGFA of DMSO control) (B and F). ‡P<0.05, ‡‡‡P<0.001 versus PBS of Con.siRNA (D and E). § P<0.05, §§§ P<0.001 versus PBS of STAT3 siRNA (D and E).

FIGS. 41A, 41B, 41C, 41D, 41E, 41F, and 41G show that mRNA of VEGFA splice variants is localized in the inner nuclear layer (INL) corresponding to Müller cells in the rat 50/10 OIR model. FISH of VEGFA splice variants (VEGF120, VEGF188, and VEGF164) in retinal cryosections at p14 shows the VEGFA splice variant message in regions where CRALBP-labeled Müller cells were present (A) in the rat 50/10 OIR model (B-D) and in a room air-raised pup at p14 (RA; E-G). The expression of VEGFA is also present in the external limiting layer, retinal pigment epithelium (RPE), and photoreceptor regions. GCL, ganglion cell layer; ONL, outer nuclear layer.

FIG. 48 shows a table of shRNA sequences. From top to bottom the sequences are SEQ ID NOs: 7, 8, 9, 4, 5, 6, 1, 2, 3, and 55, respectively.

DETAILED DESCRIPTION

Figure 1:
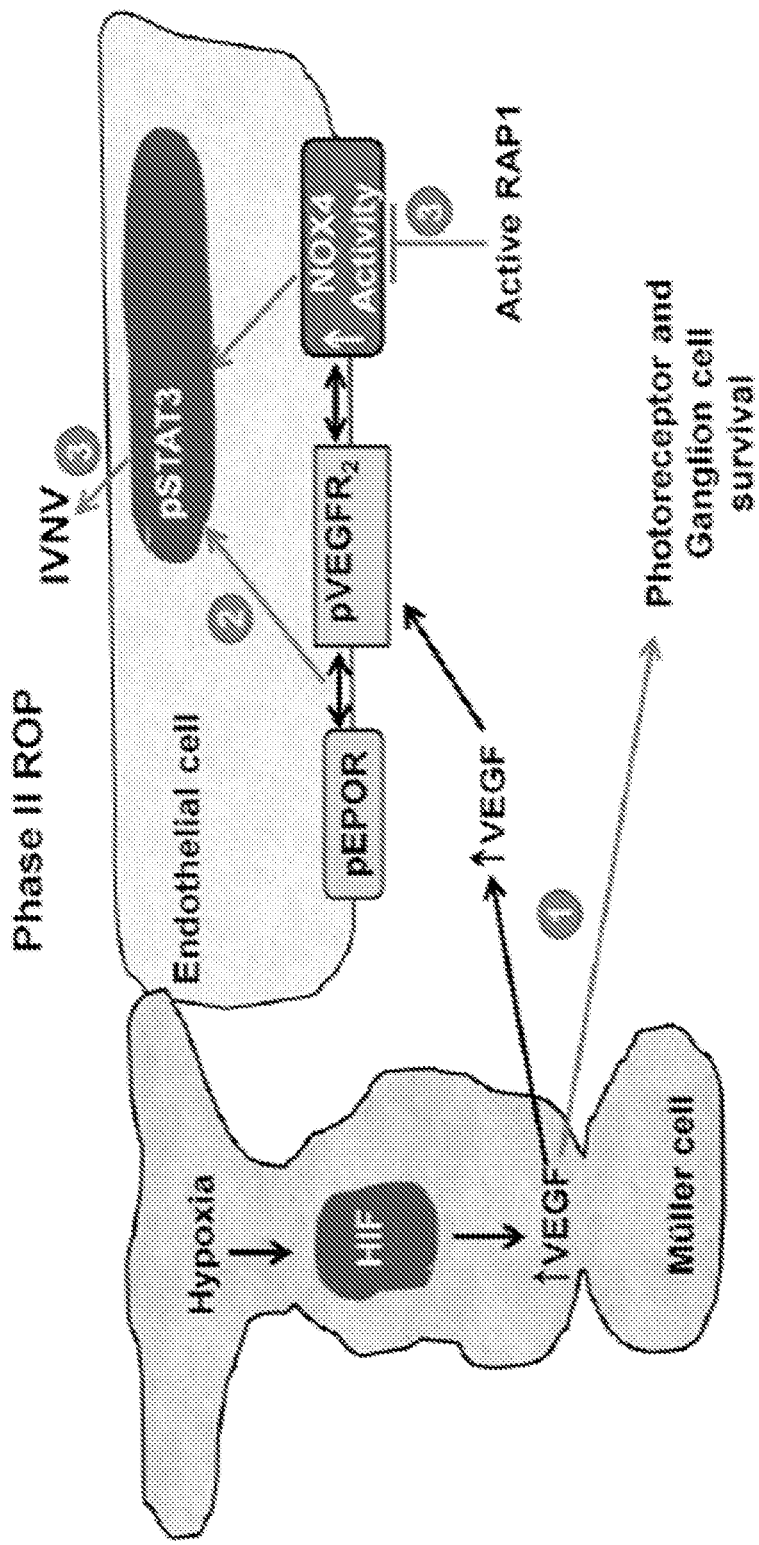
FIG. 1 shows that [a] VEGF produced by Müller Cells (MCs) promotes survival in photoreceptors, retinal neurons, and MCs. However, [b] VEGF also binds and phosphorylates VEGFR2 in Endothelial Cells (ECs) to activate EPOR and NOX4/NADPH oxidase. [c] Activated-EPOR or -NOX4 interacts with pVEGFR2 and overactivates EC-STAT3 to cause IVNV in Phase II.

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a shRNA is disclosed and discussed and a number of modifications that can be made to a number of molecules including the shRNA are discussed, each and every combination and permutation of the shRNA and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

The term "polymerase II promoter," also called pol II promoter, refers to an enzyme that catalyzes transcription of DNA to synthesize precursors of mRNA, and most snRNA and microRNA.

The phrase "embedded in microRNA" or "embedded in a microRNA construct" denotes inserting a nucleic acid sequence into a microRNA that only contains the 3' and 5' arms so that the construct will not become a mature miRNA as a part of active RNA-induced silencing complex (RISC). In some aspects, the shRNAs disclosed herein can be embedded in a microRNA construct in to allow shRNAs to be expressed in certain cells under the control of cell specific polymerase II promoters. For example, the microRNA can be miR30.

A "target sequence" is a sequence present in an mRNA of interest. The target sequence can be used to make a sense RNA strand identical to it, wherein the sense RNA is part of an shRNA.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

As used herein, the term "subject" or "patient" refers to any organism to which a composition of this invention may be administered, e.g., for experimental, diagnostic, and/or therapeutic purposes. Typical subjects include animals (e.g., mammals such as non-human primates, and humans; avians; domestic household or farm animals such as cats, dogs, sheep, goats, cattle, horses and pigs; laboratory animals such as mice, rats and guinea pigs; rabbits; fish; reptiles; zoo and wild animals). Typically, "subjects" are animals, including mammals such as humans and primates and the like.

By "treat" is meant to administer a compound or molecule described herein to a subject, such as a human or other mammal (for example, an animal model), that has an increased susceptibility for developing a proliferative retinopathy associated with intravitreal neovascularization, or that has a proliferative retinopathy associated with intravitreal neovascularization, in order to prevent or delay a worsening of the effects of the disease or condition, or to partially or fully reverse the effects of the disease. For example, the proliferative retinopathy associated with intravitreal neovascularizationcan be retinopathy of prematurity (ROP), proliferative diabetic retinopathy or neovascularization associated with vein occlusions.

It must be noted that as used herein and in the appended claims, the singular forms "a", "an", and "the" include plural reference unless the context clearly dictates otherwise. Thus, for example, reference to "a shRNA" can include a plurality of such shRNAs, reference to "the vector" is a reference to one or more vectors and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range¬ from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

Those skilled in the art will recognize, or be able to ascertain using no more than routine experimentation, many equivalents to the specific embodiments of the method and compositions described herein.

B. Vectors

Disclosed are vectors comprising a polymerase II (pol II) promoter and an shRNA, wherein the shRNA has a sense RNA strand and an antisense RNA strand, wherein the sense and the antisense RNA strands form an RNA duplex, and wherein the sense RNA strand comprises a nucleotide sequence identical to a target sequence in STAT3, VEGFR, or EPOR mRNA.

The vectors disclosed herein comprise a pol II promoter, wherein the pol II promoter can be an endothelial cell-specific promoter. For example, the endothelial cell-specific promoter can be a VE-cad promoter. The pol II promoter can also be a retina-specific promoter such as a Tie2 promoter or PECAM or endothelin-1 promoters. RPE specific promoters can also be used in the vectors described herein.

The vectors disclosed herein can be a viral vectors. The viral vector can be a retroviral vector. For example, a retroviral vector can be a lentiviral vector. Other examples of viral vectors are provided elsewhere herein.

1. STAT3

Disclosed are vectors comprising a pol II promoter and an shRNA, wherein the shRNA has a sense RNA strand and an antisense RNA strand, wherein the sense and the antisense RNA strands form an RNA duplex, and wherein the sense RNA strand comprises a nucleotide sequence identical to a target sequence in STAT3.

The *homo sapiens* STAT3 sequence can be identified as Gene ID: NM_139276. The *rattus norvegicus* STAT3 CDS sequence can be identified as Gene ID: NM_012747.2. Any of the sequences disclosed in the rat sequence can be used to produce shRNAs. The prediction of thermodynamic ensemble and the optimal secondary structure with minumus free energy can be helpful for determining which shRNA to use. For example, compared to STAT3 shRNA1, the STAT3 shRNA 2, which was picked for in vivo studies, shows less free energy for both thermodynamic ensemble and secondary structure (−1.7 vs −2.8). However, shRNAs can be tested in cell studies to confirm the shRNA with the best knock-down efficiency and specificity.

Target sequences in *Rattus norvegicus* STAT3 can be, but are not limited to, CATGCAGGATCTGAATGGAAAC (SEQ ID NO:28), GATCGTGGATCTGTTCAGAAAC, (SEQ ID NO:29), or CAGAGGGTCTCGGAAATTTAAC (SEQ ID NO:30). STAT3 shRNAs can be made from SEQ ID NOs:28-30 and include, but are not limited to TGCTGTTGACAGTGAGCG AATGCAGGATCTGAATGGAAACTAGTGAAGCCACAGAT GTAGTTTCCATTCAGATCCTGCATGTGCCTACTGCCTCGGA (SEQ ID NO:1); TGCTGTTGACAGTGAGCG AATCGTGGATCTGTTCAGAAACTAGTGAAGCCACAGAT GTAGTTTCTGAACAGATCCACGATCTGCCTACTGCCTCGGA (SEQ ID NO:2); or TGCTGTTGACAGTGAGCG AAGAGGGTCTCGGAAATTTAACTAGTGAAGCCACAGAT GTAGTTAAATTTCCGAGACCCTCTGTGCCTACTGCCTCGGA (SEQ ID NO:3). The underlined sequences are based on the target sequence of STAT3.

Due to an amino acid substitution in the STAT3 sequence when making the shRNAs, the STAT3 target sequences can also be AATGCAGGATCTGAATGGAAAC (SEQ ID NO:31), AATCGTGGATCTGTTCAGAAAC (SEQ ID NO:32), or AAGAGGGTCTCGGAAATTTAAC (SEQ ID NO:33).

Target sequences in homo sapiens STAT3 can also be, but are not limited to, GTTTCATAATCTCCTGGGAGAG (SEQ ID NO:10), GGTAGAGAATCTCCAGGATGAC (SEQ ID NO:11); or AATCGTGGAGCTGTTTAGAAAC (SEQ ID NO:12). STAT3 shRNAs that can be made from SEQ ID NOs:10-12 include, but are not limited to, TGCTGTTGACAGTGAGCG ATTTCATAATCTCCTGGGAGAGTAGTGAAGCCACAGATG TACTCTCCCAGGAGATTATGAAACTGCCTACTGCCTCGGA (SEQ ID NO:13); TGCTGTTGACAGTGAGCG AGTAGAGAATCTCCAGGATGACTAGTGAAGCCACAGAT GTA GTCATCCTGGAGATTCTCTACCTGCCTACTGCCTCGGA (SEQ ID NO:14); or TGCTGTTGACAGTGAGCG CATCGTGGAGCTGTTTAGAAACTAGTGAAGCCACAGAT GTA GTTTCTAAACAGCTCCACGATTTGCCTACTGCCTCGGA (SEQ ID NO:15), respectively.

Due to an amino acid substitution in the STAT3 sequence when making the shRNAs, the STAT3 target sequences can also be ATTTCATAATCTCCTGGGAGAG (SEQ ID NO:34), AGTAGAGAATCTCCAGGATGAC (SEQ ID NO:35), or CATCGTGGAGCTGTTTAGAAAC (SEQ ID NO:36).

Disclosed are vectors comprising a pol II promoter and an shRNA wherein the shRNA has a sense RNA strand and an antisense RNA strand, wherein the sense and the antisense RNA strands form an RNA duplex, and wherein the sense RNA strand comprises a nucleotide sequence identical to a target sequence in STAT3 consisting of SEQ ID NO:28, SEQ ID NO:29, SEQ ID NO:30, SEQ ID NO:10, SEQ ID NO:11, SEQ ID NO:12, SEQ ID NO:31, SEQ ID NO:32, SEQ ID NO:33, SEQ ID NO:34, SEQ ID NO:35, or SEQ ID NO:36.

In some instances the shRNA consists of SEQ ID NO:1, SEQ ID NO:2, SEQ ID NO:3, SEQ ID NO:13, SEQ ID NO:14, or SEQ ID NO:15.

2. VEGFR

Disclosed are vectors comprising a pol II promoter and an shRNA, wherein the shRNA has a sense RNA strand and an antisense RNA strand, wherein the sense and the antisense RNA strands form an RNA duplex, and wherein the sense RNA strand comprises a nucleotide sequence identical to a target sequence in VEGFR.

The homo sapiens VEGFR2 sequence can be identified as Gene ID: NM_002253. The rattus norvegicus VEGFR2 CDS sequence can be identified as Gene ID: NM_013062. Any of the sequences disclosed in the rat sequence can be used to produce shRNAs. The prediction of thermodynamic ensemble and the optimal secondary structure with minumus free energy can be helpful for determining which shRNA to use. However, shRNAs can be tested in cell studies to confirm the shRNA with the best knockdown efficiency and specificity.

Target sequences in Rattus norvegicus VEGFR can be VEGFR2 sequences. Target sequences in VEGFR2 can be, but are not limited to, CATCGTTTATGTCTATGTTCAA (SEQ ID NO:37), GACCCATTGAGTCCAATTACAC (SEQ ID NO:38), or CATGGTCTCTCTGGTTGTGAAT (SEQ ID NO:39). VEGFR shRNAs can be made from SEQ ID NOs:37-39 and include, but are not limited to TGCTGTTGACAGTGAGCG AATCGTTTATGTCTATGTTCAATA GTGAAGCCACAGATG TA TTGAACATAGACATAAACGATGTGCCTACTGCCTCGGA (SEQ ID NO:4); TGCTGTTGACAGTGAGCG AACCCATTGAGTCCAATTACACTAGTGAAGCCACAGATG TAGTGTAATTGGACTCAATGGGTCTGCCTACTGCCTCGGA (SEQ ID NO:5); or TGCTGTTGACAGTGAGCG AATGGTCTCTCTGGTTGTGAATTAGTGAAGCCACAGATG TAATTCACAACCAGAGAGACCATGTGCCTACTGCCTCGGA (SEQ ID NO:6). The underlined sequences are based on the target sequence of VEGFR.

Due to an amino acid substitution in the VEGFR sequence when making the shRNAs, the VEGFR target sequences can also be AATCGTTTATGTCTATGTTCAA (SEQ ID NO:40), AACCCATTGAGTCCAATTACAC (SEQ ID NO:41), or AATGGTCTCTCTGGTTGTGAAT (SEQ ID NO:42).

Target sequences in homo sapien VEGFR can also be, but are not limited to, CTTGGAGCATCTCATCTGTTAC (SEQ ID NO:16), ATGCCACCATGTTCTCTAATAG (SEQ ID NO:17); or CTGAGTCCGTCTCATGGAATTG (SEQ ID NO:18). VEGFR shRNAs that can be made from SEQ ID NOs:16-18 include, but are not limited to, TGCTGTTGACAGTGAGCG ATTGGAGCATCTCATCTGTTACTAGTGAAGCCACAGATG TAGTAACAGATGAGATGCTCCAAGTGCCTACTGCCTCGGA (SEQ ID NO:19); TGCTGTTGACAGTGAGCGCTGCCACCATGTTCTCTAATAGTAGTGAAGCCACAGATG TA CTATTAGAGAACATGGTGGCATTGCCTACTGCCTCGGA (SEQ ID NO:20); or TGCTGTTGACAGTGAGCG ATGAGTCCGTCTCATGGAATTGTAGTGAAGCCACAGATG TACAATTCCATGAGACGGACTCAGTGCCTACTGCCTCGGA (SEQ ID NO:21), respectively.

Due to an amino acid substitution in the VEGFR sequence when making the shRNAs, the VEGFR target sequences can also be ATTGGAGCATCTCATCTGTTAC (SEQ ID NO:43), CTGCCACCATGTTCTCTAATAG (SEQ ID NO:44); or ATGAGTCCGTCTCATGGAATTG (SEQ ID NO:45).

Disclosed are vectors comprising a pol II promoter and an shRNA wherein the shRNA has a sense RNA strand and an antisense RNA strand, wherein the sense and the antisense RNA strands form an RNA duplex, and wherein the sense RNA strand comprises a nucleotide sequence identical to a target sequence in VEGFR consisting of SEQ ID NO:37, SEQ ID NO:38, SEQ ID NO:39, SEQ ID NO:16, SEQ ID NO:17, SEQ ID NO:18, SEQ ID NO:40, SEQ ID NO:41, SEQ ID NO:42, SEQ ID NO:44, SEQ ID NO:45, or SEQ ID NO:46. In some instances the shRNA consists of SEQ ID NO:4, SEQ ID NO:5, SEQ ID NO:6, SEQ ID NO:19, SEQ ID NO:20, or SEQ ID NO:21.

3. EPOR

Disclosed are vectors comprising a pol II promoter and an shRNA, wherein the shRNA has a sense RNA strand and an antisense RNA strand, wherein the sense and the antisense RNA strands form an RNA duplex, and wherein the sense RNA strand comprises a nucleotide sequence identical to a target sequence in EPOR.

The *homo sapiens* EPOR sequence can be identified as Gene ID: NM_000121. The *rattus norvegicus* EPOR CDS sequence can be identified as Gene ID: NM_017002.2. Any of the sequences disclosed in the rat sequence can be used to produce shRNAs. The prediction of thermodynamic ensemble and the optimal secondary structure with minumus free energy can be helpful for determining which shRNA to use. However, shRNAs can be tested in cell studies to confirm the shRNA with the best knockdown efficiency and specificity.

Target sequences in *Rattus norvegicus* EPOR can be, but are not limited to, CACTGAGTGTGTCCTGAGCAAC (SEQ ID NO:46), GTCTCTCATTCTCGTCCTCATC (SEQ ID NO:47), or CGGGCACTGCCTCCTGAGCTAC (SEQ ID NO:48). EPOR shRNAs can be made from SEQ ID NOs:46-48 and include, but are not limited to, TGCTGTTGACAGTGAGCG<u>AACTGAGTGTGTCCTGAGCAAC</u>TAGTGAAGCCACAGAT GTA GTTGCTCAGG<u>ACACACTCAGTGTGCCTA</u>CTGCCTCGGA (SEQ ID NO:7); TGCTGTTGACAGTGAGCG<u>ATCTCTCATTCTCGTCCTCATC</u>TAGTGAAGCCACAGATG TA<u>GATGAGGACGAGAATGAGAGA</u>CTGCCTACTGCCTCGGA (SEQ ID NO:8); or TGCTGTTGACAGTGAGCG<u>AGGGCACTGCCTCCTGAGCTAC</u>TAGTGAAGCCACAGAT GTA GTAGCTCAGG<u>AGGCAGTGCCCG</u>TGCCTACTGCCTCGGA (SEQ ID NO:9). The underlined sequences are based on the target sequence of EPOR.

Due to an amino acid substitution in the EPOR sequence when making the shRNAs, the EPOR target sequences can also be AACTGAGTGTGTCCTGAGCAAC (SEQ ID NO:49), ATCTCTCATTCTCGTCCTCATC (SEQ ID NO:50), or AGGGCACTGCCTCCTGAGCTAC (SEQ ID NO:51).

Target sequences in *homo sapien* EPOR can also be, but are not limited to, CACCGAGTGTGTGCTGAGCAAC (SEQ ID NO:22), TTCCCTGGAAGTCCTCTCAGAG (SEQ ID NO:23); or CCGCCGGGCTCTGAAGCAGAAG (SEQ ID NO:24). EPOR shRNAs that can be made from SEQ ID NOs:22-24 include, but are not limited to, TGCTGTTGACAGTGAGCG<u>AACCGAGTGTGTGCTGAGCAAC</u>TAGTGAAGCCACAGAT GTA GTTGCTCAGC<u>ACACACTCGGTGTGCCTA</u>CTGCCTCGGA (SEQ ID NO:25); TGCTGTTGACAGTGAGCG<u>CTCCCTGGAAGTCCTCTCAGAG</u>TAGTGAAGCCACAGATG TA CTCTGAGAGG<u>ACTTCCAGGGA</u>ATGCCTACTGCCTCGGA (SEQ ID NO:26); or TGCTGTTGACAGTGAGCG<u>ACGCCGGGCTCTGAAGCAGAAG</u>TAGTGAAGCCACAGAT GTA CTTCTGCTTCAG<u>AGCCCGGCGG</u>TGCCTACTGCTCGGA (SEQ ID NO:27), respectively.

Due to an amino acid substitution in the EPOR sequence when making the shRNAs, the EPOR target sequences can also be AACCGAGTGTGTGCTGAGCAAC (SEQ ID NO:52), CTCCCTGGAAGTCCTCTCAGAG (SEQ ID NO:53); or ACGCCGGGCTCTGAAGCAGAAG (SEQ ID NO:54).

Disclosed are vectors comprising a pol II promoter and an shRNA wherein the shRNA has a sense RNA strand and an antisense RNA strand, wherein the sense and the antisense RNA strands form an RNA duplex, and wherein the sense RNA strand comprises a nucleotide sequence identical to a target sequence in EPOR consisting of SEQ ID NO:46, SEQ ID NO:47, SEQ ID NO:48, SEQ ID NO:22, SEQ ID NO:23, SEQ ID NO:24, SEQ ID NO:49, SEQ ID NO:50, SEQ ID NO:51, SEQ ID NO:52, SEQ ID NO:53, or SEQ ID NO:54.

In some instances, the shRNA consists of SEQ ID NO:7, SEQ ID NO:8, SEQ ID NO:9, SEQ ID NO:25, SEQ ID NO:26, or SEQ ID NO:27.

4. Delivery of Vectors

In the methods described herein, delivery of the vectors or compositions to cells can be via a variety of mechanisms. As defined above, disclosed herein are compositions comprising any one or more of the nucleic acids, vectors and/or antibodies described herein can be used to produce a composition which may also include a carrier such as a pharmaceutically acceptable carrier. For example, disclosed are pharmaceutical compositions, comprising the shRNAs disclosed herein, and a pharmaceutically acceptable carrier.

αvβ3 RGD functionalized siRNA-loaded poly(latched-co-glycolytic) acid (PLGA) nanoparticles (NPs) and VE-cadherin (ve-cad) promoter driven shRNA loaded PLGA NPs can also be used in the methods described herein.

The nucleic acid or vector can be in solution or in suspension (for example, incorporated into microparticles, nanoparticles, liposomes, or cells). These compositions can be targeted to a particular cell type via antibodies, receptors, or receptor ligands. One of skill in the art knows how to make and use such targeting agents with the compositions of the invention. A targeting agent can be a vehicle such as antibody conjugated liposomes; receptor mediated targeting of DNA through cell specific ligands, and highly specific retroviral targeting of cells in vivo. Any such vehicles can be part of the composition of the invention. In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, ligand valency, and ligand concentration.

For example, the compositions described herein can comprise a pharmaceutically acceptable carrier. By "pharmaceutically acceptable" is meant a material or carrier that would be selected to minimize any degradation of the active ingredient and to minimize any adverse side effects in the subject, as would be well known to one of skill in the art. Examples of carriers include dimyristoylphosphatidyl (DMPC), phosphate buffered saline or a multivesicular liposome. For example, PG:PC:Cholesterol:peptide or PC:peptide can be used as carriers in this invention. Other suitable pharmaceutically acceptable carriers and their formulations are described in Remington: The Science and Practice of Pharmacy (19th ed.) ed. A.R. Gennaro, Mack Publishing Company, Easton, Pa. 1995. Typically, an appropriate amount of pharmaceutically-acceptable salt is used in the formulation to render the formulation isotonic. Other examples of the pharmaceutically-acceptable carrier include, but are not limited to, saline, Ringer's solution and dextrose solution. The pH of the solution can be from about 5 to about 8, or from about 7 to about 7.5. Further carriers include sustained release preparations such as semi-permeable matrices of solid hydrophobic polymers containing the composition, which matrices are in the form of shaped articles, e.g., films, stents (which are implanted in vessels during an angioplasty procedure), liposomes or microparticles. It will be apparent to those persons skilled in the art that certain carriers may be more preferable depending upon, for instance, the route of administration and concentration of composition being administered. These most typically would be standard carriers for administration of drugs to humans, including solutions such as sterile water, saline, and buffered solutions at physiological pH.

Pharmaceutical compositions may also include carriers, thickeners, diluents, buffers, preservatives and the like, as long as the intended activity of the polypeptide, peptide, nucleic acid, vector of the invention is not compromised. Pharmaceutical compositions may also include one or more active ingredients (in addition to the composition of the invention) such as antimicrobial agents, anti-inflammatory agents, anesthetics, and the like. The pharmaceutical composition may be administered in a number of ways depending on whether local or systemic treatment is desired, and on the area to be treated.

Preparations of parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium choloride solution, Ringer's dextrose, dextrose and sodium choloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for optical administration may include ointments, lotions, creams, gels, drops, suppositories, sprays, liquids and powders. Conventional pharmaceutical carriers, aqueous, powder or oily bases, thickeners and the like may be necessary or desirable. Optical administration can include subretinal injections and intravitreal injections.

Compositions for oral administration include powders or granules, suspensions or solutions in water or non-aqueous media, capsules, sachets, or tablets. Thickeners, flavorings, diluents, emulsifiers, dispersing aids, or binders may be desirable. Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mon-, di-, trialkyl and aryl amines and substituted ethanolamines.

Also disclosed are vectors comprising the shRNAs or shRNAs embedded in microRNA described herein. shRNAs can include, but are not limited to, any one of SEQ ID NOS: 1-9, 13-15, 19-21 and 25-27.

Also disclosed herein are host cells transformed or transfected with an expression vector comprising the polynucleotides described elsewhere herein. Also disclosed are host cells comprising the expression vectors described herein. For example, disclosed is a host cell comprising an expression vector comprising the polynucleotides described elsewhere herein, operably linked to a control element. Host cells can be eukaryotic or prokaryotic cells. Also disclosed are recombinant cells comprising the disclosed shRNAs. Further disclosed are recombinant cells producing the disclosed shRNAs or shRNAs embedded in microRNA.

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. Further, these methods can be used to target certain diseases and cell populations by using the targeting characteristics of the carrier.

Expression vectors can be any nucleotide construction used to deliver nucleic acids into cells (e.g., a plasmid), or as part of a general strategy to deliver nucleic acids, e.g., as part of recombinant retrovirus or adenovirus (Ram et al. Cancer Res. 53:83-88, (1993)). For example, disclosed herein are expression vectors comprising an one or more of the disclosed shRNAs.

The term "vector" is used to refer to a carrier molecule into which a nucleic acid sequence can be inserted for introduction into a cell. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., 1989 and Ausubel et al., 1996, both incorporated herein by reference. Vectors can comprise targeting molecules. A targeting molecule is one that directs the desired nucleic acid to a particular organ, tissue, cell, or other location in a subject's body.

The term "expression vector" refers to a vector containing a nucleic acid sequence coding for at least part of a gene product capable of being transcribed. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described. There are a number of ways in which expression vectors may be introduced into cells. In certain embodiments of the invention, the expression vector comprises a virus or engineered vector derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986).

The retroviruses are a group of single-stranded RNA viruses characterized by an ability to convert their RNA to double-stranded DNA in infected cells; they can also be used as vectors. Other viral vectors may be employed as expression constructs in the present invention. Vectors derived from viruses such as vaccinia virus (Ridgeway, 1988; Baichwal and Sugden, 1986; Coupar et al., 1988), adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990). Different subtypes of these vectors can be used in the methods described herein. For example, self-complementary AAV2 vectors can be used in the methods described herein.

Other suitable methods for nucleic acid delivery to effect expression of the disclosed compositions are believed to include virtually any method (viral and non-viral) by which a nucleic acid can be introduced into an organelle, a cell, a tissue or an organism, as described herein or as would be known to one of ordinary skill in the art. Such methods include, but are not limited to, direct delivery of nucleic acids such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

The expression vectors can include a nucleic acid sequence encoding a marker product. This marker product can be used to determine if the nucleic acid has been delivered to the cell and once delivered is being expressed. Preferred marker genes are the *E. coli* lacZ gene, which encodes β-galactosidase, and the gene encoding the green fluorescent protein.

As used herein, plasmid or viral vectors are agents that transport the disclosed nucleic acids, such as the shRNAs into the cell without degradation and include a promoter yielding expression of the nucleic acid in the cells into which it is delivered. Viral vectors can be, for example, Lentivirus, Adenovirus, Adeno-associated virus, Herpes virus, Vaccinia virus, Polio virus, neuronal trophic virus, Sindbis and other RNA viruses, including these viruses with the HIV backbone. Also preferred are any viral families that share the properties of these viruses, which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason, are commonly used vectors. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature.

Viral vectors can have higher transaction abilities (i.e., ability to introduce genes) than chemical or physical methods of introducing genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

Retroviral vectors, in general, are described by Verma, I. M., Retroviral vectors for gene transfer. In Microbiology, Amer. Soc. for Microbiology, pp. 229-232, Washington, (1985), which is hereby incorporated by reference in its entirety. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference in their entirety for their teaching of methods for using retroviral vectors for gene therapy.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serves as the priming site for the synthesis of the second strand of DNA synthesis, and specific sequences near the ends of the LTRs that enable the insertion of the DNA state of the retrovirus to insert into the host genome. This amount of nucleic acid is sufficient for the delivery of one to many genes depending on the size of each transcript. Positive or negative selectable markers can be included along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery but lacks any packaging signal. When the vector carrying the DNA of choice is transfected into these cell lines, the vector containing the shRNA is replicated and packaged into new retroviral particles, by the machinery provided in cis by the helper cell. The genomes for the machinery are not packaged because they lack the necessary signals.

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)) the teachings of which are incorporated herein by reference in their entirety for their teaching of methods for using retroviral vectors for gene therapy. Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol., 4:1528-1533 (1984); Varga et al., J. Virology 65:6061-6070 (1991); Wickham et al., Cell 73:309-319 (1993)).

A viral vector can be one based on an adenovirus which has had the E1 gene removed and these virons are generated in a cell line such as the human 293 cell line. Optionally, both the E1 and E3 genes are removed from the adenovirus genome.

Another type of viral vector that can be used to introduce the polynucleotides of the invention into a cell is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. This type of vector can be the P4.1 C vector produced by Avigen, San Francisco, Calif., which can contain the herpes simplex virus thymidine kinase gene, HSV-tk, or a marker gene, such as the gene encoding the green fluorescent protein, GFP.

In another type of AAV virus, the AAV contains a pair of inverted terminal repeats (ITRs) which flank at least one cassette containing a promoter that directs cell-specific expression operably linked to a heterologous gene. Heterologous in this context refers to any nucleotide sequence or gene, which is not native to the AAV or B19 parvovirus. Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference in its entirety for material related to the AAV vector.

The inserted genes in viral and retroviral vectors usually contain promoters, or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Other useful systems include, for example, replicating and host-restricted non-replicating vaccinia virus vectors. In addition, the disclosed polynucleotides can be delivered to a target cell in a non-nucleic acid based system. For example, the disclosed polynucleotides can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed expression vectors, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood, to a target organ, or inhaled into the respiratory tract to target cells of the respiratory tract. For example, a composition comprising a polynucleotide described herein and a cationic liposome can be administered to a subjects lung cells. Regarding liposomes, see, e.g., Brigham et al. Am. J. Resp. Cell. Mol. Biol. 1:95 100 (1989); Felgner et al. Proc. Natl. Acad. Sci USA 84:7413 7417 (1987); U.S. Pat. No. 4,897, 355. Furthermore, the compound can be administered as a component of a microcapsule that can be targeted to specific cell types, such as macrophages, or where the diffusion of the compound or delivery of the compound from the microcapsule is designed for a specific rate or dosage.

C. Methods of Treating Proliferative Retinopathies Associated with Intravitreal Neovascularization Disclosed are methods of treating proliferative retinopathies associated with intravitreal neovascularization comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition is administered via subretinal injection.

Disclosed are methods of treating proliferative retinopathies associated with intravitreal neovascularization comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition is administered via subretinal injection, wherein the vector is a viral vector. In some instances, the viral vector can be a retroviral vector. For example, the retroviral vector can be a lentiviral vector.

Disclosed are methods of treating proliferative retinopathies associated with intravitreal neovascularization comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition is administered via subretinal injection, wherein the pol II promoter is an endothelial cell-specific promoter. For example, the endothelial cell-specific promoter can be a VE-cad promoter.

Disclosed are methods of treating proliferative retinopathies associated with intravitreal neovascularization comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition is administered via subretinal injection, wherein the IVNV phase of ROP is inhibited without interfering with physiologic retinal vascular development (PRVD).

Disclosed are methods of treating proliferative retinopathies associated with intravitreal neovascularization comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition is administered via subretinal injection, wherein the subject has been previously diagnosed with ROP.

Proliferative retinopathies associated with intravitreal neovascularization, include, but are not limited to, retinopathy of prematurity (ROP), proliferative diabetic retinopathy, neovascularization associated with vein occlusions, and aberrant neovascularization of the iris, angle, and cornea.

1. Treating with STAT3 shRNA

Disclosed are methods of treating proliferative retinopathies associated with intravitreal neovascularization comprising administering to a subject a composition comprising a vector, wherein the vector comprises a pol II promoter and a first shRNA, wherein the shRNA is embedded in a microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition is administered via subretinal injection, wherein the sense RNA strand comprises a nucleotide sequence identical to a target sequence in STAT3.

Disclosed are methods of treating proliferative retinopathies associated with intravitreal neovascularization comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition is administered via subretinal injection, wherein the sense RNA strand comprises a nucleotide sequence identical to a target sequence in STAT3, wherein the nucleotide sequence identical to a target sequence in STAT3 consists of SEQ ID NO:28, SEQ ID NO:29, SEQ ID NO:30, SEQ ID NO:10, SEQ ID NO:11, SEQ ID NO:12, SEQ ID NO:31, SEQ ID NO:32, SEQ ID NO:33, SEQ ID NO:34, SEQ ID NO:35, or SEQ ID NO:36.

Disclosed are methods of treating proliferative retinopathies associated with intravitreal neovascularization comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition is administered via subretinal injection, wherein the sense RNA strand comprises a nucleotide sequence identical to a target sequence in STAT3, wherein the first shRNA consists SEQ ID NO:1, SEQ ID NO:2, SEQ ID NO:3, SEQ ID NO:13, SEQ ID NO:14, or SEQ ID NO:15.

2. Treating with VEGFR shRNA

Disclosed are methods of treating proliferative retinopathies associated with intravitreal neovascularization comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition is administered via subretinal injection, wherein the sense RNA strand comprises a nucleotide sequence identical to a target sequence in VEGFR.

Disclosed are methods of treating proliferative retinopathies associated with intravitreal neovascularization comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition is administered via subretinal injection, wherein the sense RNA strand comprises a nucleotide sequence identical to a target sequence in VEGFR, wherein the VEGFR is VEGFR2.

Disclosed are methods of treating proliferative retinopathies associated with intravitreal neovascularization comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition is administered via subretinal injection, wherein the sense RNA strand comprises a nucleotide sequence identical to a target sequence in VEGFR, wherein the VEGFR is VEGFR2, wherein the nucleotide sequence identical to a target sequence in VEGFR consists of SEQ ID NO:37, SEQ ID NO:38, SEQ ID NO:39, SEQ ID NO:16, SEQ ID NO:17, SEQ ID NO:18, SEQ ID NO:40, SEQ ID NO:41, SEQ ID NO:42, SEQ ID NO:43, SEQ ID NO:44, or SEQ ID NO:45.

Disclosed are methods of treating proliferative retinopathies associated with intravitreal neovascularization comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition is administered via subretinal injection, wherein the sense RNA strand comprises a nucleotide sequence identical to a target sequence in VEGFR, wherein the VEGFR is VEGFR2, wherein the first shRNA consists of SEQ ID NO:4, SEQ ID NO:5, SEQ ID NO:6, SEQ ID NO:19, SEQ ID NO:20, or SEQ ID NO:21.

3. Treating with EPOR shRNA

Disclosed are methods of treating proliferative retinopathies associated with intravitreal neovascularization comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition is administered via subretinal injection, wherein the sense RNA strand comprises a nucleotide sequence identical to a target sequence in EPOR.

Disclosed are methods of treating proliferative retinopathies associated with intravitreal neovascularization comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition is administered via subretinal injection, wherein the sense RNA strand comprises a nucleotide sequence identical to a target sequence in EPOR, wherein the nucleotide sequence identical to a target sequence in EPOR consists of SEQ ID NO:46, SEQ ID NO:47, SEQ ID NO:48, SEQ ID NO:22, SEQ ID NO:23, SEQ ID NO:24, SEQ ID NO:49, SEQ ID NO:50, SEQ ID NO:51, SEQ ID NO:52, SEQ ID NO:53, or SEQ ID NO:54.

Disclosed are methods of treating proliferative retinopathies associated with intravitreal neovascularization comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition is administered via subretinal injection, wherein the sense RNA strand comprises a nucleotide sequence identical to a target sequence in EPOR, wherein the first shRNA consists of SEQ ID NO:7, SEQ ID NO:8, SEQ ID NO:9, SEQ ID NO:25, SEQ ID NO:26, or SEQ ID NO:27.

4. Treating with a First and Second shRNA

Also disclosed are methods of treating proliferative retinopathies associated with intravitreal neovascularization comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition is administered via subretinal injection further comprising administering a second shRNA.

Disclosed are methods of treating proliferative retinopathies associated with intravitreal neovascularization comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition is administered via subretinal injection further comprising administering a second shRNA, wherein the second shRNA has a sense RNA strand and an antisense RNA strand, wherein the sense and the antisense RNA strands form an RNA duplex, and wherein the sense RNA strand comprises a nucleotide sequence identical to a target sequence in STAT3, VEGFR, EPOR, or VEGFA mRNA, and wherein the second shRNA is different than the first shRNA.

In some aspects, if the first shRNA has a sense RNA strand and an antisense RNA strand, wherein the sense and the antisense RNA strands form an RNA duplex, wherein the sense RNA strand comprises a nucleotide sequence identical to a target sequence in STAT3, then the second shRNA can have a sense RNA strand and an antisense RNA strand, wherein the sense and the antisense RNA strands form an RNA duplex, wherein the sense RNA strand comprises a nucleotide sequence identical to a target sequence in VEGFR or EPOR.

In one aspect, if the first shRNA has a sense RNA strand and an antisense RNA strand, wherein the sense and the antisense RNA strands form an RNA duplex, wherein the sense RNA strand comprises a nucleotide sequence identical to a target sequence in STAT3, then the second shRNA can have a sense RNA strand and an antisense RNA strand, wherein the sense and the antisense RNA strands form an RNA duplex, wherein the sense RNA strand comprises a nucleotide sequence identical to a target sequence in STAT3, wherein the nucleotide sequence identical to a target sequence in STAT3 consists of SEQ ID NO:1, then the second shRNA can have a sense RNA strand and an antisense RNA strand, wherein the sense and the antisense RNA strands form an RNA duplex, wherein the sense RNA strand comprises a nucleotide sequence identical to a target sequence in STAT3 consisting of SEQ ID NO:2 or SEQ ID NO:3. In other words, the first shRNA and second shRNA can comprise nucleotide sequences from the same gene sequence (e.g. STAT3, VEGFR, EPOR) as long as the first shRNA and second shRNA comprise different nucleotide sequences from the same gene sequence.

Also disclosed are methods of treating proliferative retinopathies associated with intravitreal neovascularization comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition is administered via subretinal injection further comprising administering a second shRNA, wherein the second shRNA is in the same vector as the first shRNA.

Disclosed are methods of treating proliferative retinopathies associated with intravitreal neovascularization comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition is administered via subretinal injection further comprising administering a second shRNA, wherein the second shRNA is in a different vector than the first shRNA.

In some aspects, the methods comprising administering a first and second shRNA, wherein the second shRNA is in a different vector than the first shRNA refers to the first and second shRNA being in separate vectors, not necessarily that the two separate vectors are different types of vectors. For example, the first shRNA can be delivered by a lentiviral vector. The second shRNA can also be delivered by a lentiviral vector but cannot be delivered within the same lentiviral vector as the first shRNA. As long as the second shRNA is delivered by a separate lentiviral vector, the first and second shRNAs can both be present in lentiviral vectors. In some instances, the first and second shRNAs are in different vectors and the first shRNA is delivered by a lentiviral vector and the second shRNA is delivered by an adenoviral vector. The vectors disclosed herein can be used to deliver the first and second shRNAs.

Also disclosed are methods of treating proliferative retinopathies associated with intravitreal neovascularization comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition is administered via subretinal injection further comprising administering a second shRNA, wherein the second shRNA is administered in a separate composition from the first shRNA.

Methods comprising administering a first and second shRNA, wherein the second shRNA is administered in a separate composition from the first shRNA include administering the separate compositions together or consecutively. Administering the compositions together includes mixing the two compositions just prior to administration. Administering together also includes administering the separate compositions within one, two, three, four, five, six, seven, eight, nine or ten minutes of each other. Consecutive administration refers to administering the compositions at separate times greater than 10 minutes apart. For example, consecutive administration includes administering one composition at least 10, 15, 20, 25, 30, 60, 120 minutes after the administration of the other composition. In some instances, one composition can be administered 1, 2, 3, 4, 5, 6, 7, 8, 9, 10, 15, 20, 24 hours after administration of the other composition. In some instances, one composition can be administered 1, 2, 3, 4, 5, 6, 7, 8, 9, 10, 11, 12, 13, 14, 21, 28, 29, 30, or 31 days after administration of the other composition. In some instances, one composition can be administered 1, 2, 3, 4, 5, 6, 7, 8, 9, 10, 11, or 12 months after administration of the other composition.

D. Methods of Inhibiting Expression

Disclosed are methods of inhibiting expression of STAT3, EPOR, or VEGFR comprising administering to a subject a composition comprising a vector, wherein the vector comprises a pol II promoter and a first shRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, EPOR, or VEGFR mRNA, respectively, and wherein the composition is administered via subretinal injection.

In some aspects, the methods of inhibiting expression of STAT3, EPOR, or VEGFR comprise administering to a subject a composition comprising one or more of the vectors disclosed herein.

Disclosed are methods of inhibiting expression of STAT3, EPOR, or VEGFR comprising administering to a subject a composition comprising a vector, wherein the vector comprises a pol II promoter and a first shRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, EPOR, or VEGFR mRNA, respectively, and wherein the composition is administered via subretinal injection, wherein the shRNA is embedded in microRNA.

Disclosed are methods of inhibiting expression of STAT3, EPOR, or VEGFR comprising administering to a subject a composition comprising a vector, wherein the vector comprises a pol II promoter and a first shRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, EPOR, or VEGFR mRNA, respectively, and wherein the composition is administered via subretinal injection, wherein the vector is a viral vector. In some instances, the viral vector is a retroviral vector. For example, the retroviral vector is a lentiviral vector.

Disclosed are methods of inhibiting expression of STAT3, EPOR, or VEGFR comprising administering to a subject a composition comprising a vector, wherein the vector comprises a pol II promoter and a first shRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, EPOR, or VEGFR mRNA, respectively, and wherein the composition is administered via subretinal injection, wherein the pol II promoter is an endothelial cell-specific promoter. For example, the endothelial cell-specific promoter can be a VE-cad promoter.

1. Methods of Inhibiting Expression of STAT3

Disclosed are methods of inhibiting expression of STAT3 comprising administering to a subject a composition comprising a vector, wherein the vector comprises a pol II promoter and a first shRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3 mRNA, and wherein the composition is administered via subretinal injection.

Disclosed are methods of inhibiting expression of STAT3 comprising administering to a subject a composition comprising a vector, wherein the vector comprises a pol II promoter and a first shRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3 mRNA, and wherein the composition is administered via subretinal injection, wherein the nucleotide sequence identical to a target sequence in STAT3 mRNA consists of SEQ ID NO:28, SEQ ID NO:29, SEQ ID NO:30, SEQ ID NO:10, SEQ ID NO:11, SEQ ID NO:12, SEQ ID NO:31, SEQ ID NO:32, SEQ ID NO:33, SEQ ID NO:34, SEQ ID NO:35, or SEQ ID NO:36.

Disclosed are methods of inhibiting expression of STAT3 comprising administering to a subject a composition comprising a vector, wherein the vector comprises a pol II promoter and a first shRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3 mRNA, and wherein the composition is administered via subretinal injection, wherein the first shRNA consists of SEQ ID NO:1, SEQ ID NO:2, SEQ ID NO:3, SEQ ID NO:13, SEQ ID NO:14, or SEQ ID NO:15.

Also disclosed are methods of inhibiting expression of STAT3 comprising administering to a subject a composition comprising a vector, wherein the vector comprises a pol II promoter and a first shRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3 mRNA, and wherein the composition is administered via subretinal injection, further comprising administering a second shRNA. In some instances, the second shRNA can be different than the first shRNA. The first and second shRNAs can both comprise sequences identical to a target sequence in STAT3 but not the same target sequence. For example, if the first shRNA consists of SEQ ID NO:1, then the second shRNA can be any shRNA other than SEQ ID NO:1, wherein the shRNA comprises a sequence identical to a target sequence in STAT3. In some instances, the first shRNA consists of SEQ ID NO:1 and the second shRNA consists of SEQ ID NO:2 or SEQ ID NO:3.

2. Methods of Inhibiting Expression of VEGFR

Disclosed are methods of inhibiting expression of VEGFR comprising administering to a subject a composition comprising a vector, wherein the vector comprises a pol II promoter and a first shRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in VEGFR mRNA, and wherein the composition is administered via subretinal injection.

Disclosed are methods of inhibiting expression of VEGFR comprising administering to a subject a composition comprising a vector, wherein the vector comprises a pol II promoter and a first shRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in VEGFR mRNA, and wherein the composition is administered via subretinal injection, wherein the nucleotide sequence identical to a target sequence in VEGFR consists of SEQ ID NO:37, SEQ ID NO:38, SEQ ID NO:39, SEQ ID NO:16, SEQ ID NO:17, SEQ ID NO:18, SEQ ID NO:40, SEQ ID NO:41, SEQ ID NO:42, SEQ ID NO:43, SEQ ID NO:44, or SEQ ID NO 45.

Disclosed are methods of inhibiting expression of VEGFR comprising administering to a subject a composition comprising a vector, wherein the vector comprises a pol II promoter and a first shRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in VEGFR mRNA, and wherein the composition is administered via subretinal injection, wherein the first shRNA consists of SEQ ID NO:4, SEQ ID NO:5, SEQ ID NO:6, SEQ ID NO:19, SEQ ID NO:20, or SEQ ID NO:21.

Also disclosed are methods of inhibiting expression of VEGFR comprising administering to a subject a composition comprising a vector, wherein the vector comprises a pol II promoter and a first shRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in VEGFR mRNA, and wherein the composition is administered via subretinal injection, further comprising administering a second shRNA. In some instances, the second shRNA can be different than the first shRNA. The first and second shRNAs can both be sequences identical to a target sequence in VEGFR but not the same target sequence. For example, if the first shRNA consists of SEQ ID NO:4, then the second shRNA can be any shRNA other than SEQ ID NO:4, wherein the shRNA comprises a sequence identical to a target sequence in VEGFR. In some instances, the first consists of SEQ ID NO:4 and the second consists of SEQ ID NO:5 or SEQ ID NO:6.

3. Methods of Inhibiting Expression of EPOR

Disclosed are methods of inhibiting expression of EPOR comprising administering to a subject a composition comprising a vector, wherein the vector comprises a pol II promoter and a first shRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in EPOR mRNA, and wherein the composition is administered via subretinal injection.

Disclosed are methods of inhibiting expression of EPOR comprising administering to a subject a composition comprising a vector, wherein the vector comprises a pol II promoter and a first shRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in EPOR mRNA, and wherein the composition is administered via subretinal injection, wherein the nucleotide sequence identical to a target sequence in EPOR consists of a sequence selected from the group consisting of: SEQ ID NO:46, SEQ ID NO:47, SEQ ID NO:48, SEQ ID NO:22, SEQ ID NO:23, SEQ ID NO:24, SEQ ID NO:49, SEQ ID NO:50, SEQ ID NO:51, SEQ ID NO:52, SEQ ID NO:53, or SEQ ID NO:54.

Disclosed are methods of inhibiting expression of EPOR comprising administering to a subject a composition comprising a vector, wherein the vector comprises a pol II promoter and a first shRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in EPOR mRNA, and wherein the composition is administered via subretinal injection, wherein the first shRNA consists of SEQ ID NO:7, SEQ ID NO:8, SEQ ID NO:9, SEQ ID NO:25, SEQ ID NO:26, or SEQ ID NO:27.

Also disclosed are methods of inhibiting expression of EPOR comprising administering to a subject a composition comprising a vector, wherein the vector comprises a pol II promoter and a first shRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in EPOR mRNA, and wherein the composition is administered via subretinal injection, further comprising administering a second shRNA. In some instances, the second shRNA can be different than the first shRNA. The first and second shRNAs can both be sequences identical to a target sequence in EPOR but not the same target sequence. For example, if the first shRNA consists of SEQ ID NO:7, then the second shRNA can be any shRNA other than SEQ ID NO:7, wherein the shRNA comprises a sequence identical to a target sequence in EPOR. In some instances, the first shRNA consists of SEQ ID NO:7 and the second shRNA consists of SEQ ID NO:8 or SEQ ID NO:9.

4. Methods of Inhibiting Expression with a First and Second shRNA

Disclosed are methods of inhibiting expression of STAT3, EPOR, or VEGFR comprising administering to a subject a composition comprising a vector, wherein the vector comprises a pol II promoter and a first shRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, EPOR, or VEGFR mRNA, respectively, and wherein the composition is administered via subretinal injection, further comprising administering a second shRNA. The second shRNA can be in the same vector or a different vector from the first shRNA.

Methods comprising administering a first and second shRNA, wherein the second shRNA is in a different vector than the first shRNA refers to the first and second shRNA being in separate vectors, not necessarily that the two separate vectors are different types of vectors. For example, the first shRNA can be delivered by a lentiviral vector. The second shRNA can also be delivered by a lentiviral vector but cannot be delivered within the same lentiviral vector as the first shRNA. As long as the second shRNA is delivered by a separate lentiviral vector, the first and second shRNAs can both be present in lentiviral vectors. In some instances, the first and second shRNAs are in different vectors and the first shRNA is delivered by a lentiviral vector and the second shRNA is delivered by an adenoviral vector. The vectors disclosed herein can be used to deliver the first and second shRNAs.

In some instances, the first and second shRNAs are not only administered in separate vectors but are also administered in separate compositions. Methods comprising administering a first and second shRNA, wherein the second shRNA is administered in a separate composition from the first shRNA include administering the separate compositions together or consecutively. Administering the compositions together includes mixing the two compositions just prior to administration. Administering together also includes administering the separate compositions within one, two, three, four, five, six, seven, eight, nine or ten minutes of each other. Consecutive administration refers to administering the compositions at separate times greater than 10 minutes apart. For example, consecutive administration includes administering one composition at least 10, 15, 20, 25, 30, 60, 120 minutes after the administration of the other composition. In some instances, one composition can be administered 1, 2, 3, 4, 5, 6, 7, 8, 9, 10, 15, 20, 24 hours after administration of the other composition. In some instances, one composition can be administered 1, 2, 3, 4, 5, 6, 7, 8, 9, 10, 11, 12, 13, 14, 21, 28, 29, 30, or 31 days after administration of the other composition. In some instances, one composition can be administered 1, 2, 3, 4, 5, 6, 7, 8, 9, 10, 11, or 12 months after administration of the other composition.

E. Methods of Regulating Signaling Events Associated with Intravitreal Neovascularization Disclosed are methods of regulating signaling events associated with IVNV comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR, or EPOR mRNA, and wherein the composition is administered via subretinal injection.

Disclosed are methods of regulating signaling events associated with IVNV comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR, or EPOR mRNA, and wherein the composition is administered via subretinal injection, wherein the vector is a viral vector. In some instances, the viral vector can be a retroviral vector. For example, the retroviral vector can be a lentiviral vector.

Disclosed are methods of regulating signaling events associated with IVNV comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR, or EPOR mRNA, and wherein the composition is administered via subretinal injection, wherein the pol II promoter is an endothelial cell-specific promoter. For example, the endothelial cell-specific promoter can be a VE-cad promoter.

1. Methods of Regulating Signaling Events Associated with IVNV Using STAT3 shRNA Disclosed are methods of regulating signaling events associated with IVNV comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR, or EPOR mRNA, and wherein the composition is administered via subretinal injection, wherein the sense RNA strand comprises a nucleotide sequence identical to a target sequence in STAT3.

Disclosed are methods of regulating signaling events associated with IVNV comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR, or EPOR mRNA, and wherein the composition is administered via subretinal injection, wherein the sense RNA strand comprises a nucleotide sequence identical to a target sequence in STAT3, wherein the nucleotide sequence identical to a target sequence in STAT3 consists of SEQ ID NO:28, SEQ ID NO:29, SEQ ID NO:30, SEQ ID NO:10, SEQ ID NO:11, SEQ ID NO:12, SEQ ID NO:31, SEQ ID NO:32, SEQ ID NO:33, SEQ ID NO:34, SEQ ID NO:35, or SEQ ID NO:36.

Disclosed are methods of regulating signaling events associated with IVNV comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR, or EPOR mRNA, and wherein the composition is administered via subretinal injection, wherein the sense RNA strand comprises a nucleotide sequence identical to a target sequence in STAT3, wherein the shRNA consists of SEQ ID NO:1, SEQ ID NO:2, SEQ ID NO:3, SEQ ID NO:13, SEQ ID NO:14, or SEQ ID NO:15.

2. Methods of Regulating Signaling Events Associated with IVNV Using VEGFR shRNA Disclosed are methods of regulating signaling events associated with IVNV comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR, or EPOR mRNA, and wherein the composition is administered via subretinal injection, wherein the sense RNA strand comprises a nucleotide sequence identical to a target sequence in VEGFR. In some instances, the VEGFR can be VEGFR2. For example, the nucleotide sequence identical to a target sequence in VEGFR consists of SEQ ID NO:37, SEQ ID NO:38, SEQ ID NO:39, SEQ ID NO:16, SEQ ID NO:17, SEQ ID NO:18, SEQ ID NO:40, SEQ ID NO:41, SEQ ID NO:42, SEQ ID NO:43, SEQ ID NO:44, or SEQ ID NO 45.

Disclosed are methods of regulating signaling events associated with IVNV comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR, or EPOR mRNA, and wherein the composition is administered via subretinal injection, wherein the first shRNA consists of SEQ ID NO:4, SEQ ID NO:5, SEQ ID NO:6, SEQ ID NO:19, SEQ ID NO:20, or SEQ ID NO:21.

3. Methods of Regulating Signaling Events Associated with IVNV Using EPOR shRNA

Disclosed are methods of regulating signaling events associated with IVNV comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR, or EPOR mRNA, and wherein the composition is administered via subretinal injection, wherein the sense RNA strand comprises a nucleotide sequence identical to a target sequence in EPOR.

Disclosed are methods of regulating signaling events associated with IVNV comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR, or EPOR mRNA, and wherein the composition is administered via subretinal injection, wherein the sense RNA strand comprises a nucleotide sequence identical to a target sequence in EPOR, wherein the nucleotide sequence identical to a target sequence in EPOR consists of SEQ ID NO:46, SEQ ID NO:47, SEQ ID NO:48, SEQ ID NO:22, SEQ ID NO:23, SEQ ID NO:24, SEQ ID NO:49, SEQ ID NO:50, SEQ ID NO:51, SEQ ID NO:52, SEQ ID NO:53, or SEQ ID NO:54.

Disclosed are methods of regulating signaling events associated with IVNV comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR, or EPOR mRNA, and wherein the composition is administered via subretinal injection, wherein the sense RNA strand comprises a nucleotide sequence identical to a target sequence in EPOR, wherein the first shRNA consists of SEQ ID NO:7, SEQ ID NO:8, SEQ ID NO:9, SEQ ID NO:25, SEQ ID NO:26, or SEQ ID NO:27.

4. Methods of Regulating Signaling Events with a First and Second shRNA

Disclosed are methods of regulating signaling events associated with IVNV comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR, or EPOR mRNA, and wherein the composition is administered via subretinal injection further comprising administering a second shRNA.

Disclosed are methods of regulating signaling events associated with IVNV comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR, or EPOR mRNA, and wherein the composition is administered via subretinal injection further comprising administering a second shRNA, wherein the second shRNA has a sense RNA strand and an antisense RNA strand, wherein the sense and the antisense RNA strands form an RNA duplex, and wherein the sense RNA strand comprises a nucleotide sequence identical to a target sequence in STAT3, VEGFR, or EPOR mRNA, and wherein the second shRNA is different than the first shRNA.

Disclosed are methods of regulating signaling events associated with IVNV comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR, or EPOR mRNA, and wherein the composition is administered via subretinal injection further comprising administering a second shRNA, wherein the second shRNA has a sense RNA strand and an antisense RNA strand, wherein the sense and the antisense RNA strands form an RNA duplex, and wherein the sense RNA strand comprises a nucleotide sequence identical to a target sequence in STAT3, VEGFR, or EPOR mRNA, and wherein the second shRNA is different than the first shRNA, wherein the second shRNA is in the same vector as the first shRNA.

Disclosed are methods of regulating signaling events associated with IVNV comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR, or EPOR mRNA, and wherein the composition is administered via subretinal injection further comprising administering a second shRNA, wherein the second shRNA has a sense RNA strand and an antisense RNA strand, wherein the sense and the antisense RNA strands form an RNA duplex, and wherein the sense RNA strand comprises a nucleotide sequence identical to a target sequence in STAT3, VEGFR, or EPOR mRNA, and wherein the second shRNA is different than the first shRNA, wherein the second shRNA is in a different vector than the first shRNA.

Methods comprising administering a first and second shRNA, wherein the second shRNA is in a different vector than the first shRNA refers to the first and second shRNA being in separate vectors, not necessarily that the two separate vectors are different types of vectors. For example, the first shRNA can be delivered by a lentiviral vector. The second shRNA can also be delivered by a lentiviral vector but cannot be delivered within the same lentiviral vector as the first shRNA. As long as the second shRNA is delivered by a separate lentiviral vector, the first and second shRNAs can both be present in lentiviral vectors. In some instances, the first and second shRNAs are in different vectors and the first shRNA is delivered by a lentiviral vector and the second shRNA is delivered by an adenoviral vector. The vectors disclosed herein can be used to deliver the first and second shRNAs.

Disclosed are methods of regulating signaling events associated with IVNV comprising administering to a subject a composition comprising a vector, wherein the vector comprises a pol II promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR, or EPOR mRNA, and wherein the composition is administered via subretinal injection further comprising administering a second shRNA, wherein the second shRNA is administered in a separate composition from the first shRNA.

F. Cells

Also disclosed herein are host cells transformed or transfected with an expression vector comprising the nucleic acid sequences described elsewhere herein. Also disclosed are host cells comprising the expression vectors described herein. For example, disclosed is a host cell comprising an expression vector comprising the nucleic acid sequences described elsewhere herein, operably linked to a control element. Host cells can be eukaryotic or prokaryotic cells. Also disclosed are recombinant cells comprising the disclosed nucleic acid sequences or recombinant peptides. Further disclosed are recombinant cells producing the disclosed recombinant peptides.

G. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for producing vectors, the kit comprising any of the disclosed shRNAs. The kits also can contain a viral vector.

EXAMPLES

H. Example 1

Retinopathy of prematurity (ROP) is a leading cause of childhood blindness worldwide. This study examines two important sequential phases of ROP: Phase I, in which physiologic retinal vascular development (PRVD) is delayed; followed by Phase II, in which vasoproliferative intravitreal neovascularization (IVNV) in turn increases risk of blindness. Standard-of-care laser treatment and anti-angiogenic strategies, such as inhibitors of vascular endothelial growth factor (VEGF), intended to treat Phase II, are destructive of developing retinal tissue or delay PRVD, thereby prolonging Phase I. Treatments intended to reduce the delay period of Phase I and to advance PRVD can worsen IVNV in Phase II. Better treatments are needed, and the objective of this study is to develop strategies that inhibit IVNV, but do not interfere with PRVD, and are safe for preterm infants.

Potential targets were identified to safely reduce IVNV and not delay PRVD. First, in a rat model of human ROP, STAT3 contributed to outcomes during Phase I or Phase II based on the cell type in which the STAT3 was activated. In Müller cells (MCs), activated-STAT3 inhibited erythropoietin (EPO) expression and was a cause of Phase I. In endothelial cells (ECs), activated STAT3 mediated IVNV in Phase II. Second, in cultured ECs, activation of VEGF receptor 2 (VEGFR2) in turn activated and then interacted with EPOR or NOX4 to enhance STAT3-mediated angiogenesis. Third, using microRNA-embedded shRNAs to knock down VEGF overexpression in MCs, Phase II IVNV was significantly inhibited without retarding pup growth, but outer retinal apoptosis occurred. These findings indicate: [a] VEGF produced by MCs promotes survival in photoreceptors, retinal neurons, and MCs. However, [b] VEGF also binds and phosphorylates VEGFR2 in ECs to activate EPOR and NOX4/NADPH oxidase. [c] Activated-EPOR or -NOX4 interacts with pVEGFR2 and overactivates EC-STAT3 to cause IVNV in Phase II (FIG. 1). These results were tested in the rat ROP model, which was adapted using lentivectors to efficiently express shRNAs in specific cell types:

Objective 1. Testing whether knockdown of overexpressed VEGF164 in MCs to retinal VEGF levels that inhibit IVNV and not delay PRVD allows retinal neuronal survival and function.

Objective 2. Testing whether knockdown of EPOR in ECs reduce IVNV in phase II ROP and not delay PRVD in phase I.

Objective 3. Testing whether STAT3 knockdown in ECs safely inhibits IVNV and not delay PRVD. A pharmacologic means to regulate NOX4/VEGFR2-mediated STAT3 activation to reduce IVNV was examined.

IMPACT: Although VEGF is involved in Phase II IVNV, it is also necessary for PRVD to prevent Phase I. Therefore, regulating VEGFR2 signaling, but not blocking it, by interrupting interactions that overactivate VEGFR2 signaling in ECs can safely inhibit IVNV and not delay PRVD. Through knowledge of signaling pathways gained from these experiments, additional treatments can be developed (eg, EC-specific STAT3 inhibitors or regulators of NOX4). These studies will also add important knowledge about the effects of MC-generated VEGF on retinal health and function, oxidative signaling in EC-STAT3-activation and IVNV, and the role of EPO signaling in ROP. In preterm infants, past treatment with broad antioxidants (eg., vitamin E) led to adverse effects. The knowledge that can be generated from these experiments will also have implications for current clinical practice in which forms of EPO are being tested for neuroprotection, and in which anti-VEGF agents are used to treat severe ROP even though agents, doses or long-term safety effects remain unknown.

I. Example 2

Retinopathy of prematurity (ROP) is a leading cause of childhood blindness worldwide and is increasing as emerging countries develop technology to save preterm infants but lack resources to provide optimal care. In the US, ~14% of childhood blindness is attributed to ROP and in some developing nations, estimates are >20%. ROP is characterized by two phases based on clinical observations and animal models. In Phase I ROP, mainly peripheral avascular retina occurs from a delay in physiologic retinal vascular development (PRVD) and, in places with insufficient resources to regulate oxygen, hyperoxia-induced vaso-attenuation. In Phase II ROP, hypoxia-induced intravitreal neovascularization (IVNV) occurs. Treatments of IVNV in human severe ROP include laser ablation of peripheral avascular retina, which destroys developing retina, or intravitreal anti-VEGF agents, which can lead to persistent avascular retina, recurrent IVNV, and even blindness from retinal detachment. Intravitreal anti-VEGF agents reduce serum VEGF levels for weeks in human preterm infants, and inhibit postnatal growth in pups in a rat model of ROP raising additional safety concerns. Some experimental methods to promote PRVD (eg., insulin-like growth factor-1 or erythropoietin [EPO]) can worsen Phase II IVNV, whereas agents to inhibit IVNV (eg., anti-VEGF) can cause persistent avascular retina, a stimulus for later IVNV. Therefore, the strategy for ROP in these fragile preterm infants is to understand mechanisms to allow target of specific cells and to regulate signaling events involved in IVNV without interfering with PRVD.

Figure 2:
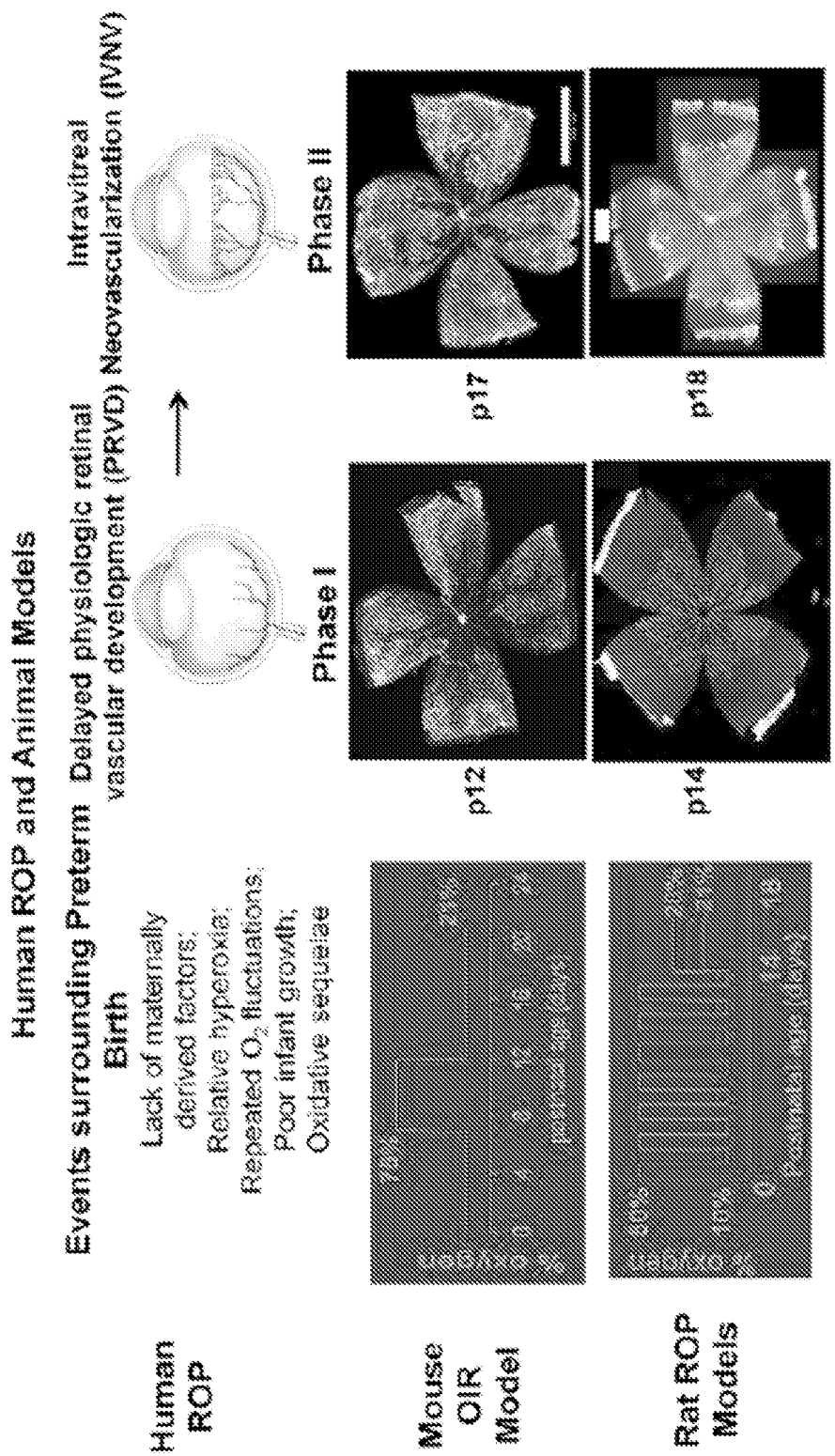
FIG. 2 shows that Phase I=postnatal day (p)12 in mouse OIR model and p14 in rat ROP model. (In room air development, retinal vascularization is complete in mouse ~p7 and in rat ~p14). Phase II=p17 in mouse OIR model and p18 in rat ROP models. Analyses: AVA=% avascular/total retinal area; IVNV+% intravitreal neovascular/total retinal area.

Compared to adult angiogenic eye diseases, additional challenges exist in studying ROP. The preterm infant eye has persistent hyaloid vasculature, firm vitreoretinal adhesions that cannot be mechanically relieved, and less than a 1.0 mm wide zone to enter the vitreous cavity without injuring lens or retina. Therefore, it is not possible to safely obtain tissue or vitreous samples from the preterm infant eye without risks of bleeding, cataract, or inoperable retinal detachment. The preterm infant blood volume, often <250 mL, limits blood sampling for study. Models of oxygen-induced retinopathy (OIR) in species that vascularize their retinas postnatally (unlike the human infant) are used. The mouse OIR model exposes newborn mice to high oxygen levels and can reflect ROP in places that lack resources to regulate oxygen or that occurred in the US and UK in the 1950's. Using transgenic mice, the mouse OIR model is helpful to study mechanisms of angiogenesis, high oxygen and relative hypoxia. The rat 50/10 OIR model ("rat ROP model") reflects human ROP: it causes extrauterine growth restriction, fluctuations in oxygen levels that reproduce arterial oxygen levels of infants with severe ROP, and appears like severe ROP (FIG. 2). It is the most representative model of ROP today, but mechanistic studies rely mainly on pharmacologic manipulations. To study molecular events, the rat ROP model was adapted to target VEGF in Müller cells (MCs) or effectors of VEGF signaling in endothelial cells (ECs) using lentivectors with specific polymerase II promoters that drive shRNAs efficiently when embedded in microRNAs. Some causes of Phases I and II differ in mouse OIR and rat ROP models. Therefore, to understand pathomechanisms in human ROP, human infants were examined and both mouse and rat models were used to identify cells that express ligands or receptors and determine signaling events that cause delayed PRVD/vasoattenuation in Phase I and IVNV in Phase II.

Identifying Safe and Effective Methods to Regulate VEGFR2 Signaling Involved in Phases of ROP. Many ligands and receptors are involved in OIR and potentially, ROP (eg, hypoxia-inducible factor (HIF)-regulated factors [eg, VEGF members and splice variants, EPO, angiopoietins], tissue plasminogen activator, membrane metalloproteinases (MMPs), Notch, reactive oxygen species (ROS), inflammatory pathways, low IGF-1/IGFBPs, etc.). This study focused on VEGFA/VEGFR2, because this pathway causes IVNV, but it is also important in PRVD. Overactivation of VEGFR2 disordered developmental retinal angiogenesis, and when VEGFR2 signaling was restored to room air levels, Phase II IVNV was inhibited and retinal vascular morphology was improved. VEGFR2 activation was regulated by targeting proteins that interact with EC-VEGFR2 and thereby inhibit overactivated EC-STAT3 in order to inhibit Phase II IVNV (FIG. 1).

Targeted inhibition of VEGF produced by MCs reduced IVNV in Phase II, but MCs required VEGF to survive and produce important neurotrophic factors for retinal function and health. The effect of knockdown of MC-VEGFA, compared to splice variant VEGF164, on survival and function of developing retina is tested in Objective 1. This is important, since preterm infants throughout the world are treated with anti-VEGF agents that reduce VEGF several weeks after intravitreal delivery, but effects on safety remain unknown. EPO has neuroprotective effects but also has been associated with IVNV and severe ROP. Early EPO administration does not reduce IVNV even though it promotes PRVD, indicating that timing of EPO delivery alone does not explain EPO's role in severe ROP. In the rat ROP model, the data showed thatVEGF, not EPO or EPOR, were increased in Phase I and that VEGF activated both EPOR and VEGFR2 in Phase II. In cultured ECs, VEGF-activated EPOR interacted with pVEGFR2 to exacerbate STAT3-induced EC proliferation. In Objective 2, the study tests whether knockdown of EPOR specifically in ECs will regulate VEGFR2 signaling and inhibit IVNV but not delay PRVD, whereas knockdown of VEGFR2 in ECs will inhibit IVNV and delay PRVD.

NADPH oxidase is involved in mouse OIR and rat ROP models, but outcomes depend on oxygen level and cells and NOX isoform involved. NADPH oxidase-generated ROS fight invading microbes, making broad inhibition unsafe in immunosuppressed human preterm infants. Activated isoform NOX4 interacts with VEGFR2 in ECs and induces STAT3-mediated angiogenesis. In Objective 3, the study tests whether knockdown of STAT3 in ECs will inhibit IVNV and not delay PRVD. This study also tests whethera strategy to inhibit NOX4NADPH oxidase activation chemically can regulate VEGFR2-induced STAT3 and inhibit IVNV.

These experiments are among the first to study mechanisms to promote PRVD in order to inhibit hypoxia-induced IVNV and identify mechanisms of delayed PRVD: overactivated VEGFR2 disorders dividing ECs in the ROP model; VEGF-induced STAT3 reduces MC-expressed EPO; NADPH oxidase-induces apoptosis and delays PRVD.

The rat ROP model was modified to study molecular mechanisms in specific retinal cell types, MCs or ECs, using lentivectors with polymerase II promoters that efficiently drive shRNAs when embedded in microRNAs.

The study sought to regulate rather than block VEGF signaling by targeting protein interactions with pVEGFR2.

Accepted ideas were challenged regarding the cause of recurrent IVNV after intravitreal neutralizing antibody to VEGF: compensatory angiogenic signaling through VEGF and VEGF-induced EPO signaling in rat ROP model-identified NADPH oxidase-induced JAK/STAT signaling in Phase I and Phase II based on cell type in which STAT3 was activated showing a need to study targeted STAT3 inhibition.

To determine if hypoxia from fluctuations in oxygen leads to disoriented angiogenesis via local increases in Müller cell VEGF and endothelial VEGFR2 signaling, thereby contributing to avascular retina. (FIGS. 2-6).

Figure 3:
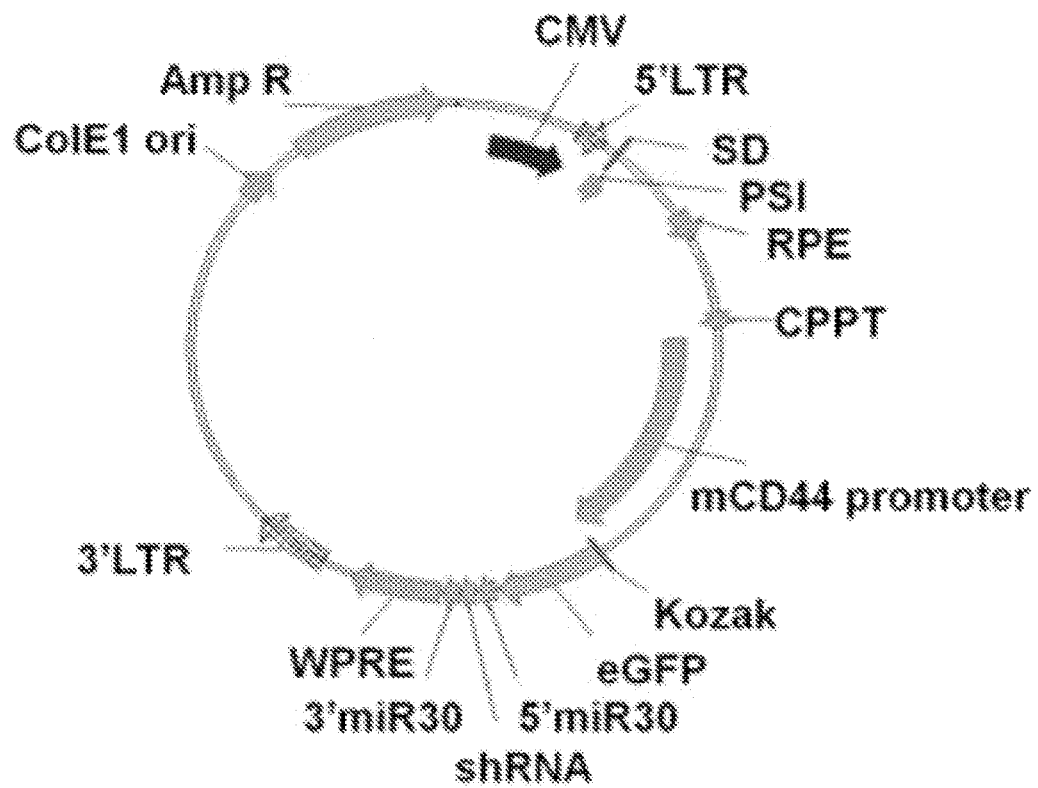
FIG. 3 shows pFmCD44. 1GW lentivector plasmid containing MC-specific CD44 promoter driving miR30-based shRNA cassette and GPF marker.
Figure 4A:
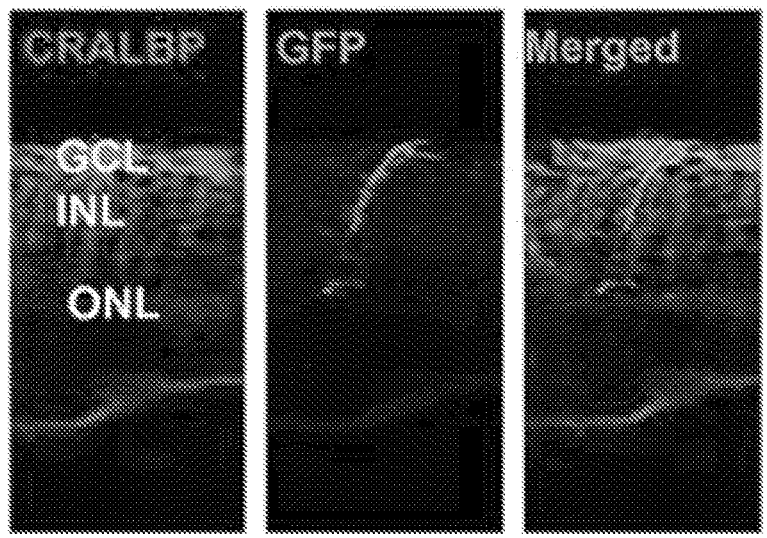
FIG. 4 shows that subretinal lentivector-VEGFA.shRNA or VEGF164.shRNA (1×106 viral particles/eye in 1 μL) show: A) GFP colocalized with CRALBP-labeled MCs; B) reduced retinal VEGF (*p<0.001 vs. uninjected RA; ++p<0.01 vs. PBS ROP; #p<0.05 vs. Luc.shRNA ROP); C) reduced IVNV and D) not weight gain, but neutralizing anti-VEGF reduced C) IVNV and D) weight gain (p<0.01, ***p<0.001 vs. Luc.shRNA; +p<0.05, ++p<0.01 vs. IgG); E) VEGFA.shRNA or VEGF164.shRNA improved retinal vascular morphology compared to anti-VEGF antibody. All p18 rat ROP model, unless specified RA. Statistics—ANOVA, post hoc Newman Keuls. (Luc.shRNA is shRNA to luciferase as a control)
Figure 4B:
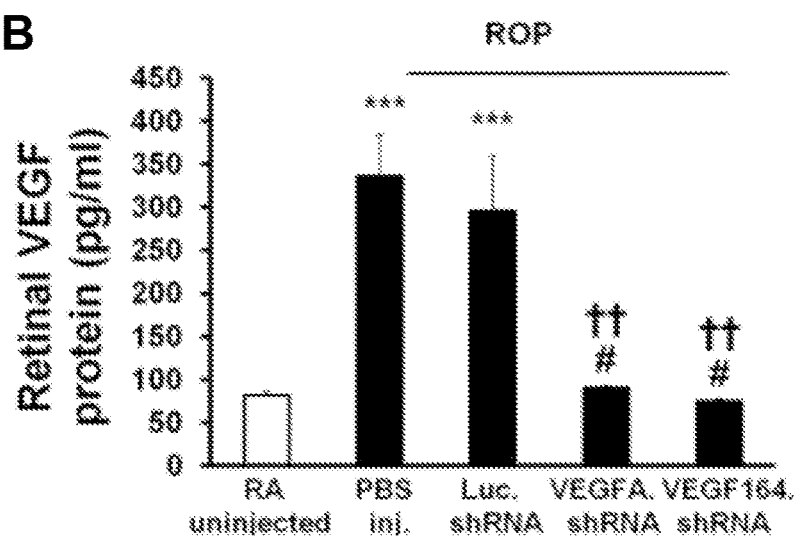
Figures 4C, 4D, 4E:
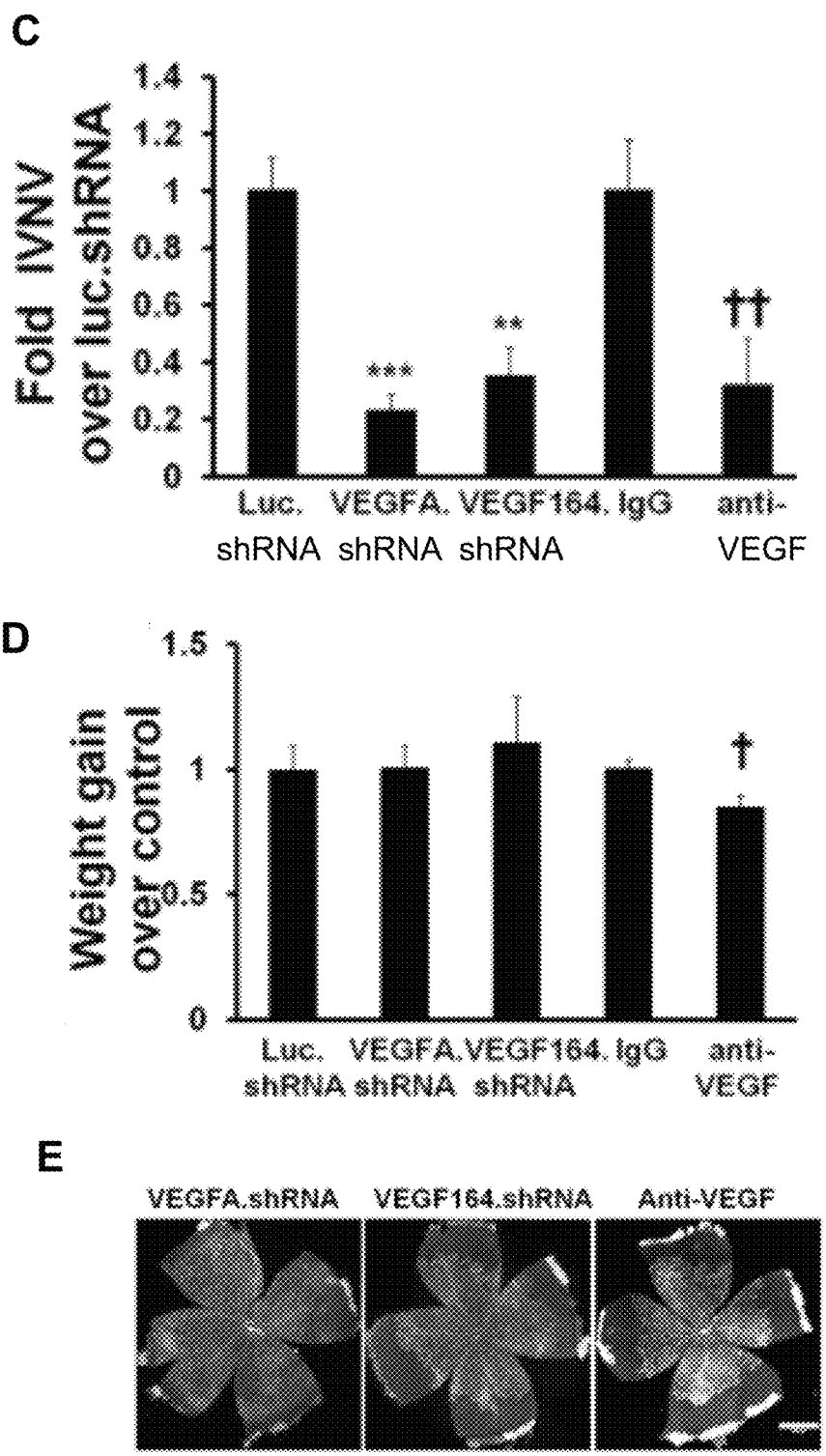
Figures 5A, 5B, 5C, 5D:
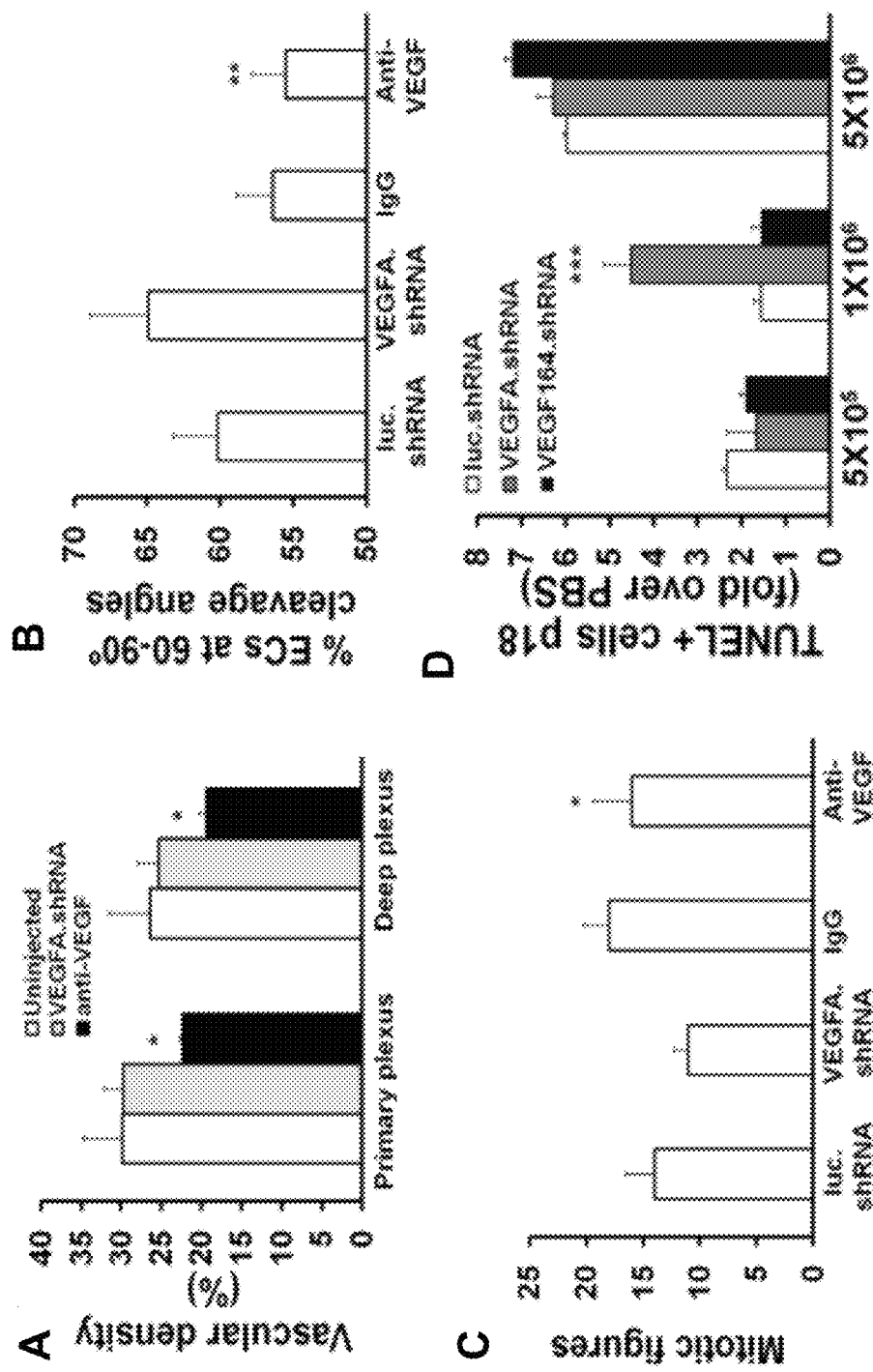
FIG. 5 shows that at p18 ROP, anti-VEGF A) reduced vascular density (pixels fluorescence/total area) compared to VEGFA.shRNA or uninjected, caused B) fewer EC cleavage angles/total dividing ECs at 60-90° (predict vessel elongation) and C) more mitotic figures stained with p-Histone H3 (*p<0.05, p<0.01 vs. VEGFA.shRNA); D) VEGFA.shRNA caused more TUNEL+ cells in ONL at 106 viral particles/eye (*p<0.001 vs. luc.shRNA); 5×10$^5$ viral particles/eye did not inhibit IVNV; 5×106 viral particles/eye increased TUNEL+ cells in all conditions.

Retinal expression of VEGF splice variants, receptors, and pigment epithelial derived factor (PEDF) were tested in Phases I and II of the ROP model and in room air-raised (RA) pups of the same developmental ages. VEGF164, VEGFR2, PEDF mRNAs, and VEGF and PEDF protein were associated with the ROP model and older developmental age, but VEGF120, VEGF188 and VEGFR1 were associated only with older developmental age. Retinal VEGF164, VEGFR2, and neuropilin1 and 2 mRNAs were increased not only at p18 with Phase II IVNV, but also at p14 with Phase I delayed PRVD in the rat ROP model. In contrast, other angiogenic proteins (eg, EPOR, IGF-1, IGF-1R) were increased only in Phase II or reduced in both phases as was EPO (FIG. 11); this differs from the mouse OIR model in which EPO was increased in Phase II. VEGF-induced STAT3 activation in MCs delayed PRVD in Phase I, but VEGF-VEGFR2 signaling caused IVNV in Phase II. Broad inhibition of VEGF with a neutralizing antibody inhibited IVNV and did not delay PRVD but led to recurrent IVNV at p25 and reduced both body weight gain (FIG. 4D) and serum VEGF. These data supported VEGFR2 involvement in both Phases I and II of the rat ROP model and the need for targeted VEGF inhibition. VEGF splice variant mRNAs were detected in retinal sections using in situ hybridization (ISH). VEGF splice variants localized to inner nuclear layer (INL) cells corresponding to CRALBP-labeled MCs. The rat ROP model was adapted to efficiently knockdown VEGFA or VEGF164 in MCs using lentivectors containing an shRNA expression system permitting multi-cistronic cotranscription of GFP driven by a polymerase II promoter embedded in a microRNA30 (miR30) (FIG. 3). The pol II promoter, CD44, targets MCs in vivo. Compared to luciferase control shRNA (luc.shRNA), subretinal, but not intravitreal, lentivectors at p8 transduced MCs (FIG. 4A), not astrocytes or ganglion cells, and significantly reduced retinal VEGF, pVEGFR2 colabeled with lectin-stained ECs and IVNV without reducing pup weight gain (FIGS. 4B, 4C, and 4D) or capillary density of the primary and deep plexi at p18 (FIG. 5A). Compared to intravitreal anti-VEGF antibody, MC-VEGFA knockdown improved vascular morphology (FIG. 4E), oriented divisions toward physiologic vascularization (FIG. 5B), and reduced the number of anti-phosphohistone H3+ dividing vascular cells (FIG. 5C). MC-VEGFA knockdown appeared more effective and safer than anti-VEGF antibody. However, knock-down of MC-VEGFA, but not MC-VEGF164, significantly increased TUNEL+ cells in the outer nuclear layer (ONL) at p18 (FIG. 5D). These data indicate that local overproduced VEGF in MCs disorients vascular cells and causes IVNV, and that targeted knockdown improves physiologic vascularization. Study is needed to determine longer-term safety of knockdown of MC-VEGFA or VEGF164 as both inhibit IVNV, but VEGFA knockdown increased TUNEL+ cells in the ONL. The data also indicate that activated STAT3 was increased in the rat ROP model compared to room air and colocalized with lectin stained ECs in retinal sections and inhibition of STAT3 significantly reduced Phase II IVNV, indicating the role of EC-STAT3 in Phase II IVNV (FIG. 6).

J. Example 3

Objective:

To determine if differential activation of NADPH oxidase by different 02 stresses triggers signaling leading to EC apoptosis or disoriented angiogenesis of ECs, thereby contributing to avascular retina [FIGS. 7-10].

Figures 8A, 8B, 8C:
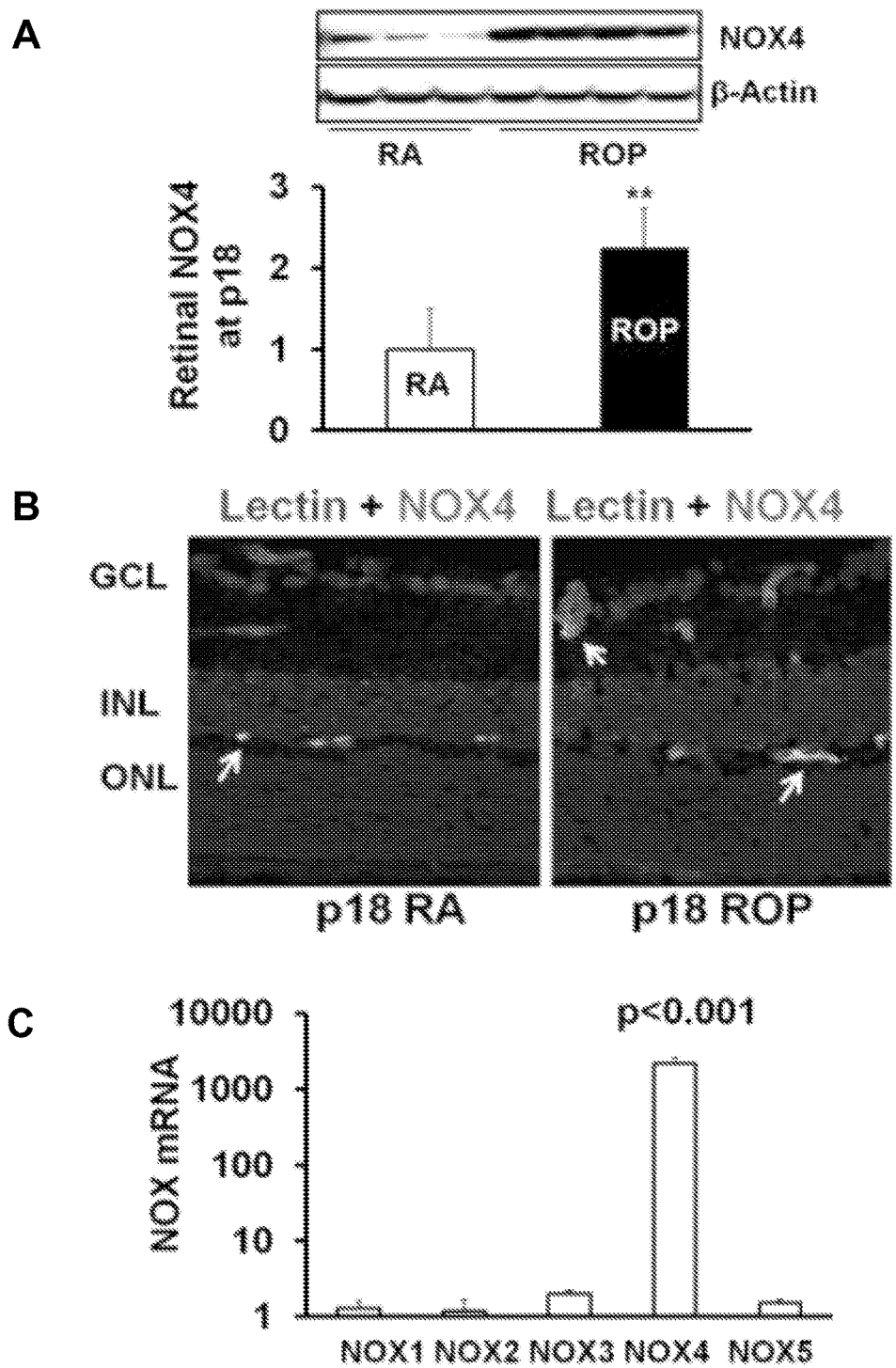
FIG. 8 shows that NOX4: increased A) in retina B) colabel (see arrows) with lectin at p18 rat ROP, C) greater in human retinal microvascular endothelial cells (hRMVECs) (**p<0.01 vs. RA, ANOVA).
Figure 9A:
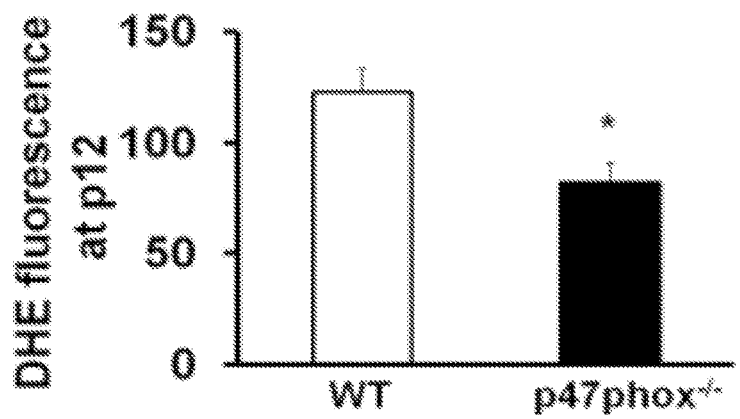
FIG. 9 shows A) DHE reduced in p47phox-1- at p12 after 5 days in 75% 02. At p17 OIR (relative hypoxia), B) T15 staining in retinal ECs and C) IVNV increased in p47phox-1-mice (*p<0.05 vs. WT).
Figure 9B:
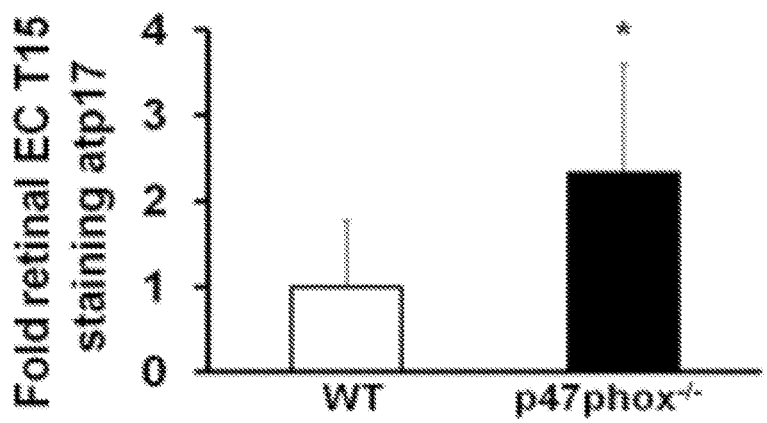
Figure 9C:
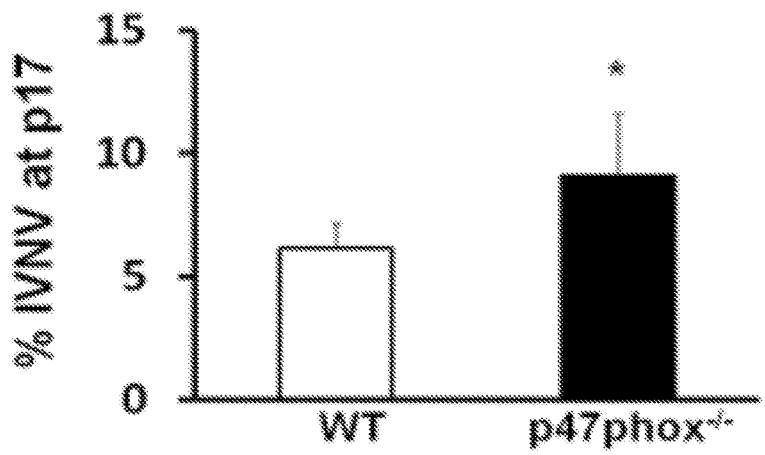
Figure 10A:
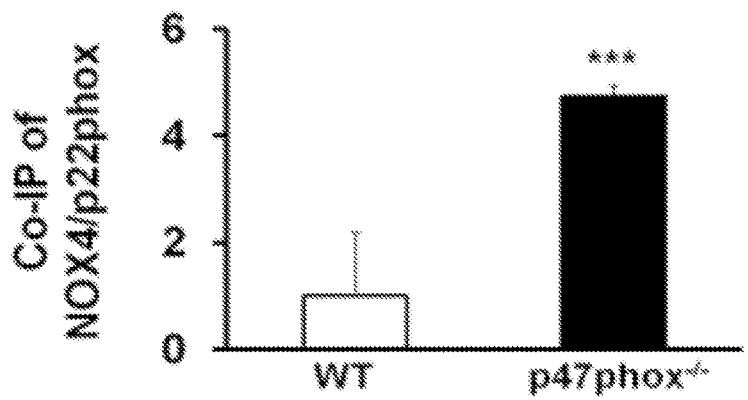
FIG. 10 shows that retinal NOX4 activity, expression increased in p47phox-1- at p17OIR: A) co-IP of NOX4/p22phox; B) NOX4 (green) colocalizes with ECs (lectin-red). C) pSTAT3 (Y705) increased in p47phox-1-p17 OIR (*p<0.05, ***p<0.001 vs. WT). ANOVA.
Figure 10B:
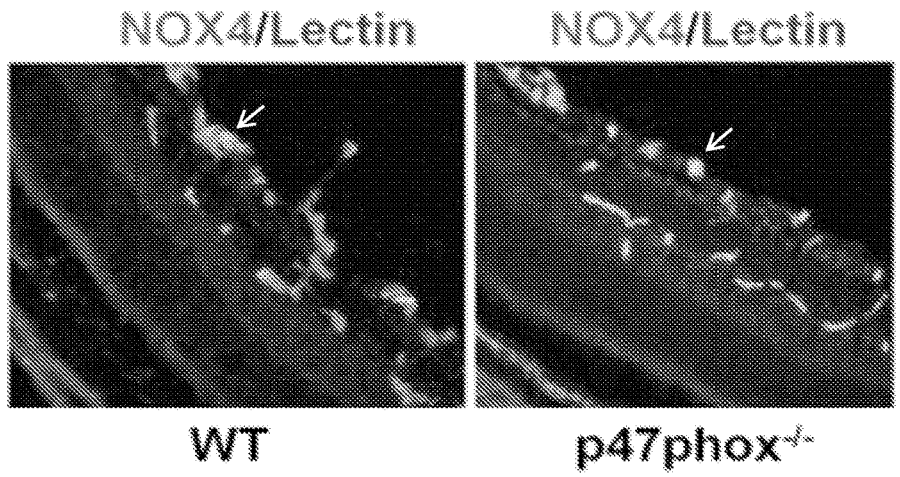
Figure 10C:
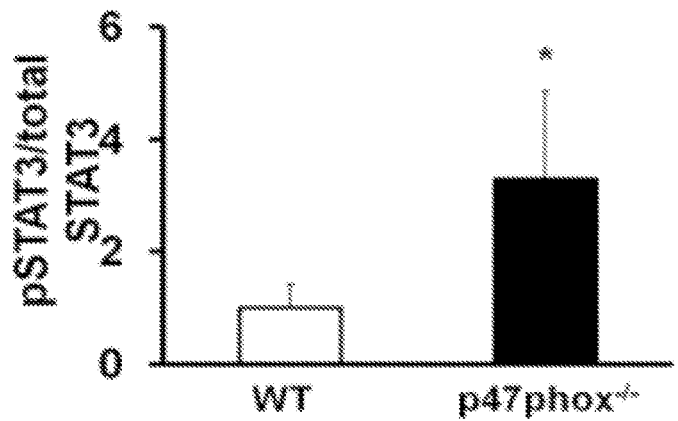

The data show that NADPH oxidase caused apoptosis and delayed PRVD in the rat ROP model but caused IVNV mediated through STAT3 in the rat ROP model rescued in 28% supplemental oxygen (ROP+SO model; FIG. 2), indicating signaling through NADPH oxidase was regulated by different 02 stresses to lead to apoptosis or angiogenesis. Activation of NADPH oxidase generally requires aggregation of a NOX isoform (NOX1-5, Duox1 or 2) with membrane bound p22phox; for NOX1-3 activation, aggregation with Rac1 and cytoplasmic subunits p47phox, p67phox or homologs is also required. Few studies address oxygen effects on NADPH oxidase regulated signaling in ROP or development. Studying NADPH oxidase in vivo is also complicated, because 1) of compensation from NOX isoforms or homologs, which differ in different tissues, and 2) most inhibitors are not specific. In this example, oxygen stresses were varied by using 3 different OIR models: ROP and ROP+SO models in rat and OIR model in mouse. NADPH oxidase-induced signaling in ECs was targeted by reducing leukocyte/macrophages, which generate ROS through NADPH oxidase, or with a transgenic mouse. In rat ROP and ROP+SO models, macrophages ~75% (FIG. 7A) were reduced with 1 uL intravitreal clodronate). IVNV (FIG. 7B), but not AVA or dihydroethidium staining (DHE, FIG. 7C) was significantly reduced in clodronate treated pups in the ROP model supporting the role of macrophages in IVNV, but indicated other cell sources of ROS. Macrophages have multiple effects on angiogenesis including through non-NADPH oxidase mechanisms, so a more specific method was used to study NADPH oxidase-related signaling. NOX 1, 2, 4 are known to be involved in pathologic retinal angiogenesis; NOX2 is in macrophages and ECs. Therefore p47phox−/− mice were used to reduce NADPH oxidase activation from NOX 1-3. The data show that p47phox−/− mice had reduced DHE in RPE/choroid and less choroidal neovascularization (CNV) following laser55. As expected, after hyperoxia at p12, DHE staining was reduced in p47phox−/− compared to wild type (WT) mice (FIG. 9A), indicating that hyperoxia activated NOX 1-3, but there was no difference in vasoattenuated retina even though retinal VEGF was reduced in p47phox−/− mice. At p17 OIR, compared to WT, IVNV (FIG. 9C), AVA, EC-pVEGFR2 colabeling (but not retinal VEGF), STAT3 activities (FIG. 10), and p-histone labeled mitotic figures were increased in p47phox−/− mice. Compensation from other NOX isoforms was suspected. The data show that NOX4 was prevalent in human retinal ECs (hRMVECs) and increased in the ROP model (FIG. 8). After relative hypoxia at p17, NOX4/NADPH oxidase activation was increased (FIG. 9B, FIG. 10A) (no compensatory increase in NOX4 occurred in RA at p4, p'7, p12 or following hyperoxia at p12). Also, neither cleaved caspase 3 nor TUNEL+ cells were increased, but disoriented EC divisions were increased, as with increased VEGFR2 induced IVNV. VEGF level was also not increased, but pVEGFR2 was. In cultured hRMVECs, NOX4 and pVEGFR2 interacted structurally and exacerbated STAT3-mediated hRMVEC proliferation [FIG. 17, Objective 3]. From these data, the study can focus on NOX4-VEGFR2 interaction in exacerbating STAT3 induced IVNV in Phase II ROP. The potential effect of the NOXO1 homolog of p47phox that can activate NOX1/NADPH oxidase even in the p47phox−/− mouse and effects from other sources of ROS, such as mitochondria can also be examined. The data indicate that NOX4/NADPH oxidase was activated by hypoxia, not hyperoxia, and in association with activated STAT3 and IVNV, whereas NOX1-3 isoforms are activated by hyperoxia.

Experimental Designs—

7 experiments were conducted to accomplish three specific objectives. The following animal models were used, in the Animal-BSL2 (ABSL2) certified room, as follows (see also FIG. 2): Rat ROP Model: The data show that dams must nurse at least 12 pups/litter to reproduce Phase I delayed PRVD and Phase II IVNV. Pup weights were monitored. Flat mount analyses were performed in pups within +/−2 g of the average weight for age in the model. For all experiments: ROP model=24 hr of 50% 02 alternating with 24 hr of 10% 02 for 14 days (rat Oxycycler, Biospherix), followed by 21% 02. At p14, Phase I delayed PRVD=avascular/total retinal area (AVA); at p18, Phase II IVNV=IVNV/total area (IVNV).

Mouse Model (OIR):

p7 mice (transgenic and WT littermate, genotyped at p6) and dams in constant 75% 02 (Oxycycler, Biospherix) for 5 days, then 21% 02. Maximal IVNV occurs at p17. IVNV is number of ECs above the inner limiting membrane (ILM) or area of IVNV.

Sample Size, Power, and Statistics:

Sample sizes for experiments were calculated to detect moderate effects (35% difference among groups) at an alpha of 0.05 and power of 80% based on one eye/pup, but analyses on both eyes are used as within subject replication to aid in the analysis of variability in factorial ANOVAs. Quantitative results expressed as means and confidence intervals or standard deviations are analyzed using multifactorial ANOVA. For post-hoc mean separation, t tests with alpha levels protected for the number of multiple comparisons performed using a simulation method were used. For IVNV and AVA, 18 data points are estimated; for secondary questions (ERG, protein, mRNA, IHC, ISH), 8 to 10 data points. Both eyes of the same pup are injected with the same lentivector or compounds to minimize confounding from cross-over effects. In each litter, pups in control and experimental groups are used and distinguished by tattooing. For flat mounts, one data point=one eye of a pup, and the fellow eye is used for secondary questions. For each experiment, at least 3 litters are used to control for intra-litter effects. IVNV, AVA and IHC measured by 2 masked reviewers.

Objective 1:

To test whether knockdown of overexpressed VEGF164 in MCs to retinal VEGF levels that inhibit IVNV and not delay PRVD will allow retinal neuronal survival and function.

Rationale:

VEGF is necessary for MC health and for survival of ganglion cells, retinal pigment epithelium (RPE), and photoreceptors. Conditional knockout of MCs caused photoreceptor degeneration in mice. Knockdown of VEGFA or splice variant, VEGF164, reduced IVNV, but knockdown of VEGFA, and not of VEGF164, increased ONL apoptosis in the rat ROP model raising concern for photoreceptor health [FIG. 5D]. The effect of reducing MC-VEGFA or MC-VEGF164 on MCs and photoreceptors is unknown, particularly in the developing preterm infant and retina. Lentivirus is incorporated into the genome and provides a robust means to test the prediction that long term MC-VEGF164 knockdown will not adversely affect the retina, but MC-VEGFA knockdown will lead to photoreceptor injury and reduce a-wave amplitude first, then affect bipolar cells and reduce postreceptor synaptic processing and b-wave amplitude. At sequential time points, analyses of electroretinography (ERG, Part A), spectral domain optical coherence tomography (sdOCT, Part B), and neurotrophic factors (Part C) are compared. The p25 time point corresponds to ~2 weeks of reduced VEGF that occurs in preterm infants after intravitreal anti-VEGF. The p32 time point is tested for potential repair.

Example 4

Lentivectors with VEGFA.shRNA or VEGF164.shRNA (1×106 viral particles in 1 µL subretinal injection) can be tested. Controls include luciferase (luc.shRNA) to compare to VEGF knockdown, subretinal PBS to assess toxicity effects from subretinal lentivirus, uninjected ROP to assess effects from ocular injection, which releases PEDF and other factors, and RA raised rats of the same developmental ages as a standard for normal retinal vascular morphology and VEGF expression (6 groups total). Subretinal injections (1 µL) of the same type of lentivector can be given to each eye at p8. Live measurements can be performed at p14, p18, p25, p32 and tissue sampling at p18, p25, p32; 1 eye can be processed for flat mounts and the fellow eye for protein, RNA or IHC.

Part A: Functional Effects from Knockdown of MC-VEGFA or MC-VEGF164.

Electroretinography (ERG, BigSHot, LKC Technologies) can be performed at p18, p25, p32 in the NEI-sponsored Vision Core. Pups can be dark adapted overnight, anesthetized in dim red light, dilated and measurements made between gold corneal and stainless-steel scalp electrodes with a 0.3-500 Hz band-pass filter. Scotopic, followed by photopic, ERGs in a 135 lux background, can be recorded with increasing flash intensities from 0.0025 to 250 cd·s/m2 and 0.25 to 250 cd·s/m2, respectively. At least 5 a- and b-wave traces are averaged for each stimulus, and mean amplitude and latency compared with unpaired two-tailed t-test (post-hoc testing with Bonferroni).

Outcome Measures:

a and b wave amplitudes to discern effects on photoreceptors (a-waves) or inner retina (bipolar cells, b-waves), ratio of b/a amplitudes, latency for responses, ELISA of retinal VEGF protein.

Results and Interpretation:

Pups injected with VEGF164.shRNA, which did not cause apoptosis at p18 [FIG. 5D], can have normal ERG responses at all time points. In contrast, VEGFA.shRNA can have reduced a-wave amplitudes at an early time point (eg., p18) followed by reduced b-wave amplitudes later (eg., p25); reduced function can persist or worsen at p32 and can be associated with retinal thinning or structural changes (see Part B). Also MCs, ganglion cells or other neurons can be injured by knocked down MC-VEGFA before photoreceptors. If mild MC injury occurs, there can be GFAP or vimentin labeling of MCs (see Part C). With greater injury, b-wave amplitudes can be reduced from overall inner retinal/bipolar dysfunction before a-waves. If lentivirus and/or knockdown activate MCs, neurotrophic factors can be expressed (Part C) and ERG function can recover at later time points (eg, p32).

Part B: Longitudinal Structural Effects from Knockdown of MC-VEGFA or MC-VEGF164.

At p18, imaging of GFP in retinas can be performed (Micron III imaging). Regions of GFP+ transduced MCs can be mapped and recorded. After hyaloid regression at ~p25, sdOCT (Bioptigen, NC) and Micron III imaging can be performed.

Outcome Measures:

sdOCT to determine retinal layer structure, presence of cysts and thickness in areas of transduced MCs (GFP+ by Micron imaging at p18) and non-transduced MCs (no GFP), measured at p25, p32.

Results:

VEGF164.shRNA cannot cause adverse structural effects, but VEGFA.shRNA can cause regions of injured MCs, inner retinal abnormalities or possibly cyst-like structures (similar to OCTs in preterm infant retinas), or possibly, photoreceptor loss and thinning of ONL. A subretinal injection of VEGFA.shRNA or VEGF164.shRNA transduces MCs in ~30% of a retinal flat mount but is sufficient to significantly inhibit IVNV in the entire retina. In areas of non-transduced MCs, there can be a healthy retina, but VEGF knockdown can also affect non-transduced retina, by reducing secreted VEGF that can then bind and activate receptors on remote cells and neurons.

Part C: Retinal Neurotrophic Factors with MC-VEGFA or MC-VEGF164 Knockdown.

MCs can be activated by lentivirus or VEGFA or VEGF164 knockdown and induce neurotrophic factor release. With longer duration of VEGF knockdown or greater stress, MCs can die, no longer produce neurotrophic factors, and later ganglion cell and photoreceptor death can occur. Effects of VEGF or VEGF164 knockdown can be compared to controls.

Outcome Measures:

At each time point (p18, p25, p32), after in vivo testing (Parts A, B), and euthanasia. One eye to be processed for western blot: pSTAT3, EPO, pAkt, VEGF (or ELISA), phospho/total VEGFR1,2,3, EPOR, pEPOR, and BDNF (BDNF variants associated with human severe ROP in multicenter candidate gene study, ARVO 2013, #601, May 5); immunohistochemistry (IHC) retinal sections labeled with lectin [ECs]; glutamine synthetase (GS), CRALBP [MCs], GFAP, vimentin [activated MCs]; pan-Brn3, Thy-1 [ganglion cells]; rhodopsin [rods]; NG-2, $\alpha$SMA, desmin [pericytes]; CD34 [EPCs], CD39 [angioblasts]; TUNEL; some IHC colabeling with pVEGFR2, pEPOR, cleaved caspase-3, pERK; real-time PCR for VEGF, EPO, EPOR and BDNF; some for in situ hybridization (ISH). Fellow eye for lectin-stained flat mounts for IVNV area and avascular retinal area (AVA), capillary density; some colabeled for ganglion cells [Thy-1, pan-Brn3+].

Results:

VEGF164.shRNA can haveretinal VEGF164 and pVEGFR2 reduced to levels of RA pups, and reduced IVNV but not increased AVA; ERG and sdOCT can be similar to that of luc.shRNA. VEGFA.shRNA cancause more apoptosis or GFAP labeling of MCs than VEGF164.shRNA or luc.shRNA. Knockdown of MC-VEGFA or MC-VEGF164 can lead to different neurotrophic factor expression and can recover retinal structure and ERG at later time points. Capillary density can decrease and new IVNV occur with MC damage; methods to perform fluorescein angiography in live pups can be used.

ECs, precursors (EPCs) and angioblasts interact with different cells to undergo ordered developmental angiogenesis: ganglion cells for inner retinal plexus; astrocytes attract migrating ECs to form capillaries in some species; pericytes stabilize newly formed blood vessels; and these and other cells can be considered first by detecting them with IHC. ERG measures total retinal function and focal dysfunction can be missed. If discrepancies between structure and function exist, ways to perform focal ERGs can be explored such as with Micron imaging. Besides systematic analysis of densitometry of pVEGFR2 colabeled with MC markers, quantitative analysis can be performed from pooled retinas using flow cytometry gating on GFP labeled cells or immunoprecipitation (IP) to pull down GFP and assay for pVEGFR2. Subretinal injections can activate MCs and cause nonspecific effects on retinal neurons through cytokine release. Glial activity can be assessed with GFAP or vimentin labeling on IHC, comparing experimental and control eyes, and assay for cytokines, like TNF$\alpha$, as in Part C. A study in adult mice that overexpress VEGF in photoreceptors reported no retinal apoptosis from long-term treatment with a VEGFR tyrosine kinase inhibitor (SU4312) administered periocularly and dosed to inhibit CNV. However, the study did not address developing retina or if periocular dosing affected MCs or photoreceptors. This study focuses on VEGFA and VEGF164, but considers: extracellular matrix products, VEGF splice variants including VEGFxxxb that inhibit VEGF-induced VEGFR2 signaling; members like VEGFC/VEGFR3 that reinforces Notch to convert EC tip to stalk cells; other neurotrophic factors (eg, LIF, NGF, CNTF, IGFBP5, CTGF, bFGF and GDNF); adenosine 5'-triphosphate (ATP)-degrading ectoenzymes that increase availability of adenosine or antioxidants. Photoreceptors express endothelin to initiate an injury response involving MCs and glia. MC-derived factors can be considered if b-waves are reduced early or MCs express GFAP, vimentin or pERK. If there is trouble labeling with antibodies, other antibodies can be used. Other time points can be considered for injection or analysis and additional viral titers in separate experiments. Cysts found in human ROP can occur from increased VEGF. They can be anticipated in controls, but if cysts occur with VEGF knockdown, other factors, eg, angiopoietin-4 can be considered. Astrocytes were not transduced by lentivectors, and CRALBP can be used to distinguish MCs from astrocytes. TUNEL is not specific for apoptosis and other assays (eg., c-caspase 3) can be considered.

Animal Numbers Anticipated:

Also see Sample Size Power and Statistics. For ERG and structural assessment, n=10; for biochemical analyses, n=8. 6 groups (VEGFA.shRNA, VEGF164.shRNA, luc.shRNA, PBS, ROP noninjected, RA noninjected)×3 time points for 18 data points for primary question=27 litters.

Figures 11A, 11B, 11C:
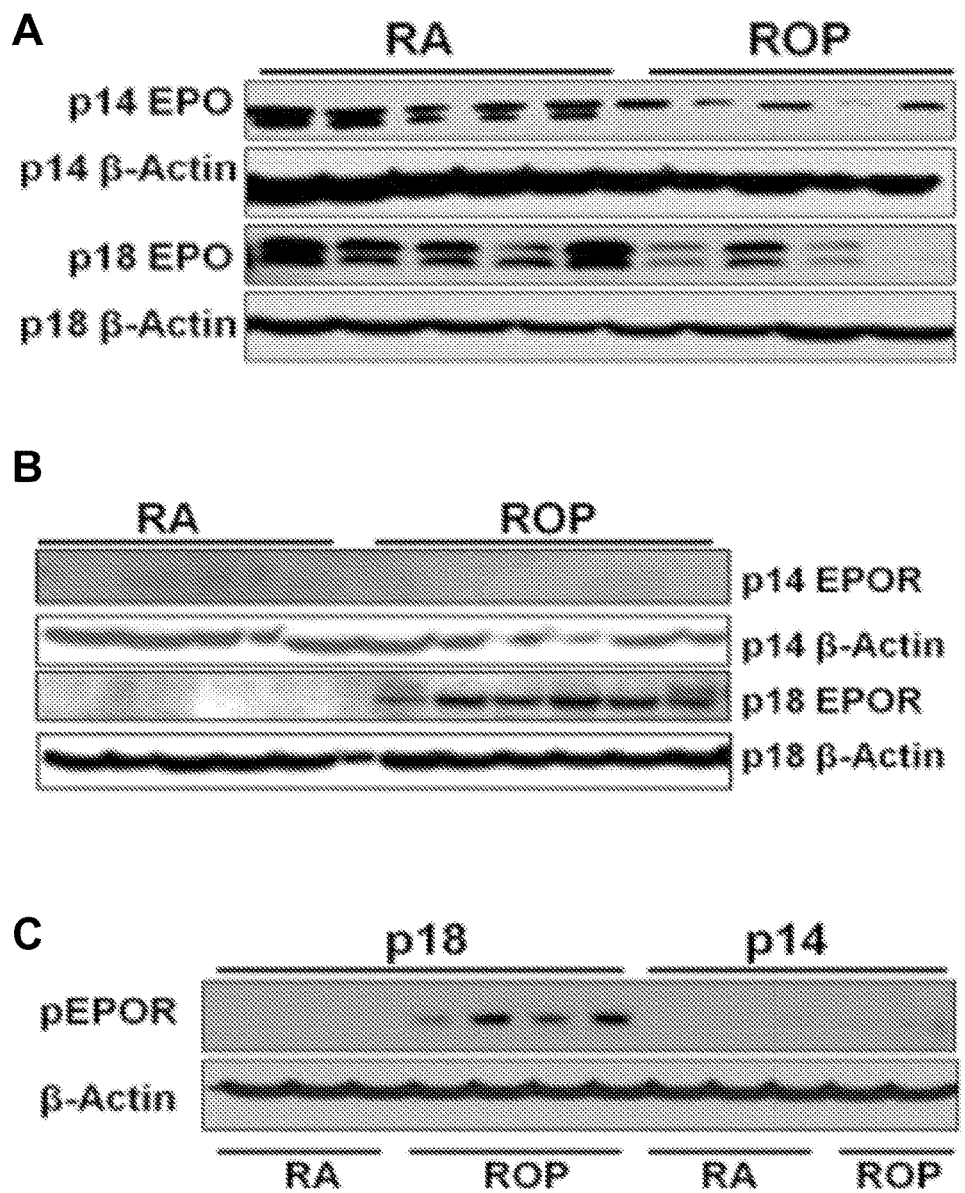
FIG. 11 shows that the ROP model has A) decreased erythropoietin (EPO) at p14 and p18 (lower bands), and increased B) Retinal EPO receptor (EPOR), C) pEPOR, D) pEPOR/lectin colabel (see arrows) (E) quantification at p18 (*p<0.05, **p<0.01 vs. RA).
Figure 11D:
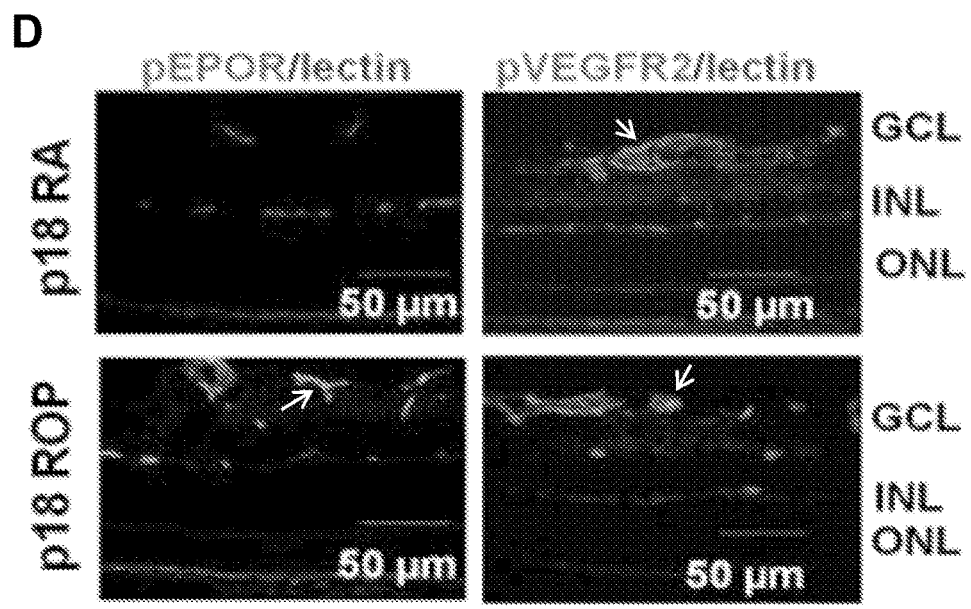
Figure 11E:
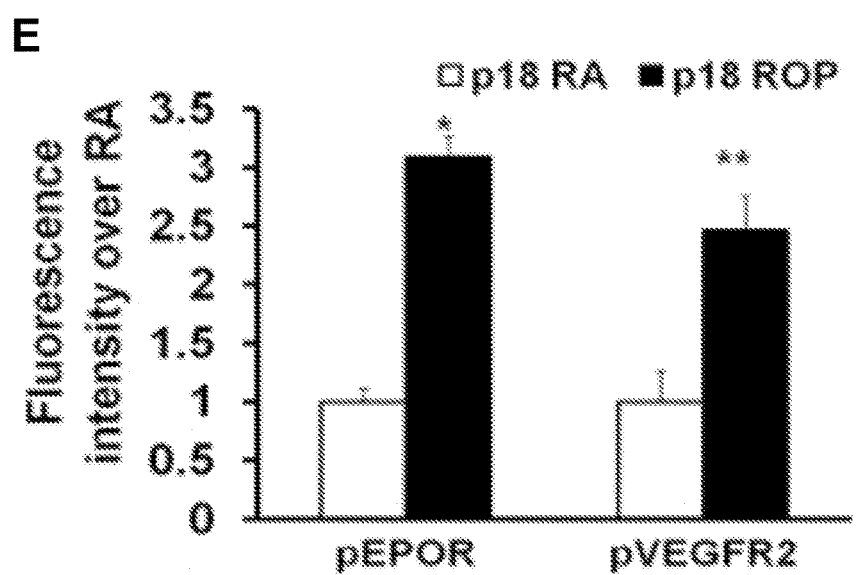
Figures 12A, 12B:
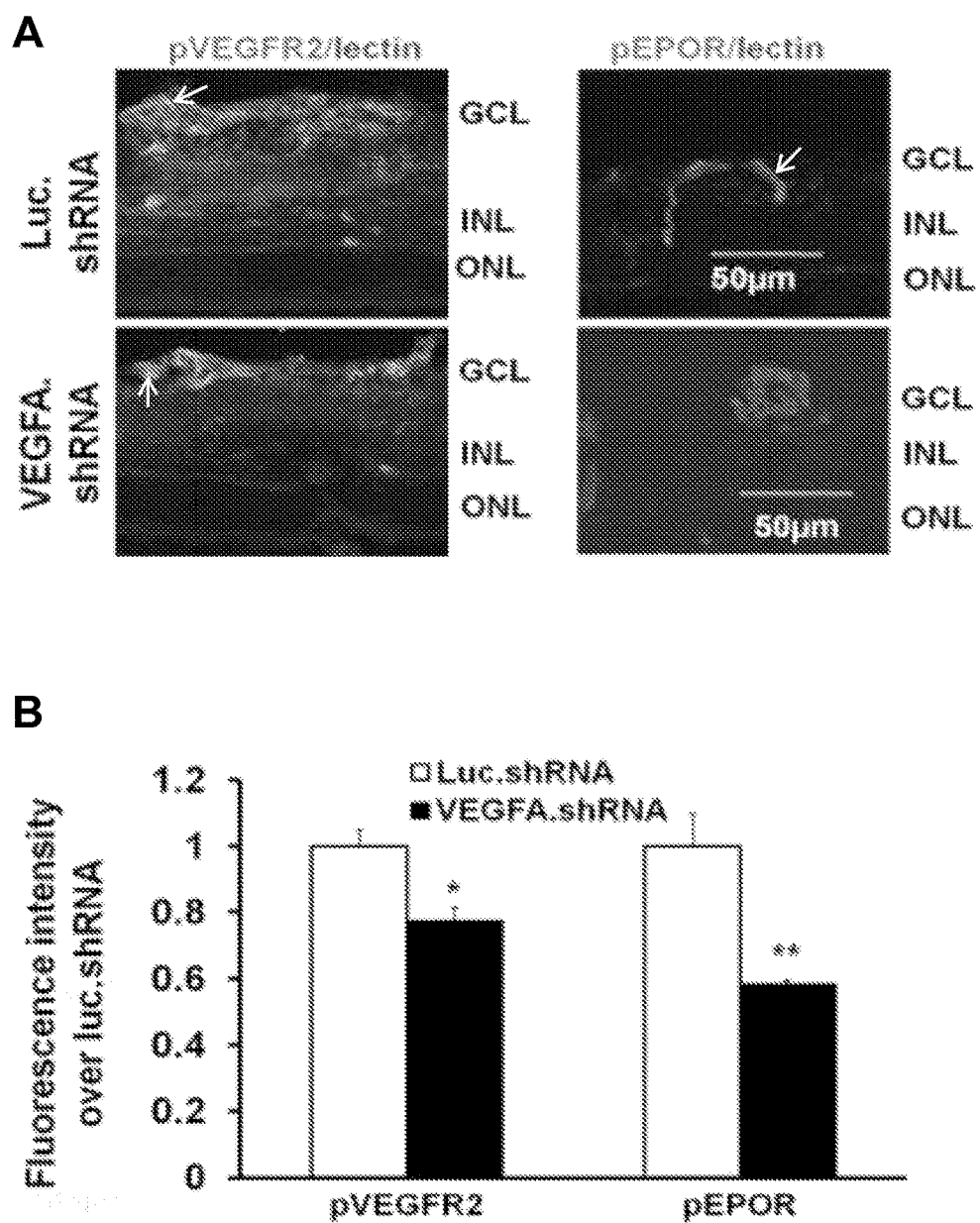
FIG. 12 shows pVEGFR2 and pEPOR A) colabel with lectin (see arrows) (B) quantification reduced in p18 ROP model with VEGFA.shRNA (*p<0.05, **p<0.01 vs. LUC-.shRNA). Statistics all ANOVA.
Figures 13A, 13B, 13C, 13D:
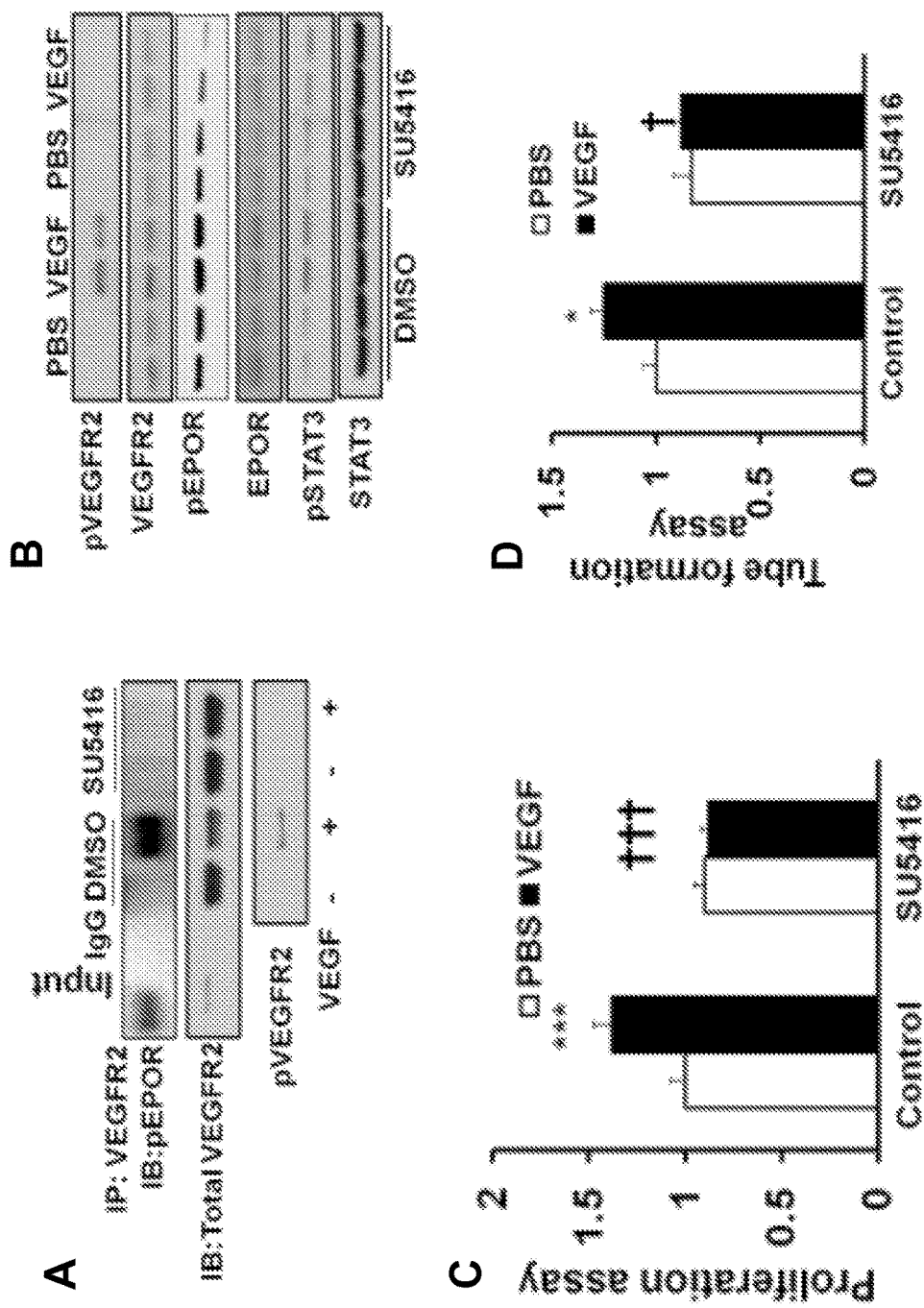
FIG. 13 shows that A) VEGFR2 interaction with pEPOR is blocked by SU5416. SU5416 inhibits B) VEGF-induced pVEGFR2, pEPOR, pSTAT3, c) hRMVEC proliferation and D) tube formation (*p<0.05, ***p<0.001 vs. PBS of Control; †p<0.05, †††p<0.001 vs. VEGF of Control). EPOR knockdown reduces E) VEGFR2/EPOR interaction, F) VEGF-induced pVEGFR2, pEPOR, pSTAT3, G) hRMVEC proliferation and H) tube formation (*p<0.05, vs. PBS of con.siRNA; †p<0.05 vs. VEGF of Con.siRNA; #p<0.05 vs. PBS of EPOR.siRNA). Statistics all ANOVA with post-hoc Neuman Keuls.
Figures 13E, 13F, 13G, 13H:
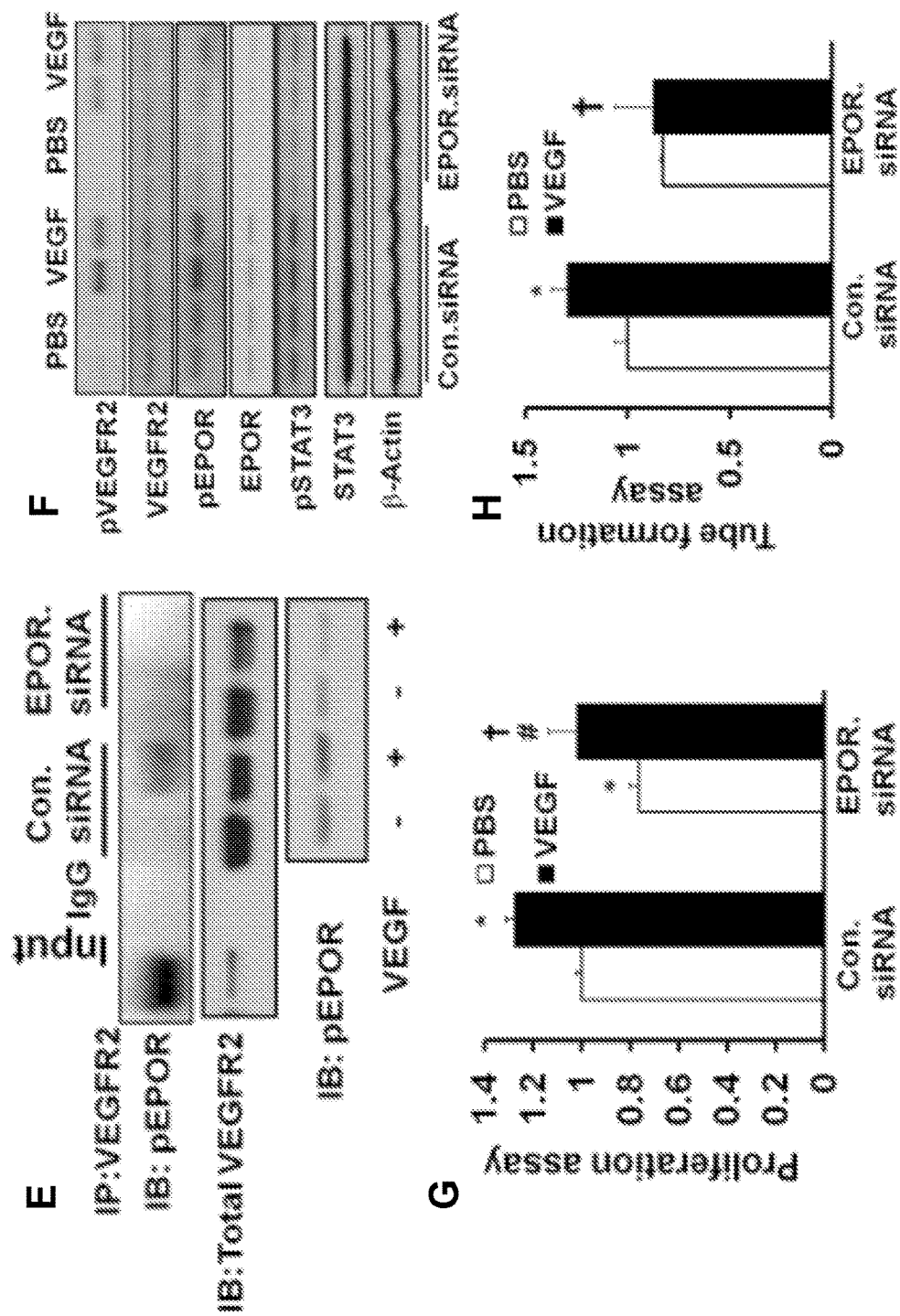

Objective 2:

To test whether knockdown of EPOR in ECs will reduce IVNV in Phase II ROP and not delay PRVD in Phase I [FIGS. 11-13]

Rationale:

Erythropoietin (EPO) treats anemia but has neuroprotective, angiogenic, antiapoptotic and antioxidative properties. Studies reported exogenous EPO was associated with severe ROP. In the mouse OIR model, EPO was a target for Phase II IVNV, but when administered at early ages was found protective, indicating timing of delivery was important. In the ROP model, exogenous EPO delivered at early ages restored PRVD in Phase I, but did not reduce Phase II IVNV. In recent clinical studies in preterm infants, EPO derivatives tested for cognitive development did not increase or reduce IVNV in severe ROP indicating that beneficial effects of EPO are not based on timing of administration alone. In hematopoiesis, EPO binds EPO Receptor® to form a homodimer and activates JAK/STAT signaling. EPOR can form heterodimers with the beta common receptor (βcR) as a tissue protective receptor or VEGFR2 to be angiogenic. Carbamylated EPO (CEPO) binds βcR and is protective in stroke models, but βcR was barely detectable in retina, and CEPO compared to EPO or PBS increased Phase II IVNV in the ROP model. Retinal EPO/EPORs and VEGFR2 were examined in the ROP model. Compared to RA, EPO, EPOR, pEPOR, and pEPOR co-labeled-ECs were not increased in Phase I. However, EPOR and pEPOR (but not EPO) in retinal lysates and pEPOR co-labeled-ECs in retinal sections were increased in Phase II (FIG. 11). In contrast, VEGF and pVEGFR2 were increased in both Phase I and Phase II. These data support VEGF, not EPO, as associated with activated EPOR in the rat ROP model. Because ECs make up a small fraction of cells in the retina, densitometry of lectin stained retinal sections colabeled with pVEGFR2 ($p<0.05$) or pEPOR ($p<0.01$) was measured. Colabeling was lower in VEGFA.shRNA treated eyes compared to luc.shRNA (FIGS. 12A and 12B). In vitro, VEGF-induced-pVEGFR2 and -pEPOR formed a structural interaction that triggered EC-STAT3 activation and enhanced hRMVEC proliferation (FIG. 13) (Reduced total VEGFR2 [FIG. 13A] can be from VEGFR2 ubiquitination). Inhibition of pVEGFR2 with SU5416 or EPOR siRNA inhibited STAT3 activation and VEGF-induced angiogenesis (FIG. 13). These data indicate that EPOR knockdown regulates VEGFR2 mediated overactivation of EC-STAT3. Increased VEGF in Phase I activates VEGFR2 and EPOR in Phase II, which interact to cause IVNV. Knockdown of EPOR in ECs can inhibit IVNV and not delay PRVD. The rat ROP model and lentivectors with shRNA to EPOR or VEGFR2, efficiently driven by a rat ve-cadherin promoter that targets ECs only were used [FIGS. 14-15]. Lentivirus, an integrating virus, were used so shRNAs can be expressed in proliferating cells. The experiment will also provide knowledge of VEGF-induced VEGFR2-EPOR interactions in ECs.

Objective 2.1:

To determine efficiency and specificity of EPOR or VEGFR2 knockdown in ECs

Example 5

Efficiency of EPOR or VEGFR2 Knockdown

The strategy can be similar to knockdown of MC-expressed VEGFA, except a ve-cadherin promoter to target ECs can be used. The ve-cadherin promoter recruits polymerase II to drive miR30 embedded shRNAs. 3 shRNAs specific to rat EPOR (EPOR.shRNAs) and rat VEGFR2 (VEGFR2.shRNAs) were developed and tested (FIG. 14B) to determine shRNAs with the best knockdown. For control, shRNA targeted to luciferase (luc.shRNA), a nonmammalian gene, was used. Into a plasmid DNA expressing a Flag-tagged wild type (wt) coding sequence (wt-cDNA) for EPOR or VEGFR2, point mutations in the cognate region of the cDNA can be introduced where the shRNA binds to render the cDNA resistant to RISC cleavage without changing the native amino acid sequence (mut-cDNA). Then cotransfect 293T cells with either VEGFR2.shRNA or EPOR.shRNA and respective wt-cDNA or mut-cDNA. Off target effects can be determined by western blots of Flag expression or from interferon-induced genes using BLOCK-iT RNAi Stress Response Control Kit (Invitrogen, CA). Groups can be: rat EPOR.shRNAs+rat EPOR-wt-cDNA, rat EPOR. shRNAs+rat EPOR-mut-cDNA, rat VEGFR2.shRNA+rat VEGFR2-wt-cDNA or rat VEGFR2.shRNA+rat VEGFR2-mut-cDNA. Luc.shRNA and no DNA transfection can be controls. For specificity (FIG. 14A), lentiviral transduction of rECs, rat MCs (rMC-1s), human ARPE can be tested.

Outcome Measures:

rat EPOR, VEGFR2 mRNAs (real-time PCR); Flag expression levels by western blot.

Results:

Compared to control, at least one shRNA to EPOR and one to VEGFR2 can reduce respective mRNA and protein in 293T and rECs, but not in rMC-1s or ARPE. 293T co-transfected with shRNA+EPOR-wt-cDNA can have reduced Flag expression levels compared to respective rat shRNAs+mut-cDNA. Lentivirus driven by rat VE-cadherin promoter can be transduced in rECs, not rMC-1s or human ARPE.

Example 6

Optimizing silencing from lentivector containing EPOR shRNA Viral packaging components (VSV-G, pMDLg/pRRE and pRSV-REV) and each transfer vector containing the shRNA with optimal knockdown in Example 5 can be transfected using polyethylenimine (PEI) into HEK 293A cells to produce complete packaged virus particles for in vivo testing. Groups can be complete viruses with shRNAs to EPOR (EPOR.shRNA), VEGFR2 (VEGFR2.shRNA) and luc.shRNA. At the start of 50% 02 at p10, (optimal transduction and knockdown, FIGS. 15A and 15B), 1 μL subretinal, 106 viral particles total, can be injected. Other controls include subretinal PBS, non-injected ROP, and non-injected RA. Outcomes can be at p18 and p25.

Outcome Measures:

Viral titer by Lenti-X™ p24 Rapid Titer Kit (Clontech). Transduction in ROP model monitored with Micron III for GFP and by flat mount analysis. Knockdown of EPOR or VEGFR2 by western blot for EPOR and pEPOR or VEGFR2 and pVEGFR2, respectively, compared to luc.shRNA and RA uninjected pups of the same developmental ages. IHC for EPOR and pEPOR or VEGFR2 and pVEGFR2 colabeled with CD31 or lectin (ECs) or with other cell markers based on colocalization with GFP in IHC.

Anticipated Outcomes:

Viral titers can be determined by ELISA (Titer kit). In vivo, EPOR.shRNA can reduce colabeling of EPOR and pEPOR with lectin in IHC, reduce pEPOR on western blot compared to luc.shRNA and noninjected ROP, and be similar to RA rats of the same developmental ages. Similar findings can be anticipated for VEGFR2.shRNA compared to controls.

The preliminary studies show efficient transduction of ECs in vivo (FIG. 15). If there is difficulty in efficiently and sufficiently knocking down target genes, shRNAs directed to other sequences in relevant open reading frames can be tested. Also, high vector titers obtained can allow to further increase viral concentration in vivo. The ve-cadherin promoter was initially chosen because it is specific to ECs, whereas Tie-2 can also affect hematopoiesis, and the ubiquitously active CMV promoter cannot support cell specific shRNA/gene expression. If necessary the CRISPR-based gene editing system can be employed to obtain cell specific, regulated knockdown in vivo. Here, the lentivector can express CAS9 cDNA under the control of the ve-cadherin promoter, and the U6 promoter can drive expression of the guide-RNA directed to the target exon(s). (If needed, a tetracycline inducible promoter can be introduced to support doxycycline regulated expression of a CRISPR-resistant cDNA to replace the CRISPR-mutated endogenous target gene and stop the knockout; this can be done as a single vector system and requires a transgenic rat in which the doxycycline regulated transactivator is ubiquitously expressed. Viral transduction and target gene knockout can be limited to retina (no ve-cadherin was found in hyaloid), but can analyze pooled vitreous, RPE/choroids and vasculature outside the eye by western blot or IHC in shRNA groups and controls. Other approaches include AAV-DJ and functionalized nanoparticles, but these do not integrate into host DNA and are less ideal to test the knockdown of generations of dividing ECs. Nanoparticles require specific surface proteins to target ECs, and these can be determined for the ROP model. Time points of delivery and analysis can be adjusted as needed. ECs make up a small proportion of retinal cells, so ECs can be concentrated from pooled retinas using flow cytometry or IP for GFP and western blot to measure pEPOR and CD31 similar as described in Objective 1, if needed. The mouse OIR is not ideal to test this objective but if there is difficulty, inducible retinal vascular EC conditional knockout of EPOR with (VE-cadherin)-Cre-Loxp-EPOR mice cane be created by crossbreeding Cdh5 (VE-cadherin) mice with mice carrying a loxP-flanked EPOR gene and treating newborn mice with subretinal tamoxifen to induce Cre activity only in retina. Induction with subretinal tamoxifen can cause retinal damage, and controls to assess this can be used. This method can be adapted for rat. Another method to knockdown proteins in retinal endothelial cells only is to create a transgenic rat that will express the avian retrovirus receptor only in endothelial cells and give lentiviral vectors containing specific shRNAs and with a ubiquitous promoter.

Objective 2.2:

To test whether EPOR, compared to VEGFR2, is necessary for aberrant IVNV and whether knockdown in ECs will reduce IVNV but not delay PRVD.

EPO/EPOR has neuroprotective effects; therefore, it is not the goal of the study to broadly inhibit it. In the ROP model, EPOR is activated in retinal ECs in Phase II by VEGF-induced pVEGFR2 [FIGS. 11-12]. Interactions between pEPOR and pVEGFR2 [FIG. 13] cause IVNV and knockdown of EPOR in ECs only can inhibit Phase II IVNV and not delay PRVD, whereas EC-knocked down VEGFR2 can inhibit IVNV and delay PRVD.

Example 7

Effects of EPOR or VEGFR2 Inhibition on IVNV and Effects on AVA

Both eyes of each pup can receive 1 uL subretinal injections at p10 with the same lentivector-delivered shRNAs to control for cross over effects and allow sufficient time for EC transduction: in a litter, 1/3 pups injected with EPOR.shRNA; 1/3, VEGFR2.shRNA; 1/3, luc.shRNA. Groups include 2 lentivector doses (eg, $1\times10^6$ or $2\times10^6$ viral particles/inj.); additional controls include: PBS injected, uninjected ROP, RA. Analyses (p18, p25).

Measured Outcomes:

IVNV and AVA in lectin stained flat mounts. Retinal sections: GFP colabeled with ECs (lectin or CD31) to assess transduction; pEPOR, pVEGFR2 colabeled with EC markers (lectin or CD31); TUNEL, cleaved (c-)caspase 3 and retinal thickness for retinal health. EPOR mRNA (real-time PCR); EPOR protein, pEPOR, pSTATs (1,3, 5), pAkt, pERK, pVEGFR1,2,3, VEGF, VEGFRs, c-caspase 3 (western blot).

Results:

The data show knockdown of EPOR reduces angiogenesis [FIG. 13]. At least one titer of EPOR.shRNA can reduce IVNV and not increase AVA and IHC can not show increased apoptosis of ECs in physiologic vessels, whereas VEGFR2.shRNA can reduce IVNV, increase AVA and can show apoptosis in ECs in the normal vasculature and IVNV. Luc.shRNA can not affect IVNV and AVA significantly compared to uninjected eyes. pEPOR can be reduced in EPOR.shRNA- and VEGFR2.shRNA-injected; pVEGFR2 can be reduced in VEGFR2.shRNA-injected and less so in EPOR.shRNA-injected. Different angiogenic signaling profiles (eg, pAkt, pERK, pSTATs, etc.) after knockdown of each receptor can be found.

If transduction is inadequate, titers and postnatal age of injection can be adjusted. If retinal thickness is reduced or apoptosis in luc.shRNA is increased compared to uninjected ROP, viral doses can be lowered. Phagocytic cells can ingest lentivectors and express shRNA. If this occurs, label for macrophages (CD68, F4/80), microglia (Iba), RPE (RPE65). To reduce macrophages, clodronate (progress report) or other methods and appropriate controls can be used. If VEGFR2 is not reduced by VEGFR2.shRNA, consider mechanisms that inhibit receptor ubiquitination, such as the adaptor, PDCL3, which can stabilize VEGFR2 activation by inhibiting receptor ubiquitination. Effects of EC-EPOR knockdown can occur only in regions where GFP is expressed.

Knockdown of EPOR did not abolish angiogenesis in vitro, but if EPOR knockdown reduces Phase II IVNV and PRVD, inject EPOR.shRNA or luc.shRNA as described above, and administer intraperitoneal (IP) EPO, which has been tested for cognitive development in preterm infants, to determine if compared to PBS, EPO binding EPOR in non-endothelial cells can be neuroprotective or restore PRVD, potentially through neurovascular effects. Brain bcl-2 mRNA was reduced in the rat ROP model in Phase I. Bcl-2 inhibits apoptosis. Retinas and brains can be assessed for TUNEL+ cells and c-caspase-3 in EPO-treated pups in both EPOR.shRNA and luc.shRNA groups compared to PBS control groups. Crosstalk between EPOR and VEGFR2 can be examined, particularly induced by VEGF, including Src, a classic effector of VEGFR signaling, and IQGAP or PDCL3, which are important adaptors for VEGF signaling. The data show that VEGF does not bind EPOR directly. However, if the data prove otherwise, this can be tested using receptor/ligand binding affinity.

Animal Numbers Anticipated:

Also see Sample Size Power and Statistics. For Example 6:~12 litters. For Example 7, (n=18 for primary question of IVNV and AVA, n=6-8 for secondary questions) 2 time points×3 shRNAs×2 doses=12 groups, and for 18 data points/group, 18 litters. Additional controls (RA, injected ROP, PBS); IHC, mRNA, protein not provided by fellow eyes, 0.34 litters×8 data points×5 assays=~14 litters. 32 litters for Example 7.

Objective 3:

To test whether STAT3 knockdown in ECs will safely inhibit IVNV and not delay PRVD. A pharmacologic means to regulate NOX4/VEGFR2-mediated STAT3 activation to reduce IVNV can be tested.

Figures 6A, 6B, 6C:
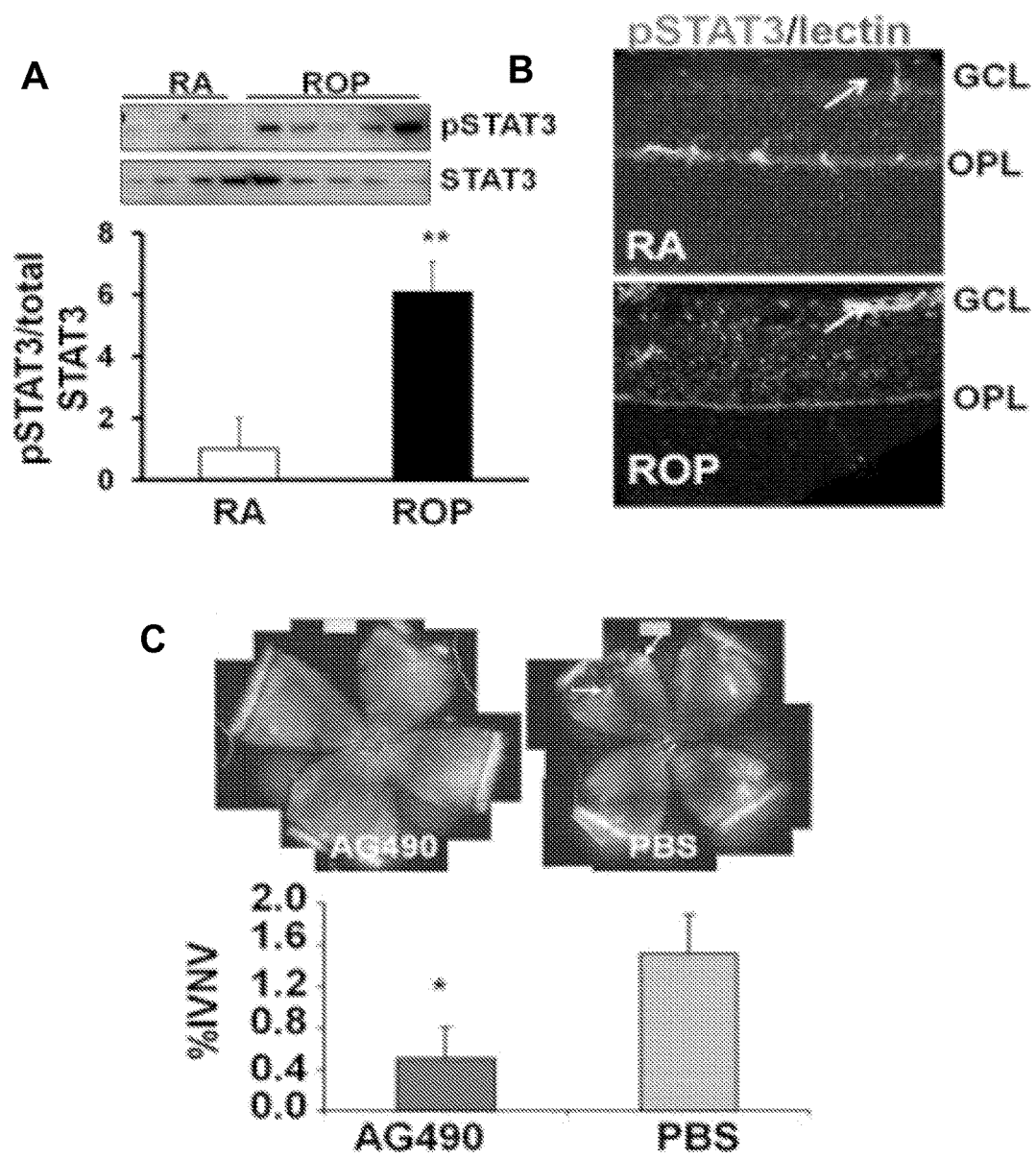
FIG. 6 shows increased pSTAT3 A) in retina at p18 ROP and B) colabeled (see arrows) with lectin at primary plexus in p14 ROP model (**p<0.01 vs. RA); C) Intraperitoneal JAK2/STAT3 inhibitor, AG490, reduced IVNV at p18 ROP model rescued in 28% oxygen (*p<0.05 vs. PBS). ANOVA/Newman keuls.
Figures 7A, 7B, 7C:
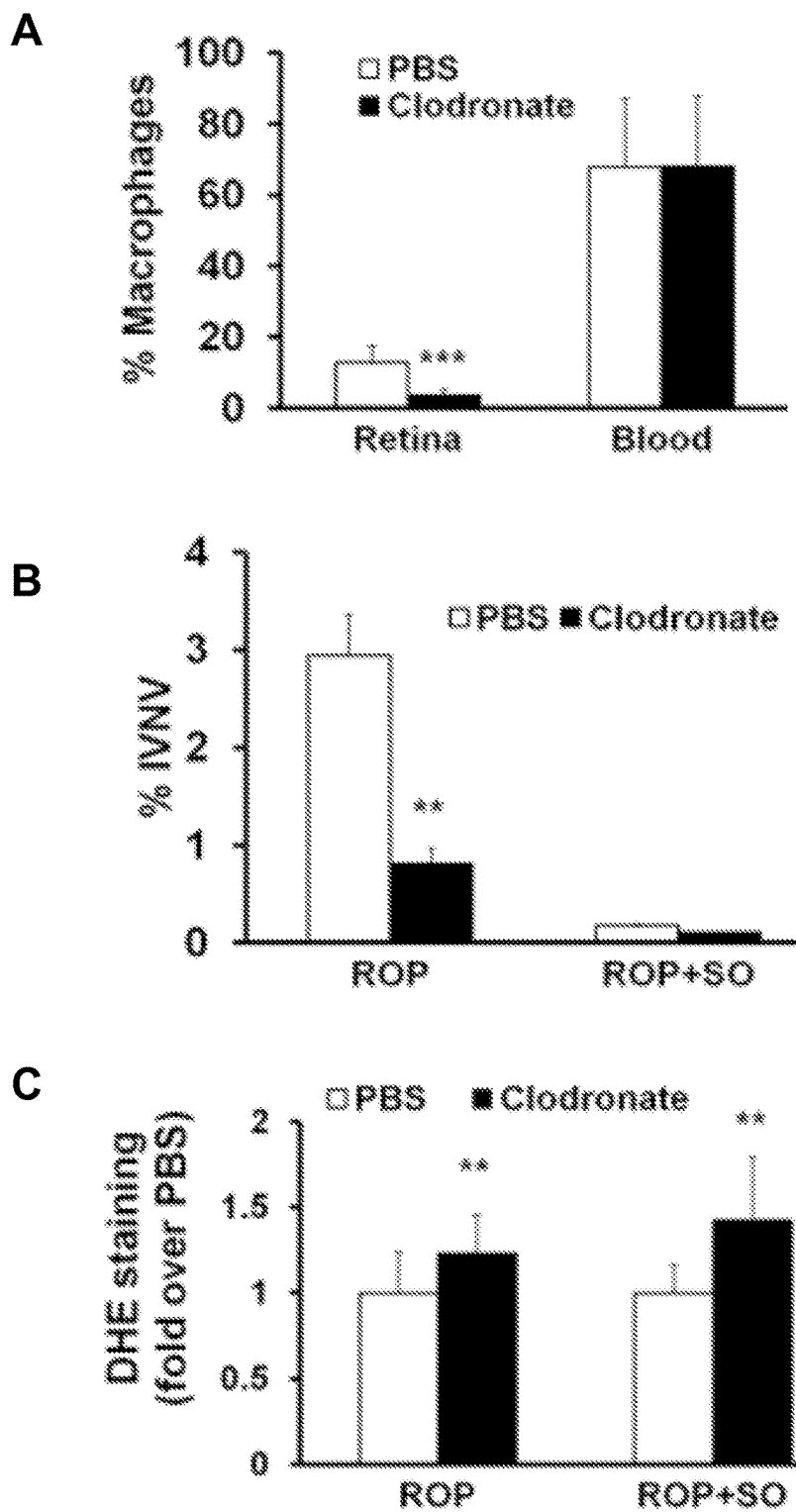
FIG. 7 shows intravitreal clodronate (1 μL) reduced A) macrophages B) IVNV in ROP model and C) increased dihydroethidium (DHE) in ROP/ROP+SO models (p<0.001, *p<0.001 vs. PBS).

Rationale:

Overexpressed MC-VEGF activates EC-VEGFR2 and causes IVNV, showing that MCs express VEGF that triggers EC signaling to cause IVNV. To protect MCs, signaling effectors on ECs that are activated by MC-produced VEGF can be targeted. Interactions between EC-VEGFR2 and EPOR [FIG. 13] or EC-VEGFR2 and NOX4 [FIGS. 16-17] overactivate EC-STAT3. It is also possible that EPOR knockdown can lead to greater EC-activated STAT3 through other signaling mechanisms. Therefore, this study examines whether the knockdown of STAT3 can inhibit IVNV. Activated STAT3 mediates Phase II IVNV and localizes to ECs in the ROP model (FIGS. 6A and 6B). Systemic STAT3 inhibitors are effective to treat cancerous tumors, autoimmune diseases, uveitis and IVNV (FIG. 6C), but total knockout of STAT3 is lethal in mice, and innate STAT3 is needed to clear methicillin resistant *S. aureus* pneumonia that affects 28% of preterm infants with *S. aureus* bacteremia. Thus, broad inhibition of STAT3 is not safe in preterm infants. Photoreceptor STAT3 provides protection from light-induced toxicity, so intravitreal delivery of a STAT3 inhibitor can be harmful. Inhibition of VEGF-induced STAT3 in MCs increased EPO, which is angiogenic. Thus, broad STAT3 inhibition can counteract EC-STAT3 inhibition and partly explain why systemic JAK2/STAT3 inhibitor, AG490, inhibited Phase II IVNV in the ROP+SO, but not ROP, model.

Objective 3.1:

To determine if activated STAT3 in ECs mediates IVNV in the rat ROP model.

Figures 14A, 14B, 14C, 14D:
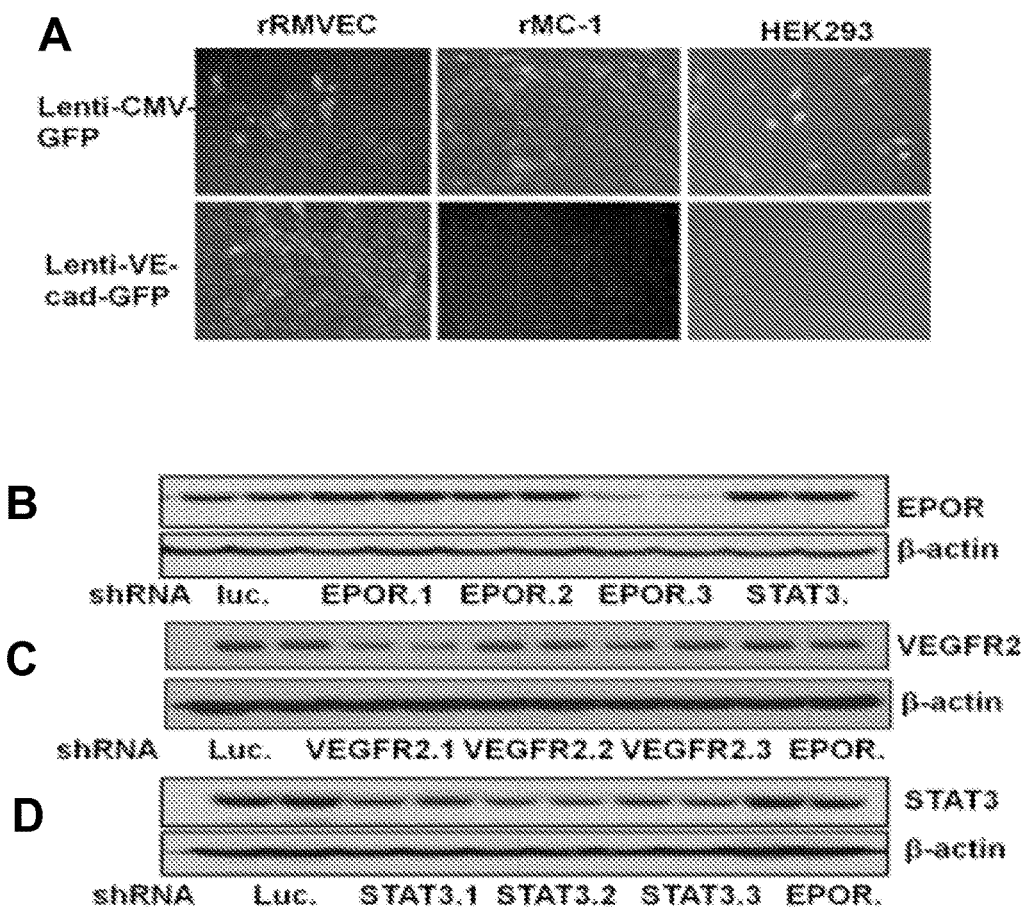
FIG. 14 shows that A) Lentivirus with CMV promoter (Lenti-CMV-GFP) tranduces rat retinal micro-vascular ECs (rMVECs), rat MC-1s, 293T, but lentivirus with ve-cadherin promoter (Lenti-VE-cad-GFP) only transduces rMVECs (106 viral particles/well) with 90+% efficiency. Western blots of B) EPOR, C) VEGFR2, D) STAT3 in 293T cotranfected with Lenti-VE-cad-GFP-driven shRNA and plasmid DNA expressing coding sequence of gene of interest.
Figure 15A:
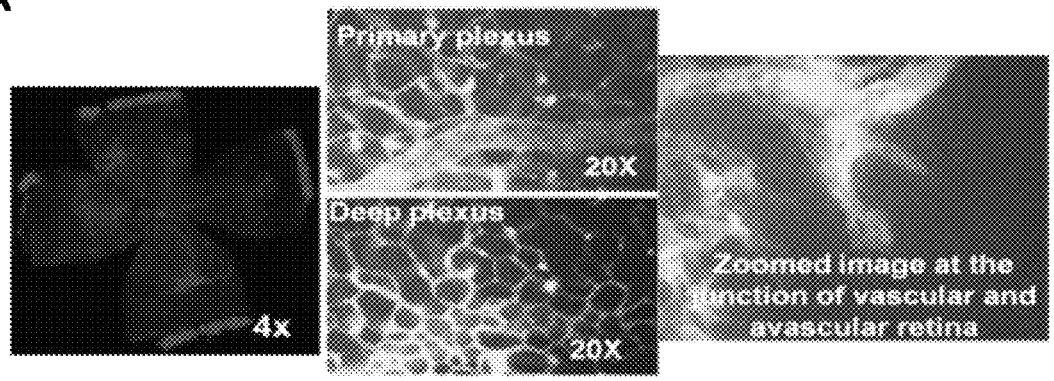
FIG. 15 shows p18 ROP injected at p10 with Lenti-VE-cad-GFP driving luc.shRNA or STAT3.shRNA (10$^6$ viral particles/inj) shows A) GFP colocalized with lectin in primary and deep plexi in retinal flatmount, and greater colocalization at the junction of vascular and avascular retina where IVNV occurs, B) Densitometry of IHC pSTAT3 with lectin reduced by STAT3.shRNA (**p<0.01 vs. luc.shRNA, ANOVA).
Figure 15B:
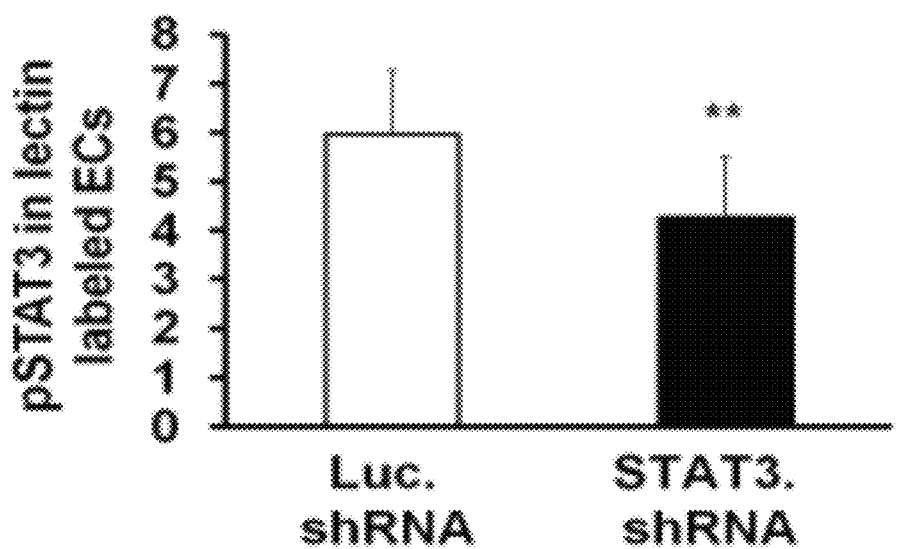

Rationale:

Using methods as in Example 5, 3 STAT3.shRNAs for knockdown in 293 Ts (FIG. 14D) were developed and tested. A lentivector-ve-cadherin STAT3.shRNA with the best knockdown (STAT3.shRNA2) was developed: (sequence: TGCTGTTGACAGTGAGCGAATCGTGGATCTGTTCA-GAAACTAGTGAAGCC ACAGATGTAGTTTCT-GAACAGATCCACGATCTGCCTACTGCCTCGGA) and showed specificity for rat MVECs and in the ROP model (FIGS. 14A and 15A). STAT3-lectin colabeling was reduced in sections from the ROP model (FIG. 15B). As in Examples 5 and 6, the viral dose, times of delivery and assays can be optimized to assure adequate transduction.

Example 8

Effects of STAT3 Inhibition on IVNV, PRVD and Retinal Apoptosis

Both eyes of each pup can receive the same lentivectors (1 uL subretinal STAT3.shRNA2 or luc.shRNA) at p10. Two doses (106 viral particles/inj or 2×106/inj) can be analyzed at p18 and 25 (similar to methods in Example 7).

Measured Outcomes:

AVA, IVNV of lectin-stained flat mounts in one eye. In fellow eyes: real-time PCR-STAT3; western blot-pSTAT3/STAT3, pEPOR, pAkt, pERK, c-caspase-3; IHC-pSTAT3, pEPOR, pVEGFR2, c-caspase-3 colabeled for ECs (CD31, lectin); TUNEL+ cells.

Figure 17A:
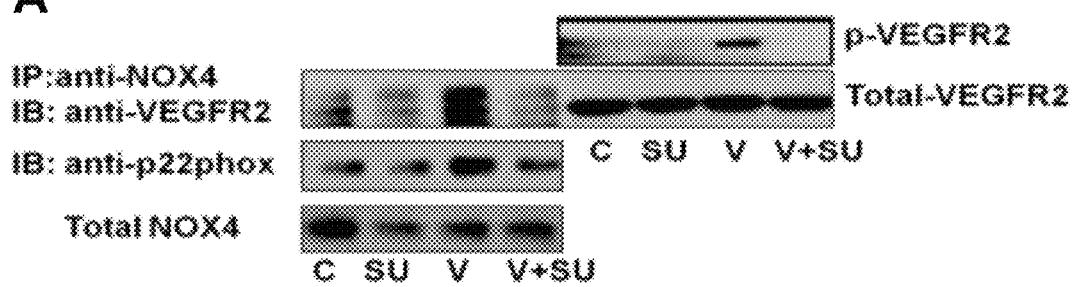
FIG. 17 shows that in hRMVECs, A) VEGF induced pVEGFR2 1) activates NOX4 (p22phox/NOX4 co-IP) and 2) interacts with NOX4 (co-IP NOX4/VEGFR2; C, control; SU, SU5416; V, VEGF; V+SU, VEGF+SU5416) to B) trigger pSTAT3. VEGF induces NOX4-dependent C) ROS generation and D) EC growth (***p<0.001 vs. PBS of Con.siRNA; †††p<0.001 vs. VEGF of Con.siRNA); E) pSTAT3 inhibition by AG490 increases TUNEL+ cells (*p<0.05 vs. DMSO). ANOVA, Newman Keuls.
Figure 17B:
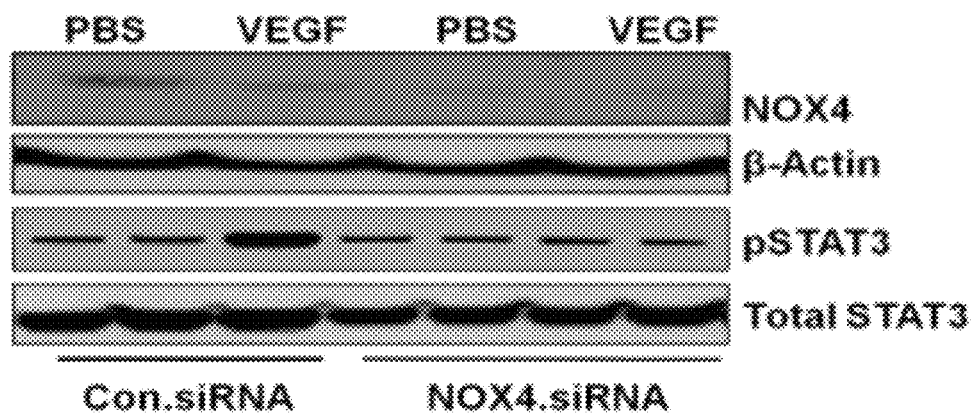
Figure 17C:
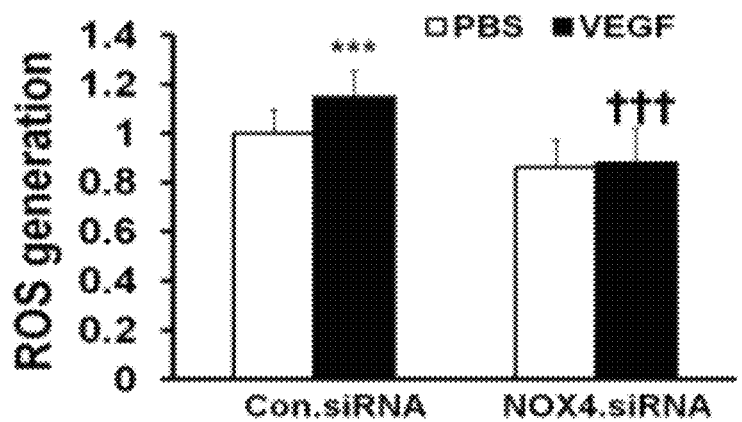
Figure 17D:
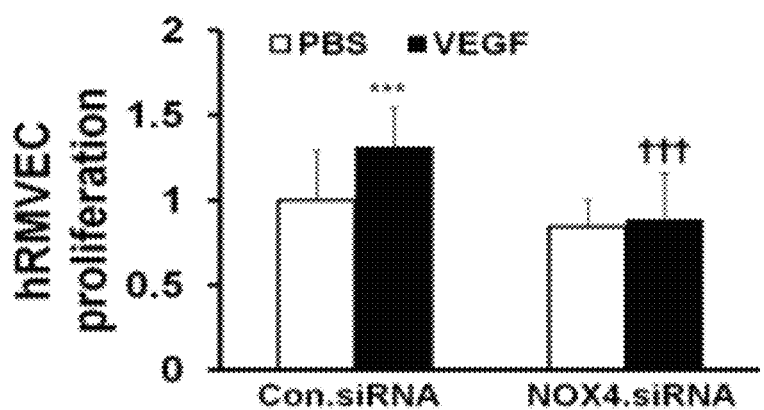
Figure 17E:
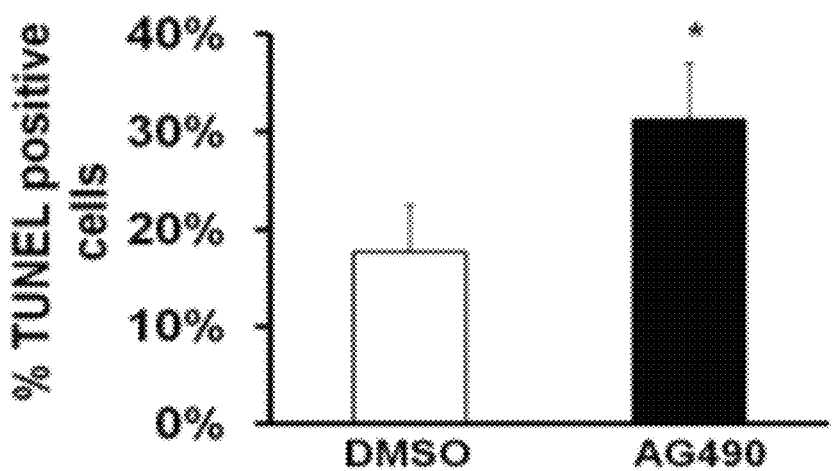
Figure 18A:
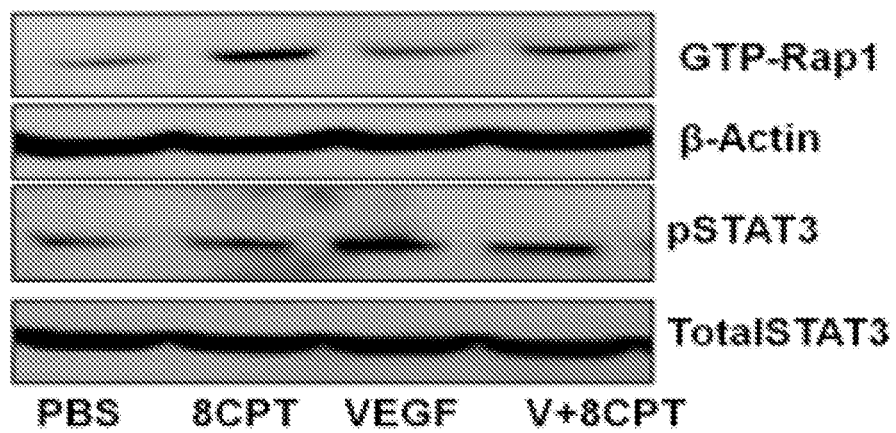
FIG. 18 shows In hRMVECs, A) Activation of Rap1 with 8CPT inhibits VEGF (V)-induced STAT3 activation, B) basal and VEGF-induced ROS generation mediated by NOX4 (*p<0.001, p<0.01 vs. PBS; †††p<0.001 vs. 8CPT; ##p<0.01 vs. VEGF, all of con.siRNA), STAT3 knockdown blocks C) VEGF induced pSTAT3, not pVEGFR2, and D) VEGF-induced hRMVEC proliferation (**p<0.01 vs. PBS of Con.siRNA; †††p<0.001 vs. VEGF of Con.siRNA). ANOVA, post-hoc Neuman Keuls.
Figure 18B:
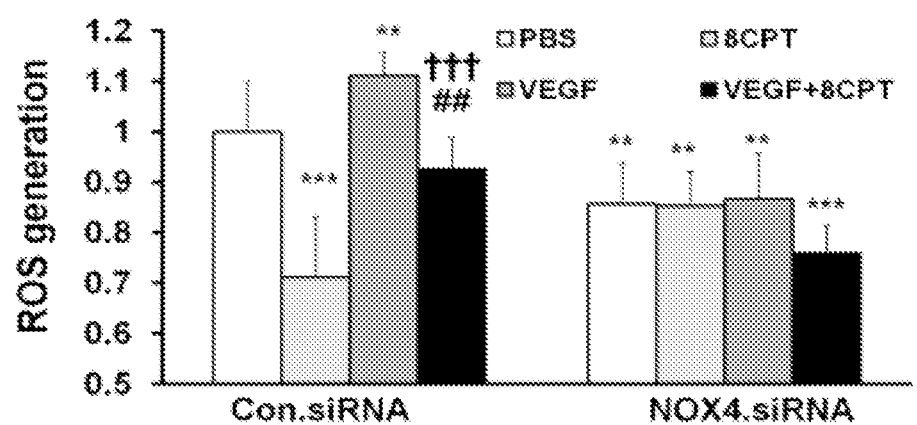
Figure 18C:
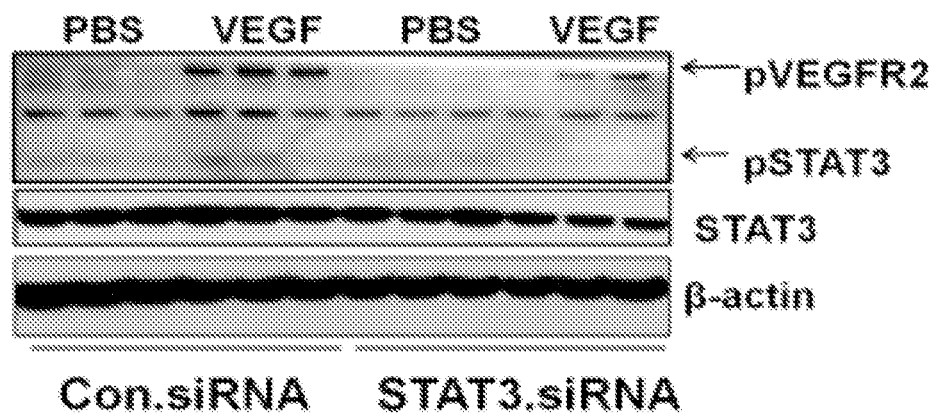
Figure 18D:
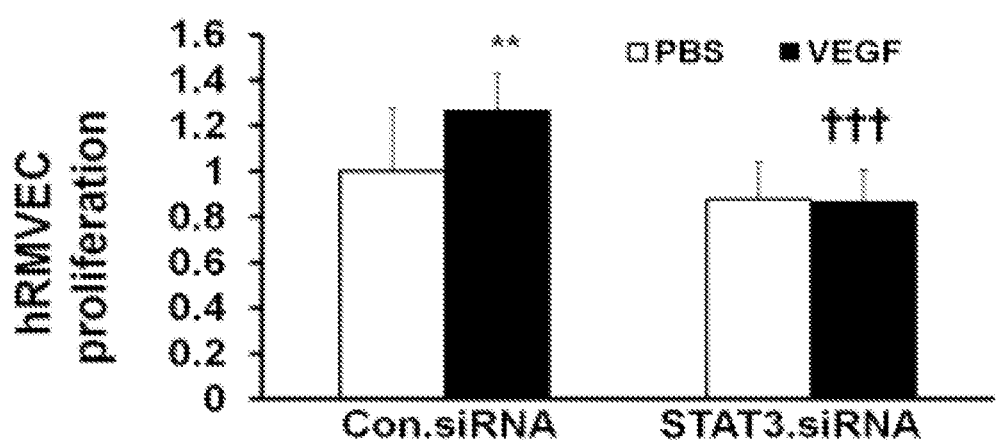
Figure 19A:
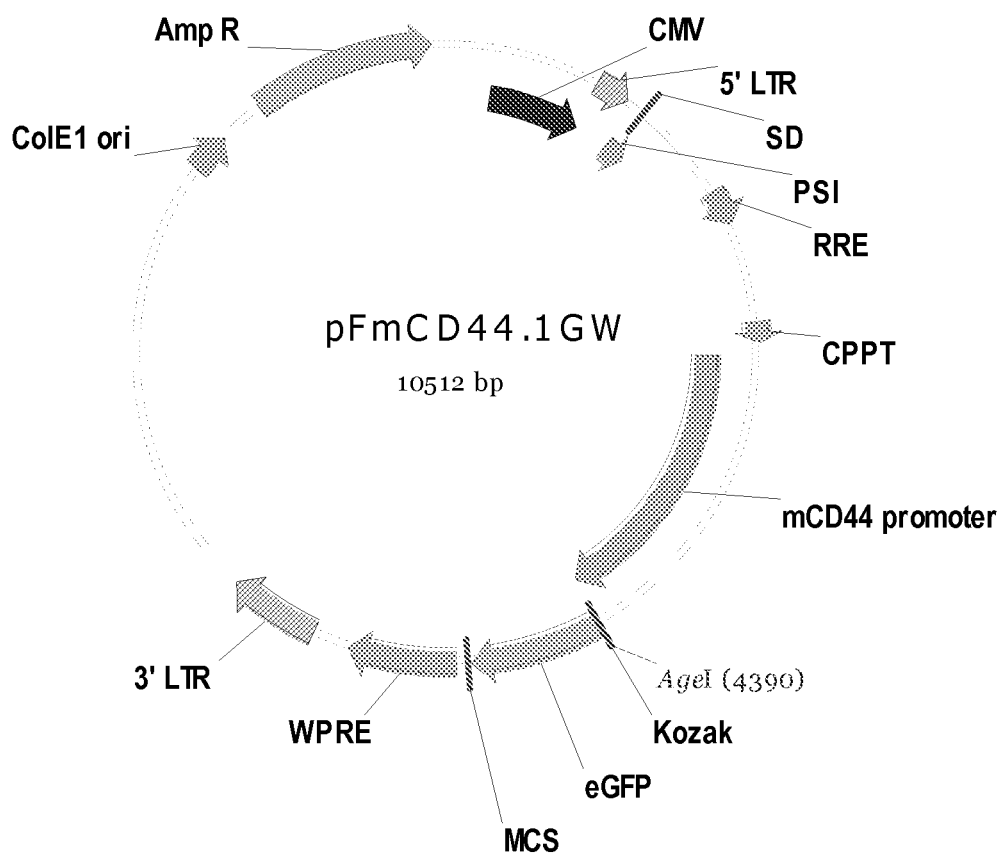
FIG. 19 shows the A) pFmCD44.1GW lentivector (no shRNAs); and B) VEGF overexpressed with CD44 pro.
Figure 19B:
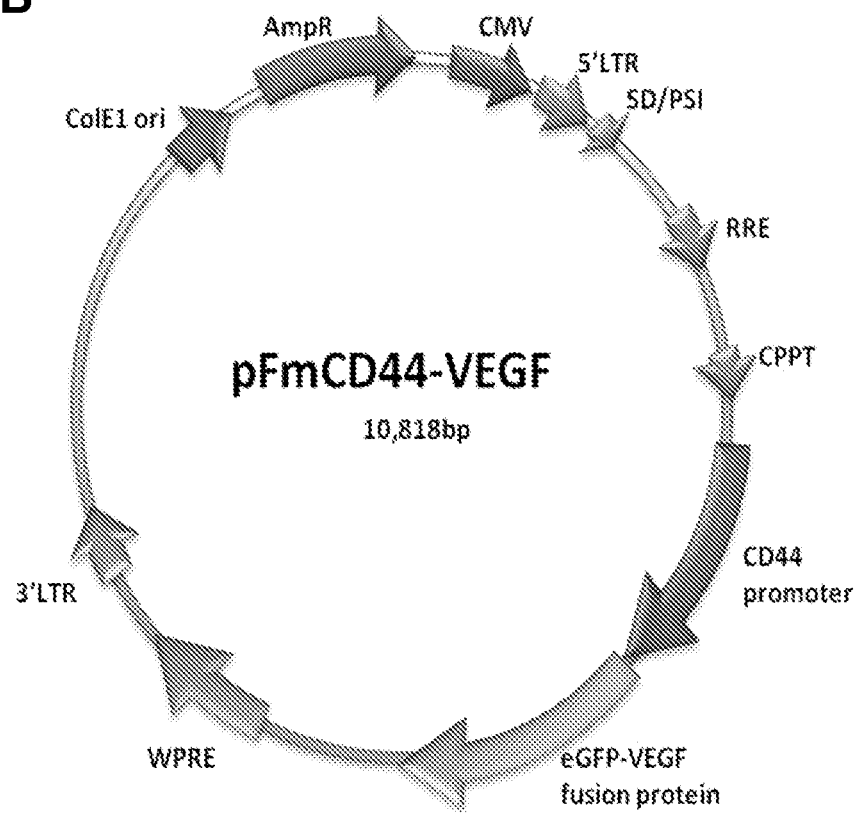
Figure 20A:
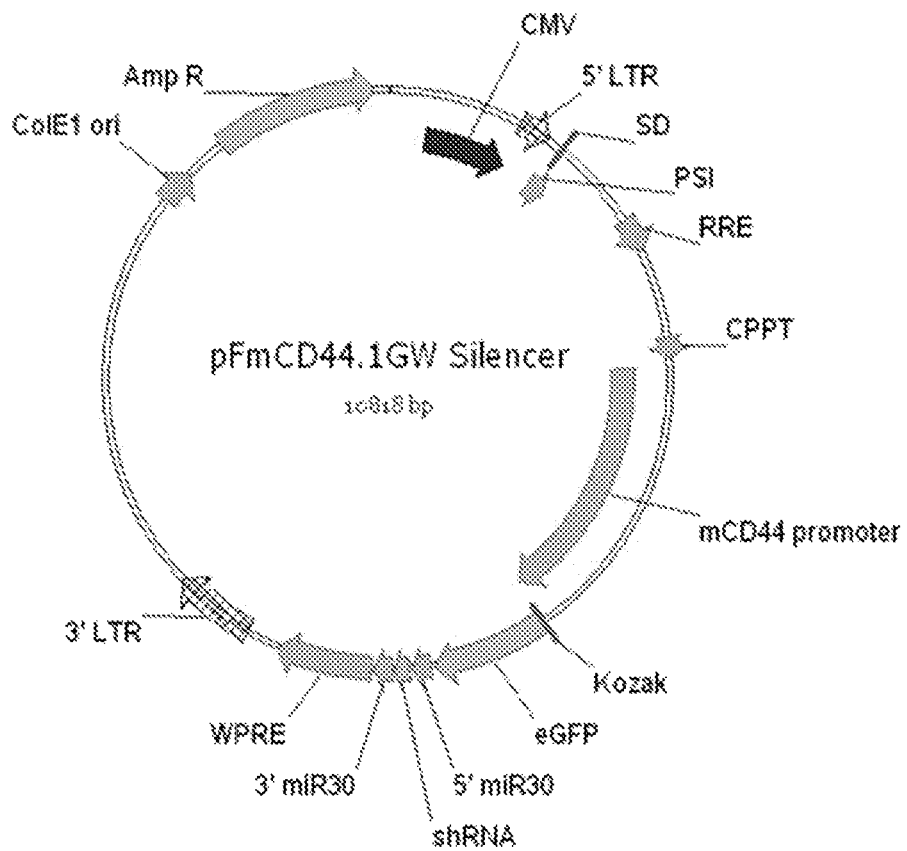
FIGS. 20A and 20B show the A) vector from FIG. 19A with the cloned in shRNA embedded within a miR30 construct and B) with the promoter II replaced with ve-cadherin.
Figure 20B:
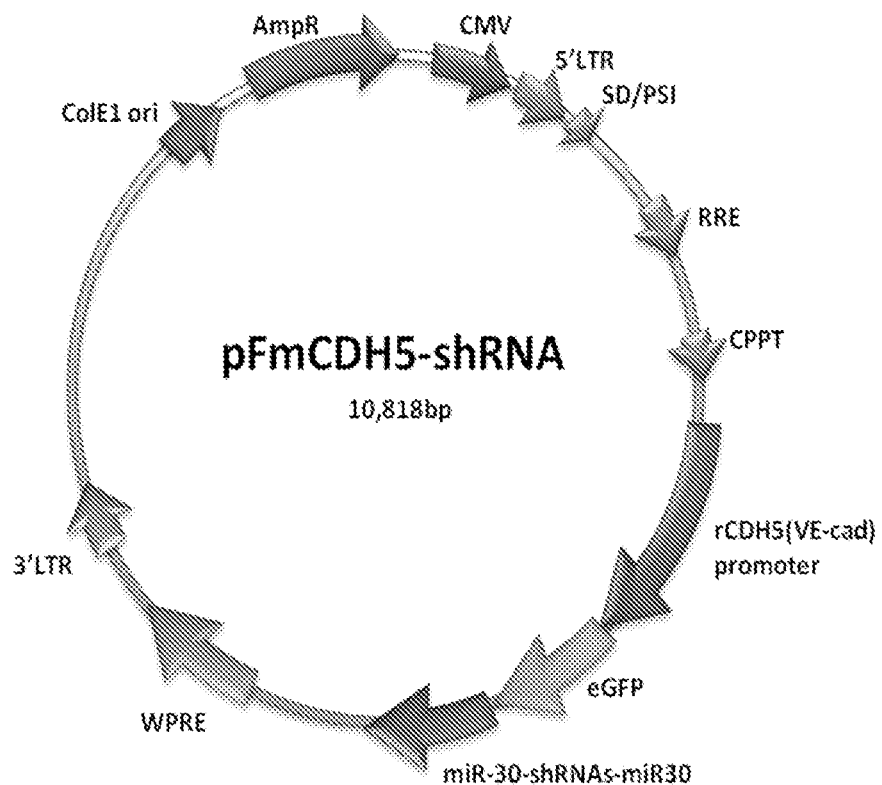
Figure 21:
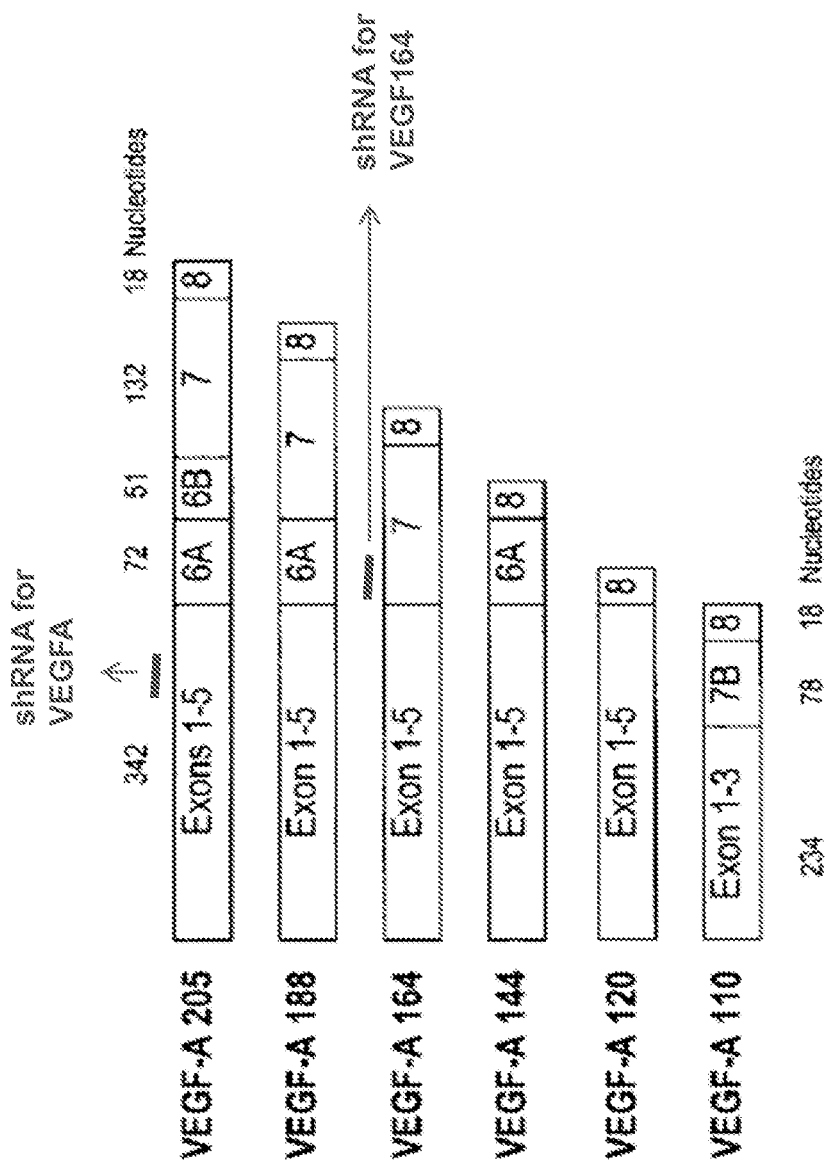
FIG. 21 shows the splice variants of the human VEGF gene and the targeting sites of shRNAs to VEGFA and VEGF164.
Figures 22A, 22B, 22C:
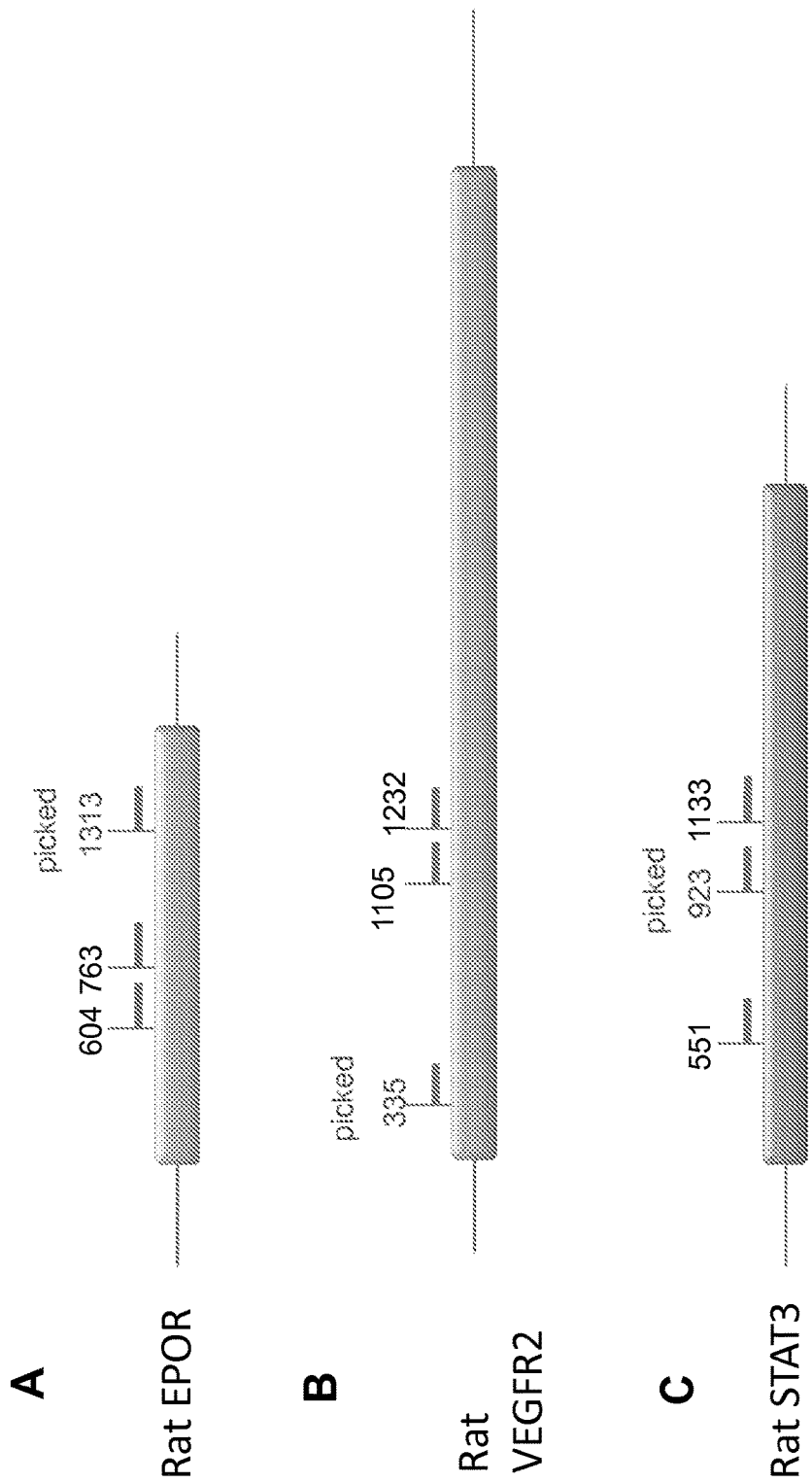
FIG. 22 shows the targeting sites of shRNAs designed and picked for rat EPOR (A), VEGFR2 (B), and STAT3 (C).

Results:

In areas of STAT3 knockdown, EC pSTAT3/STAT3 and IVNV can be reduced at p18 and p25, and AVA cannot be increased. In GFP(−) areas, there is no reduced IVNV or pSTAT3/STAT3. If STAT3 knockdown does not reduce IVNV, measure pVEGFR2 or pEPOR by IHC and western blot for activation of potential compensatory angiogenic pathways (eg, pVEGFR2, pEPOR; PI3-kinase/Akt, ERK, or other effectors). Increased apoptosis (TUNEL+ cells or c-caspase-3) in neural retina is not anticipated, but expected in IVNV as STAT3 inhibition can cause EC apoptosis (FIG. 17E).

pSTAT3 in other cells can be considered and colabeled for markers, e.g., GS or CRALBP for MCs, Thy-1 or pan Brn3 for GCs, CD68, F4/80 for macrophages, Iba1 for microglia, or RPE65 for RPE. Other STATs (STAT1, 5) are not found but can be considered. Besides VEGFA and VEGFR2, other ligands and receptors, like VEGFC/VEGFR3 that affects tip cells can be considered. STAT3 knockdown in ECs can reduce PRVD. If this occurs, test if intraperitoneal EPO (vs. PBS) can facilitate PRVD and not IVNV in pups with STAT3.shRNA compared to control. There was no difficulty visualizing transduced retina, but an anti-GFP antibody can be used, if needed, to visualize GFP+ areas of the retina. If STAT3 knockdown is insufficient, clone into a lentivector shRNAs to EPOR and STAT3 (or another molecule) each driven by ve-cadherin.

Objective 3.2:

To understand the effects of STAT3 activation on gene regulation in ECs

Example 9

Downstream Regulation from STAT3

Figures 16A, 16B, 16C:
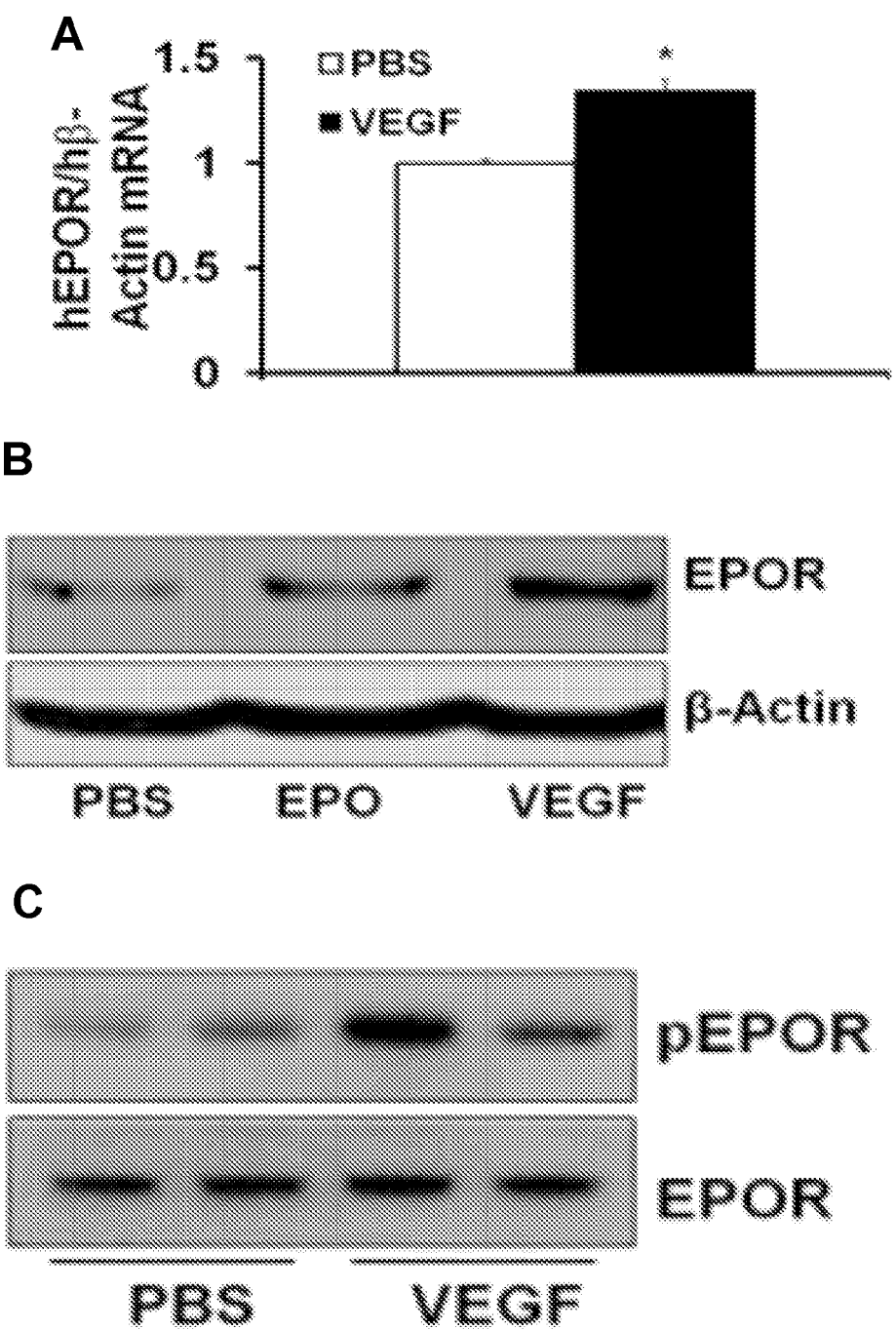
FIG. 16 shows that VEGF upregulates A) mRNA, B) protein (12 hr VEGF incubation), and C) activates EPOR (30 min VEGF incubation) (*p<0.05 vs. PBS).

Rationale:

VEGF induced an interaction between activated NOX4 and pVEGFR2 that augments angiogenesis through active STAT3 [FIGS. 16-17]. pSTAT3 dimers move from cytoplasm to nucleus and regulate gene transcription. In ECs, STAT3 inhibition induced apoptosis (FIG. 17E). In ECs, VEGF activated STAT3 [FIGS. 16-17] and upregulates and activates EPOR (FIG. 16). This can lead to a positive loop further exacerbating IVNV. To study STAT3 regulation of angiogenesis, gene expression in hRMVECs transfected with STAT3 siRNA or control and stimulated with VEGF or control can be measured.

Measured Outcomes:

Real time PCR of EPOR, VEGFR2, Bcl-2, Bcl-XL, survivin, Cyclin Dl.

Results:

STAT3.siRNA can reduce VEGF-induced EPOR expression and decrease anti-apoptosis gene, bcl-2, compared to control and VEGFR2 expression can not be affected by STAT3 knockdown. STAT3 knockdown can inhibit survivin and/or cyclin Dl. Protein of affected genes can be detected by labeling retinal sections with IHC and measure mRNA expression with real-time PCR in the ROP model injected with STAT3.shRNA or control.

Other signaling pathways, which can be regulated by STAT3 can be considered (eg, STAT3 can affect Notch regulation, which is important in cancer stem cells and in EC tip/stalk proliferation in PRVD and IVNV). Molecular mechanisms can be examined by ChIP and promoter activity assays and recruitment of co-regulators that are involved in gene transcriptional regulation by STAT3, such as CBP/p300 and NCoA/SRC1a, or corepressors, like Tip60 and SMRT (NCOR2 gene) can be considered.

Also, SOCS3, which inhibits pathologic angiogenesis in the mouse OIR model by negatively regulating JAK/STAT signaling can be considered. MicroRNAs, eg miRNA-21, can be regulated by STAT3 to affect cell invasion in cancer and can affect EC migration. Other microRNAs, eg miR-126, -92a or -329 inhibit angiogenesis by regulating VEGFR2 or coreceptor, CD146. If there are unexpected effects on PRVD in Objective 3.1, miRNAs, like -126, -210, or -27b, important in physiologic angiogenesis can be considered.

Objective 3.3:

To study a potential method to regulate NOX4 induced STAT3 and IVNV

Example 10

Regulation of NOX4 Induced IVNV by Activating Rap1 GTP

Rationale:

For activation of NOX4, the most prominent isoform in retinal ECs, aggregation with p22phox is important. The data show that activated NOX4 regulates VEGFR2-induced STAT3 activation. NOX4 activation can be regulated by a GTPase of the Ras family, Rap1 [FIG. 18]. Active Rap1 can also bind to p22phox to inhibit other NOX isoform (NOX1-4)/activated NADPH oxidases. Therefore, activating Rap1 can be more effective in inhibiting NADPH oxidase-mediated angiogenesis than available NADPH oxidase inhibitors, which cannot affect all NOX isoforms. This example examines the potential translational impact to determine if activation of Rap1 with chemical, 8CPT 2′OMe-cAMP (8CPT, Biolog), will regulate VEGF-induced NOX4 activation and reduce Phase II IVNV. The ROP model can be used. Intravitreal 8CPT (2.05 µM, 20.5 µM) or PBS can be given at p12 during the 50% 02 cycle; pups can return to the model until p18.

8CPT can also be used to inhibit TNF-α induced neovascularization. For example, 8CPT can also be used to inhibit TNF-α induced neovascularization in age-related macular degeneration. Pathologic angiogenesis can be reduced by inhibiting NADPH oxidase in age-related macular degeneration.

Measured Outcomes:

IVNV, AVA in retinal flat mounts; ROS (DHE, T15, p47phox/p22phox); NOX4 activation (NOX4, NOX4/p22phox); pSTAT3; Rap1GTP pull down assay (active Rap1); IHC-NOX4 colabeled with lectin.

Results:

Rap1 activation can increase Rap1GTP in pulldown assays, reduce T15 and pSTAT3 compared to control and reduce IVNV in flat mounts.

If there is no difference from activation of Rap1, other time points or doses can be tested. The mouse OIR can be tested using WT and p47phox−/− mice (enriched for NOX4). If active Rap1 reduces IVNV, other means to activate Rap 1 can be studied, eg., forskolin eye drops proposed for glaucoma previously; specific formulations to target cells with unique signatures or through ligand-modified quantum dots and nanoparticles. Potential mechanisms including through β-catenin can also be examined. Sources of ROS other than NADPH oxidase can be involved in ROP and OIR, like nitric oxide synthetases, mitochondria, xanthine oxidase; specific inhibitors (eg, rotenone to inhibit mitochondria) can be used. Compensation from other NOX isoforms can be determined.

Animal Numbers Anticipated:

Also see Sample Size Power and Statistics. For Example 8, (n=18 for primary question of IVNV and AVA, n=6-8 for secondary questions); 2 time points×2 shRNAs×2 doses=8 groups, and for 18 data points/group, 12 litters. For additional controls, IHC, RNA, protein not provided by fellow eyes, 0.34 litters×8 data points×5 assays=~14 litters or 26 litters for Example 8 Example 10, 1 time point×2 conditions×2 doses=4 groups, and for 18 data points/group, 6 litters. For additional controls, IHC, RNA, protein not provided by fellow eyes, 0.34 litters×8 data points×5 assays=~14 litters or 20 litters for Example 10.

Example 11

Targeting Müller Cell-Derived $VEGF_{164}$ to Reduce Intravitreal Neovascularization in the Rat Model of Retinopathy of Prematurity Objective:

To determine whether knockdown of Müller cell-derived VEGFA-splice variant, $VEGF_{164}$, which is upregulated in the rat retinopathy of prematurity (ROP) model, safely inhibits intravitreal neovascularization (IVNV).

Methods:

Short hairpin RNAs for $VEGF_{164}$ ($VEGF_{164}$.shRNAs) or luciferase.shRNA control were cloned into lentivectors with CD44 promoters that specifically target Müller cells. Knockdown efficiency, off-target effects, and specificity were tested in HEK reporter cell lines that expressed green fluorescent protein (GFP)-tagged $VEGF_{164}$ or $VEGF_{120}$ with flow cytometry or in rat Müller cells (rMC-1) by real-time PCR. In the rat oxygen-induced retinopathy (OIR) ROP model, pups received 1 μL subretinal lentivector-driven luciferase.shRNA, VEGFA.shRNA, or $VEGF_{164}$.shRNA at postnatal day 8 (P8). Analyses at P18 and P25 included: IVNV and avascular retina (AVA); retinal and serum VEGF (ELISA); density of phosphorylated VEGFR2 (p-VEGFR2) in lectin-labeled retinal endothelial cells (ECs; immunohistochemistry); TUNEL staining and thickness of inner nuclear (INL) and outer nuclear layers (ONL) in retinal cryosections; and pup weight gain.

Results:

In HEK reporter and in rMC-1 cells and in comparison to luciferase.shRNA, VEGFA.shRNA reduced both $VEGF_{120}$ and $VEGF_{164}$, but $VEGF_{164}$.shRNA only reduced $VEGF_{164}$. Compared with luciferase.shRNA, VEGFA.shRNA and VEGF164.shRNA reduced retinal VEGF and IVNV without affecting AVA at P18 and P25. At P25, VEGF164.shRNA more effectively maintained IVNV inhibition than VEGFA.shRNA. VEGFA.shRNA and VEGF164.shRNA reduced pVEGFR2 in retinal ECs at P18, but VEGFA.shRNA increased it at P25. VEGFA.shRNA increased TUNEL+ cells at P18 and decreased ONL thickness at P18 and P25. VEGFA.shRNA and VEGF164.shRNA did not affect pup weight gain and serum VEGF.

Conclusions:

shRNA to Müller cell $VEGF_{164}$ maintained long-term inhibition of IVNV and limited cell death compared with shRNA to VEGFA.

VEGF is important in several angiogenic eye diseases, including AMD, diabetic retinopathy, retinal vein occlusion, and retinopathy of prematurity (ROP). The data herein shows that overactivation of VEGF receptor 2 (VEGFR2) led to disordered developmental angiogenesis in a similar pattern as seen in intravitreal neovascularization (IVNV) in severe ROP. Broad inhibition of VEGF with an intravitreal neutralizing antibody reduced IVNV in a rat model of ROP, but also reduced pup growth and serum VEGF levels. To target pathologic effects of VEGFA without affecting physiologic ones, VEGFA splice variant mRNAs were localized to cellular retinaldehyde-binding protein (CRALBP)-labeled Müller cells, RPE, and cells in the ganglion cell layer in the retina of a rat model of ROP at a time point when total retinal VEGFA expression was significantly increased compared with room air-raised pups.

Lentivectors that used CD44 promoters and efficiently drove VEGFA shRNA specifically in Müller cells when delivered into the subretinal space were created. In the short-term, IVNV was inhibited without affecting serum VEGFA, pup growth, or retinal apoptosis. However, Müller cells also depend on VEGFA for survival and this strategy can have adverse effects. Therefore, in this study, lentivectors with CD44 promoters that specifically targeted Müller cell-$VEGF_{164}$ were created, which leads to pathologic angiogenesis and which was found to be the most prevalent splice variant in the ROP model. The study tested whether the lentivector shRNA to rat $VEGF_{164}$ in Müller cells safely and effectively reduces IVNV compared with knockdown of VEGFA or control and also the efficacy and retinal cell survival at a later time point in the ROP model. It was found that targeted lentivector delivery of shRNAs to VEGFA or $VEGF_{164}$ reduced IVNV, but that shRNA to $VEGF_{164}$ maintained long-term inhibition of IVNV and limited cell death compared with shRNA to VEGFA.

Methods:

Rat Model of ROP (Rat 50/10 OIR Model)

In the well-described rat oxygen-induced retinopathy (OIR) model (rat model of ROP), Sprague-Dawley (Charles River Laboratories, Inc., Wilmington, Mass.) dams and pups were placed into a dual channel/dual gas controller (OxyCycler; BioSpherix, Ltd., Lacona, N.Y.) within 6 hours of birth, where oxygen is cycled between 50% and 10% every 24 hours. At postnatal day (P)14, litters were placed into room air until P18 or P25. Litter size was maintained at 12 to 16 pups. Pup weight was obtained at P8, P18, and P25. Pups were euthanized by intraperitoneal injection (IP) of ketamine (60 mg/kg) and xylazine (18 mg/kg) followed by IP pentobarbital (80 mg/kg). For all pups, one eye was processed for flatmount analysis and the fellow eye for protein or immunohistochemistry (IHC). After oxygen fluctuations at P14, pups are returned to room air (21% oxygen), supplemental oxygen (28% oxygen) or other levels.

Construction of Lentivector-Driven shRNA shRNAs targeting rat VEGFA (NM_031836, VEGFA.shRNA); rat $VEGF_{164}$ (AF260425, VEGF164.shRNA); or nonmammalian gene luciferase (M15077, luciferase.shRNA) were developed. shRNAs were embedded within a microRNA (miR-30) context as an efficient method to knock down a gene. The shRNAmicroRNA30 was each cloned into a lentiviral transfer vector driven by a CD44 promoter specific to Müller cells (pFmCD44.1GW) and with multicistronic cotranscription of green fluorescent protein (GFP) or red fluorescent protein (RFP). The VEGFA.shRNAs were developed and tested for off-target effects and efficiency. Here, methods for lentivectors with VEGF164.shRNAs are described. Knockdown and off-target efficiency was tested in rMC-1 cells) and $VEGF_{120}$ and $VEGF_{164}$HEK reporter cell lines, with the goal to choose shRNAs with better knockdown efficiency in $VEGF_{164}$ but not $VEGF_{120}$.

Cell Culture and Assay for In Vitro-Knockdown Efficiency rMC-1 cells, $VEGF_{120}$, and $VEGF_{164}$HEK reporter cell lines were maintained in DMEM/high glucose (Gibco/Life Technologies, Grand Island, N.Y.) containing 10% fetal bovine serum (FBS) and 1% penicillin-streptomycin. Both $VEGF_{120}$ and $VEGF_{164}$ HEK reporter cell lines were transfected with plasmid DNA-pFmCD44.1GW containing VEGF164.shRNA-1 or VEGF164.shRNA-2 expressed with RFP or an empty vector without shRNA as control. Forty-eight hours after transfection, the knockdown efficiency of VEGF164.shRNAs was determined by flow cytometry of GFP fluorescence in RFP positive cells. Silencing was calculated as a percentage of GFP to control vector transfected-cells. The shRNA with better knockdown efficiency in $VEGF_{164}$ but not $VEGF_{120}$ was chosen for all following experiments and designated VEGF164.shRNA. rMC-1 cells in 6-well plates (Corning, Inc., Corning, N.Y.) with 80% confluence were infected with lentivirus ($5.0 \times 10^6$ viral particles/mL) containing VEGFA.shRNA, VEGF164.shRNA, luciferase.shRNA, or vehicle without viral infection. After 48 hours, cells were extracted and real-time PCR was performed. Each condition was performed in triplicate.

Subretinal Injection

At the beginning of P8 (50% oxygen cycle), pups were anesthetized by IP ketamine (20 mg/kg) and xylazine (2.5 mg/kg). Subretinal injections were performed by creating an initial opening beneath the limbus with a 30-gauge needle. One µL of $1 \times 10^9$ viral particles/mL (VP/mL) of VEGFA.shRNA, VEGF164.shRNA, or control luciferase.shRNA was delivered into the subretinal space using a 33-gauge needle attached to a syringe (Hamilton Company, Reno, N.Y.). In some pups, 1 µL of subretinal PBS was used as an additional control. The created retinal detachments resolved within 24 hours. The same virus and dose were used in each eye of the same pup. Attempts were made to represent all lentivector types in each litter and to inject the same number of pups with each lentivector preparation in each litter. Pups weighing less than 7 g were not used and all pups analyzed were within ±2 g of mean pup weight based on overall growth chart.

In Vivo Retinal Imaging

Pupil dilation was achieved with tropicamide (1% solution; Bausch & Lomb Pharmaceuticals, Inc., Rochester, N.Y.). Genteal gel (Novartis Pharmaceuticals Corp., East Hanover, N.J.) was the coupling agent for retinal imaging with a commercial applanation imaging system (Micron III; Phoenix Research Laboratories, Inc., Pleasanton, Calif.) and multiple camera recording software (StreamPix 5; Norpix, Inc., Montreal, Quebec, Canada). Both GFP and bright field were used for imaging.

The eyes can also be imaged using optical coherence tomography.

Retinal Flatmount Preparation, Imaging, and Analysis

After euthanasia, eyes were enucleated, pierced through the cornea with a 30-gauge needle, placed into freshly made 4% paraformaldehyde (PFA) containing 10 mM sodium orthovanadate for 2 hours on ice, and then transferred to PBS. Corneas, lenses, and vitreous were removed, and retinas were dissected from the RPE/choroid/sclera. Retinal flatmounts were labeled using 5 µg/mL AlexaFluor 568 conjugated isolectin GS-IB4 from *Griffonia simplicifolia* (Bandeiraea; Molecular Probes, Eugene, Oreg.) and imaged using an inverted fluorescence microscope ([Olympus IX81]; Olympus Corp., Tokyo, Japan). Whole retinal flatmount images were stitched using the scan-slide stitching function of imaging software (Metamorph version 7.0; Molecular Devices, Inc., Sunnyvale, Calif.). The avascular retina (AVA) and IVNV areas were analyzed by two masked reviewers and calculated as a percentage of total retinal area for each flatmount using Java-based imaging software (ImageJ version 1.46; National Institutes of Health, Bethesda, Md.).

Cryosection Preparation and Immunofluorescence Staining and Quantification

Whole eye globes were fixed in 4% PFA containing 10 mM sodium orthovanadate for 10 minutes. Corneas and lenses were removed, and posterior eyecups were fixed for another 15 minutes in 4% PFA, then incubated in 30% sucrose/PBS at 4° C. overnight, and mounted in optimal cutting temperature compound (Tissue-Tek; Electron Microscopy Sciences, Hatfield, Pa.). Cryosections (12 µm) were cut sequentially and stained for immunofluorescence analysis. Cryosections were incubated with rabbit anti-phosphorylated VEGFR2 (p-VEGFR2 at Y951; Santa Cruz Biotechnology, Santa Cruz, Calif.) overnight at 4° C. After washes, sections were incubated with AlexaFluor 405 conjugated goat anti-rabbit second antibody for p-VEGFR2 and lectin for 1 hour. Sections stained with only secondary antibody and DAPI were controls. TUNEL staining was performed per instructions in the cell death detection kit (In Situ Cell Death Detection Kit, TMR red; Roche Diagnostics, Indianapolis, Ind.). DNase-treated sections were used as positive controls. Images were captured with confocal microscopy (Olympus IX81; Olympus Corp.). To determine the effects of knockdown on retinal VEGFR2 activation in captured images, semiquantitative assessment of the density of p-VEGFR2 was performed in sections of retina extending from the ganglion cell layer to lectin stained choroidal vessels depicting the RPE/choroid layer using Java-based imaging software (NIH). For p-VEGFR2 in retinal vessels, the density of p-VEGFR2 colabeling with lectin-stained ECs of the primary vascular plexus at the junctions between avascular retina and vascular retina was measured with the threshold function of the Java-based imaging software (NIH). TUNEL-positive cells colabeled with tetramethylrhodamine red (TMR red) and diamino-2-phenylindole (DAPI) were counted in retinal sections imaged at ×4 magnification. Retinal thickness was measured from ganglion cell to ONL in DAPI-stained sections captured at ×40 magnification using Java-based imaging software (NIH). In total, six sections taken at 60-µm intervals from three eyes of three pups in three litters were used for immunohistochemical analyses.

Retinal Protein Preparation and VEGF ELISA

Retinas were homogenized in modified radio-immunoprecipitation assay buffer containing 2 mM orthovanadate and protease inhibitors (Roche Diagnostics). Protein concentration was determined by bicinchocinic acid (BCA) protein assay (Pierce Biotechnology, Inc., Rockford, Ill.). Total retinal and serum VEGF concentration was measured using a commercial ELISA kit (Quantikine Rat VEGFA RRVOO; R&D Systems, Minneapolis, Minn.) following manufacturer's instructions. Serum (50 µL) or 50 µg protein of retinal lysates was used for each sample, and samples were in duplicate.

Statistical Analysis

Significant differences between treatment groups were determined with ANOVA and Newman-Keuls multiple comparison test. For each test, a minimum value of $P<0.05$ was considered statistically significant. Except where indicated otherwise, at least eight flat mounts, six samples for Western blot, and four samples for ELISA were analyzed. All samples were taken from different pups from at least three different litters. Results are mean±SD.

Results:

Generation and Knockdown Efficiency of Lentivector-Driven $VEGF_{164}$-shRNA

Figure 23A:
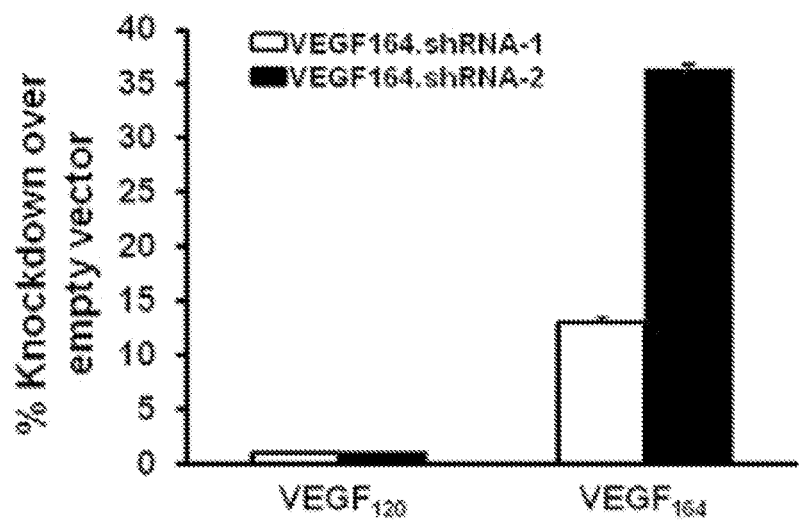
FIGS. 23A and B show the generation of lentivector-delivered shRNA for specific knockdown of VEGF164 in Müller cells. HEK reporter cell lines expressed GFP-tagged VEGF120 or VEGF164 were transfected with RFP-expressed lentivector VEGF164.shRNA plasmids or empty vector without shRNA. (A) Quantification of percent silencing of VEGF120 and VEGF164 by VEGF164 shRNAs from FACS analysis. (B) Real-time PCR of mRNA of VEGF120 and VEGF164 in rat Müller cells (rMC-1) infected without lentivirus (uninfected) or with lentivector driven shRNA to luciferase (luc.shRNA), VEGFA (VEGFA.shRNA) or VEGF164 (VEGF164.shRNA). *P<0.05 and **P<0.01 versus luc.shRNA).

Two different shRNAs were designed for the rat $VEGF_{164}$ coding sequence (GenBank: AF260425) and each was cloned into the lentivector pFmCD44.1 GW, which contains a CD44 promoter specific to Müller cells and drives a microRNA30 (miR-30)-based shRNA cassette and either RFP or GFP. To test knockdown efficiency of the designed shRNAs, lentivector plasmids containing either of the two shRNAs and an RFP tag or an empty vector were transfected into one of two HEK293 reporter cell lines that expressed either GFP-tagged rat $VEGF_{120}$ or $VEGF_{164}$. GFP fluorescence intensity in RFP-expressed cells containing the shRNAs or empty vector was read using flow cytometry. Neither VEGF164.shRNA-1 nor -2 had an effect on knockdown of $VEGF_{120}$ (FIG. 23A). Compared with cells transfected with empty vector, VEGF164.shRNA-2 caused 35% knockdown of $VEGF_{164}$, whereas VEGF164.shRNA-1 only caused 15% knockdown of $VEGF_{164}$. Therefore, VEGF164.shRNA-2 (designated hereafter as VEGF164.shRNA) was chosen for later experiments. The sequence of VEGF164.shRNA was: 5'-TGCTGTTGACAG TGAGCGCAGCCAGAAAAT-CACTGTGAGCTAGTGAAGCCACAGATGTAGCT-CACAGTGATT TTCTGGCTTTGCCTACTGCCTCGGA-3'. The data herein show how lentivectors targeting rat Müller cell VEGFA were designed and tested and a VEGFA.shRNA that caused 35% reduction in $VEGF_{120}$ and 50% of $VEGF_{164}$ in HEK reporter cell lines was chosen.

Figure 23B:
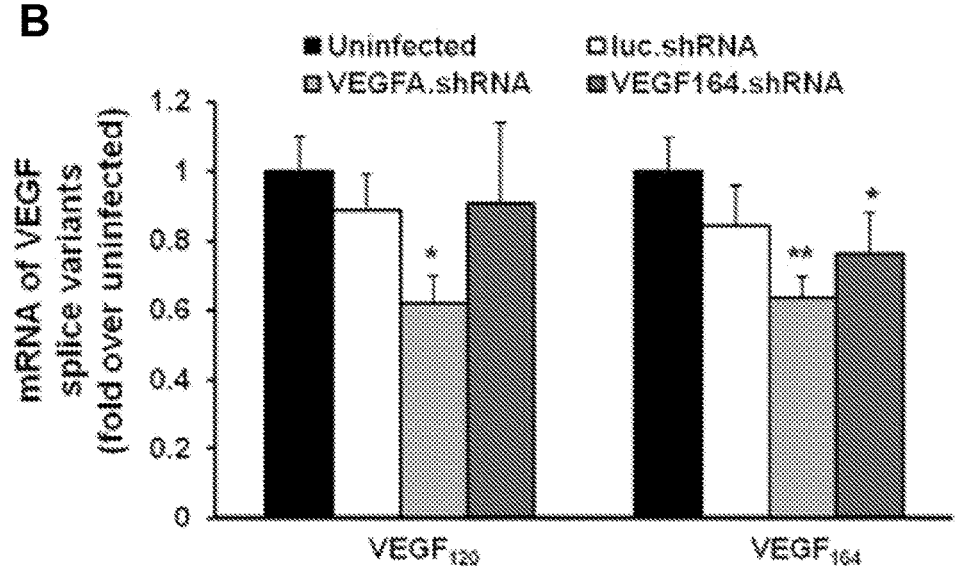

To test knockdown efficiency and specificity of lentivector-driven VEGF164.shRNA and VEGFA.shRNA in Müller cells, rMC-1s, a rat Müller cell line, was infected with lentivectors containing the CD44 promoter driving GFP and one of the three different shRNAs (luciferase.shRNA, VEGFA.shRNA, VEGF164.shRNA) or an uninfected control. After 48 hours, rMC-1s were analyzed with real-time PCR for $VEGF_{120}$ or $VEGF_{164}$ mRNAs and expressed as fold difference compared with the mRNA from the uninfected control. There was no difference in mRNA level of $VEGF_{120}$ and $VEGF_{164}$ splice variants between uninfected and luciferase.shRNA. Compared with luciferase.shRNA, VEGFA.shRNA reduced expression of both $VEGF_{120}$ and $VEGF_{164}$ (FIG. 23B), whereas only $VEGF_{164}$ mRNA was reduced in the VEGF164.shRNA group. These results indicate that VEGF164.shRNA specifically knocked down $VEGF_{164}$ mRNA and not $VEGF_{120}$.

Knockdown of $VEGF_{164}$ Reduced IVNV at P18 and P25

Figure 24A:
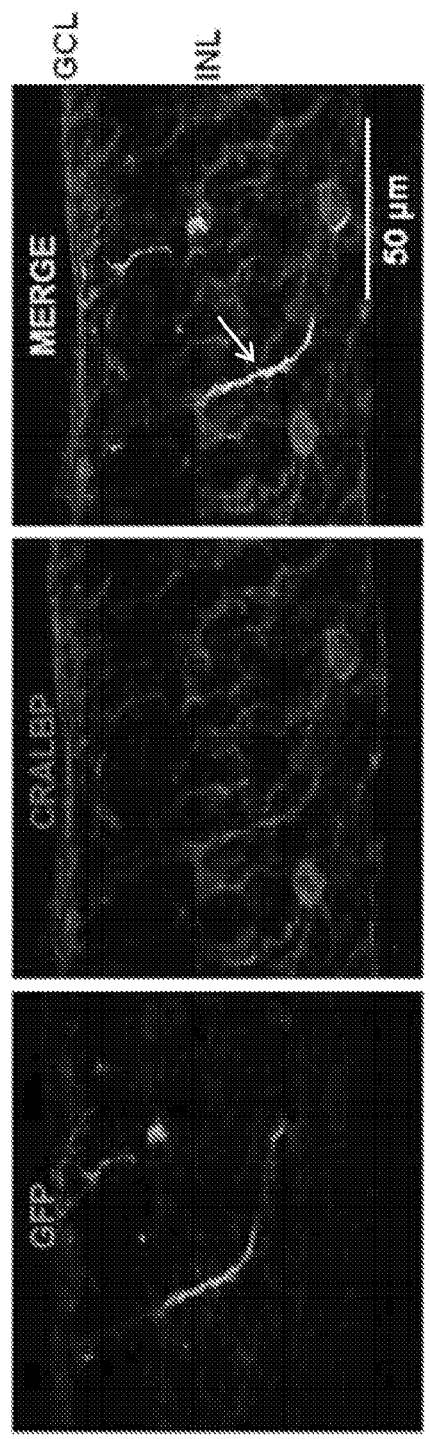
FIGS. 24A and 24B shows in vivo analysis of lentivector-delivered shRNA transduction in retina of pups raised in the rat ROP model at P18 and P25 following subretinal injection at P8. (A) GFP expression is localized with CRALBP-labeled Müller cells in retinal cryosections at P25 (see arrows). (B) ELISA of retinal VEGFA protein at P18 and P25. *P<0.05. **P<0.001 versus luc.shRNA at P18. †P<0.05. ††P<0.01 versus luc.shRNA at P25.
Figure 24B:
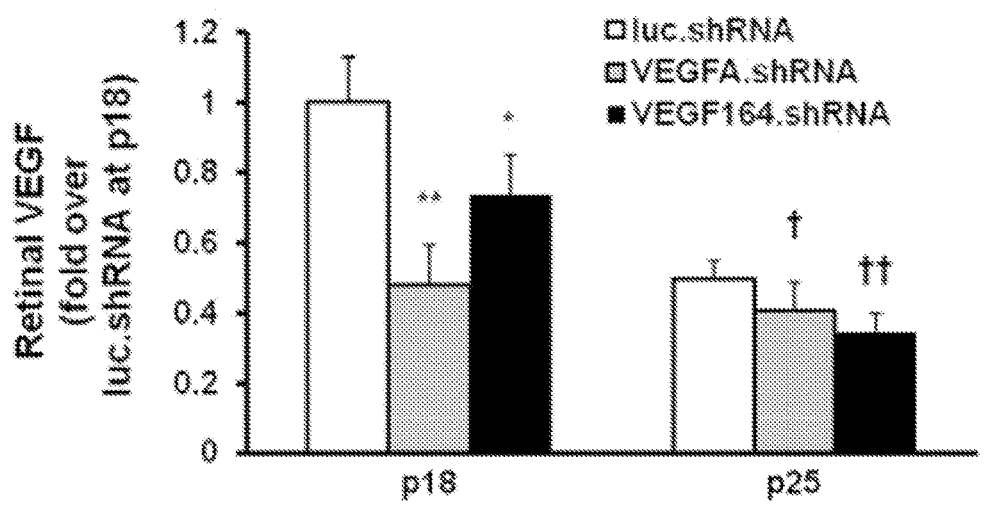

Images were taken before euthanasia using an applanation imaging system (Phoenix Research Laboratories, Inc.) to assess transduction of each of the three lentivectors that had been delivered as subretinal injections to P8 pup eyes. At P25, GFP fluorescence demonstrated that approximately 33% of the retina was transduced by each subretinal injection of lentivector shRNA and not with the PBS injection. Müller cell specificity was determined by colabeling of GFP and CRALBP in retinal cryosections (FIG. 24A). To determine knockdown efficiency of VEGF in vivo, total retina lysates were analyzed for VEGF by ELISA. Compared with respective luciferase.shRNA controls at P18 and P25, retinal VEGF was significantly decreased by treatment with lentivector VEGFA. shRNA or VEGF164.shRNA at both time points (FIG. 24B).

Figure 25A:
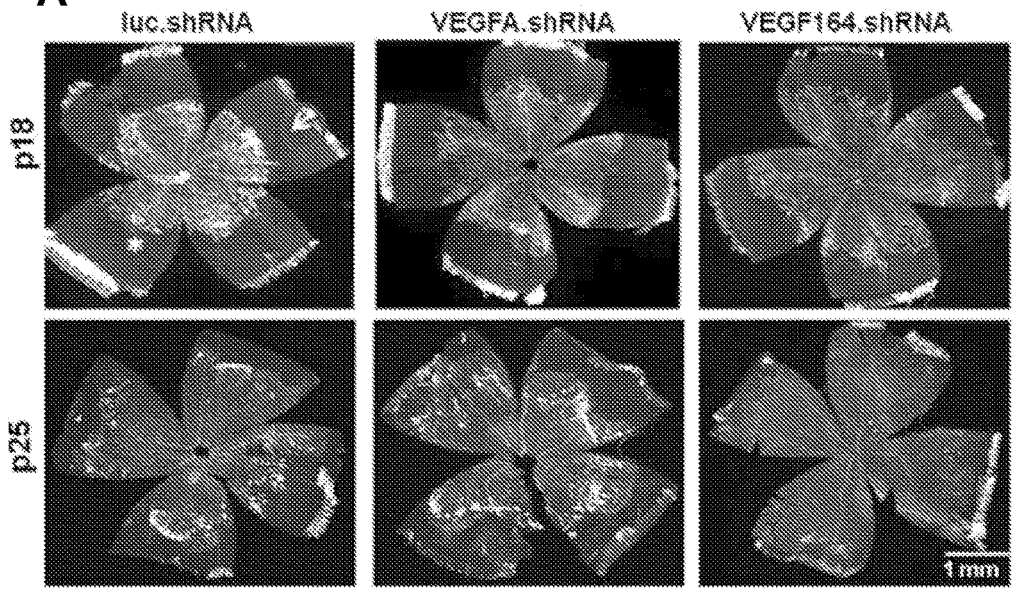
FIG. 25 shows lentivector-derived shRNA to VEGFA or VEGF164 reduces IVNV without affecting physiological retinal vascular development (AVA) in the rat ROP model. Images of retinal flatmounts at P18 and P25 following subretinal injections in each group. (A) luc.shRNA, VEGFA.shRNA, and VEGF164.shRNA * A white arrow in the avascular retina of p18 luc.shRNA points toward the lectin labeled IVNV at the junction of the vascular and avascular retina. (B) Quantification of IVNV. *P<0.05. ***P<0.001 versus luc.shRNA at P8. †P<0.01 versus VEGFA.shRNA at P25. ###P<0.001 versus VEGFA.shRNA at P18. (C) AVA.
Figures 25B, 25C:
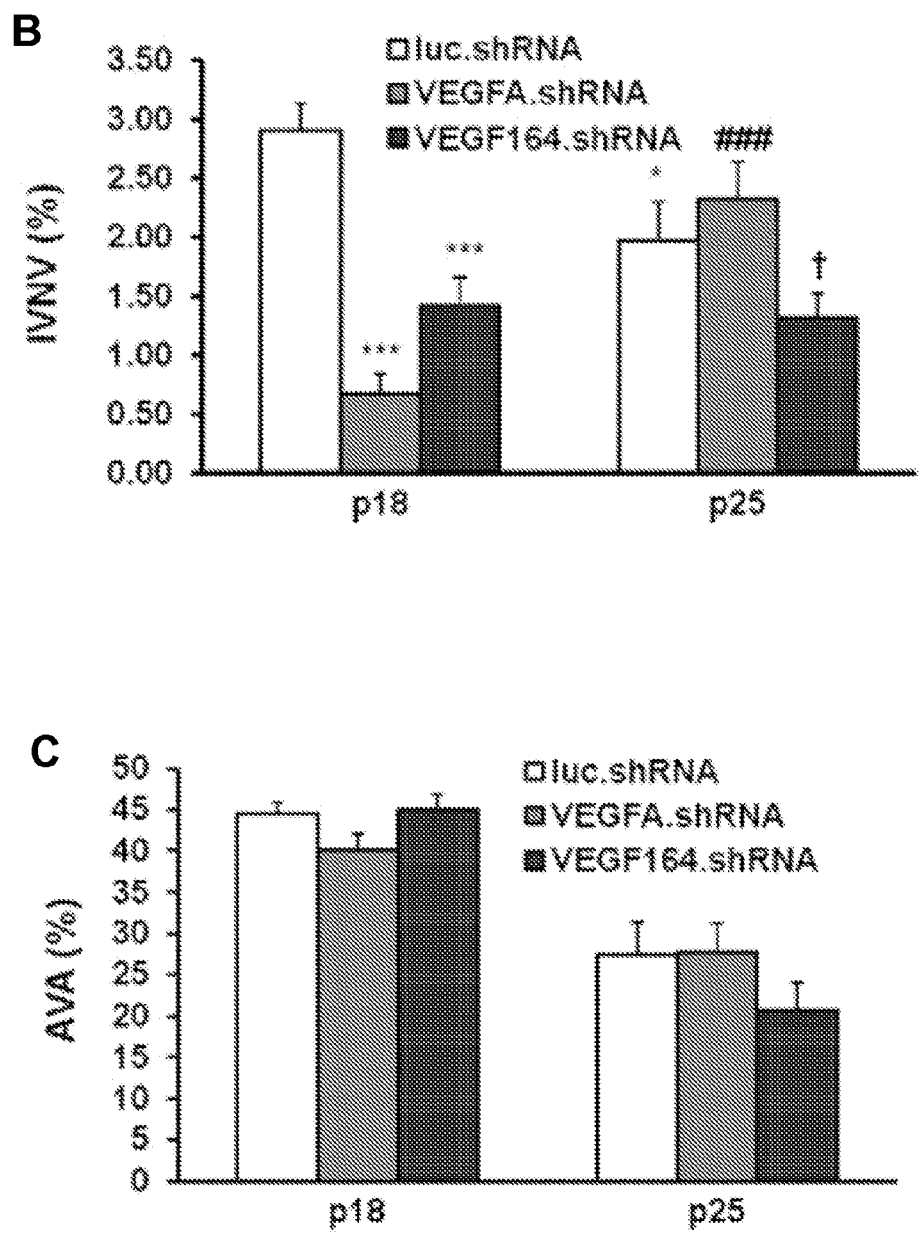

VEGFA.shRNA and VEGF164.shRNA each significantly inhibited IVNV at P18 compared with luciferase.shRNA (FIGS. 25A, 25B). At P25, IVNV was significantly reduced in pup eyes treated with the luciferase.shRNA compared with those treated at P18. This was anticipated, because IVNV naturally regresses in the ROP model. At P25, VEGF164.shRNA significantly inhibited IVNV compared with VEGFA.shRNA, whereas VEGFA. shRNA increased IVNV at P25 compared with P18. These findings indicate that VEGF164.shRNA, but not VEGFA.shRNA, was superior in maintaining inhibition of IVNV (FIGS. 25A, 25B), and that VEGFA.shRNA-treated eyes had recurrent IVNV. Neither VEGFA.shRNA nor VEGF164.shRNA had an effect on AVA at either P18 or P25, compared with luciferase.shRNA (FIGS. 25A, 25C).

VEGFR2 Activation in Retinal ECs after Targeted VEGFA.shRNA or VEGF164.shRNA

Figures 26A, 26B:
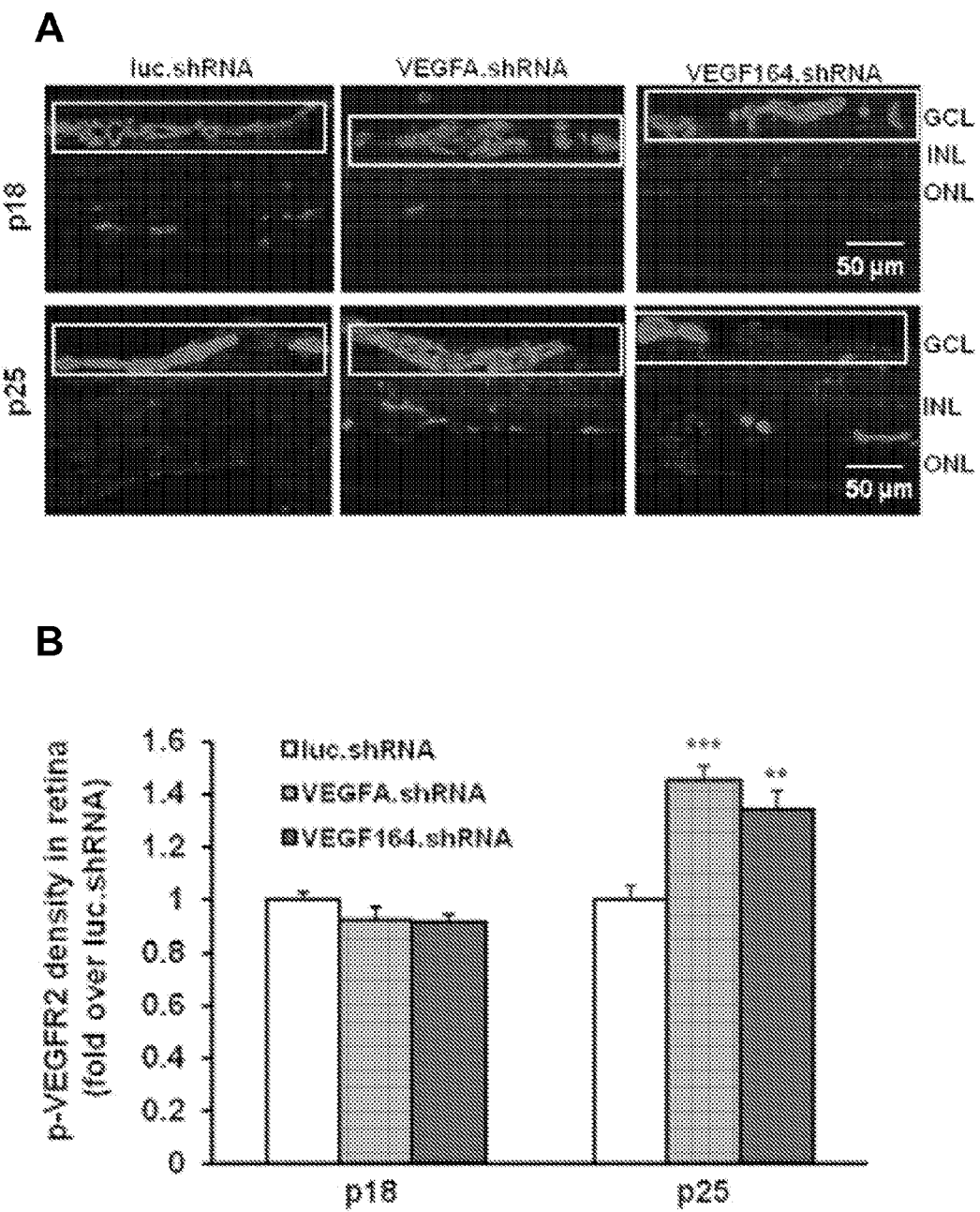
FIGS. 26A, 26B, and 26C show an analysis of VEGFR2 activation in pups treated with subretinal injections of lentivector-driven shRNAs in the rat ROP model. (A) IHC of p-VEGFR2 in retinal cryosections. (B) Semiquantification of p-VEGFR2 (blue) in total retina (***P<0.001 versus luc.shRNA at P25). (C) Colabeling of p-VEGFR2 (blue) in lectin (red)-labeled ECs in the primary plexus (depicted within boxes; *P<0.05, **P<0.01 versus luc.shRNA at P18; ††P<0.01 versus luc.shRNA at P25) from P18 and P25 pups treated with luc.shRNA, VEGFA.shRNA and VEGF164.shRNA.
Figure 26C:
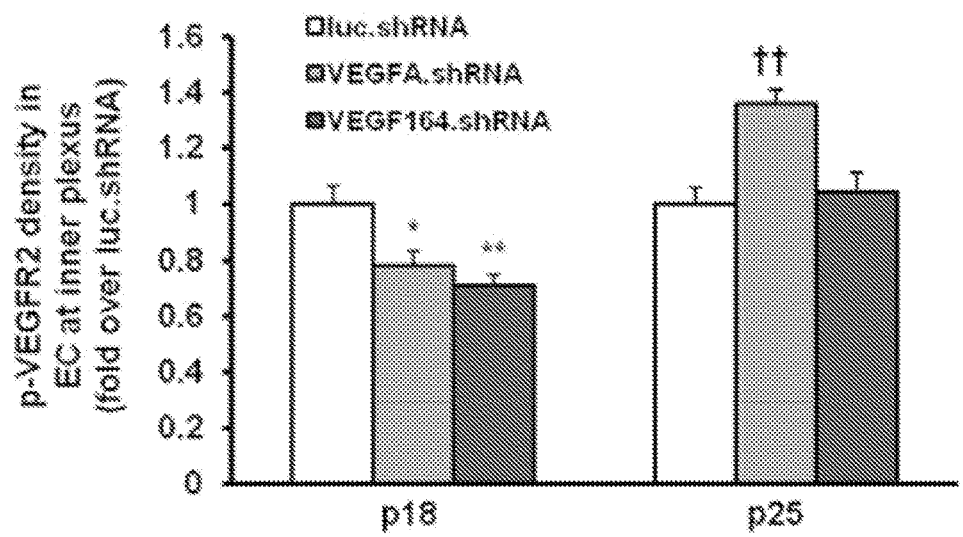

To determine if targeted treatment with VEGFA.shRNA or VEGF164.shRNA inhibited total retinal VEGFR2 signaling, densitometry of p-VEGFR2 was measured from the ganglion cell layer to the RPE/choroid layer in cryosections colabeled with p-VEGFR2 and lectin (FIGS. 26A, 26B). To determine the effect of VEGFA.shRNA or VEGF164.shRNA on VEGFR2 activation in endothelial cells, lectin and p-VEGFR2 colabeling was analyzed with densitometry in the cryosections at the junctions between avascular and vascular retina in the inner plexus (FIGS. 26A, 26C). At P18, neither treatment significantly inhibited total retinal p-VEGFR2 density (FIG. 26B) compared with luciferase.shRNA, but VEGFA.shRNA and VEGF164.shRNA each reduced colabeling of lectin and p-VEGFR2 in the vascular/avascular junction where IVNV developed (FIG. 26C). At P25, there was increased p-VEGFR2 labeling in the retina in both VEGFA and VEGF164.shRNA sections compared with luciferase.shRNA (FIG. 26B). There was also increased p-VEGFR2 colabeling with endothelial cells in VEGFA.shRNA-treated sections but not in VEGF164.shRNA-treated ones (FIG. 26C).

Figure 27A:
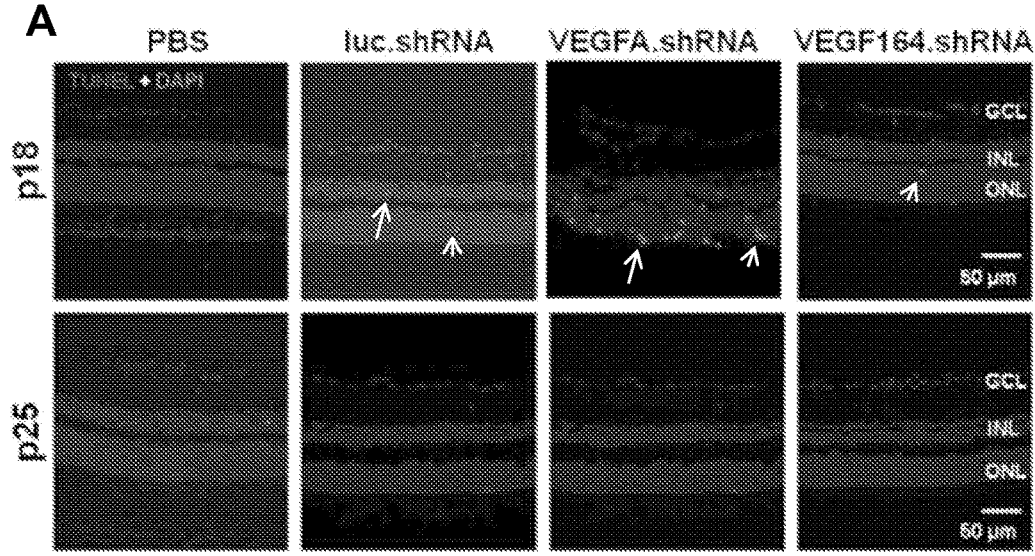
FIGS. 27A, 27B, 27C and 27D shows an analysis of retinal apoptosis and retinal morphological changes in the pups treated with lentivector-driven shRNAs in the rat ROP model. Images of TUNEL staining (A) and number of TUNEL positive cells (see arrows) (B) in retinal DAPI stained cryosections from P18 and P25 pups treated with luc.shRNA, VEGFA.shRNA, and VEGF164.shRNA (P<0.01, *P<0.001 versus PBS at P18; †††P<0.001 versus luc.shRNA at P18). Quantification of the thickness of the INL (C) (*P<0.001 versus PBS at P18; ††P<0.01 versus luc.shRNA at P25) and the ONL (D) (*P<0.001 versus luc.shRNA at P18; ††P<0.001 versus luc.shRNA at P25) in DAPI-stained retinal cryosections from P18 and P25 OIR pups treated with luciferase.shRNA, VEGFA.shRNA, and VEGF164.shRNA.
Figure 27B:
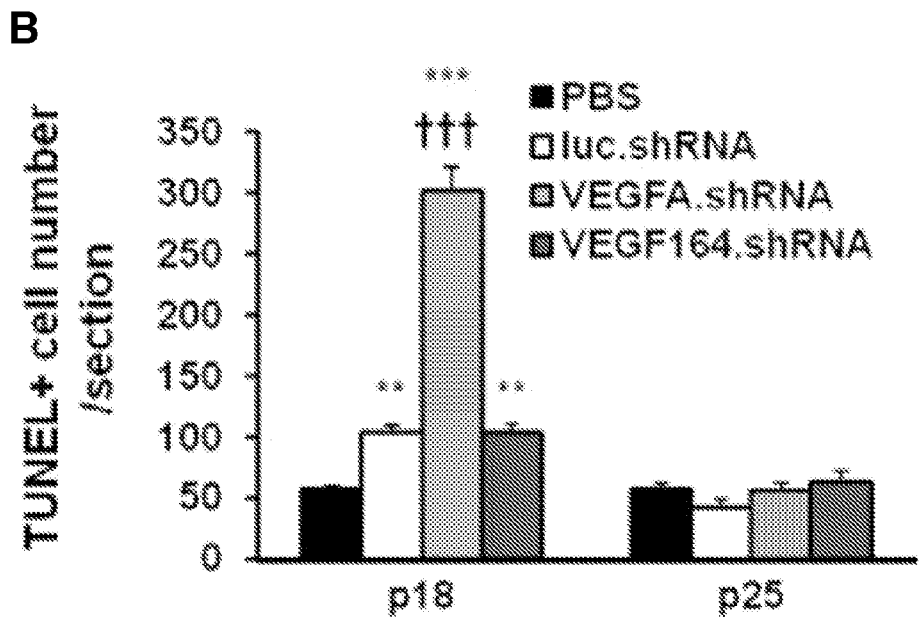
Figure 27C:
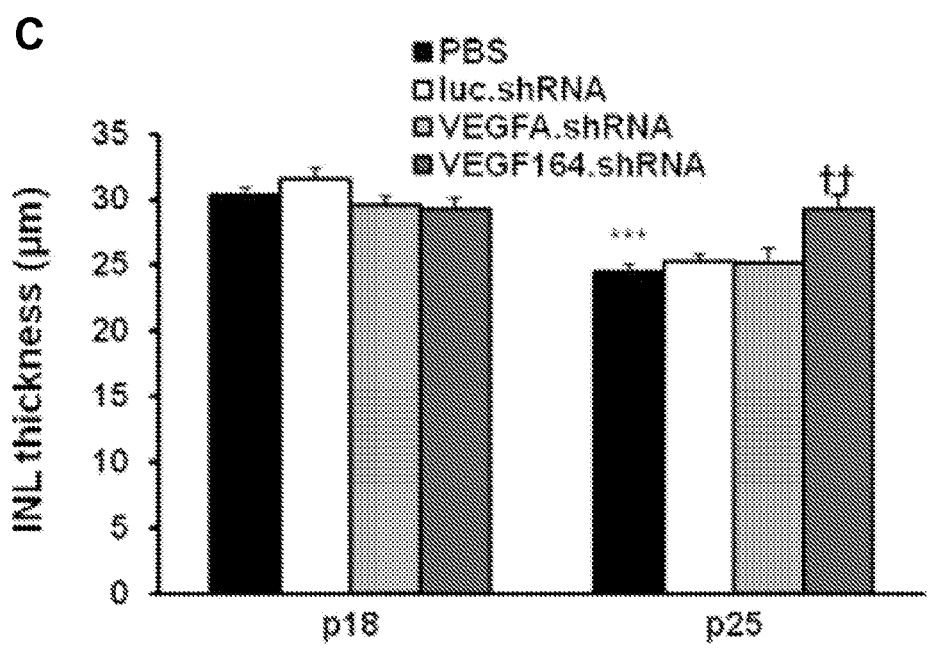
Figure 27D:
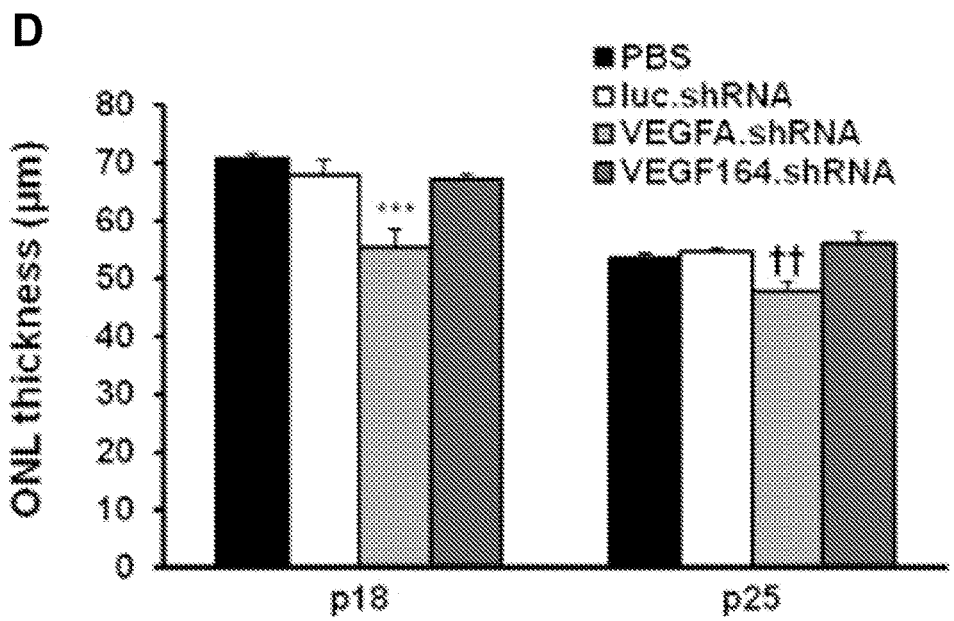
Figure 28A:
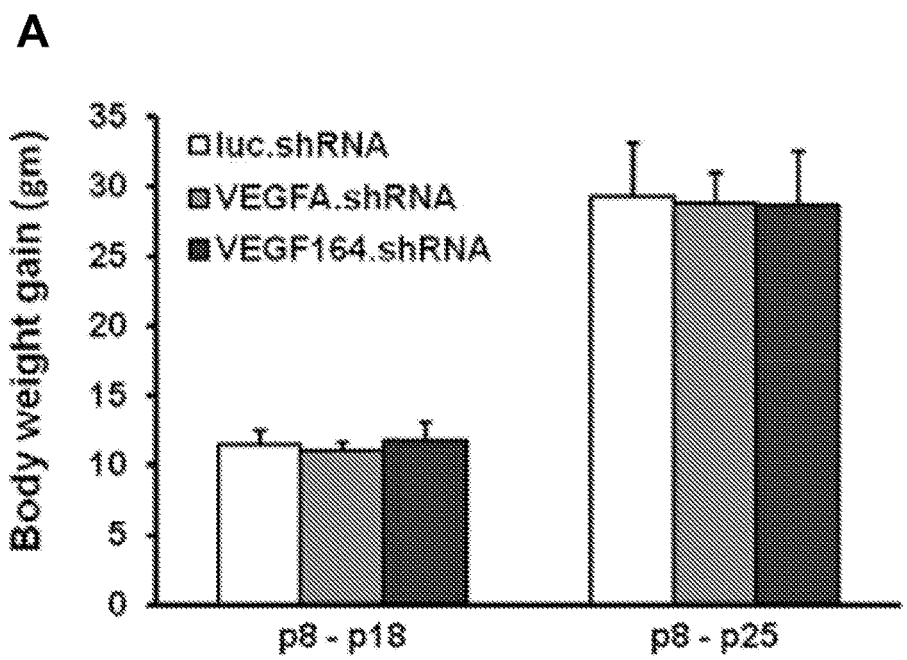
FIGS. 28A and 28B show that lentivector-driven shRNAs treatment has no effect on pup growth and serum VEGF. Pup weight gains from P8 to P18 or P25 (A) and ELISA of serum VEGF in retina from P18 or P25 pups treated with luc.shRNA, VEGFA.shRNA, and VEGF164.shRNA in the rat ROP model.
Figure 28B:
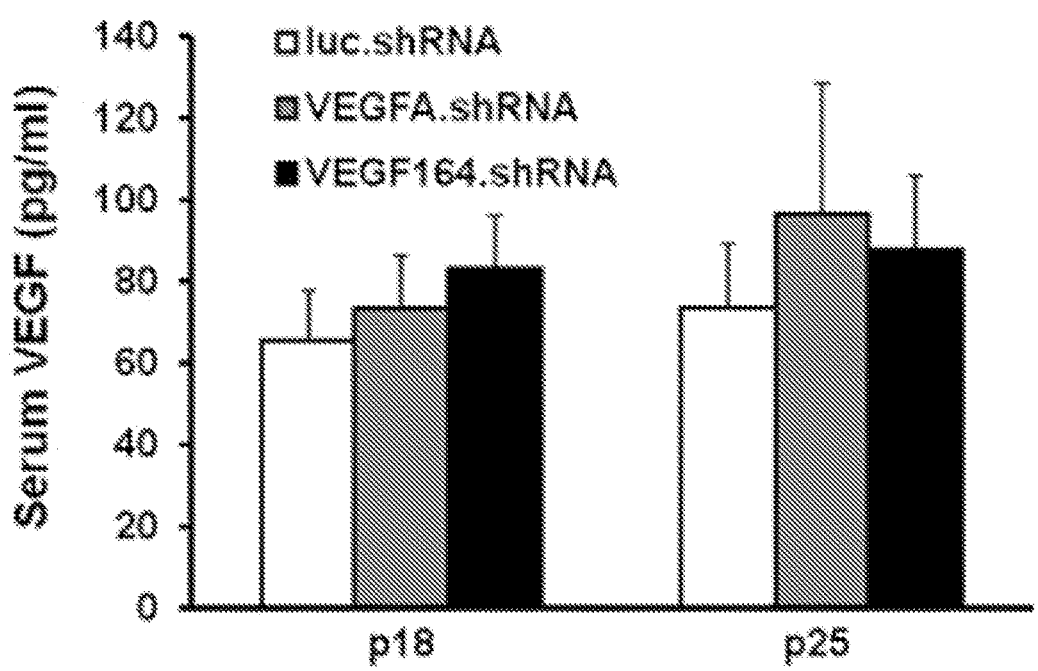

VEGFA.shRNA and VEGF164.shRNA Effects on Retinal Survival, Serum VEGF, and Pup Growth VEGF is important to Müller cell health and neuroprotection. Therefore, the study examined whether shRNAs to either VEGFA or $VEGF_{164}$ affected retinal cell survival at P18 or P25 by assessing TUNEL staining (FIG. 27A). Compared with PBS, luciferase.shRNA increased TUNEL+ cells at P18 but not at P25 (FIG. 27B). Although the data show that VEGFA knockdown did not increase apoptosis in P18 retinal lysates, sections from VEGFA.shRNA, not VEGF164.shRNA treated eyes had significantly increased TUNEL+ cells in both INL and ONL compared with luciferase.shRNA at P18. At P25, TUNEL+ cells were significantly reduced compared with respective groups at P18, and there were no significant differences in TUNEL+ cells among the groups at P25. Compared with PBS, luciferase.shRNA treatment did not alter the thickness of the retina, the INL (FIG. 27C) or ONL (FIG. 27D). However, eyes treated with the VEGFA.shRNA had significantly reduced ONL thickness compared with luciferase.shRNA at both P18 and P25 (FIG. 27D). Compared with luciferase.shRNA, no differences in thickness of total retina at P18 or P25 or INL at P18 were detected after VEGFA.shRNA or VEGF164.shRNA injections (FIG. 27C). At P25, the INL was thicker in the VEGF164.shRNA group than the other groups (FIG. 27C). Subretinal VEGFA.shRNA or VEGF164.shRNA did not affect body weight gain (FIG. 28A) or serum VEGF (FIG. 28B) compared with luciferase-.shRNA at either time point.

Discussion:

The data herein show that targeting Müller cells with an shRNA to one splice variant of VEGF, $VEGF_{164}$, was safer and more effective at inhibiting and maintaining inhibition of IVNV than targeting all splice variants of VEGFA in a rat model representative of human ROP. Müller cells were targeted, because VEGF-splice variant mRNAs localized to cells in the INL corresponding to CRALBP-labeled Müller cells and knockdown of VEGFA in Müller cells inhibited IVNV at the early time point, P18. Previously, Bai et al. found that Müller cell-expressed VEGF was important in causing IVNV by developing and testing a Müller cell conditional VEGF knockout in the mouse OIR model. This study not only differs by testing long-term safety and comparing knockdown of a Müller cell-expressed splice variant—$VEGF_{164}$—to knockdown of Müller cell-VEGFA, but also studies the rat OIR model, which is a representative model of human ROP in places where oxygen is regulated.

Studies in human preterm infants show that IVNV can recur following anti-VEGF treatments. Experimentally, broad inhibition of VEGF with an intravitreal neutralizing antibody led to upregulation of angiogenic compounds in association with recurrent IVNV. The study examined whether inhibition of all VEGF splice variants affects both pathologic and physiologic processes and can lead to cell death or compensatory upregulation of angiogenic pathways. Therefore, one splice variant of VEGF was targeted to inhibit pathologic angiogenesis and potentially preserve physiologic effects from VEGF. $VEGF_{164}$ was chosen based on the finding that of the three rat splice variants of VEGFA ($VEGF_{120}$, $VEGF_{164}$, and $VEGF_{188}$), $VEGF_{164}$ was the most prevalent and unlike $VEGF_{120}$ or $VEGF_{188}$, was increased in association with both older developmental age and the ROP model compared with RA. The data also show that $VEGF_{164}$ was upregulated by repeated fluctuations in oxygenation, whereas $VEGF_{120}$ was upregulated by hypoxia alone. Physiologic events can be stimulated by hypoxia alone. Also, evidence is accumulating that fluctuations in oxygenation are important in ROP. Others have reported $VEGF_{164}$ as the splice variant most likely to cause inflammation and abnormal angiogenesis. For all these reasons, this study compared the efficacy and safety of targeting Müller cell-$VEGF_{164}$ or -VEGFA with shRNAs in the rat model of ROP. A lentivector was chosen because lentivirus is incorporated into the genome and provides a robust means to study VEGF knockdown longitudinally.

Although the data show that targeting $VEGF_{164}$ with shRNA was more effective at maintaining inhibition of IVNV than targeting VEGFA, the two cannot be directly compared. The shRNA to VEGFA had greater knockdown in HEK164 reporter cell lines than did $VEGF_{164}$-specific shRNA, which was selective to $VEGF_{164}$ and not $VEGF_{120}$. Therefore, the dose effect of VEGF164.shRNA in Müller cells can account for some of the outcomes. For example, there was greater knockdown of VEGF in P18 retinal lysates from eyes treated with VEGFA.shRNA than with VEGF164.shRNA; but after a longer time for lentiviral transduction, VEGF164.shRNA treatment reduced VEGF in P25 retinal lysates. $VEGF_{120}$, which was not knocked down by $VEGF_{164}$ shRNA, has soluble properties enabling it to move to other cells within the retina, and can have accounted for the lack of cell death and increased INL thickness noted in P25 sections from eyes treated with VEGF164.shRNA.

Based on densitometry of labeled retinal sections, knockdown of $VEGF_{164}$ or VEGFA had no effect on overall retinal VEGFR2 activation at P18; but at a later time point, both VEGFA.shRNA and VEGF164.shRNA each led to greater retinal p-VEGFR2. This indicates a compensatory increase in VEGFR2 activation. One explanation can be upregulation of VEGF in other cells in the retina. The ELISA technique measures only unbound VEGF and can miss VEGF bound to VEGFR. The data show that Müller cell-VEGF activates endothelial cell VEGFR2. Therefore, to detect differences in p-VEGFR2 among the groups, a semiquantitative approach was used with densitometry of labeled retinal sections for endothelial cell p-VEGFR2. This method showed reduced p-VEGFR2 densitometry in ECs at P18, but increased p-VEGFR2 in ECs at P25 retinas that had been treated with the VEGFA.shRNA, not VEGF164.shRNA, and in association with an increase in IVNV at P25, indicating compensatory signaling effects.

Targeted knockdown of overexpressed VEGFA in Müller cells reduced IVNV at P18 without adversely affecting body weight gain or causing apoptosis measured as cleaved caspase-3 in retinal lysates. Here, using TUNEL, the data show that VEGFA knockdown caused more cell death compared with luciferase.shRNA treatment. This can be because TUNEL does not discriminate apoptosis from necrosis and that the sensitivity in detecting a small group of cells undergoing apoptosis was insufficient using Western analysis of whole retinal lysates. At P25, there was no difference in TUNEL+ cells, indicating absence of ongoing cell death. However, VEGFA.shRNA also reduced ONL thickness at P25. Müller cells require VEGF for their own survival and produce VEGF and other factors important to retinal neuronal survival, including photoreceptors whose nuclei reside in the ONL. Conditional knockout of Müller cells in a mouse model led to photoreceptor degeneration. Additional studies of the effects of long-term knockdown of Müller cell-VEGF such as through electrophysiology and spectral domain optical coherence tomography can also be performed.

In summary, knockdown of splice variant, $VEGF_{164}$, in Müller cells appears safer and more effective in inhibiting IVNV in the long-term than targeted knockdown of VEGFA, indicating that maintaining the expression of some splice variants of VEGFA can improve survival of cells within the retina. Additional studies regarding potential compensatory signaling of Müller cells after VEGF inhibition and on long-term structure and function from knockdown of VEGFA or $VEGF_{164}$ are warranted. Effects of VEGF knockdown on endothelial effectors are also important to determine.

Example 12

Quantitative Analyses of Retinal Vascular Area and Density after Different Methods to Reduce VEGF in a Rat Model of Retinopathy of Prematurity Objective:

Targeted inhibition of Müller cell (MC)-produced VEGF or broad inhibition of VEGF with an intravitreal anti-VEGF antibody reduces intravitreal neovascularization in a rat model of ROP. In this study, the effects of these two approaches on retinal vascular development and capillary density in the inner and deep plexi in the rat ROP model were compared.

Methods:

In the rat model of ROP, pups received 1 µL of (1) subretinal lentivector-driven short hairpin RNA (shRNA) to knockdown MC-VEGFA (VEGFA.shRNA) or control luciferase shRNA, or (2) intravitreal anti-VEGF antibody (anti-VEGF) or control IgG. Analyses of lectin-stained flat mounts at postnatal day 18 (p18) included: vascular/total retinal areas (retinal vascular coverage) and pixels of fluorescence/total retinal area (capillary density) of the inner and deep plexi determined with the Syncroscan microscope, and angles between cleavage planes of mitotic vascular figures labeled with anti-phosphohistone H3 and vessel length.

Results:

Retinal vascular coverage and density increased in both plexi between p8 and p18 in room air (RA) pups. Compared with RA, p18 ROP pups had reduced vascular coverage and density of both plexi. Compared with respective controls, VEGFA.shRNA treatment significantly increased vascular density in the deep plexus, whereas anti-VEGF reduced vascular density in the inner and deep plexi. VEGFA.shRNA caused more cleavage angles predicting vessel elongation and fewer mitotic figures, whereas anti-VEGF treatment led to patterns of pathologic angiogenesis.

CONCLUSIONS:

Targeted treatment with lentivector-driven VEGFA.shRNA permitted physiologic vascularization of the vascular plexi and restored normal orientation of dividing vascular cells, indicating that regulation of VEGF signaling by targeted treatment can be beneficial.

Lack of retinal capillary support is a pathologic consequence that precedes intravitreal neovascularization (IVNV) in a number of diseases, including retinopathy of prematurity (ROP) and diabetic retinopathy. Loss of vascular support to the retina causes hypoxia and triggers a cascade of events that enables transcription of angiogenic factors, including VEGF, erythropoietin, angiopoietin, and others. The goals of previous clinical treatments were to destroy the avascular retina, which was believed responsible for stimulating angiogenic factor production and to reduce oxygen debt created by the avascular retina. Later approaches interfered with angiogenic growth factor-receptor binding and activation (e.g., antibodies to ligands or receptors for VEGF, platelet-derived growth factor, or tyrosine kinase inhibitors to inhibit signaling pathways) or inhibited inflammatory pathways that also increase angiogenesis (e.g., steroids and angiotensin II type I receptor). Currently, efforts seek to promote physiologic retinal vascularization through the use of growth factors or omega-3 fatty acids in growth-restricted preterm infants for ROP, to prevent metabolic damage to physiologic vascularization of the retina in diabetic retinopathy, or to regulate aberrant angiogenic signaling in endothelial cells to minimize disoriented retinal vascular growth and intravitreal angiogenesis in ROP.

Recent clinical studies reported a persistent avascular retina and recurrent IVNV following treatment with non-specific intravitreal anti-VEGF agents for severe ROP. Using the rat ROP model, the data herein indicate that a neutralizing antibody to VEGF significantly inhibited IVNV but also reduced pup weight gain and serum VEGF. These studies indicate that targeted inhibition of overproduced VEGF can be a safer strategy to treat ROP. The mRNA signal of VEGFA-splice variants were located in the regions corresponding to cellular retinaldehyde-binding protein (CRALBP)-labeled Müller cells, and therefore developed lentivector driven VEGFA short hairpin RNA (shRNA) to target Müller cell VEGFA using a CD44 promoter. Using the rat ROP model, the data indicate that the lentivector targeted knockdown of Müller cell VEGFA significantly inhibited IVNV without affecting pup weight or serum VEGF. In this study, the safety effects on the retinal vasculature and capillary density from the two methods of anti-VEGF treatment were evaluated. Targeted knockdown of VEGF in Müller cells that overproduced VEGF21 preserve normal-ordered developing intraretinal vascularization and capillary density, whereas broad anti-VEGF treatment interferes with endothelial cell receptor activation necessary for physiologic vascularization and causes a persistent avascular retina with reduced capillary density. The rat model of ROP was used to recreate pathologic features of severe ROP and capillary support in the inner and deep vascular plexi of the retina was measured by two different methods. The vascular coverage was determined as areas of vascularized retinal area and capillary density was determined as pixels fluorescence from lectin stained-flat mounts showing a vascularized retina in both inner and deep plexi. In both measurements, outcomes were normalized to total retinal area. The number and orientation of dividing vascular cells within the retina at the junction of vascularized and avascular retinas were determined. targeted VEGFA knockdown of Müller cell-VEGFA were compared to neutralizing VEGF with an antibody to rat VEGF. Both treatments were delivered at doses and time points that significantly inhibit IVNV. Here, targeted VEGFA knockdown permitted physiologic vascularization of the retinal vascular plexi and restored normal orientation of dividing vascular cells at the junction of vascular and avascular retinas. These data support additional studies to develop methods to target overproduced VEGF in order to treat IVNV.

Methods:

Rat Model of Oxygen-Induced Retinopathy (Rat ROP Model)

The rat ROP model has been described herein. Entire litters of newborn Sprague-Dawley rat pups (Charles River, Wilmington, Mass.) and dams were placed into an oxygen environment that cycled oxygen concentration between 50% and 10% every 24 hours for 14 days, and then placed into room air (RA). Pup number was maintained at 12 to 14 pups/litter. At postnatal day 18 (p18), pups were euthanized by intraperitoneal injection (IP) of ketamine (60 mg/kg) and xylazine (18 mg/kg) followed by IP pentobarbital (80 mg/kg).

Ocular Injections

Intravitreal Injections of Neutralizing Antibody to VEGF. As described herein, following anesthesia, 1 µL of 50 ng neutralizing antibody to rat $VEGF_{164}$ (anti-VEGF; R&D Systems, Minneapolis, Minn.) or isotype goat immunoglobulin G (IgG; R&D Systems, Minneapolis, Minn.) was delivered into the vitreous with a 33-gauge needle attached to a Hamilton syringe (Hamilton, Reno, Nev.) at the beginning of the 50% oxygen cycle on p12 in order to inhibit retinal secreted VEGF at its highest concentration in the model at p14 and subsequent IVNV. As shown herein, 50 ng of neutralizing antibody to rat VEGF164 significantly reduced IVNV by 3.5-fold over IgG control.

Subretinal Injections of Lentivector-Driven VEGFA.shRNA. Lentivector driven VEGFA shRNA was constructed and tested as described herein. Briefly, shRNAs were designed as microRNAs against rat VEGFA (VEGFA.shRNA) or luciferase (luc.sRNA) and cloned into the lentiviral transfer vector (pFmCD44.1GW) with the CD44 promoter, which targets Müller cells and not astrocytes, and a green fluorescence protein (GFP) reporter gene. Micron III live imaging showed that 30% of retina was transduced by subretinal injection of lentivector and achieved 80% knockdown of retinal VEGFA by VEGFA.shRNA compared with luc.shRNA determined by ELISA in retinal lysates from the rat model of ROP. However, an intravitreal injection of lentivirus yielded a poor retinal virus transduction, which was consistent with the report from Greenberg, et al. VEGFA.shRNA effectively reduced IVNV by 4-fold over luc.shRNA at p18 in the rat model of ROP.

In this study, at the beginning of the 50% oxygen cycle of the 50/10 ROP model on p8, pups received 1 µL ($1\times10^9$ viral particles/mL) of lentivectors containing VEGFA.shRNA or luc.shRNA as subretinal injections that created a transient retinal detachment, which resolved within 24 hours. Both eyes of each pup were injected with the same lentivector preparation.

Each litter typically had an equal distribution of either lentivector preparation. After the injection, topical antibiotic (0.5% erythromycin) was applied to each eye, and pups were allowed to recover on a warming pad before being returned to the Oxycycler.

For both intravitreal and subretinal injections, litters were typically out of the oxygen cycler for 3 hours. At p18, the time point of maximum IVNV in this model, pups were euthanized for analysis.

Retinal Flat-Mount Preparation, Imaging, and Analysis

Lectin-stained retinal flat mounts were prepared using Alexa Fluor 568 conjugated *Griffonia simplicifolia* (Bandeiraea) isolectin B4 (5 µg/mL; Invitrogen Molecular Probes, Eugene, Oreg.), as described herein, and imaged using an inverted fluorescence microscope (Olympus, Japan). Flat mounts were created using the scan-slide stitching function of Metamorph imaging software (Molecular Devices, Inc., Sunnyvale, Calif.). Measurements were made by two masked reviewers using ImageJ (National Institutes of Health, Bethesda, Md.). High resolution multi-Z plane images of retinal flat mounts were created by autostitching individual 20× fluorescence images of lectin-stained vasculature using the Syncroscan fluorescence microscope (Olympus). Fluorescence was converted to grayscale prior to stitching of each Z plane. The number of Z-planes needed to capture both primary and tertiary plexi was determined during imaging. The inner (primary plexus) and deep (tertiary plexus) layers were separated using filters in Adobe Photoshop CS5 extended (Version 12.1; Adobe Systems Incorporated, San Jose, Calif.). In this study, only data from the inner and deep capillary layers were analyzed. Images corresponding to inner and deep layers had different color channels in Photoshop (Adobe Systems, Inc.) to differentiate the inner and deep layers. Total pixels covered by inner and deep layers were measured using histograms in Photoshop. The flat-mount vascular and avascular areas were measured by ImageJ 1.45S (National Institutes of Health). Retinal vascular coverage was defined as area of vascular extent to total retina area. Retinal vascular density was the pixels of lectin fluorescence to total retinal area.

Phosphohistone Labeling and Measurement of Mitoses and Cleavage Angles

Quantitative image analysis was performed using the freeware ImageTool, version 3 (University of Texas, Austin, Tex.). As described herein, cell division cleavage planes were identified in Alexa Fluor 568-conjugated isolectin-stained vessels by bisection of the separating chromosomes labeled with Alexa Fluor 488-conjugated anti-phosphohistone H3 (10 µg/mL; EMD Millipore, Billerica, Mass.) during late metaphase to anaphase. Mitotic figures were identified as cells labeled with isolectin and phosphohistone H3. Lines were drawn using image management software (Photoshop 7.0; Adobe Systems, Inc.) along the cleavage plane and along the long axis of the blood vessel for each mitotic division. The angle between these two lines was calculated. Angles of 0° predicted widening and 90° elongation of vessels. Angles between these values predict disordered divisions.

Statistical Analysis

Significant differences between treatment groups were determined by ANOVA. A minimum value of P less than 0.05 was considered statistically significant. At least two different litters were used for each experiment to account for potential effects within individual litters. For each condition, three to five flat mounts were analyzed. For each analysis, one data point was one eye from an individual pup.

Figures 29A, 29B:
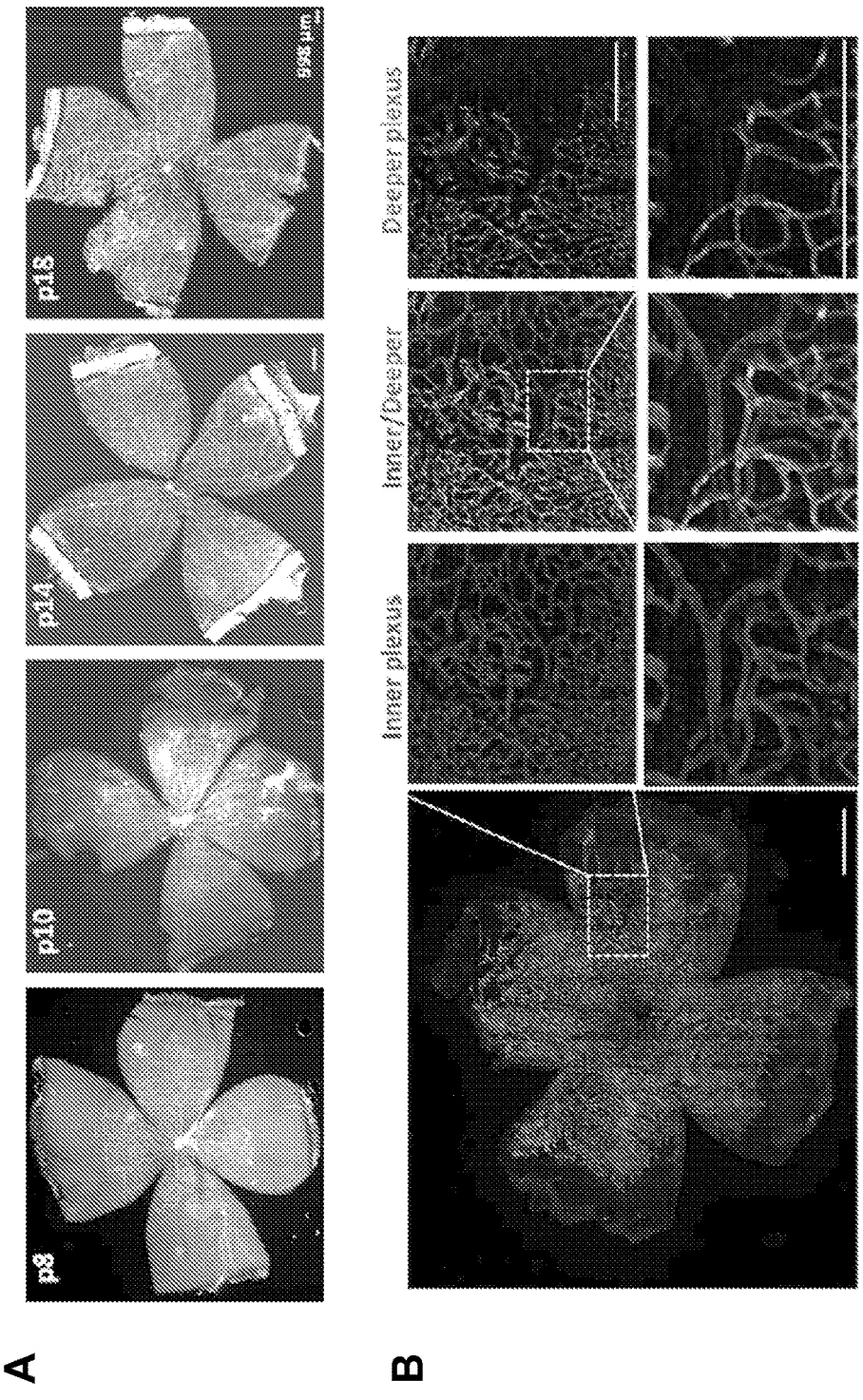
FIGS. 29A, 29B, 29C, and 29D shows that retinal vascular coverage and density in the inner and deeper plexi are increased during development at p8, p10, p14, and p18 in RA. (A) Syncroscan images of lectin-stained retinal flat mounts. (B) A portion of p18 VEGFA.shRNA-treated flat mount in the ROP model showing inner plexus, deep plexus, and combined image of both plexi assigned different colors (inner and deep plexi offset to permit visualization; lines indicate magnification size at the same unit). (C) Vascular coverage determined by vascular area normalized to total retina area. (D) Vascular density determined by the number of pixels of lectin fluorescence normalized to total retinal area (overall one-way ANOVA ***P<0.001; results are means±SD).
Figure 29C:
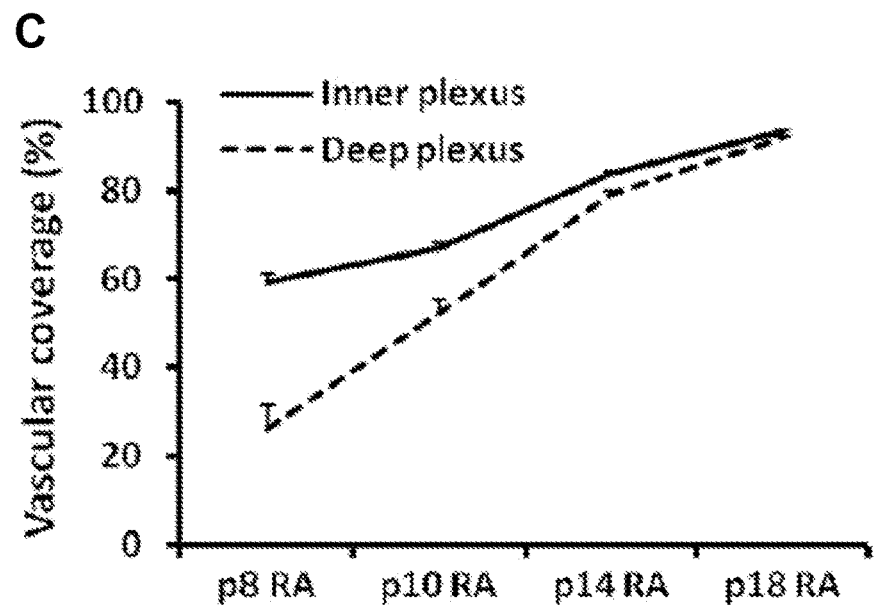
Figure 29D:
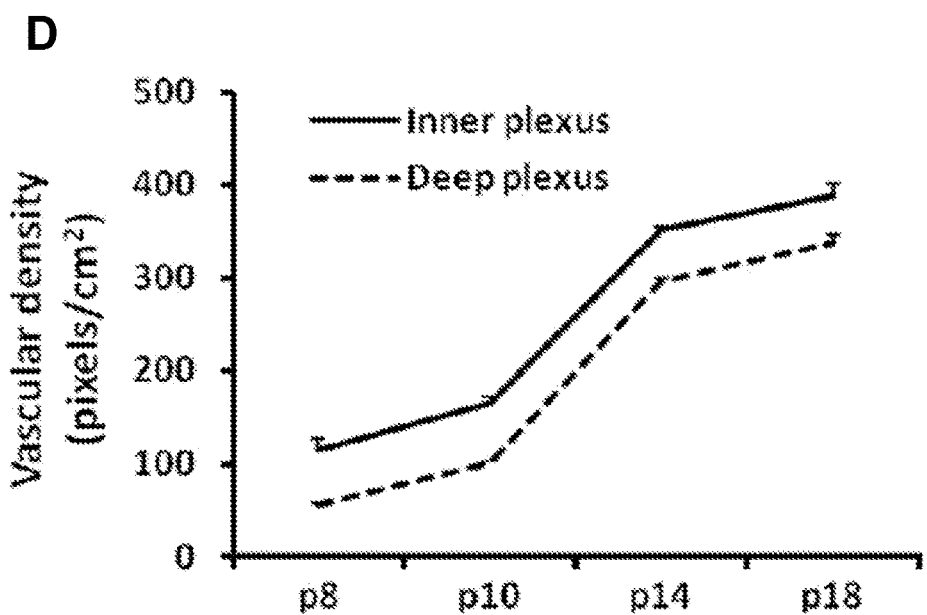

Results:

Retinal Vascular Coverage and Density in the Inner and Deep Plexi at Different Time Points During Development To analyze retinal vascular development in inner and deep plexi at various time points in development, two different approaches were used. In the first, the extent of the retina covered by blood vessels as vascular/total retinal area for each plexus (termed vascular coverage) in retinal flat mounts was measured (FIG. 29A). In the second, the number of pixels of lectin-stained fluorescence/total retinal area in the inner and deep vascular plexi (termed vascular density) were measured, separated by assigning different colors to the plexi (FIG. 29B). The second approach measured not only retinal vascular/total retinal area, but incorporated capillary density/total retinal area. At time points from p8 to p18 in RA-raised rats, the data indicate that vascular coverage increased on average 1.5-fold in the inner plexus and 3.5-fold in the deep plexus (FIG. 29C). Vascular density increased 3.5-fold in the inner plexus and 6-fold in the deep plexus from p8 to p18 (FIG. 29D). Even though the slope of vascular coverage of the deep plexus was steeper than that of the inner plexus at the time points measured, the vascular density of the deep plexus increased with a similar slope as the inner plexus, indicating that maintaining capillary density can be important to overall retinal development.

Figures 30A, 30B, 30C:
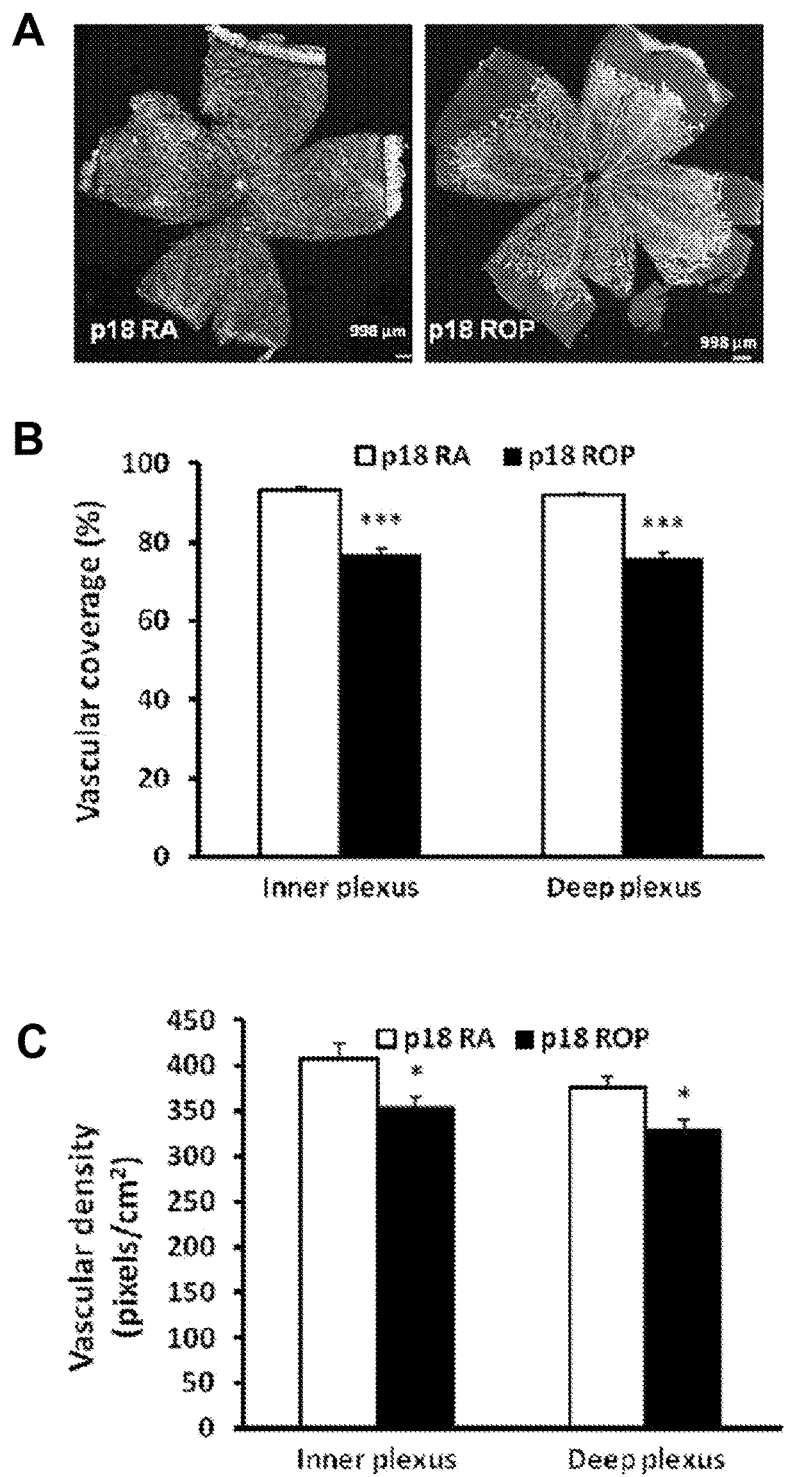
FIGS. 30A, 30B, and 30C show that retinal vascular coverage and density are reduced in both inner and deep plexi of pups raised in the ROP model at p18. (A) Images of retinal flat mounts of pups raised in RA or exposed to the ROP model. (B) Retinal vascular coverage and (C) retinal vascular density in the inner and deep plexi (*P<0.05, ***P<0.001 versus RA, two-way ANOVA; results are means±SD).

Retinal Vascular Coverage and Density in the Inner and Deep Plexi is Reduced in the Rat ROP Model Delayed physiological retinal vascular development accounts for much of the avascular retina in phase I ROP in places in which oxygen is regulated. When rat pups are exposed to the ROP model, retinal vascular coverage in the inner and deep plexi was decreased compared with RA-raised pups at p18 (FIG. 30A, 30B). At p18, RA vascular coverage in both inner and deep plexi was 96% on average; however, for pups exposed to the ROP model, both vascular coverage (FIG. 30B) and vascular density (FIG. 30C) were significantly reduced in both inner and deep plexi compared with RA-raised pups.

Figures 31A, 31B, 31C, 31D:
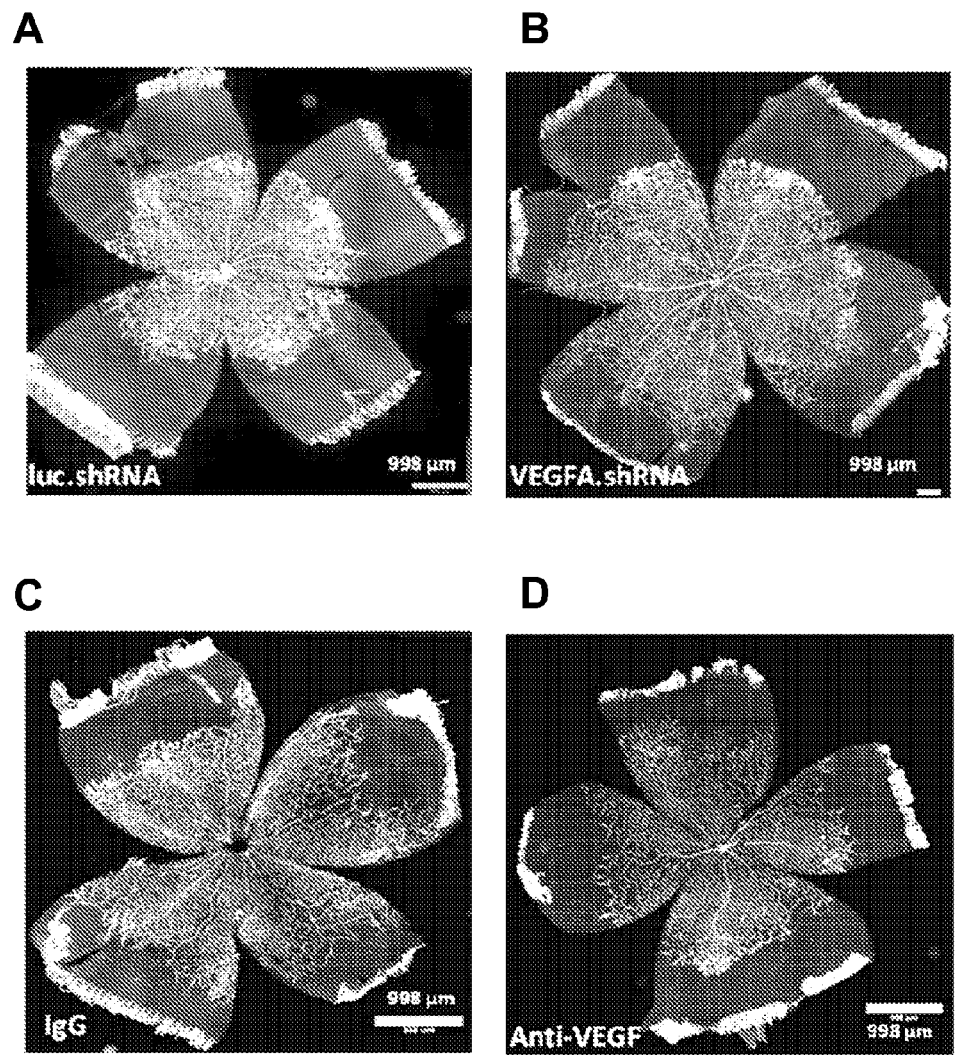
FIGS. 31A, 31B, 31C, and 31D show vascular endothelial growth factor-A.shRNA versus anti-VEGF treatments on retinal vascular morphology. Images of lectin-stained retinal flat mounts from pups treated with (A) luc.shRNA, (B) VEGFA.shRNA, (C) IgG, and (D) anti-VEGF, at p18 in the ROP model.
Figures 32A, 32B:
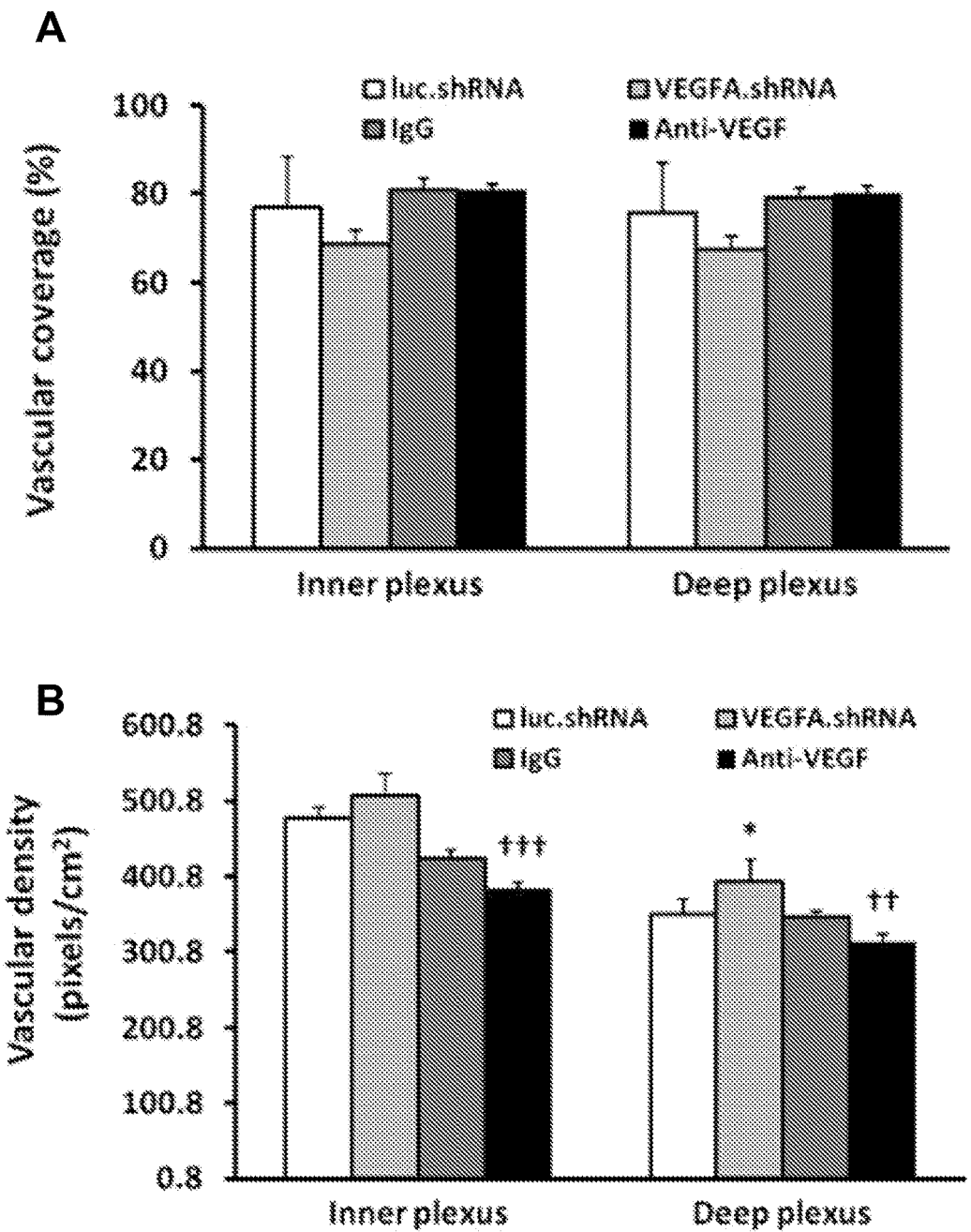
FIGS. 32A and 32B show retinal vascular coverage and density in the inner and deep plexi of pups treated with VEGFA.shRNA or anti-VEGF in the ROP model at p18 compared with respective controls. (A) Retinal vascular coverage and (B) vascular density (*P<0.05 versus luc.shRNA; ††P<0.01 and †††P<0.001 versus IgG, two-way ANOVA; results are means±SD).

Effects of Methods to Inhibit VEGF on Vascular Density and the Extent of Vascular Coverage in Inner and Deep Plexi Two different methods to reduce VEGF at doses found to successfully inhibit VEGF-induced IVNV were tested. In one, intravitreal anti-VEGF antibody (anti-VEGF) was compared with its control nonimmune IgG and in the other a subretinal injection of lentivectors carrying VEGFA shRNA (VEGFA.shRNA) that knocked down Müller cell VEGF was compared with control shRNA to the nonmammalian gene, luciferase (luc.shRNA). Vascular coverage and vascular density of the inner and deep plexi in lectin stained flat mounts were measured at p18 ROP (FIG. 31). Compared with respective controls, luc.shRNA or IgG-treated ROP pups, VEGFA.shRNA or anti-VEGF did not significantly affect vascular coverage in the inner and deep plexi (FIG. 32A). However, compared with respective controls, anti-VEGF significantly reduced vascular density of the inner and deep plexus, and VEGFA.shRNA treatment significantly increased vascular density of the deep plexus (FIG. 32B). Therefore, compared with respective controls, anti-VEGF treatment reduced capillary density in the inner and deep plexi of the retina in the ROP model, and targeted knockdown of VEGFA increased vascular density in the deep plexus, even though both treatments had no effect on the vascular coverage.

Figures 33A, 33B:
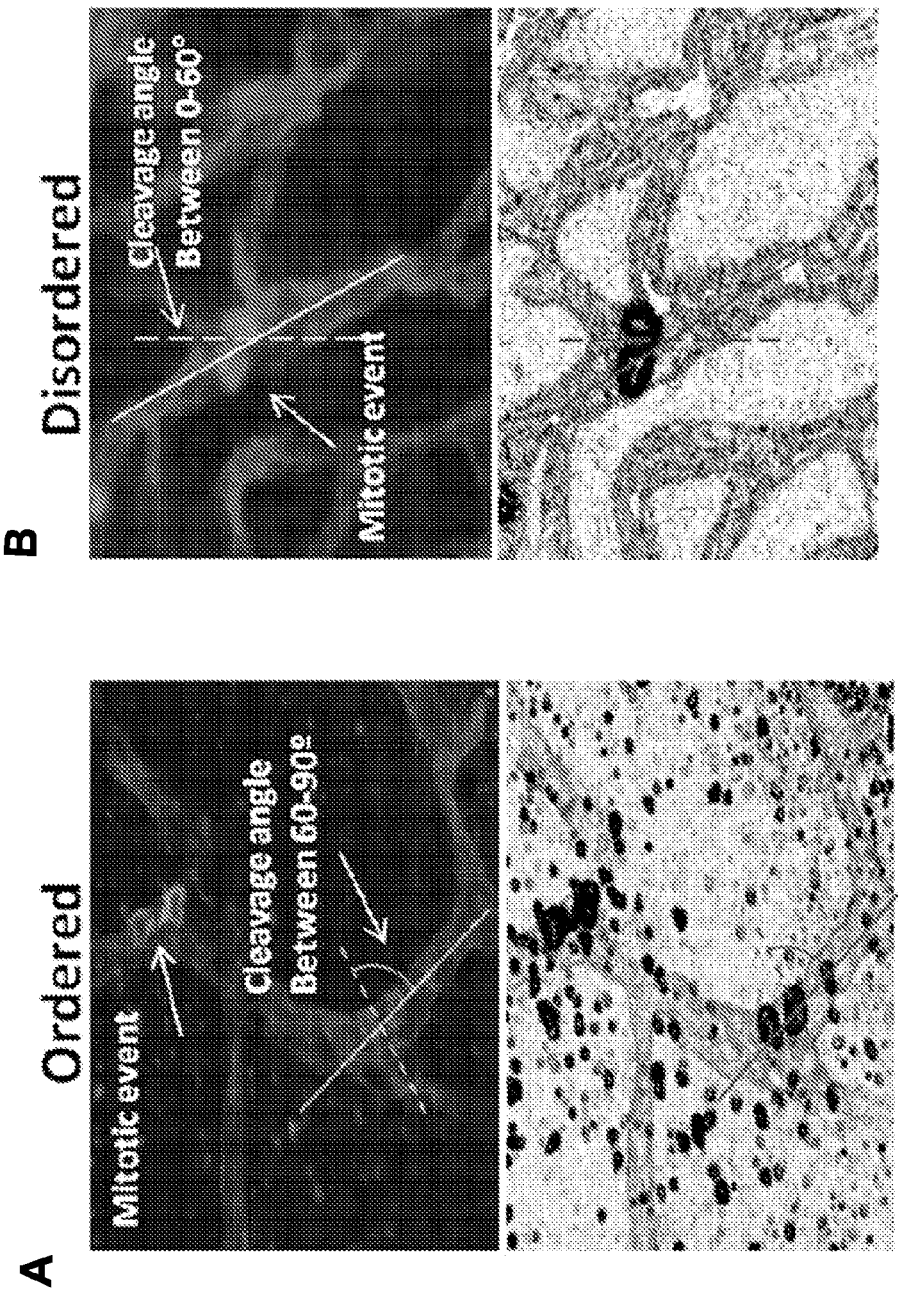
FIGS. 33A, 33B, 33C, and 33D show vascular endothelial growth factor-A.shRNA treatment reduces disordered angiogenesis in the ROP model. Diagram of cleavage angles produced from lectin-stained flat mounts colabeled for phosphohistone H 3 showing cells in anaphase: (A) cleavage angles between 60° and 90° predict ordered angiogenesis; (B) cleavage angles between 0° and 60° predict widened or disordered angiogenesis; (C) percentage of ECs with cleavage angles between 60° and 908; and (D) total number of mitotic figures determined as phosphohistone H3 labeled vascular ECs in retinal flat mounts from pups treated with luc.shRNA, VEGFA.shRNA, IgG, or anti-VEGF (*P<0.05 versus luc.shRNA, two-way ANOVA; results are means±SD).

Effects of Targeted VEGF Knockdown and Anti-VEGF on Number and Angle of Proliferating Vascular Endothelial Cells The orientation of dividing endothelial cells predicts whether the subsequent vessel is elongated, widened, or disordered. The data herein indicate that excessive signaling through VEGFR2 disordered the orientation of dividing daughter endothelial cells in an embryonic stem cell model and vascular cells leading to increased vessel tortuosity in the ROP model. Knockdown of Müller cell VEGFA with shRNA appeared to reduce retinal vascular tortuosity (FIG. 31) that occurred in the ROP model compared with anti-VEGF antibody post treatment. Therefore, targeted VEGFA knockdown in Müller cells can orient dividing endothelial cells into a more ordered physiologic pattern. To test this, retinal flat mounts from pups in the ROP model were labeled after treatment with VEGFA.shRNA, luc.shRNA, anti-VEGF, or IgG with lectin, and an antibody to anti-phosphohistone H3 that manifests mitotic figures in anaphase. The number of mitotic figures were counted and the cleavage angles between the long axis of lectin-labeled vessels and the cleavage plane drawn between phosphohistone H3-labeled figures were determined (FIGS. 33A, 33B). Cleavage angles between the cleavage planes of dividing cells and respective long axes of the vessels are expected to align closer to 90° (predicting elongation or physiologic angiogenesis; FIG. 33A) with targeted VEGFA knockdown, whereas angles away from 90° (predictive of widening or disordered angiogenesis; FIG. 33B) occur after nonspecific anti-VEGF treatment.

Figure 33C:
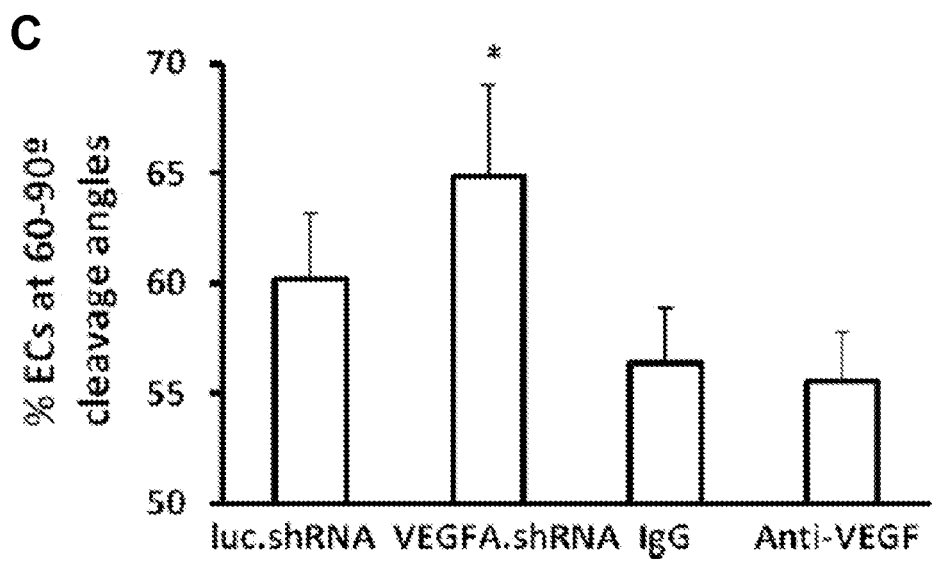
Figure 33D:
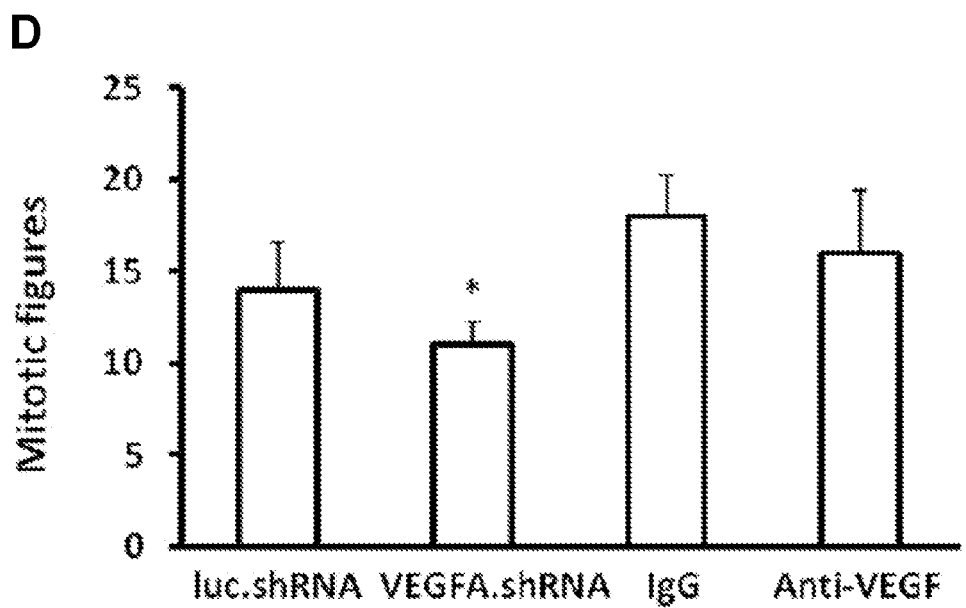

Angles were clustered into groups every 15° between 0° and 90°, and determined the absolute number of antiphosphohistone H3-labeled cells at the plane of the inner and deep plexi counted throughout retinal flat mounts. Most mitotic figures were found at the junctions between vascularized and avascular retina where IVNV occurs. Compared with luc.shRNA, the data indicate that VEGFA.shRNA treatment caused more mitotic figures clustered between 60° and 90°, predicting elongation and ordered angiogenesis (FIG. 33C). The data also indicate that the absolute number of dividing vascular cells was decreased following VEGFA.shRNA treatment compared with luc.shRNA (FIG. 33D). There was no difference in the percent of mitotic figures clustered between 60° and 90° and total mitotic figures between anti-VEGF and IgG (FIGS. 33C, 33D). In agreement with this, retinal flat mounts of inner plexi after each treatment and respective controls provided evidence that targeted overproduction of VEGF restored more normal retinal vascular morphology than did broad anti-VEGF inhibition (FIG. 31). Altogether, these data indicate that targeting overproduced VEGFA with the VEGFA.shRNA treatment restored ordered angiogenesis, whereas anti-VEGF treatment did not improve ordered angiogenesis.

Discussion:

In countries lacking resources to treat severe ROP, the use of intravitreal anti-VEGF antibodies has increased. However, there have been some reports of persistent avascular retina, recurrent IVNV, retinal detachment, and reduction in serum VEGF leading to concern about potential effects of intravitreal anti-VEGF on growth and development of preterm infants. The current guidelines for ROP treatment recommend longer follow-up after anti-VEGF treatment than for standard of care laser and only use of anti-VEGF agents for zone I stage 3+ severe ROP until more information on proper dose and safety is available. Many studies report inner plexus coverage determined by area of vascular extent as an outcome, whereas fewer have measured capillary density or the vascular extent of both inner and deep plexi. This study sought to determine the effects of different strategies to inhibit VEGF on physiologic retinal vascularization by measuring the intensity of pixel fluorescence of the inner and deep plexi in lectinstained retinal flat mounts, which provided data on capillary density and extent of these plexi. Compared with RA-raised pups of the same developmental age, the data indicate that the ROP model reduced vascular extent and density compared with normal development. This finding goes along with a previous study in which retinal hypoxia measured with Hypoxyprobe (HPI, Burlington, Mass.), which detects tissue where oxygen levels are about 1%, was increased in retinal flat mounts from p18 rat pups in the ROP model compared with RA-raised pups. Although vascular extent after treatment with either strategy to reduce VEGF was no different compared to untreated ROP, broad inhibition using an intravitreal antibody against rat VEGF at a dose shown to inhibit IVNV in the rat ROP model significantly reduced capillary density in both inner and deep retinal plexi compared with control IgG. In contrast, targeted VEGFA knockdown in Müller cells that overproduce VEGF increased capillary density in the deep plexus and did not inhibit capillary density in the inner plexus compared with luc.shRNA control. VEGF is a survival factor for endothelial cells and broad anti-VEGF needed to neutralize excess VEGF can adversely reduce VEGF essential to the survival of newly developed intraretinal capillaries. VEGF also has survival effects on retinal neurons and Müller glia, and it is increasingly clear that neurovascular interactions are important in retinovascular development and angiogenesis.

Finally, the data indicate that the number of dividing vascular cells was increased following treatment with anti-VEGF and the orientation of dividing cells predicted vessel widening or disordered angiogenesis instead of more physiologic elongation. If vascular cell divisions are disordered, they can divide outside the plane of the retina and into the vitreous as IVNV. Even though the change in area of IVNV was comparable after treatment with intravitreal anti-VEGFor subretinal VEGFA.shRNA compared with respective controls at p18 in the ROP model, it is possible that hypoxia from reduced capillary density was greater after anti-VEGF antibody and stimulated later recurrent intravitreal angiogenesis reported at p25. These findings can also lend insight into what occurs in some cases of human ROP when recurrent intravitreal angiogenesis occurs after treatment with intravitreal anti-VEGF antibody.

In summary, the data indicate that broad inhibition of VEGF was associated with reduced capillary density and led to disordered angiogenesis from retina that had too little capillary support and oxygenation. The data from these studies support the need for both greater knowledge of the effect of dose on developing angiogenesis as it relates to ROP as well as additional studies into targeted treatment of disordered angiogenesis causing IVNV.

Example 13

VEGFA Activates Erythropoietin Receptor and Enhances VEGFR1-Mediated Pathological Angiogenesis Summary:

Clinical and animal studies implicate erythropoietin (EPO) and EPO receptor (EPOR) signaling in angiogenesis. In the eye, EPO is involved in both physiological and pathological angiogenesis in the retina. This study examined whether EPOR signaling is important in pathological angiogenesis by using a rat model of oxygen-induced retinopathy that is representative of human retinopathy of prematurity. It was first shown that EPOR expression and activation were increased and that activated EPOR was localized to retinal vascular endothelial cells (ECs) in retinas at postnatal day 18 (p18), when pathological angiogenesis in the form of intravitreal neovascularization occurred. In human retinal microvascular ECs, EPOR was upregulated and activated by VEGF. Lentiviral-delivered shRNAs that knocked down Müller cell-expressed VEGF in the retinopathy of prematurity model also reduced phosphorylated EPOR (p-EPOR) and VEGFR2 (p-VEGFR2) in retinal ECs. In human retinal microvascular ECs, VEGFR2-activated EPOR caused an interaction between p-EPOR and p-VEGFR2; knockdown of EPOR by siRNA transfection reduced VEGF-induced EC proliferation in association with reduced p-VEGFR2 and p-STAT3; however, inhibition of VEGFR2 activation by siRNA transfection or semaxanib (SU5416) abolished VEGFA-induced proliferation of ECs and phosphorylation of VEGFR2, EPOR, and STAT3. The data show that VEGFA-induced p-VEGFR2 activates EPOR and causes an interaction between p-EPOR and p-VEGFR2 to enhance VEGFA-induced EC proliferation by exacerbating STAT3 activation, leading to pathological angiogenesis.

Introduction:

Retinopathy of prematurity (ROP) is an important cause of vision loss and blindness in infants worldwide. Because of the limited ability to study human preterm infant eyes, models have been established in which newborn animals that normally vascularize their retinas after birth are exposed to oxygen stresses that lead to retinal features similar to human ROP. Based on such models of oxygen-induced retinopathy (OIR) and on observations in human infants, ROP has been described as having two phases. In phase I, infants experience delayed physiological retinal vascular development and sometimes vasoattenuation from high oxygen. Phase II is characterized by aberrant disordered developmental angiogenesis in the form of vasoproliferative intravitreal neovascularization (IVNV). Several angiogenic agonists and inhibitors have been recognized as potentially involved in human ROP. Of these, the most studied is vascular endothelial growth factor A (VEGFA).

Besides being involved in human pathological angiogenic eye disease, VEGFA is also important in retinal vascular development. Inhibition of the bioactivity of VEGFA in preterm infants with severe ROP reduced the IVNV of phase II, but reports of persistent avascular retina and recurrent pathological angiogenesis raised concern. Furthermore, neutralizing VEGFA with an antibody similar to that used in human preterm infants with severe ROP initially reduced IVNV in the rat ROP model, but caused recurrent pathological angiogenesis in association with up-regulation of several angiogenic agonists, including erythropoietin (EPO).

EPO is known mainly for hematopoiesis, and it has been used to treat anemia. However, a growing body of evidence indicates that EPO has other biological effects, including neuroprotective, antiapoptotic, antioxidative, and angiogenic properties. Evidence supporting the role of EPO in angiogenesis comes from clinical and animal studies. In clinical studies, proliferative diabetic retinopathy and severe ROP have been associated with increased EPO. In proliferative diabetic retinopathy, vitreous EPO was increased, and a promoter polymorphism in the EPO gene resulting in increased production of EPO was associated with severe diabetic retinopathy in a largely European-American population. In ROP, greater risk of severe ROP was associated with EPO treatment for anemia of prematurity. In a mouse OIR model, hyperoxia down-regulated EPO expression in the retina and decreased vascular stability in association with vaso-obliterated retina, and, after relative hypoxia, retinal EPO was increased and contributed to IVNV. EPO was also identified as a target in OIR in a study using a transgenic mouse in which hypoxia inducible factor 2a (HIF-2a; alias HLF, EPAS-1) was knocked down, and EPO synergistically increased VEGFA-induced human retinal microvascular endothelial cell (hRMVEC) proliferation. However, EPO also promoted physiological retinal vascularization in a rat OIR model. Thus, the evidence is mixed, in that EPO has been associated with both physiological and pathological retinal angiogenesis. EPO is now being considered as a neuroprotective agent to promote cognitive development in preterm infants. Greater understanding is needed regarding EPO and EPO receptor (EPOR) signaling in ROP and developmental angiogenesis.

In the present study, a rat ROP model in which VEGFA is overexpressed by postnatal day 8 (p8) and causes IVNV at p18 was used. The VEGFA signal is detected in Müller cells, and a method using a lentiviral vector that targets Müller cells and knocks down VEGFA in vivo, thereby inhibiting IVNV without interfering with pup growth or serum VEGFA was developed. The present investigation of the role of EPOR adapted this lentiviral vector rat model. In phase I, EPOR activation was lower than in phase II, when VEGFA expression and VEGFR2 expression and activation were increased. In hRMVECs, VEGFA up-regulated and activated EPOR and (through crosstalk between activated VEGFR2 and EPOR) increased the activation of STAT3 to enhance angiogenesis. The data herein indicate that VEGFA activates and causes an interaction between EPOR and VEGFR2 to contribute to pathological angiogenesis.

Materials and Methods:

Rat ROP Model

A parallel to the OIR model in mouse, the rat ROP model used in this study has been described herein. Within 6 hours of birth, newborn Sprague-Dawley pups and dam (Charles River Laboratories International, Wilmington, Mass.) were placed into a regulated oxygen environment (OxyCycler; BioSpherix, Lacona, N.Y.) in which oxygen was cycled between 50% and 10% every 24 hours for 14 days, and then into ambient room air (RA) for 4 days. Phase I, delayed physiological retinal vascular development, occurred at p14 and phase II, IVNV, at p18. For each study, at least three different litters were analyzed for immunohistochemistry, quantitative real-time PCR (qPCR), or Western blotting; all litters had between 12 and 14 pups.

For knockdown of Müller cell VEGFA, a lentivirus with a CD44 promoter that drives GFP and VEGFA shRNA when embedded within a microRNA30 context was used. A subretinal injection of 1 mL of lentivirus (1×10⁹ viral particles per milliliter) with either VEGFA shRNA or control luciferase shRNA was delivered at the beginning of the 50% oxygen cycle of the ROP model, on p8, as described herein. Each pup received the same type of lentivector in each eye, to reduce the potential for confounding from crossover effects. Eyes were processed for immunohistochemistry of phosphorylated VEGFR2 (p-VEGFR2), or EPOR (p-EPOR) and lectin.

Retinal Section Preparation and Staining

Anterior segments were removed from eyes after 10 minutes of fixation in 4% paraformaldehyde (Electron Microscopy Sciences, Hatfield, Pa.); retinas were carefully dissected and placed into 4% paraformaldehyde for another 15 minutes, followed by overnight incubation in 30% sucrose. After immersion in optimal cutting temperature compound [Tissue-Tek OCT (Sakura Finetek, Torrance, Calif.); Electron Microscopy Sciences, Hatfield, Pa.], retinas were cut into 12 µm cryosections. Sections were incubated with rabbit anti-p-VEGFR2 (1:50; Abcam, Cambridge, Mass.) or anti-p-EPOR (1:50; Santa Cruz Biotechnology, Dallas, Tex.) overnight at 44° C. After rinsing, sections were incubated for 1 hour with FITC-conjugated goat anti-rabbit secondary antibody (1:200; Jackson ImmunoResearch Laboratories, West Grove, Pa.) and Alexa Fluor 594-conjugated antibody for isolectin B4 (lectin) (1:500; Life Technologies, Carlsbad, Calif.), to stain vessels. Sections stained without primary antibodies were used as controls. Labeling for all sections was performed during the same experiment session. Images were captured using confocal microscopy (Olympus IX81; Olympus, Tokyo, Japan) at ×20 or ×40 magnification.

Cell Culture, Transfection, and Proliferation Assay hRMVECs (Cell Systems, Kirkland, Wash.) were maintained in EGM-2 endothelial growth medium (Lonza, Walkers-ville, MD) supplemented with 5% fetal bovine serum. Cells of passage 3 to 5 were used for experiments. Confluent cells in six-well plates were starved for 16 hours and then treated with 20 ng/mL VEGFA or PBS for 24 hours for qPCR or 30 minutes for p-VEGFR2, p-EPOR, and p-STAT3.

For siRNA transfection, hRMVECs at 70% confluency were transfected in six-well plates with siRNAs targeting human EPOR, VEGFR2, or STAT3 (Life Technologies, Carlsbad, Calif.) using Lipofectamine 2000 reagent (Invitrogen by Life Technologies, Carlsbad, Calif.). A silencer selective negative control siRNA was used as control.

For cell proliferation assays, hRMVECs were plated into 96-well plates at a density of 5000 cells per well. At 24 hours after transfection with siRNA, cells were starved in serum-free medium for 24 hours and then were incubated with 20 ng/mL VEGFA or control PBS for another 24 hours. To inhibit VEGFR2 or STAT3 activation, cells were pretreated with 5 µmol/L of the VEGFR2 tryosine-kinase inhibitor semaxanib (SU5416), 10 µmol/L of the JAK2/STAT3 inhibitor AG490 (both from Sigma-Aldrich, St. Louis, Mo.), or dimethyl sulfoxide (DMSO) vehicle control for 1 hour before addition of VEGFA. Cell number was measured with a Vybrant MTT cell proliferation assay kit (Life Technologies, Carlsbad, Calif.).

RNA Isolation and qPCR Analysis

Total RNA of cells was extracted by TRI Reagent (Sigma-Aldrich, St. Louis, Mo.). For dissected retinas, total RNA was extracted using an RNeasy mini kit (Qiagen, Valencia, Calif.). RNA was quantified using a NanoDrop spectrophotometer (Thermo Fisher Scientific, Waltham, Mass.). cDNA was generated with the use of a high-capacity cDNA archive kit (Life Technologies, Carlsbad, Calif.). qPCR was performed on a Mastercycler ep realplex system (Eppendorf, Hauppauge, N.Y.) with the use of SYBR Green master mix (Roche Diagnostics, Indianapolis, Ind.) and primers synthesized by the core research facility of the University of Utah. Expression levels for VEGFA were normalized to the mean value of internal control β-actin. The primers (forward and reverse, respectively) were rat EPOR 5'-CATTCTCGTCCT-CATCTCACTG-3' and 5-AACTCATTCTCTG-GGCT-TGG-3', and human EPOR 5'-CCCCAAGTTCGAGAG-CAAAG-3' and 5'-GGTAGG-AGAAGCTGTAGTTGC-3'.

Protein Extraction and Western Blot Analysis

Dissected retinas and hRMVECs were lysed in radioimmunoprecipitation assay buffer with 1:100 protease inhibitors (Roche Diagnostics, Indianapolis, Ind.) and 2 mmol/L sodium orthovanadate and were homogenized and centrifuged at 13,000 rpm (15,700 g) for 10 minutes at 4° C. Total protein in the supernatant fluid was quantified by a bicinchoninic acid assay (Pierce BCA; Thermo Fisher Scientific, Waltham, Mass.). Membranes were incubated overnight at 4° C. with primary antibodies to p-STAT3 and total STAT3 (1:1000; Cell Signaling Technology, Danvers, Mass.), p-EPOR and total EPOR (1:500; Santa Cruz Biotechnology, Dallas, Tex.) and p-VEGFR2 and total VEGFR2 (1:500; Santa Cruz Biotechnology, Dallas, Tex.). Blots were visualized, and the relative densities of bands were calculated as described herein, using gel analysis software (UN-SCAN-IT gel, version 6.1; Silk Scientific, Orem, Utah). Relative activities were calculated as the ratio of phosphorylated to total protein or to β-actin and are expressed as fold difference compared with control. At least six samples from each group were measured and analyzed.

Statistical Analysis

Significant differences between treatment groups were determined by one-way analysis of variance using the Newman-Keuls multiple comparison post hoc test or a two-way analysis of variance for grouped comparison. A minimum value of P<0.05 was considered statistically significant. For proliferation assays, experiments were performed three times with n=3 per condition in each experiment. For qPCR and protein analyses, six individual samples were used (sometimes pooled from retinas of pups from the same group).

Figures 34A, 34B, 34C:
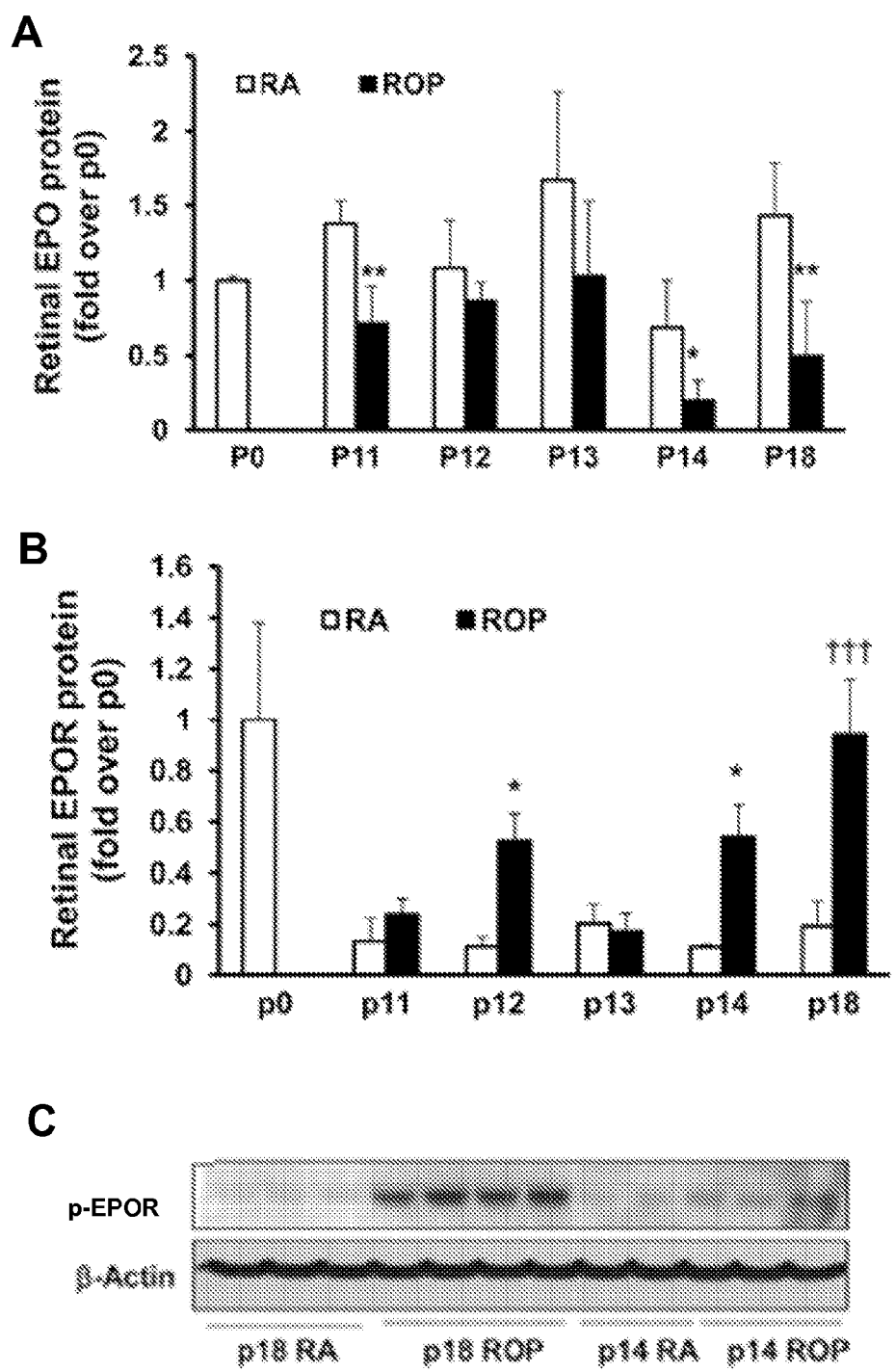
FIGS. 34A, 34B, 34C, 34D, 34E, and 34F show that EPOR expression and activation increased in vascular endothelium in the rat ROP model. A and B: Protein analyses for EPO (A) and EPOR (B) in retinas from rat pups raised in room air (RA) and ROP model pups at time points from baseline to p18. C and D: Representative Western blots of p-EPOR in retina at p14 and p18 (C) and quantification of gels (D). E and F: Immunohistochemical staining of p-EPOR (E) or p-VEGFR2 (F) colabeling with lectin in retinal cryosections at p18. The boxed region in each upper row corresponds to the adjacent image at higher magnification in the lower row. The arrows show the co-labeling. Data are expressed as means±SD (A and B) or as individual data points with means±SD (D). *P<0.05, Q20 **P<0.01 versus RA at the same developmental age. †††P<0.001, overall analysis of variance. Scale bars: 50 µm (E and F, upper rows); 10 µm (E and F, lower rows). GCL, ganglion cell layer; INL, inner nuclear layer; ONL, outer nuclear layer.

Results:

EPOR Expression and Activation is Increased in Retinal Vascular Endothelium in Association with IVNV in Rat ROP Model The data indicate that exogenous EPO restored developmental retinal vascularization by 40%. In addition, pathological angiogenesis recurred in the rat ROP model after treatment with anti-VEGFA antibody, in association with increased retinal EPO. These observations indicate a role for EPO in angiogenesis associated with the ROP model. To assess EPO signaling, the expression of retinal EPO and EPOR at several time points were measured, including phase I (p14) and phase II (p18) in the rat ROP model and in RA-raised control pups of the same developmental ages. Compared with RA, EPO protein was significantly decreased in the ROP model at p14 and p18 (FIG. 34A); this is in contrast to retinal VEGFA, which is significantly increased at both p14 and p18 in the ROP model. Also, compared with RA, EPOR protein was significantly increased in the ROP model at p14 and p18 (FIG. 34B). To determine whether EPOR was activated in the ROP model, Western blots were performed using anti-p-EPOR antibody. p-EPOR was increased in the retina in the ROP model at p18, but not at p14, compared with RA (FIGS. 34C, 34D).

Figures 34D, 34E:
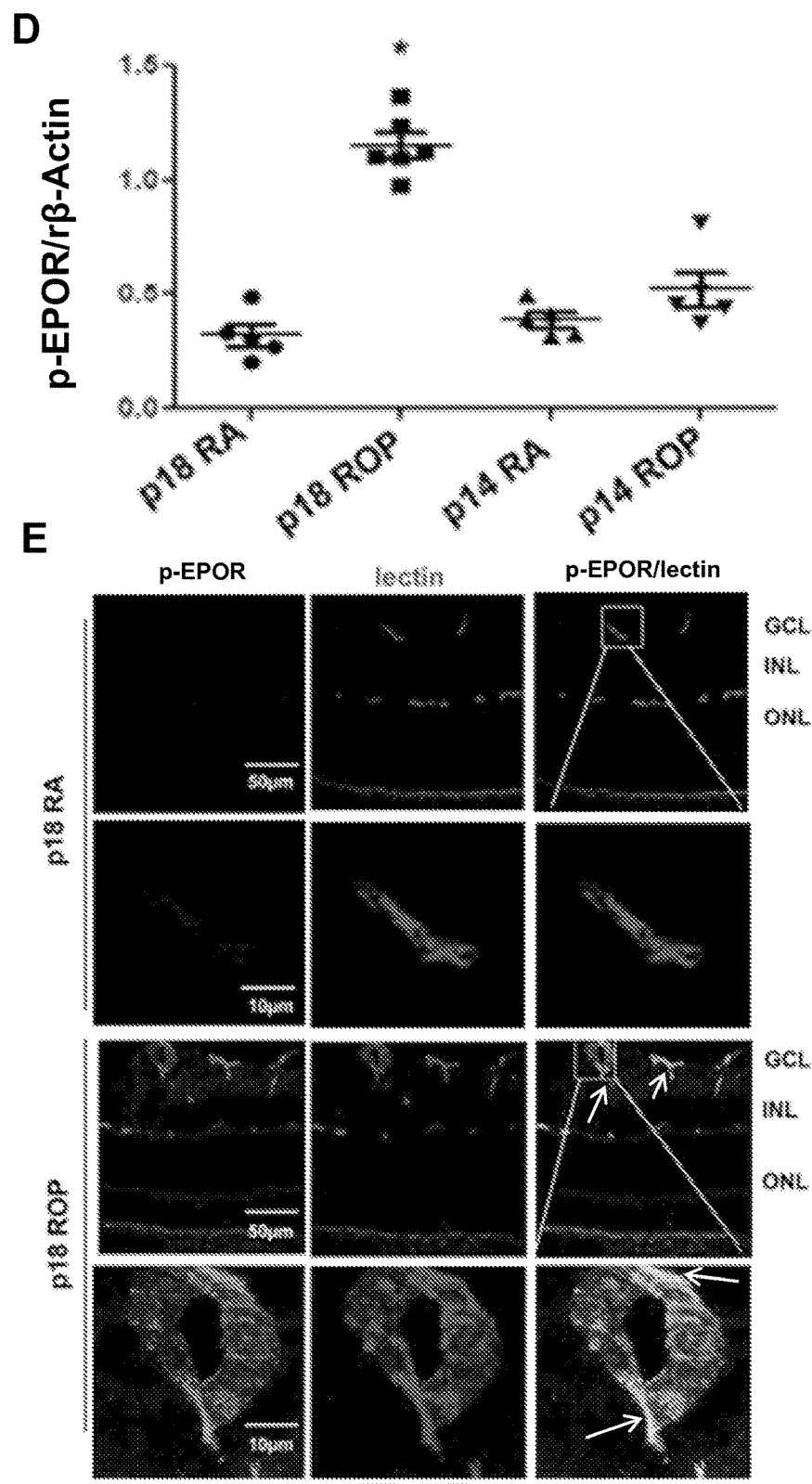
Figure 34F:
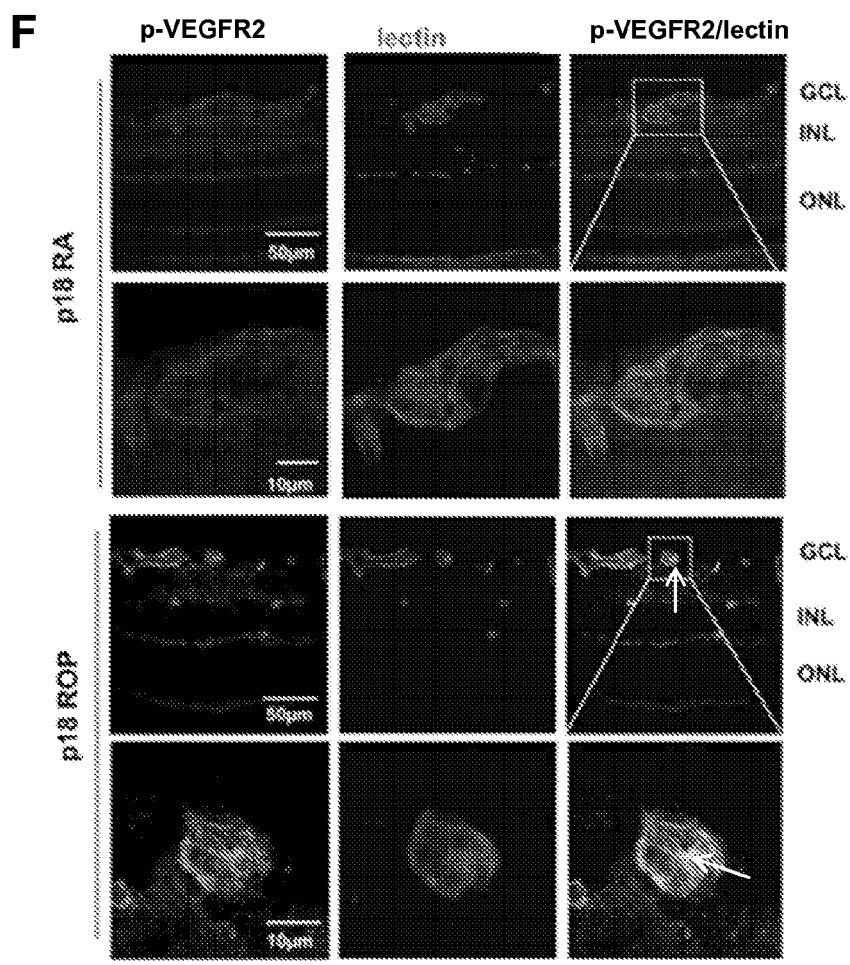

To determine the localization of EPOR activation, cryosections from RA and ROP retinas from p18 pups were colabeled with p-EPOR and lectin to stain vascular cells and, in adjacent sections, with p-VEGFR2 and lectin. p-EPOR colabeling with lectin was not strong at p18 in RA sections, but colabeled vessels were apparent at p18 in the ROP model (FIG. 34E). By contrast, p-VEGFR2 colabeled with lectin-stained vessels in both RA and ROP sections, and appeared qualitatively greater in the ROP model (FIG. 34F). Taken together, these results indicate that, like VEGFR2, EPOR is activated in ECs in the ROP model during phase II, when IVNV occurs.

EPOR in ECs is Up-Regulated and Activated by VEGFA

Figure 35A:
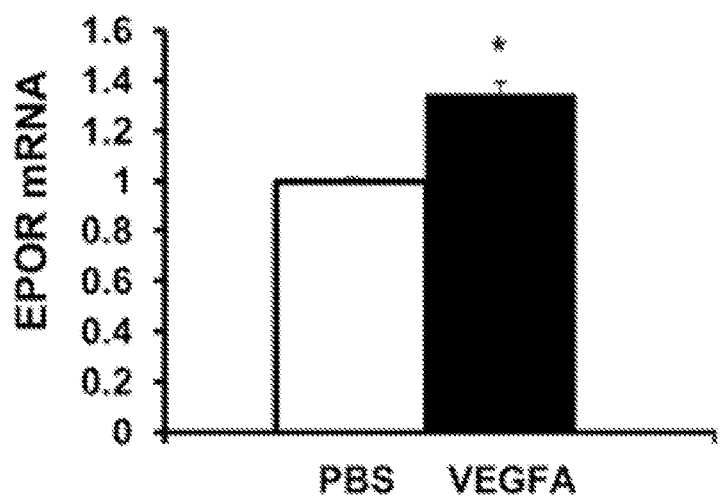
FIGS. 35A, 35B, 35C, 35D, 35E, and 35F show that EPOR is up-regulated and activated by VEGFA in vitro and in vivo. A and B: qPCR of human EPOR (A) and Western blots of EPOR protein in hRMVECs stimulated by 20 ng/mL VEGFA or 10 IU/mL EPO for 18 hours (B). Human β-actin was used as an internal control. C: Western blots of p-EPOR and total EPOR in hRMVECs stimulated with 20 ng/mL VEGFA or PBS for 30 minutes. D and E: Quantification of Western blots of p-VEGFR2 (D) and p-EPOR (E) in retina. F: IHC of p-VEGFR2 or p-EPOR colabeled with lectin in retinal sections from rat pups injected with lentivirus-delivered luciferase shRNA (Luc.shRNA) or VEGFA shRNA (VEGFA.shRNA) at p18 in rat ROP model. Arrows show co-localization. Negative controls are shown in Supplemental Figure S1B. Data expressed as means±SD, representative of three or more independent experiments. n=6. *P<0.05 versus control. Scale bar=50 µm.
Figure 35B:
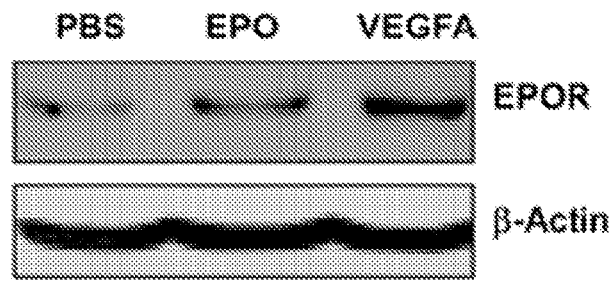
Figure 35C:
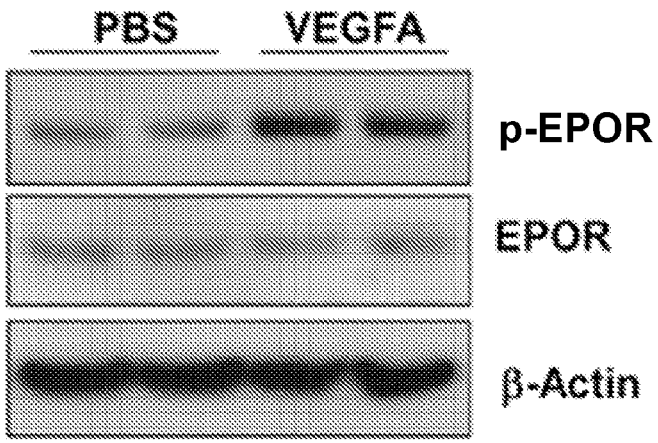

The oxygen levels used in the ROP model result in retinal hypoxia, as indicated by increased conjugated pimonidazole compared with RA. Hypoxia induces HIF stabilization, which allows transcription of angiogenic factors, including VEGFA or EPO. In the ROP model, retinal VEGFA is increased at p14, compared with RA counterparts. By contrast, EPO protein was decreased during phase I (p14) (FIG. 34A). Because both EPOR and VEGFR2 were activated in phase II, these findings raised the question of whether activation of EPOR in retinal ECs in the ROP model is affected by VEGFA. Therefore, hRMVECs were stimulated with VEGFA and EPOR expression and activation was measured. Compared with PBS control, VEGFA increased EPOR mRNA expression (FIG. 35A) and protein levels (FIG. 35B) after overnight VEGFA treatment. VEGFA activated VEGFR2, beginning at 5 minutes of treatment; EPOR peaked at 30 minutes of treatment (FIG. 35C), and STAT3 activation began at 30 minutes and peaked at 60 minutes of treatment. Therefore, 30 minutes of stimulation with VEGFA was chosen for subsequent analyses of VEGFR2, EPOR, and STAT3 activation in the same cell lysate. Overnight treatment with 10 IU/mL EPO in hRMVECs also led to an increase in EPOR protein (FIG. 35B), but the induction of EPOR by EPO was less than with VEGFA treatment; furthermore, 30 minutes of EPO treatment did not increase p-EPOR and p-VEGFR2 levels.

Figure 35D:
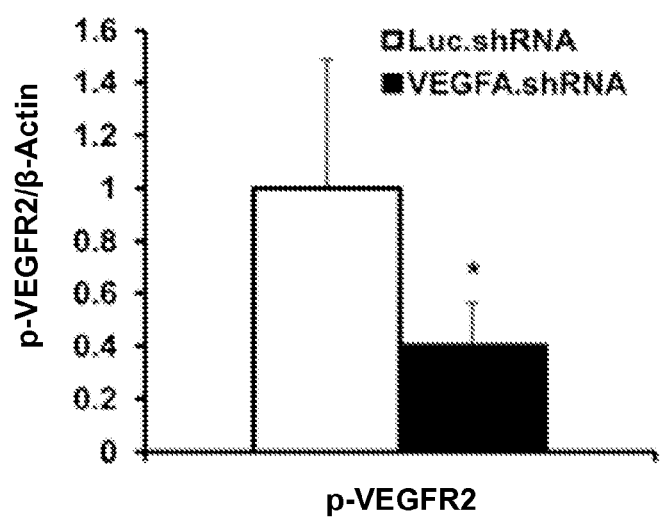
Figure 35E:
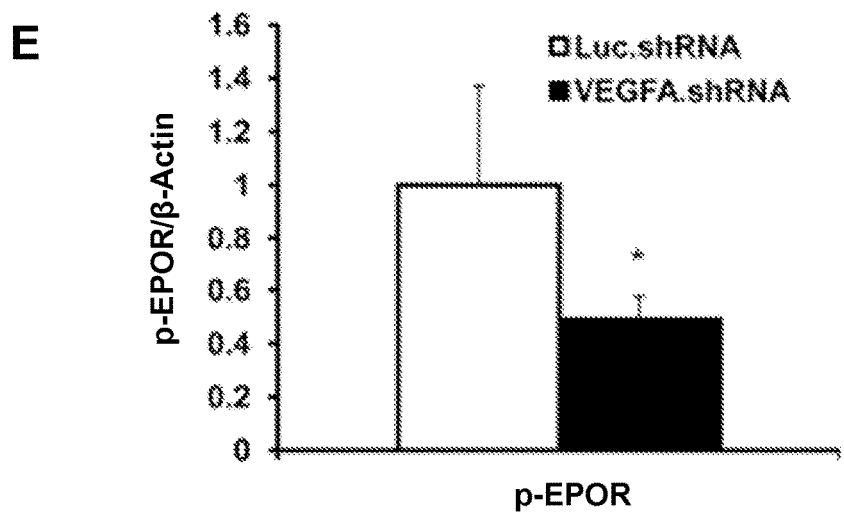
Figure 35F:
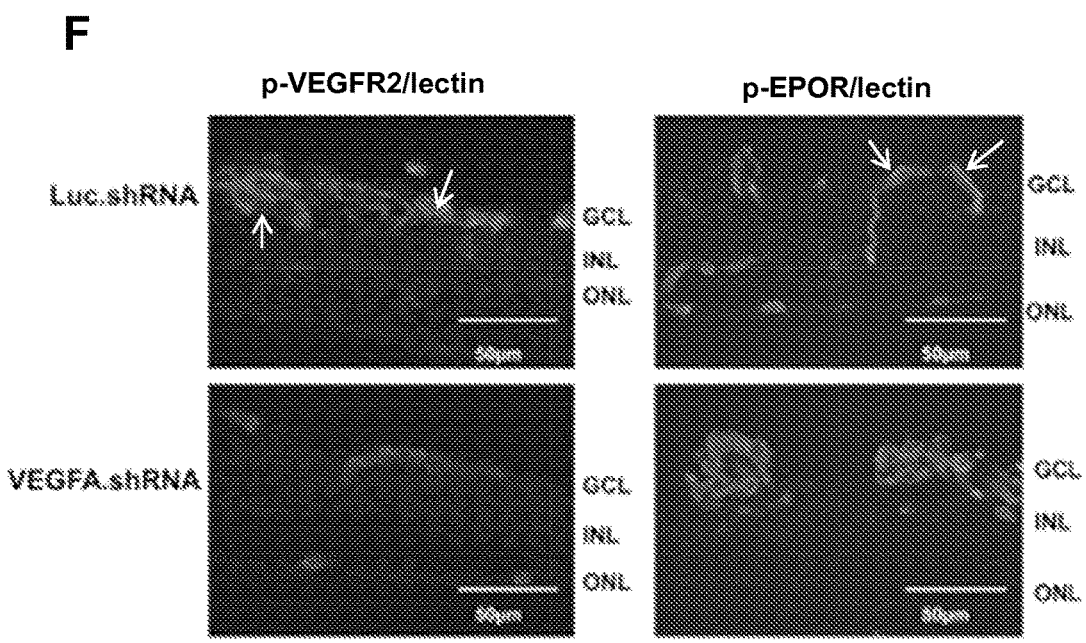

A lentivector gene therapy strategy was developed to knock down overexpressed VEGFA in Müller cells in the rat ROP model. Retinal VEGFA was reduced to levels observed in the retina of RA-raised pups, and VEGFR2 activation was inhibited in vascular ECs, in association with reduced phase II IVNV. To assess whether knockdown of Müller cell-derived VEGFA reduces activated EPOR in the rat ROP model, retinal lysates and retinal sections from p18 rat pup eyes in the ROP model that were knocked down for Müller cell VEGFA with a subretinal lentivector-driven shRNA were analyzed. Compared with the control luciferase shRNA treatment, knockdown of Müller cell VEGFA reduced p-VEGFR2 (FIG. 35D) in retinal lysates and reduced colabeling of p-VEGFR2 with lectin-stained ECs in retinal sections (FIG. 35F). In the same retinas, p-EPOR in retinal lysates (FIG. 35E) and colabeling with lectin in sections were also significantly reduced, compared with the respective luciferase shRNA controls (FIG. 35F). These findings provide strong evidence that inhibiting VEGFA reduces p-VEGFR2 and p-EPOR in vascular endothelial cells in the ROP model.

Activation of EPOR by VEGFA Enhances VEGFA-Mediated EC Proliferation

Figures 36A, 36B:
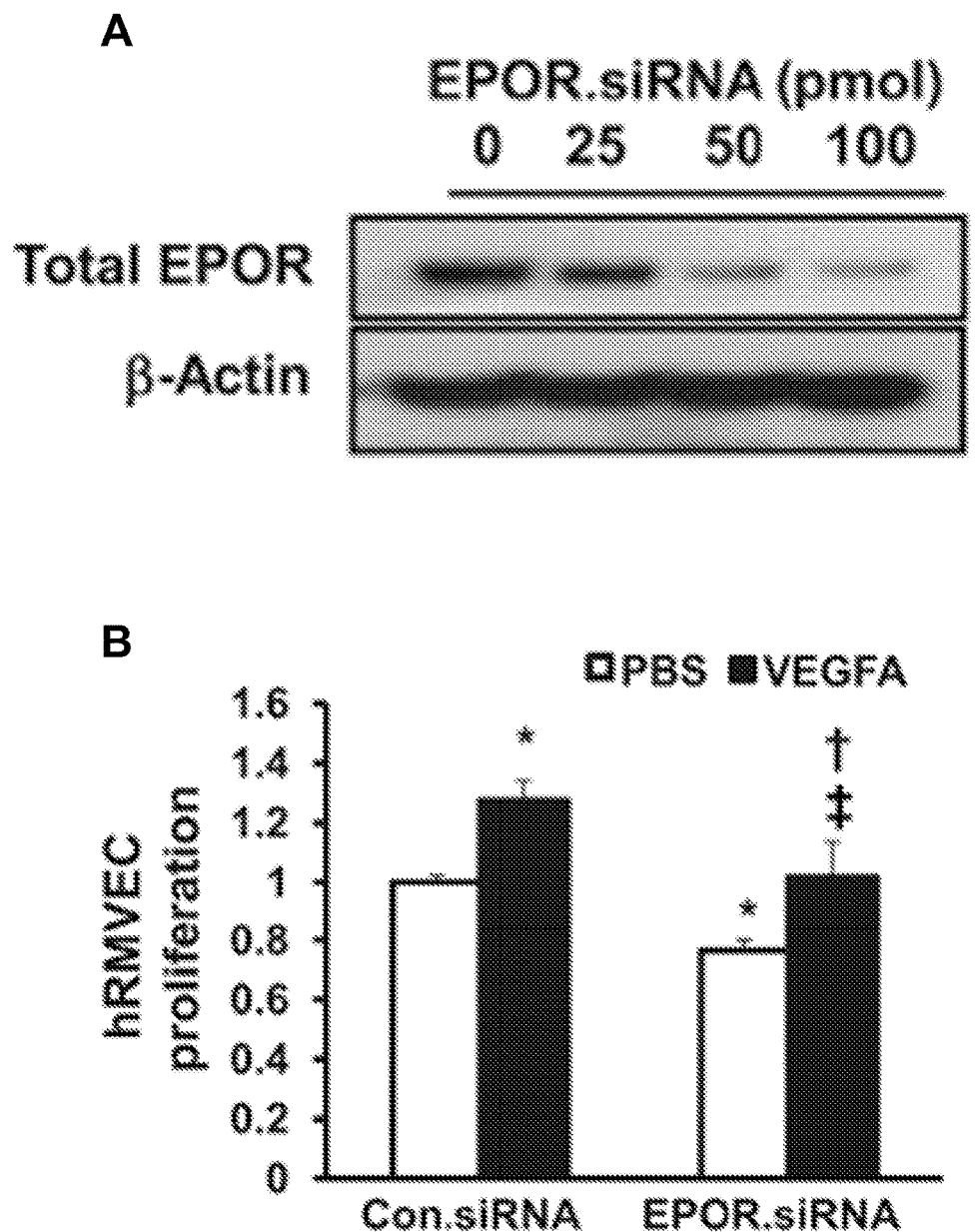
FIGS. 36A, 36B, 36C, and 36D show that the knockdown of EPOR reduces VEGFA-induced EC proliferation, and inhibition of VEGFR2 activation inhibits it, in hRMVECs. A: Western blots of total EPOR in hRMVECs transfected with 0 to 100 pmol EPOR siRNA. B-D: VEGFA-induced proliferation assay in hRMVECs transfected with control siRNA (Con.siRNA) or EPOR siRNA (B), in hRMVECs treated with SU5416 (C), and in hRMVECs transfected with Con.siRNA or VEGFR2 siRNA (D). Data are expressed as means±SD, representative of three or more independent experiments. *P<0.05 versus PBS of Con.siRNA (B and D). †P<0.05 versus VEGFA of Con.siRNA (B and D); ‡P<0.05 versus PBS of EPOR.siRNA (B). §§§ P<0.001 versus PBS of DMSO (C). ¶¶¶P<0.001 versus VEGFA of DMSO (C).
Figure 36C:
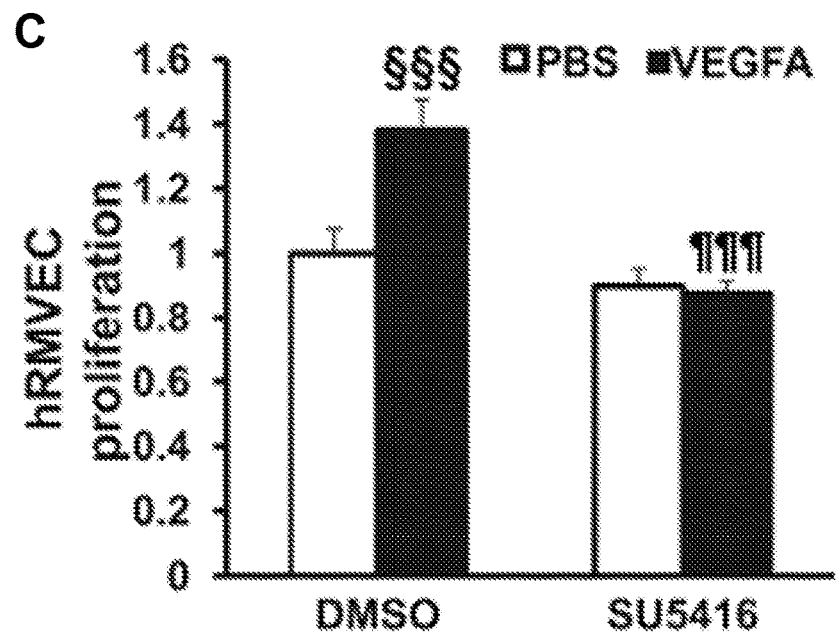
Figure 36D:
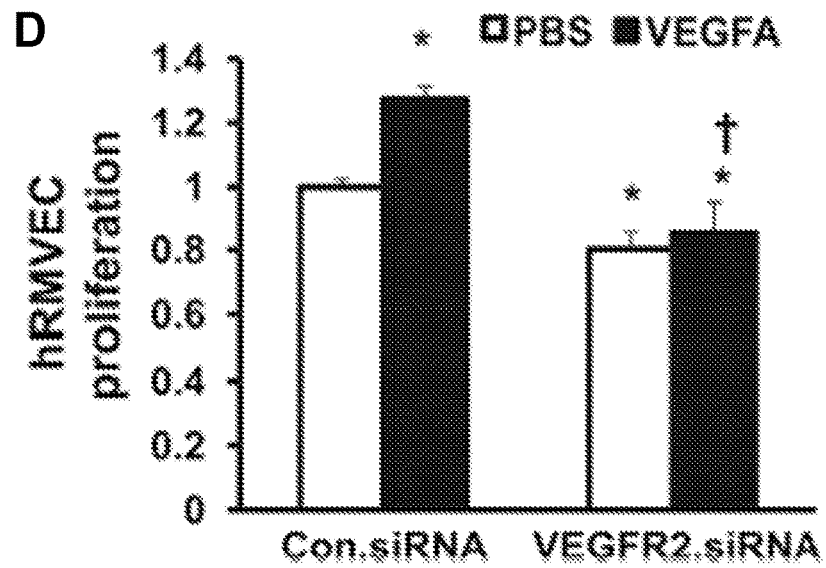

EPOR-rescued mice were reported to have a significant reduction in ischemia-induced VEGFA and VEGFR2 expression. The data herein also indicate that crosstalk exists, but that VEGFA-VEGFR2 signaling can regulate EPOR expression and activation. To assess crosstalk between EPOR and VEGFR2, hRMVECs were transfected with EPOR siRNA or control siRNA and then stimulated with VEGFA or PBS (control). EPOR siRNA significantly reduced total EPOR in a dose-dependent pattern (FIG. 36A), achieving maximum reduction at 50 pmol EPOR siRNA; this dose was used for the later experiments. The study then examined whether knockdown of EPOR affects VEGFA-induced EC proliferation. Compared with hRMVECs transfected with control siRNA, VEGFA-induced hRMVEC proliferation was partially reduced after EPOR siRNA transfection (FIG. 36B). By contrast, inhibition of VEGFR2 by the VEGFR2 inhibitor SU5416 (FIG. 36C) or by siRNA transfection (FIG. 36D) abolished VEGFA-induced proliferation. These results indicate that VEGFA-activated EPOR augments EC proliferation caused by stimulation with VEGFA, but that knockdown of EPOR does not fully abolish VEGFA-induced EC proliferation.

Activation of EPOR Interacts with VEGFR2 to Regulate STAT3 Activation

Figures 37A, 37B:
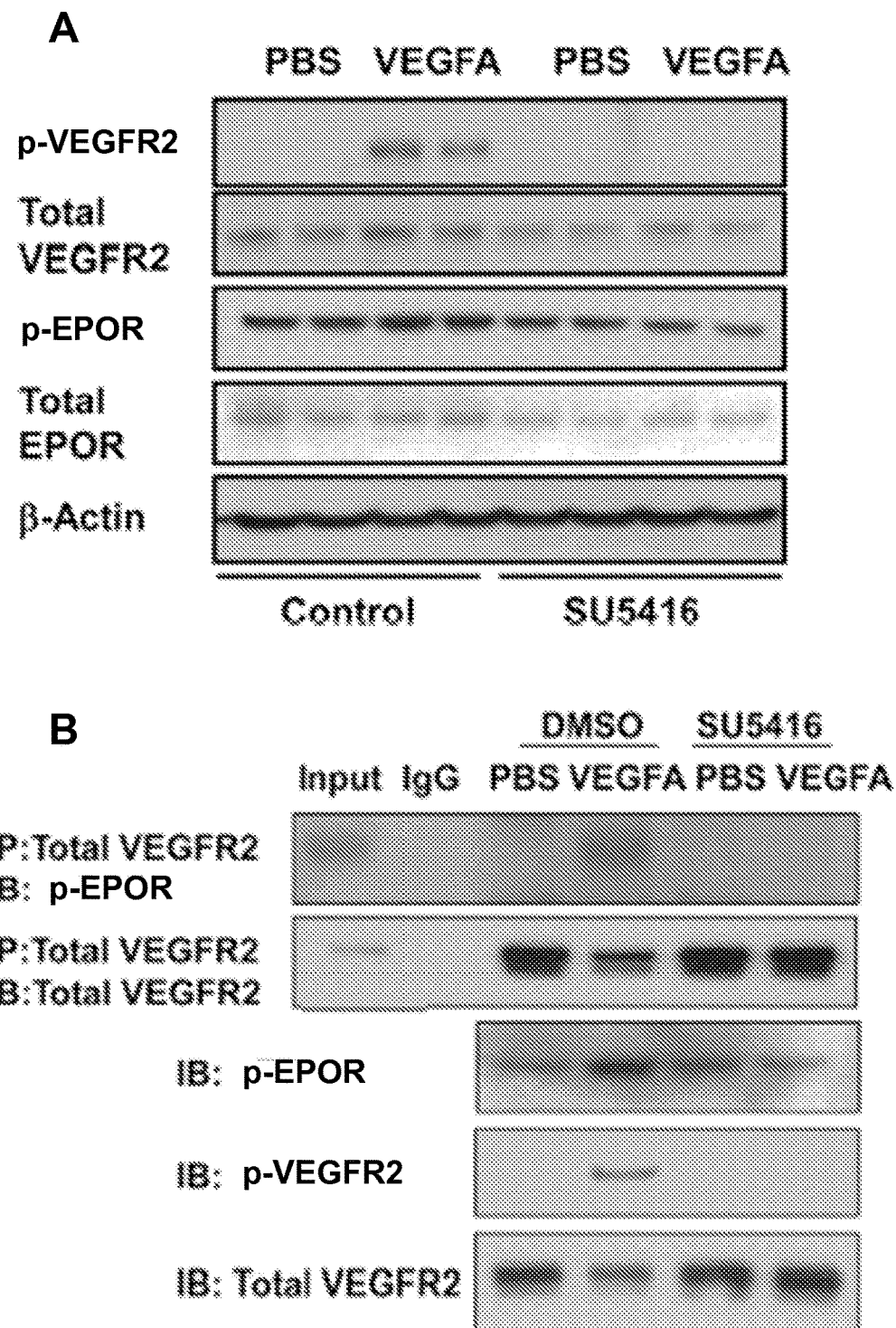

One means whereby EPOR can affect VEGFA-induced angiogenesis is through an interaction between the receptors. To determine whether there was an interaction between activated EPOR and VEGFR2, coimmunoprecipitation of EPOR and VEGFR2 was determined after stimulation with VEGFA or PBS control. After stimulation with VEGFA, both p-VEGFR2 and p-EPOR levels increased (FIG. 37A), compared with control, and in the same cell lysate coimmunoprecipitation of VEGFR2 and p-EPOR likewise increased (FIG. 37B). Activation of VEGFR2 led to reduced total VEGFR2 in lysates, which is believed to represent increased ubiquitinization of VEGFR2 on activation of the receptor. To determine whether VEGFR2 activation is required for the interaction of p-EPOR and VEGFR2, hRMVECs were pretreated with the VEGFR2 inhibitor SU5416 for 1 hour before stimulation with VEGFA. SU5416 effectively blocked VEGFA-induced p-VEGFR2 and also p-EPOR (FIG. 37A). In the same cell lysate, the VEGFA-induced coimmunoprecipitation of p-EPOR and VEGFR2 was abolished by pre-treatment with the SU5416 (FIG. 37B). hRMVECs transfected with EPOR siRNA failed to exhibit VEGFA-induced phosphorylation of EPOR or an interaction between p-EPOR and p-VEGFR2 (FIG. 37C). These findings support the notion that an interaction between the receptors occurs in response to VEGFA and that activation of either receptor is needed for the interaction.

Based on the findings that VEGFA-mediated EC proliferation was augmented through EPOR, signaling pathways affected by EPOR or VEGFR2 activation were examined. An ROP model with supplemental oxygen (ROP+SO model), originally developed by Berkowitz and Zhang, was used in which rat pups are placed into 28% instead of 21% oxygen after repeated fluctuations in oxygen concentration as a way to study the role of supplemental oxygen in ROP. The data indicated that the 28% oxygen reduces total retinal VEGFA, compared with the standard 21% oxygen model. By using the 28% oxygen model, signaling effects dominated by VEGFA-induced signaling were unmasked and activation of STAT3 was found to be important in phase II IVNV in the ROP+SO model. The present study, therefore, focused on EC-activated STAT3.

Figure 38C:
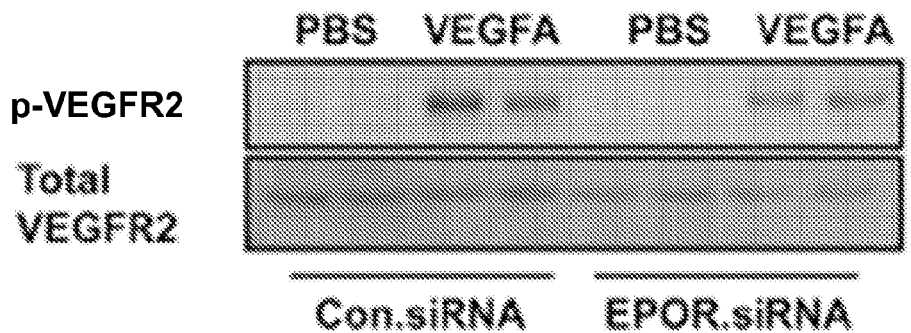
Figure 38D:
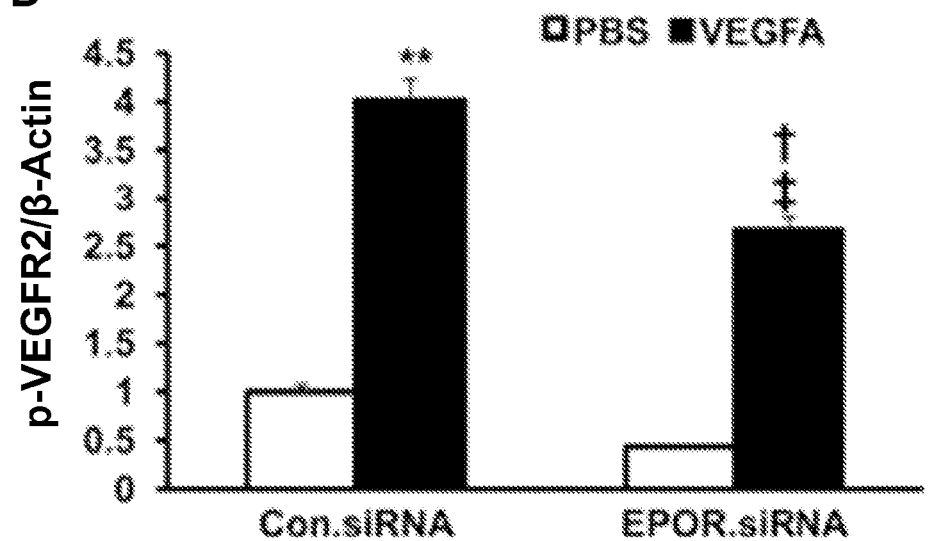
Figure 38E:
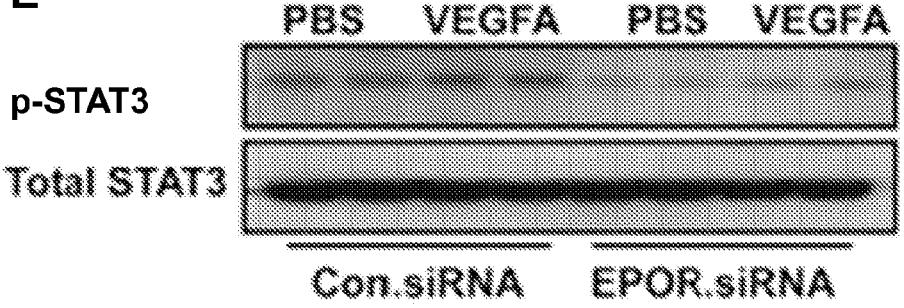
Figures 39C, 39D:
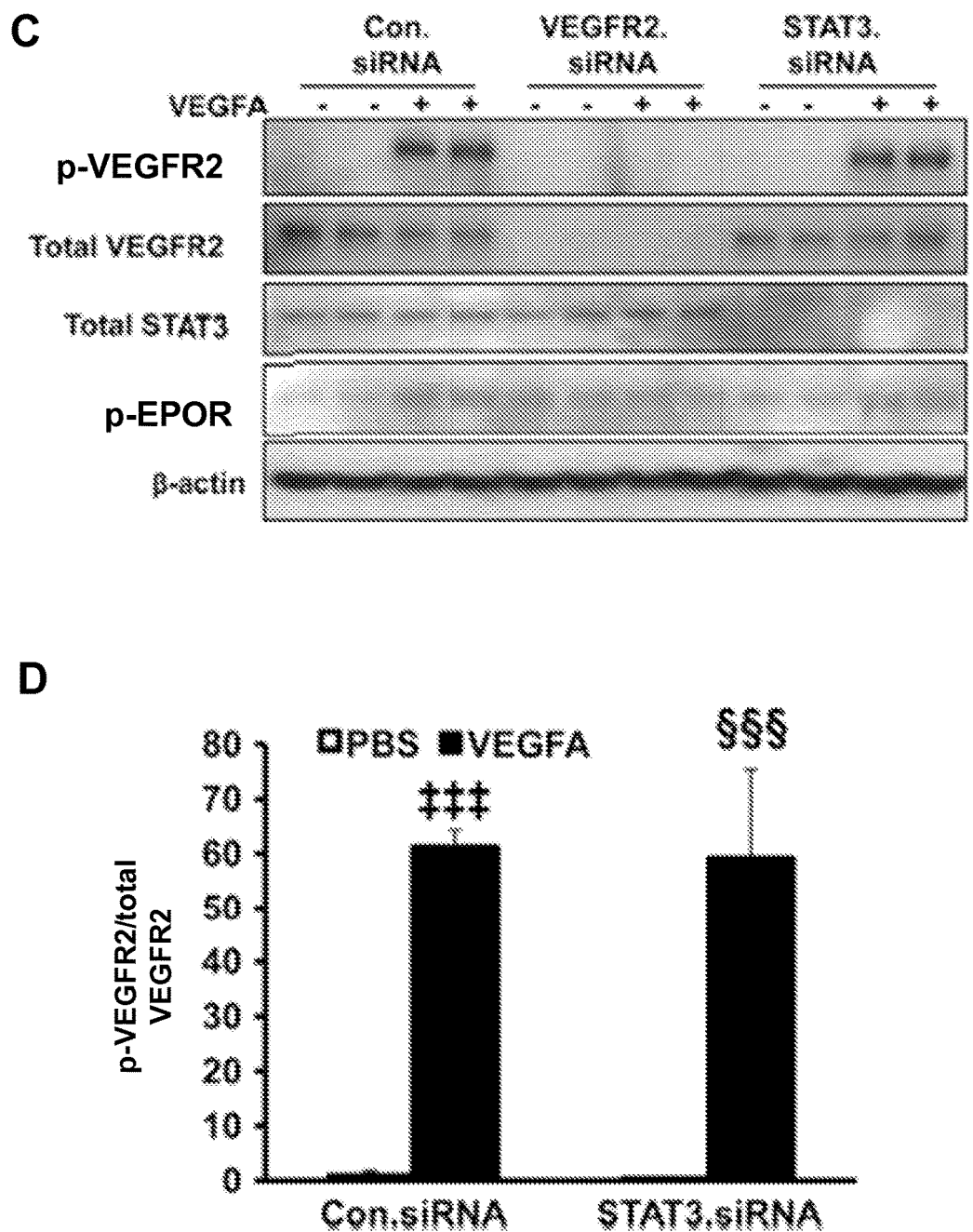
Figure 39E:
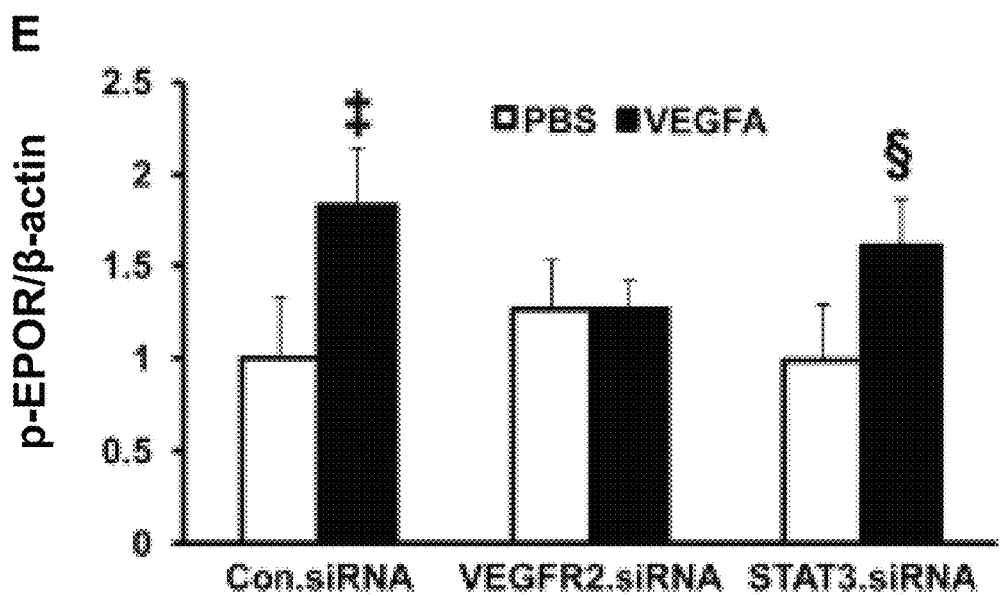
Figure 39F:
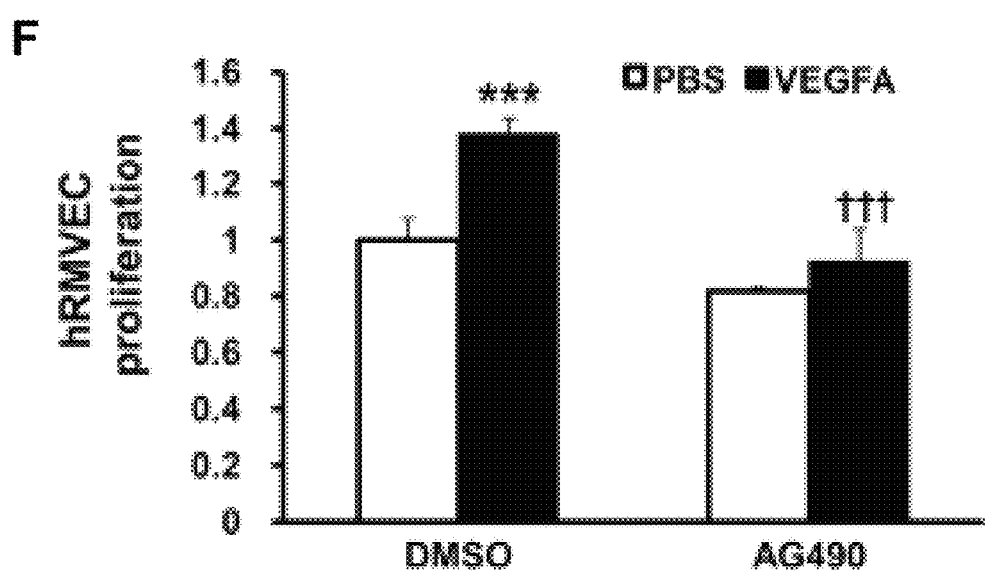

Compared with control siRNA, EPOR siRNA inhibited VEGFA-induced p-EPOR (FIGS. 38A, 38B) and p-STAT3 (FIGS. 38E, 38F), and reduced p-VEGFR2 (FIGS. 38C, 38D). Similarly, VEGFA-induced p-VEGFR2 (FIG. 37A), p-EPOR (FIG. 37A), and p-STAT3 (FIGS. 39A, 39B) were reduced to baseline in hRMVECs pretreated with the VEGFR2 inhibitor SU5416. The data further indicate that knockdown of VEGFR2 by siRNA transfection inhibited VEGFA-induced p-EPOR (FIGS. 39C, 39E), but knockdown of STAT3 by siRNA did not affect VEGFA-induced p-VEGFR2 and p-EPOR (FIGS. 39C, 39D, 39E). These findings show that p-VEGFR2 is required for VEGFA-induced p-EPOR. Furthermore, activation of p-STAT3 occurred downstream of p-VEGFR2 and p-EPOR. Inhibition of STAT3 with AG490 reduced VEGFA-induced hRM-VEC proliferation to baseline (FIG. 39F). Taken together, these findings indicate that VEGFA activates EPOR and induces an interaction between activated EPOR and VEGFR2, which augments angiogenesis through activation of STAT3.

Discussion:

With the present study, the data indicate that VEGFA activates VEGFR2, which then phosphorylates EPOR and forms an interaction with p-EPOR to exacerbate STAT3 activation and mediate the pathological angiogenesis seen in phase II ROP. The relevant ROP model in rat was used showing that p-EPOR-labeled ECs were increased during phase II IVNV, but not in phase I. Furthermore, in the rat model with knockdown for Müller cell VEGFA, p-EPOR labeling in ECs was significantly reduced, compared with luciferase shRNA control. Knockdown of EPOR only partially reduced VEGFA-induced EC proliferation, whereas inhibition of VEGFR2 by either of two methods (siRNA transfection or tyrosine kinase inhibition) appeared to reduce VEGFA-induced EC proliferation to control levels. The data further indicate that VEGFA induced an interaction between EPOR and VEGFR2, which triggered activation of STAT3 in ECs to induce EC proliferation. These findings indicate that EPOR can enhance VEGFR2 signaling and thus lead to pathological angiogenesis in the setting of increased VEGFA, as in ROP; in the physiological angiogenesis of normal development, VEGFA concentration is not as elevated.

Recombinant EPO has been used to treat anemia of prematurity, but several studies have indicated an association between severe ROP and EPO use. EPO has since been shown to have other properties besides hematopoiesis, including neuroprotection through interactions between EPOR and the 0 common receptor and angiogenesis in ischemic limb models through interactions between VEGFR2 and EPOR. In terms of ROP, inhibition of phase II IVNV with a neutralizing antibody to VEGFA caused recurrent pathological angiogenesis in association with increased retinal EPO expression. Studies in the mouse OIR model demonstrated that EPO is a target for phase II IVNV, but can be protective if delivered as an intraperitoneal injection before hyperoxia-induced vaso-obliteration in phase I. Furthermore, prolyl hydroxylase inhibitors can increase EPO and reduce phase I vaso-obliteration and phase II IVNV in the mouse OIR and rat ROP models. Increased size of the avascular retina has been associated with increased severity of ROP in several clinical studies, indicating that restoring physiological retinal vascularization and reducing avascular retina could reduce IVNV in severe ROP. Based on such studies, it was proposed that the timing of EPO administration is important and that EPO delivered early might protect against severe ROP. However, even though exogenous administration of EPO restored physiological retinal vascularization in phase I of the ROP model, phase II IVNV was not reduced. Also, in a multicenter clinical trial of darbepoietin (a derivative of erythropoietin) delivered systemically by weekly subcutaneous injections beginning immediately after birth to improve cognitive development in preterm infants (n=102), darbepoietin neither increased nor reduced the occurrence of severe ROP. The study population was small, but these findings show that timing of EPO administration is not the only consideration involved in ROP.

Previous studies have indicated a role for EPOR in cancer cell growth and in EPO-EPOR signaling in angiogenesis. In EPOR knockout mice rescued by permitting EPO signaling of hematopoiesis (Epor$^{-/-}$ rescued mice), EPOR-EPOR signaling regulated angiogenesis by up-regulating VEGFA and its receptors in a hindlimb ischemia model, indicating crosstalk between the signaling pathways. In the present study, the data indicate that VEGFA can also up-regulate EPOR and activate EPOR through p-VEGFR2, leading to an interaction between the receptors and pathological angiogenesis. Activation of STAT3 caused phase II IVNV in a model of ROP+SO. The data herein indicate that STAT3 is activated in ECs by VEGFA, leading to IVNV through an interaction between activated VEGFR2 and EPOR (which accounts for the phase II IVNV observed herein). There are several potential mechanisms whereby STAT3 activation can increase IVNV. Activated STAT3 dimers can translocate to the nucleus and regulate transcription of genes involved in angiogenesis by binding to the gene promoters. The data show that in the rat ROP model, after repeated oxygen fluctuations, VEGFA activated STAT3 in Müller cells; after translocation to the nucleus, p-STAT3 dimers bound the EPO promoter and down-regulated expression of EPO, in association with delayed physiological retinal vascular development in phase I. Thus, VEGFA-activated STAT3 can also be involved in up-regulating EPOR in ECs by directly binding to the EPOR promoter.

Figure 40:
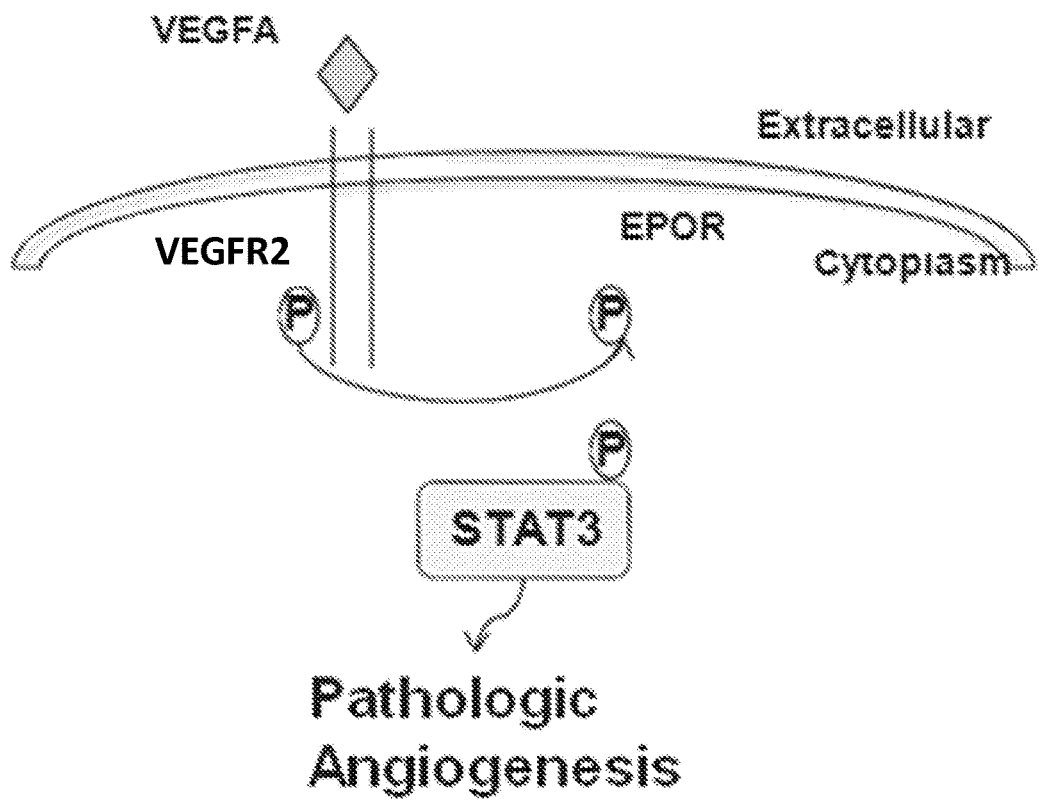
FIG. 40 shows that the hypothetical signaling pathway in pathological angiogenesis regulated by interactions of activated VEGFR2 and EPOR. VEGFA activates VEGFR2, which then phosphorylates EPOR and forms an interaction with p-EPOR to exacerbate STAT3 activation and mediate pathological angiogenesis as seen in phase II ROP.

The data also indicate that VEGFA activates VEGFR2 (which in turn activates EPOR) in phase II ROP, potentially through another downstream signaling pathway or through an adaptor protein that facilitates an interaction between the receptors (FIG. 40). Although current clinical trials show preliminary evidence that ROP is neither increased nor decreased when EPO derivatives are administered early, the present study does not directly address whether exogenous EPO can safely be used in preterm infants. These findings provide evidence of a potential role for EPOR and VEGFR2 interactions, induced by VEGFA in phase II IVNV in ROP and in other conditions associated with pathological angiogenesis.

Example 14

Short Hairpin RNA-Mediated Knockdown of VEGFA in Müller Cells Reduces Intravitreal Neovascularization in a Rat Model of Retinopathy of Prematurity Vascular endothelial growth factor (VEGF) A is implicated in aberrant angiogenesis and intravitreous neovascularization (IVNV) in retinopathy of prematurity (ROP). However, VEGFA also regulates retinal vascular development and functions as a retinal neural survival factor. By using a relevant ROP model, the 50/10 oxygen-induced retinopathy (OIR) model, the data herein indicate that broad inhibition of VEGFA bioactivity using a neutralizing antibody to rat VEGF significantly reduced IVNV area compared with control IgG but also significantly reduced body weight gain in the pups, indicating an adverse effect. Therefore, knockdown of up-regulated VEGFA in cells that overexpress it under pathological conditions can reduce IVNV without affecting physiological retinal vascular development or overall pup growth. First, the VEGFA mRNA signal was determined to be located within the inner nuclear layer corresponding to CRALBP-labeled Müller cells of pups in the 50/10 OIR model. Then, a lentiviral-delivered miR-30-embedded shRNA against VEGFA that targeted Müller cells was developed. Reduction of VEGFA by lentivector VEGFA-shRNA-targeting Müller cells efficiently reduced 50/10 OIR up-regulated VEGFA and IVNV in the model, without adversely affecting physiological retinal vascular development or pup weight gain. Knockdown of VEGFA in rat Müller cells by Lentivector VEGFA-shRNA significantly reduced VEGFR2 phosphorylation in retinal vascular endothelial cells. These results indicate that targeted knockdown of overexpressed VEGFA in Müller cells safely reduces IVNV in a relevant ROP model.

Retinopathy of prematurity (ROP) remains a leading cause of childhood blindness and is increasing in frequency in developing countries. The hypothetical proposed pathophysiological characteristics of ROP have been recently refined to be that stresses in prematurity cause delayed physiological retinal vascular development and potentially some high oxygen-induced capillary constriction that results in avascular retina. Once supplemental oxygen is removed from the preterm infant, the retina becomes hypoxic, and hypoxia stimulates the release of angiogenic factors with growth of new blood vessels into the vitreous as intravitreous neovascularization (IVNV). Many angiogenic factors can result in pathological IVNV in animal models, such as insulin-like growth factor-1, hepatocyte growth factor, erythropoietin, platelet-derived growth factor, and angiopoietins, but vascular endothelial cell growth factor A (VEGFA) has become one of the most studied factors leading to IVNV. VEGFA mRNA was found in the retina of a preterm infant eye with severe ROP, and VEGFA protein was increased in vitreous from preterm infants who underwent surgery for stage 4 ROP compared with controls. VEGFA inhibitors reduce pathological angiogenesis in adult retinal diseases, including diabetic retinopathy and age-related macular degeneration.

Therefore, there is reason to consider VEGFA in the pathological characteristics of human ROP. However, in the preterm infant retina, VEGFA is also important in the development of retinal blood vessels and other organs. After a recent clinical trial testing intravitreal delivery of a broad anti-VEGFA antibody in infants with severe ROP, there have been reports of persistent avascular retina and reactivation of IVNV with subsequent total retinal detachment, even 1 year after treatment. In addition, by using a relevant ROP model, the data herein indicate that inhibition of VEGFA bioactivity using a neutralizing antibody to rat VEGF significantly reduced IVNV area without adversely affecting physiological retinal vascular development 6 days after antibody injection, but significantly reduced body weight gain in the pups, indicating an adverse effect. Therefore, safer ways to inhibit pathological IVNV while preserving physiological retinal vascularization are needed.

One way to target pathological IVNV is to determine the cells within the retina that overproduce VEGFA during pathological stress. In preterm infant eyes, it is not possible to safely localize where VEGFA is produced. Therefore, a relevant model of ROP, the rat 50/10 oxygen-induced retinopathy (OIR) model, was used to localize the VEGFA signal within the retina and determine its role in pathological IVNV in ROP. This model causes features of severe ROP and produces extrauterine growth restriction, a risk for ROP in human preterm infants. The oxygen exposure recreates arterial oxygen fluctuations similar to those experienced by infants with severe ROP. The data described herein indicate that VEGFA and VEGFR2 were both increased as early as at postnatal day 8 (p8) in whole retinas from eyes of pups in the 50/10 OIR model compared with room air-raised counterparts.

In the retina, several cells have been shown to produce VEGFA to support retinal development and physiological functioning. These include ganglion cells, astrocytes, Müller cells, and retinal pigment epithelium. In pathological IVNV, the VEGFA signal has been localized to many of the same cells: Müller cells, astrocytes, and, possibly, ganglion cells. However, there has been disagreement as to the cell type that overproduced VEGFA to cause IVNV, and these articles also used the mouse model of OIR that exposes pups to constant and higher oxygen levels than currently used in the management of ROP.

In this example, shRNAs to VEGFA were generated and a lentiviral miRNA-based system was used to target Müller cells, where the VEGFA message was localized in the 50/10 OIR model. The study examined whether knocking down VEGFA to physiological levels in Müller cells would inhibit IVNV without adversely affecting physiological retinal vascular development.

Materials and Methods:

Rat Model of the 50/10 OIR Model

The rat 50/10 OIR model has been described herein. Entire litters of newborn Sprague-Dawley rat pups (Charles River, Wilmington, Mass.) and dams were placed into an oxygen environment (Oxycycler; Biospherix, Lacona, N.Y.) that cycled the oxygen concentration between 50% and 10% every 24 hours for 14 days. At postnatal day 14 (p14), litters were placed into room air for an additional 4 days. Pup number was maintained at 12 to 14 pups per litter. At least two litters were used for each condition. Protein, in situ hybridization, or immunohistochemistry (IHC) was performed in one eye, and flat mount analysis was performed in the fellow similarly treated eye.

In Situ Hybridization of VEGFA Splice Variants

Serial sections (10 µm thick) from fresh frozen p14 50/10 OIR uninjected eyes were processed for in situ hybridization to detect the message of VEGF120, VEGF164, and VEGF188 splice variants using the fluorescence in situ hybridization (FISH) kit (Invitrogen, Carlsbad, Calif.), per manufacturer's instructions. In comparison, serial retinal sections from a room air-raised pup at developmental day p14 were processed at the same time. Labeling of nuclei was performed using Hoechst 33342 (Invitrogen, Carlsbad, Calif.).

Construction of VEGFA shRNA Lentivectors

Studies have shown that double-stranded RNAs can bind the surface of cells and activate toll-like receptor 3. shRNAs packaged within a virus were chosen, rather than as siRNA, so the RNA will not have access to the surface toll-like receptor 3. shRNAs were embedded into the endogenous precursor miR-30 context, so that the miRNA-based shRNA is involved in the endogenous gene-silencing machinery that is transcribed predominantly by polymerase II promoters.

Target sequences for rat VEGFA (NM_031836) were selected from five online prediction algorithms based on regions predicted to work in more than two of the algorithms. Sequences were blasted to ensure no off-target effects. For VEGFA, the target sequences were selected in the region of bases between 100 and 419 so that no alternative splice sites were targeted and to ensure that all splice variants would be silenced. A sequence-targeting nonmammalian gene, luciferase (M15077), was developed as a control. The lentiviral transfer vector with a CD44 promoter and the red fluorescence protein (RFP) or green fluorescence protein (GFP) (pFmCD44.1GW), along with viral packaging constructs (VSV-G, pMDLg/pRRE, and pRSV-REV), were shown to target Müller cells in rats in vivo. shRNAs were designed against rat VEGFA (VEGFA-shRNA) or luciferase (luciferase-shRNA) and cloned into lentiviral transfer vectors (pFmCD44.1GW). Viral titers were determined using real-time quantitative PCR for viral particles, with final viral working stocks of $1\times10^9$ viral particles/mL. The sequences of VEGFA-shRNA and luciferase-shRNA were 5'-TGCTGTTGACAGTGAGCGC-CCAAAGAAAGATA-GAACAAAGTAGTGAAGC-CACAGATGTACTTTGTTCTATCTTTCTTTGGTTGC-CTACTG CCTCGGA-3' and 5'-TGCTGTTGACAGTGAGCGCGCTGAGTACTTC-GAAATGTCTAGT-GAAGCCACAGATGTAGA-CATTTCGAAGTACTCAGCGTGCCTACTGCCTCGGA-3', respectively.

Generation of VEGF120 and VEGF164 HEK Reporter Cell Lines

Two HEK reporter cell lines were generated by cloning rat $VEGF_{120}$ and $VEGF_{164}$ cDNA sequences into a pTK642 lentiviral transfer vector to test the efficacy of shRNAs to inhibit all splice variants of VEGFA. pTK642 contains a cytomegalovirus promoter, followed by an interferon response element and blasticidin/GFP. The GFP reporter was used to assess transfection efficiency, whereas the blasticidin permitted selection of cells that expressed rat $VEGF_{120}$ and rat $VEGF_{164}$. Both HEK VEGFA reporter cell lines were transfected with plasmid DNA pFmCD44.1GW containing VEGFA-shRNA expressed with RFP or an empty vector without shRNA as control. The knockdown efficiency of VEGFA-shRNA was determined by reading GFP fluorescence 48 hours after transfection of HEK VEGF reporter cell lines with flow cytometry. Red cells were gated, and the mean fluorescence intensity of GFP was measured. Silencing was calculated as the difference in GFP mean fluorescence intensity between cells transfected with the vector containing the VEGFA-shRNA and cells containing the control vector. Silencing was expressed as a percentage of control vector transfected cells.

Cell Culture and Transduction with pFmCD44-shRNA Lentivectors rMC-1 cells, a rat Müller cell line (kindly provided by Dr. Vijay Sarthy, Northwestern University, Evanston, Ill.), were maintained in Dulbecco's modified Eagle's medium/high glucose (Gibco/Life Technologies, Grand Island, N.Y.), supplemented with 10% fetal bovine serum/1% penicillin-streptomycin and grown to 80% confluence in 6-well plates (Corning, Inc., Corning, N.Y.). Human primary retinal microvascular endothelial cells at passage 3 (hRMVECs; Cell Systems, Kirkland, Wash.) were maintained in basal endothelial growth medium (Lonza, Hopkinton, Mass.), supplemented with 5% fetal bovine serum/1% penicillin-streptomycin and grown to 80% confluence in 6-well plates (Corning, Inc., Tewksbury, Mass.). Cells were infected in triplicate with VEGFA-shRNA or luciferase-shRNA lentivector-containing media ($5.0\times10^6$ viral particles/mL) or left uninfected. After 24 hours, media were replaced, and cells were then incubated for another 18 hours at 37° C. at 1% $O_2$ (Biospherix). GFP expression was imaged using an inverted fluorescence microscope (Olympus IX81; Olympus, Tokyo, Japan) at ×20 magnification with a fluorescein isothiocyanate filter. rMC-1 cells were collected for RNA extraction and analysis with real-time PCR. Media were harvested for VEGFA enzyme-linked immunosorbent assay (ELISA). All samples were frozen at −80° C. until analysis.

Co-Culture of rMC-1s and hRMVECs hRMVECs were grown on inserts (Transwell; Corning, Inc.) with 1-μm-diameter pores that were too small to allow cell migration but still allowed hRMVEC and rMC-1 cells grown on the underside of the inserts to make contact. In some experiments, rMC-1 cells were infected with lentivector VEGFA-shRNA or luciferase-shRNA, as described herein. At 48 hours after contact and virus infection, hRM-VECs were collected from the tops of the inserts and processed for VEGFR2 phosphorylation.

Subretinal Injections

At the beginning of the 50% oxygen cycle of the 50/10 OIR model on p8, pups were anesthetized by i.p. injection (IP) of 20 mg/kg ketamine and 6 mg/kg xylazine. By using a 33-gauge needle attached to a Hamilton syringe, 1 μL ($1\times10^9$ viral particles/mL) of lentivectors containing VEGFA-shRNA or luciferase-shRNA was delivered into the sub-retinal space. Sterile PBS (1 μL) was used as an additional control. Successful injections produced a retinal detachment, which was transient, and retinas reattached within 24 hours without lens injury or injury to the choroid. Both eyes of each pup were injected with the same lentivector preparation or with PBS. Each litter typically had an equal distribution of lentivector- and PBS-injected pups. After the injection, 0.5% erythromycin was topically applied to each eye, and pups were allowed to recover on a warming pad before being returned to the oxygen environment (Oxycycler). Litters were typically out of the oxygen cycler for 3 hours. At postnatal day 18 (p18), a time point that the data indicate maximum IVNV in this model, and to provide sufficient time for lentivirus transduction and VEGFA knockdown, pups were euthanized by IP of ketamine (60 mg/kg) and xylazine (18 mg/kg), followed by IP of pentobarbital (80 mg/kg). One eye was processed for retinal flat mounts, and the fellow eye was processed with the same treatment for protein or RNA analysis.

In Vivo Retinal Imaging

Pups were anesthetized for in vivo imaging of the retinas with Micron III retinal imaging microscope (Phoenix Research Laboratories, Inc., Pleasanton, Calif.) using a GFP filter during the 50% oxygen cycle and returned to the oxygen chamber for recovery within 3 hours. For euthanasia, pups received IP of pentobarbital (80 mg/kg) after deep anesthesia Retinal Flat Mount Preparation, Imaging, and Analysis Lectin-stained retinal flat mounts were prepared using 5 μg/mL Alexa Fluor 568-conjugated *Griffonia simplicifolia* (Bandeiraea) isolectin B4 (Molecular Probes, Eugene, Oreg.), as described herein, imaged using an inverted fluorescence microscope (Olympus). Flat mounts were generated using the scan-slide stitching function of Metamorph imaging software version 7.0 (Molecular Devices, Inc., Sunnyvale, Calif.). Measurements were made by two masked reviewers (Y.J. and M.M.) using ImageJ software version 1.46 (NIH, Bethesda, Md.). The avascular retinal area (AVA) and IVNV area were calculated as a percentage of total retinal area for each flat mount.

Retinal Section Preparation and Staining and Retinal Thickness Measurement

Eyes were fixed in 4% paraformaldehyde containing 10 mmol/L sodium orthovanadate for 10 minutes, and retinas were removed and placed into 4% paraformaldehyde for another 15 minutes, followed by incubation in 30% sucrose/PBS overnight. Each retina was immersed in optimal cutting temperature compound (Tissue Tek; EMS, Hatfield, Pa.). Eyes cut into cryosections (10 μm thick) were processed, as described previously, and incubated overnight at 4° C. with primary antibody, rabbit anti-phosphorylated VEGFR2

(p-VEGFR2 at Y951; Santa Cruz Biotechnology, Santa Cruz, Calif.), and mouse isolectin B4; then, they were washed and incubated for 1 hour with a 1:500 dilution of Alexa 594-conjugated goat anti-mouse secondary antibody (Invitrogen) for isolectin B4 or Alexa 488-conjugated goat anti-rabbit secondary antibody (Invitrogen) for p-VEGFR2. Some sections stained with only secondary antibody were controls. Cryosections stained with DAPI were used to measure retinal thickness. Images were captured using confocal microscopy (Olympus IX81). Exposure times for images were the same. Integrated density per image area of p-VEGFR2 and thickness of overall retina and different retinal layers were measured using ImageJ software.

VEGFA ELISA

Protein samples (50 μg) were used in the Quantikine Rat VEGFA ELISA kit (RRV00; R&D Systems, Minneapolis, Minn.) to measure total retinal VEGFA concentration between treatment groups, per manufacturer's instructions. All samples were run in duplicate.

Protein Extraction and Western Blot Analysis

The hRMVECs were lysed in modified radioimmunoprecipitation assay buffer (20 mmol/L Tris base, 120 mmol/L NaCl, 1% Triton X-100, 0.5% sodium deoxycholate, 0.1% SDS, and 10% glycerol) with 1:100 protease inhibitors (Roche Diagnostics, Indianapolis, Ind.) and 2 mmol/L orthovanadate, and were homogenized and centrifuged at 16,000×g for 10 minutes at 4° C. Total protein concentration (g/mL) in the supernatant fluid was quantified by BCA protein assay (Pierce, Rockford, Ill.). Total protein (30 μg) for each sample was used for Western blot analyses. Membranes were incubated overnight at 4° C. with primary antibodies: p-VEGFR2, VEGFR2 (1:500; Santa Cruz Biotechnology), cleaved caspase 3, and total caspase 3 (1:1000; Cell Signaling Technology Inc., Danvers, Mass.). Blots were visualized, and the relative densities of bands were calculated.10 The relative activities of STAT3 and VEGFR2 were calculated as phosphorylated/total protein and expressed as fold difference. Caspase 3 activity was analyzed by Western blot analysis and quantified as the density of the bands for the cleaved form/density of total caspase bands.

RNA Isolation and Real-Time PCR Analysis

Samples were removed from RNAlater, and total RNA was extracted with the RNeasy Mini kit (Qiagen, Valencia, Calif.). RNA was quantified using the NanoDrop spectrophotometer (Thermo Scientific, Wilmington, Del.). cDNA was generated using a High Capacity cDNA Archive Kit (Applied Biosystems, Foster City, Calif.). Real-time PCR was performed on a Mastercycler ep Realplex (Eppendorf, Westbury, N.Y.) with the use of TaqMan probes (Applied Biosystems). Expression levels for VEGFA were normalized to the mean value of internal control, glyceraldehyde-3-phosphate dehydrogenase.

Statistical Analysis

Significant differences between treatment groups were determined by one-way analysis of variance with the Bonferroni multiple-comparison post hoc test. A minimum value of $P<0.05$ was considered statistically significant.

Figures 41E, 41F, 41G:
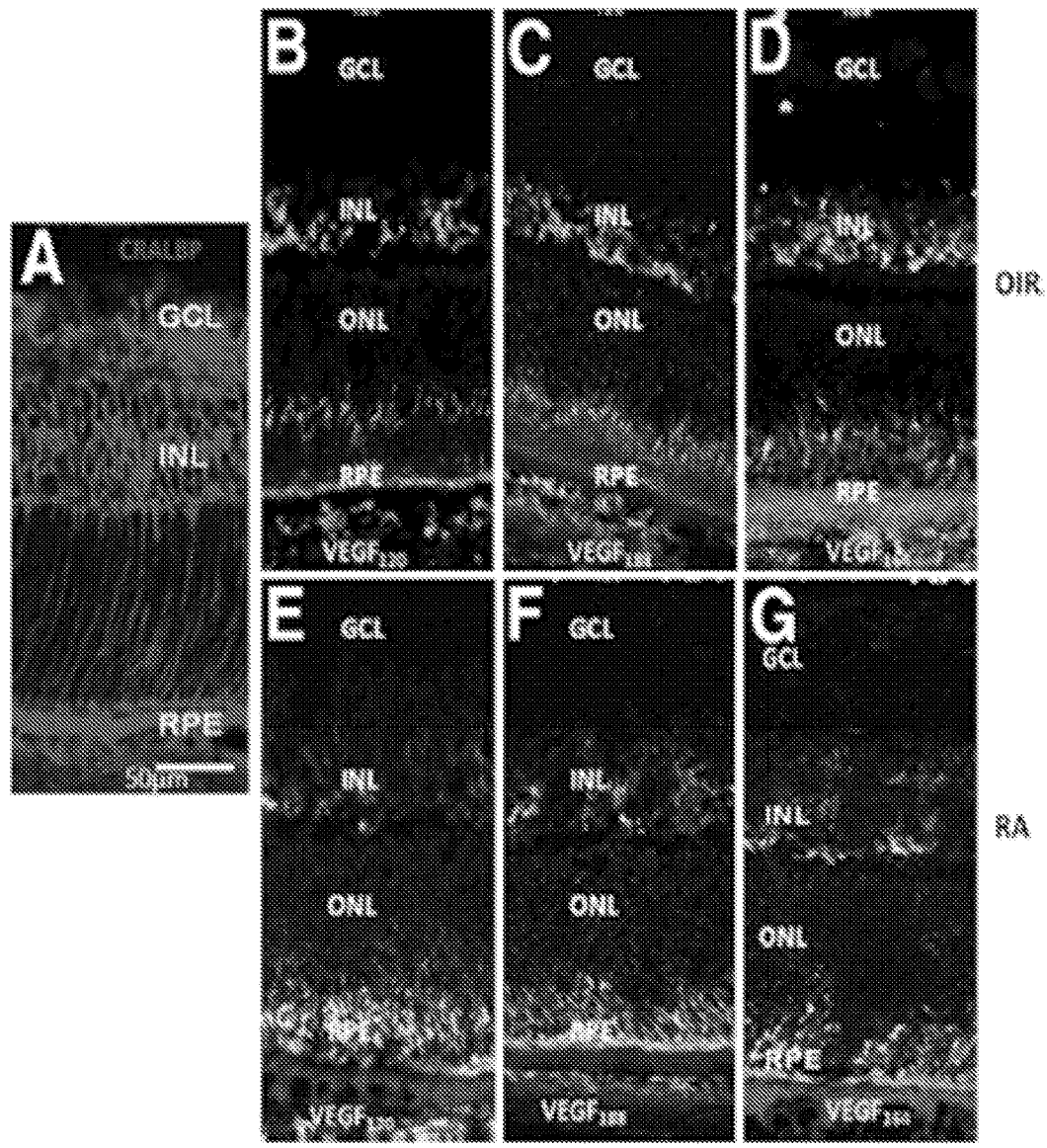

Results:

VEGFA Splice Variants Localize to Layers Corresponding to CRALBP-Labeled Müller Cells in the 50/10 OIR Model The data herein indicate that VEGFA splice variant expression increased in the retinas of rat pups exposed to the 50/10 OIR model at time points including p14 and p18, compared with retinas from age-matched pups raised in room air. Therefore, VEGFA mRNA splice variants, VEGF120, VEGF164, and VEGF188, were localized within the retinas of rat pups raised in the 50/10 OIR model and in room air at p14. The mRNA signals in both room air-raised pups and the 50/10 OIR model, determined by FISH, were mainly in the inner nuclear layer, corresponding to CRALBP-labeled Müller cells, and retinal pigment epithelium in both the 50/10 OIR model and room air (FIG. 41). These results indicate that Müller cell-produced VEGFA can be involved in VEGFA-mediated pathological angiogenesis in the 50/10 OIR model.

Generation of Lentivectors for VEGFA-shRNA Delivery to Müller Cells

Figure 42A:
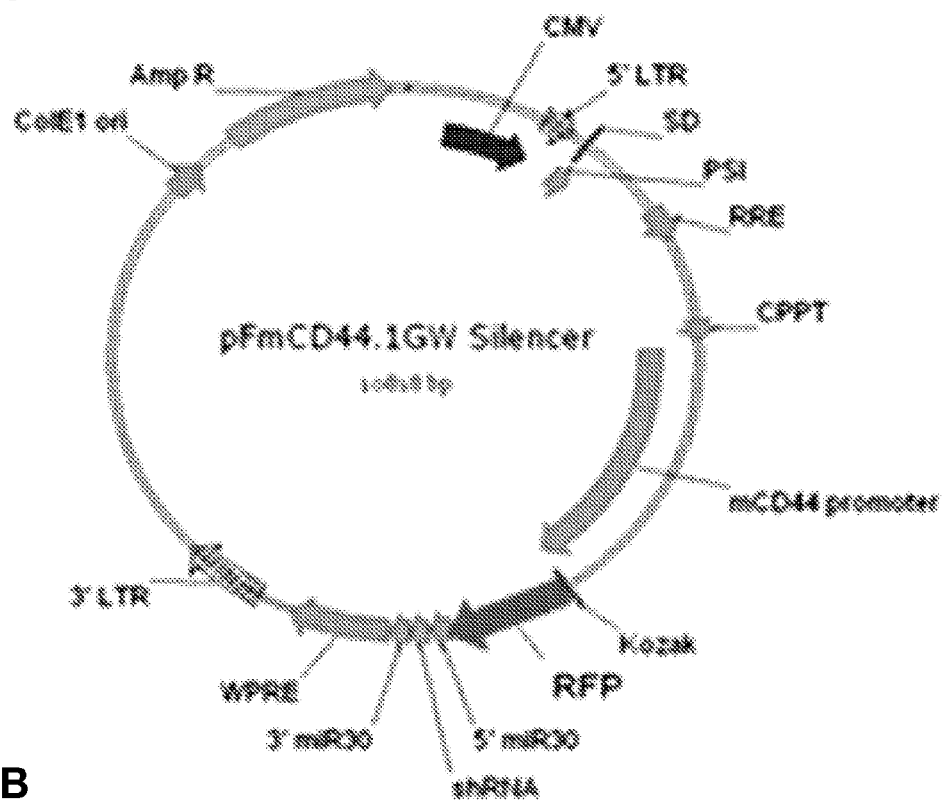
FIGS. 42A, 42B, 42C, and 42D show that the generation of lentivector-delivered shRNA for specific knockdown of VEGFA in Müller cells. (A) Diagram of the pFmCD44.1GW lentivector containing the glia-specific CD44 promoter driving an miR-30-based shRNA cassette and an RFP marker. (B) HEK293 reporter cell line expressed GFP-tagged rat VEGF120 or VEGF164. (C) HEK reporter cell lines to VEGF120 and VEGF164 were transfected with RFP-expressed lentivector VEGFA-shRNA plasmids, and GFP fluorescence (infectivity) was measured by flow cytometry. (D) Quantification of percentage silencing of VEGF120 and VEGF164 by VEGFA-shRNAs from fluorescence-activated cell sorter analysis (n=3). Results are means±SEM.
Figure 42B:
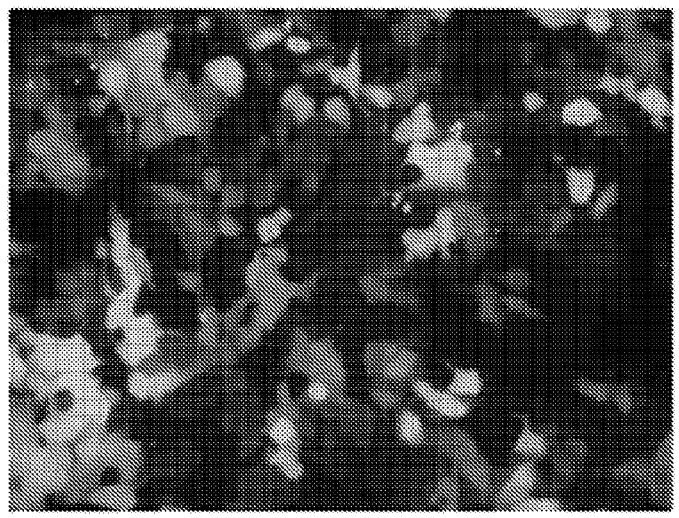
Figure 42C:
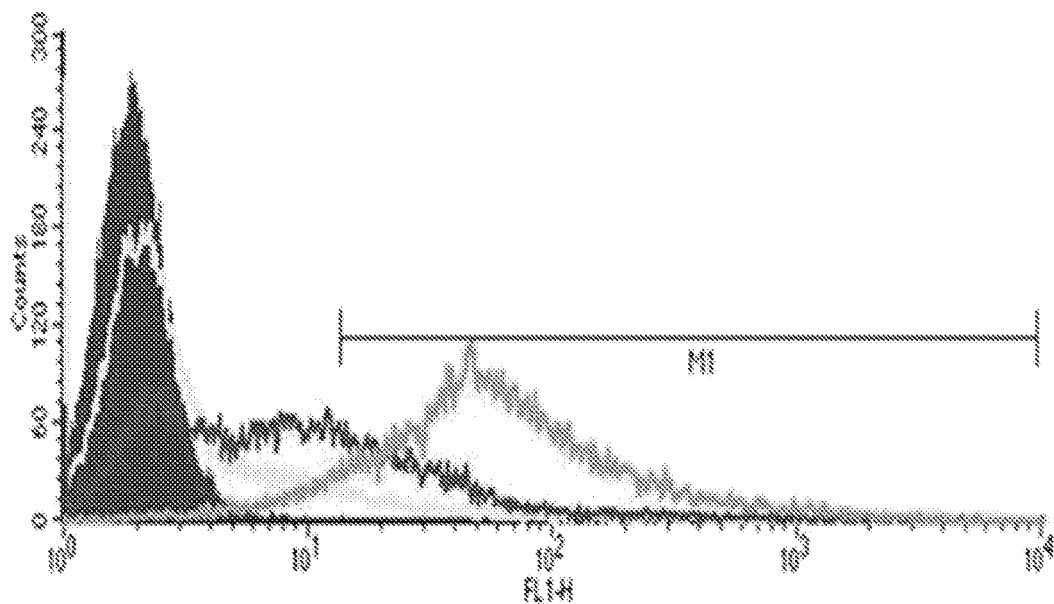
Figure 42D:
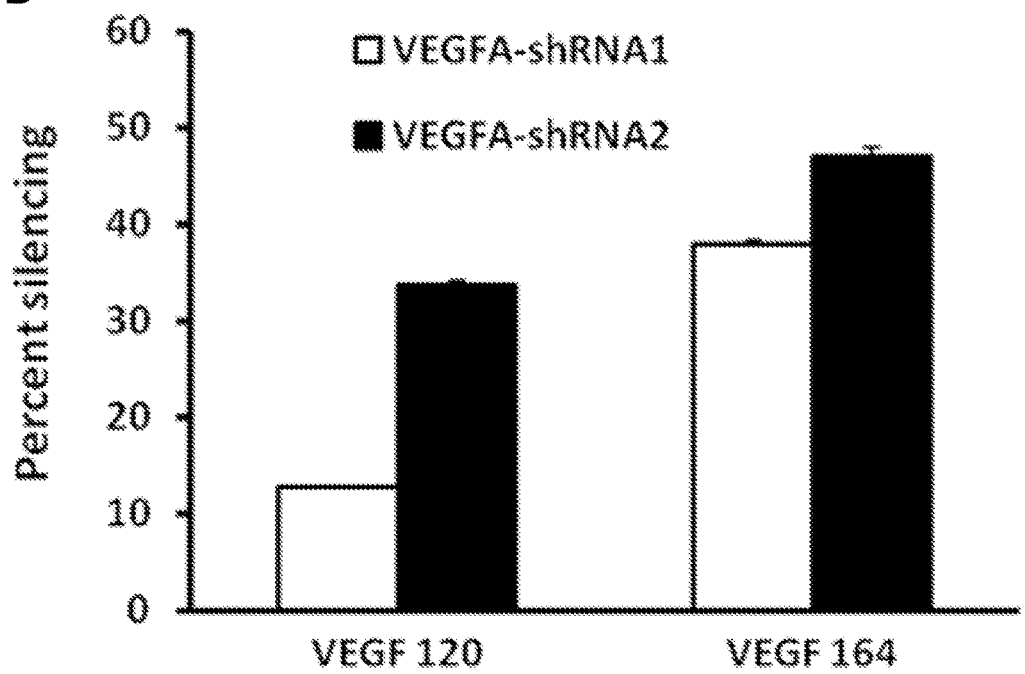

To investigate whether Müller cell-derived VEGFA contributed to IVNV, lentivectors were generated from pFmCD44.1 GW, which contains a CD44 promoter that targets Müller cells, and this was used to drive an miR-30-based shRNA cassette and RFP (FIG. 42A) or GFP (FIG. 43A) to deliver VEGFA shRNAs to Müller cells in vitro or in vivo. To ensure knockdown efficiency, two shRNAs targeting rat VEGFA coding sequences were designed, and an empty lentivector was used as a control. To test if designed shRNAs reduced VEGFA expression, HEK reporter cell lines were generated that expressed GFP-tagged rat VEGF120 or VEGF164 (FIG. 42B). Lentivector plasmid DNA containing VEGFA-shRNA with RFP expression was transfected into HEK reporter cell lines. Fluorescence-activated cell sorter analysis of GFP fluorescence in RFP-positive cells was used as a readout for the expression level of $VEGF_{120}$ and $VEGF_{164}$, two splice variants of VEGFA (FIG. 42C). As shown in FIG. 42D, VEGFA-shRNA2 showed better knockdown efficiency than VEGFA-shRNA1, with 35% reduction in $VEGF_{120}$ expression and approximately 50% reduction in $VEGF_{164}$ expression. Therefore, VEGFA-shRNA2 was used for in vivo experiments.

Figure 43A:
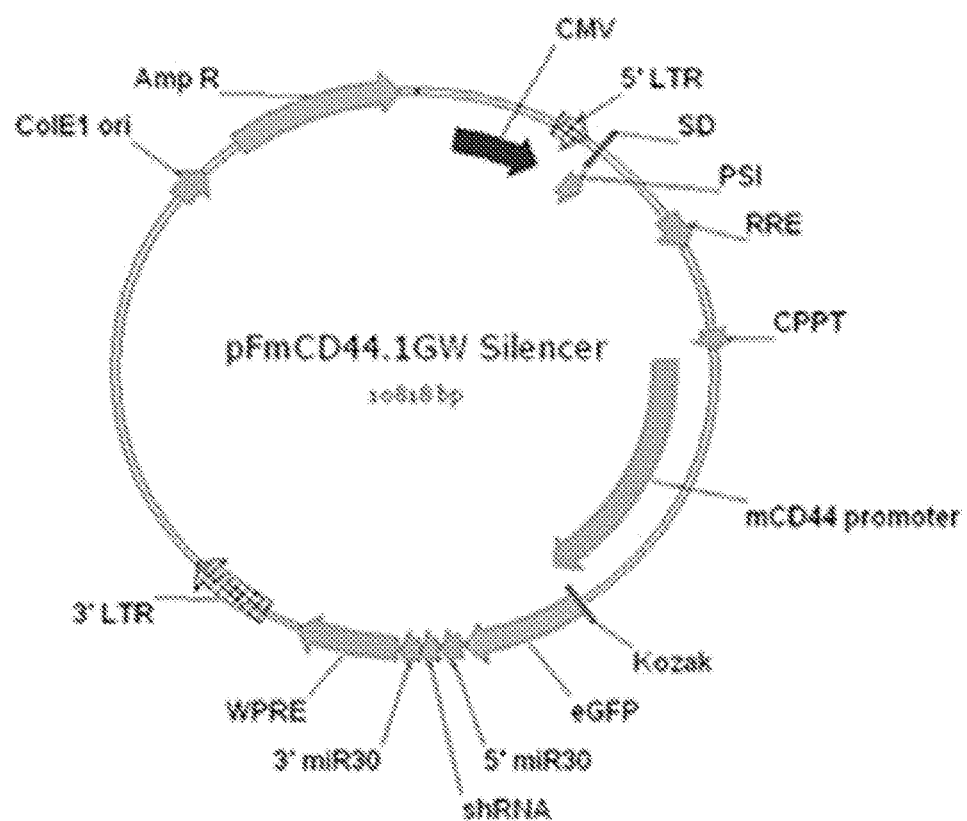
FIGS. 43A, 43B, 43C, 43D, 43E and 43F show the in vitro analysis of lentivector-delivered shRNA transduction and VEGFA knockdown in rMC-1 cells, and VEGFA signaling in a co-culture model of rMC-1 s and hRMVECs. (A) Diagram of the pFmCD44.1GW lentivector plasmid containing the glia-specific CD44 promoter driving an miR-30-based shRNA cassette and a GFP marker. (B) GFP expression in rMC-1s and hRMVECs. Real-time PCR of VEGFA mRNA in rMC-1s (C) and ELISA of VEGFA protein in culture media of rMC-1s transduced with lentivirus (D). E and F: Knockdown of VEGFA in rMC-1s by lentivector-VEGFA-shRNA reduces co-culture-induced p-VEGFR2 in hRMVECs. Representative gels of p-VEGFR2 in hRM-VECs grown in contact with lentivector VEGFA-shRNA or luciferase-shRNA-transduced rMC-1s (E) (solo cultured, treated with VEGFA, and grown in contact with rMC-1s) and in hRMVECs grown in contact with lentivector VEGFA-shRNA- or luciferase-shRNA-transduced rMC-1s (F). *P<0.05, ***P<0.001 versus uninfected; †P<0.05, †††<0.001 versus luciferase-shRNA. Data shown in C and D are representative of six independent samples. Results are means±SEM. GAPDH, glyceraldehyde-3-phosphate dehydrogenase.
Figure 43B:
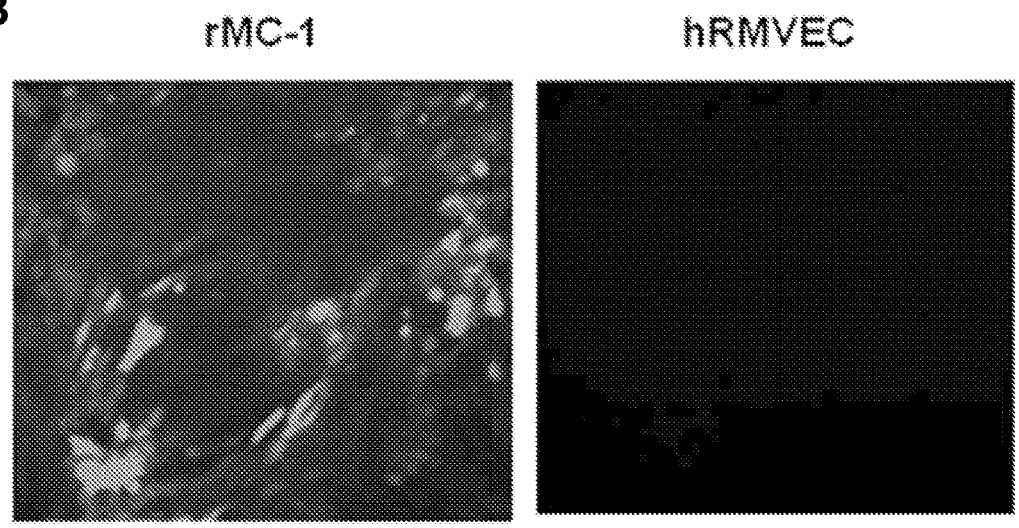
Figures 43C, 43D:
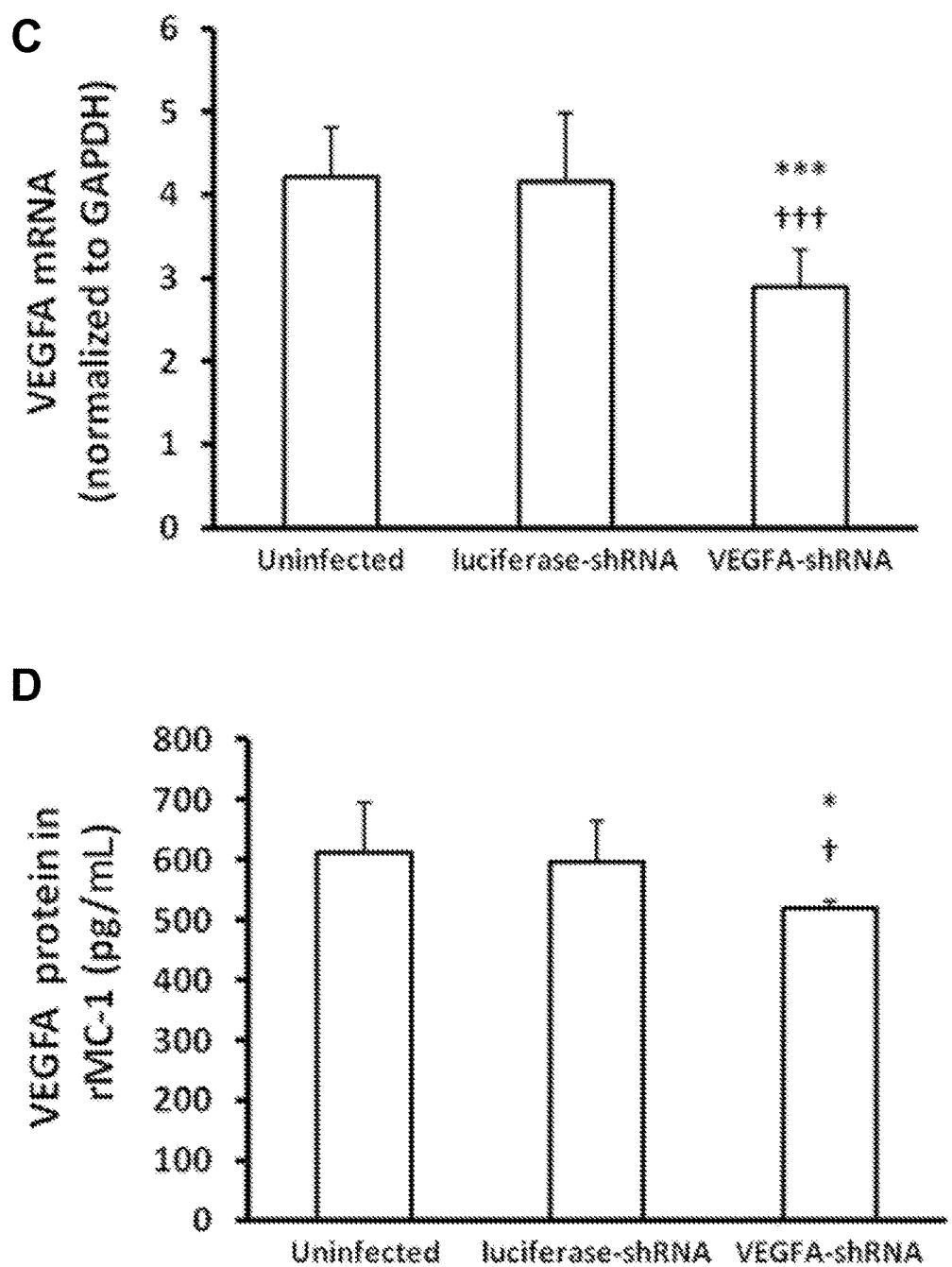

To determine whether the lentivector specifically targeted Müller cells, a rat Müller cell line, rMC-1s, and, as a comparison, hRMVECs, were infected with GFP-expressed lentivirus carrying VEGFA-shRNA2 or luciferase-shRNA control virus (FIG. 43A). Specificity to Müller cells was determined by GFP expression, as shown in FIG. 43B, where rMC-1s were GFP positive, and no hRMVECs were GFP positive. At 48 hours after viral transduction, VEGFA mRNA was significantly reduced in VEGFA-shRNA-transduced rMC-1s (FIG. 43C), and VEGFA protein was significantly decreased in the culture media of VEGFA-shRNA-transduced rMC-1s compared with uninfected cells or cells transduced with lentivector with luciferase-shRNA (FIG. 43D). These results indicate that lentivectors transporting shRNAs to VEGFA yielded a satisfactory reduction of VEGFA expression at both mRNA and protein levels.

Figure 43E:
Figure 43F:
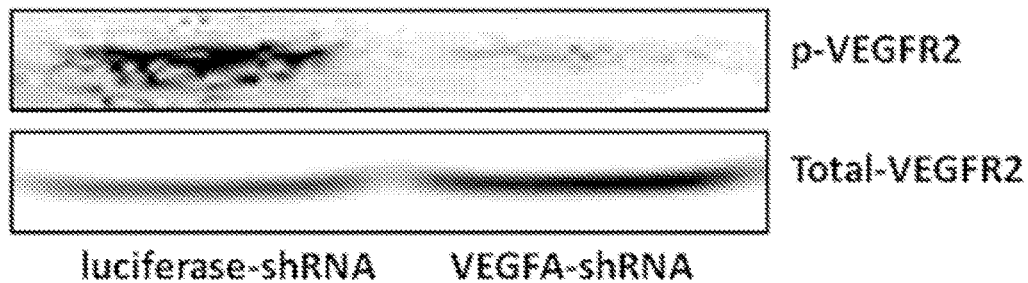

To further test if knockdown of VEGFA in rMC-1s is able to reduce VEGFA signaling in retinal endothelial cells, a co-culture model of rMC-1s and hRMVECs was used. As shown in FIG. 43E, compared with solo cultured hRMVECs, p-VEGFR2 was increased in hRMVECs either grown in contact with rMC-1 for 24 hours or treated with human VEGFA for 30 minutes. To further examine the effect of Müller cell-derived VEGFA on the activation of hRMVEC VEGFA signaling, activation of VEGFR2 was determined in hRMVECs grown in contact with rMC-1 cells transduced with lentivector VEGFA-shRNA or control luciferase-shRNA. Similar to the results shown in FIG. 43C, VEGFA mRNA was significantly reduced in rMC-1s transduced with lentivector VEGFA-shRNA, and p-VEGFR2 was also decreased in hRMVECs when cells were in contact with lentivector VEGFA-shRNA-transduced rMC-1s, compared with control luciferase-shRNA (FIG. 43F). These findings indicate that modulating VEGFA expression in rMC-1s changed VEGF-mediated angiogenic signaling in hRMVECs.

Knockdown of VEGFA in Müller Cells Reduces IVNV without Affecting Retinal Physiological Vascularization In the 50/10 OIR model, VEGFA was increased as early as p8 and was up-regulated at several time points through p18, when IVNV is at a maximal level. To investigate whether knockdown of VEGFA in Müller cells reduced IVNV in the 50/10 OIR model, lentivectors carrying VEGFA-shRNA or control luciferase-shRNA were delivered to rat pups via subretinal injections at p8, a time point that allowed sufficient time for viral transduction. It has been shown that intravitreal injections did not yield Müller cell transduction. Only pups weighing within ±2 g of the average weight of the litters received injections and were included in the following experiments; thus, body weights at p8 were similar between the virus injection and control groups. In addition, pup number was maintained between 12 and 14 in all litters to ensure consistency in the 50/10 OIR model.

Figure 44A:
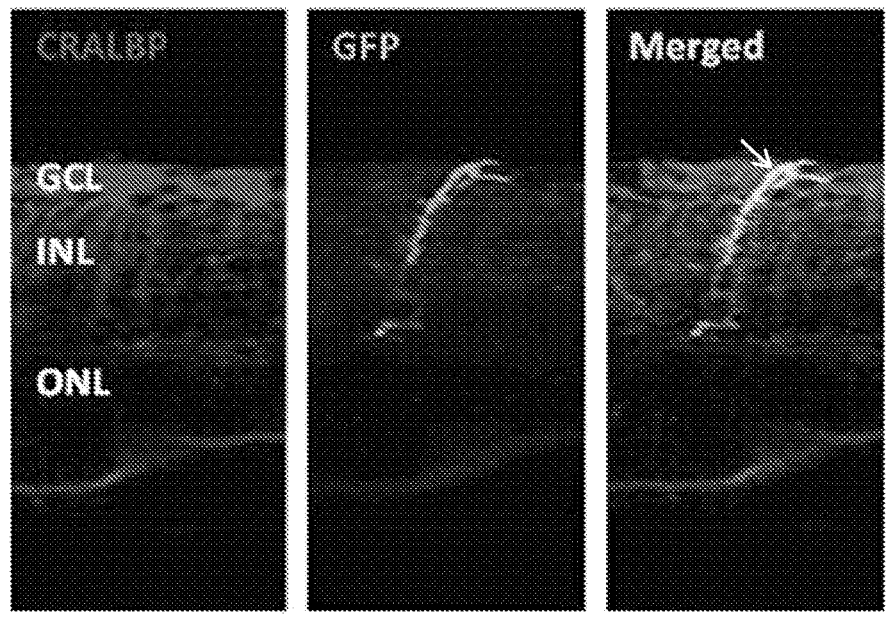
FIGS. 44A and 44B show the in vivo analysis of lentivector-delivered shRNA transduction in retina of pups raised in the rat 50/10 OIR model at p18 after subretinal injection at p8. (A) GFP expression is localized with CRALBP-labeled Müller cells in retinal cryosections at p18 taken from pup eye injected at p8 with lentivirus containing CD44 promoter driving GFP expression. The arrow represents colocalization. (B) ELISA of retinal VEGFA protein at p18. ***P<0.001 versus uninjected room air raised (RA), ††P<0.01 versus PBS, and †P<0.05 versus luciferase-shRNA. Results are means±SEM (n=6 to 8).
Figure 44B:
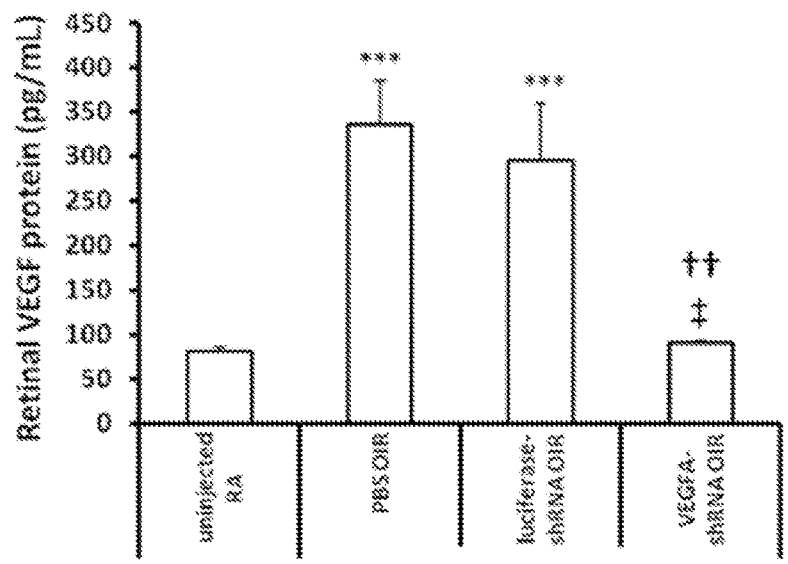

To determine the extent of viral transduction in the retina, retinal images were captured in vivo using the Micron III retinal imaging microscope. The retina had GFP fluorescence by p18. Rat pups were sacrificed at p18, and one eye was analyzed for IVNV and avascular retina, and the other for protein or IHC. By IHC, GFP was found to be colocalized with CRALBP-labeled Müller cells, as shown in an experiment using control lentivirus with the CD44 promoter to drive GFP (FIG. 44A), providing additional support that the lentivirus was transduced in Müller cells. To determine the silencing effect of the lentivector-delivered shRNA in vivo, total retinal VEGFA protein was measured by ELISA. Consistent with the data herein, VEGFA protein was increased in retinas from pups raised in the 50/10 OIR model at p18 compared with room air-raised pups (FIG. 44B). Compared with pups receiving subretinal injections of PBS or luciferase-shRNA controls, retinal VEGFA was significantly reduced in pups that received VEGFA-shRNA virus injections (FIG. 44B). However, compared with room air-raised pups of the same postnatal day ages, there was no significant difference in VEGFA levels in retinas from p18 pups in the 50/10 OIR model and treated with VEGFA-shRNA virus, indicating that lentivector VEGFA-shRNA reduced VEGFA to physiological levels required for normal retinal vascular development. To determine the VEGFA knockdown, retinal cryosections were colabeled with VEGFA and glutamine synthetase from eyes injected with lentivector VEGFA-shRNA or luciferase-shRNA. Immunoreactivity of VEGFA was reduced in sections from VEGFA-shRNA injection compared with luciferase-shRNA or uninjected eyes from the 50/10 OIR model at p18.

Figure 45A:
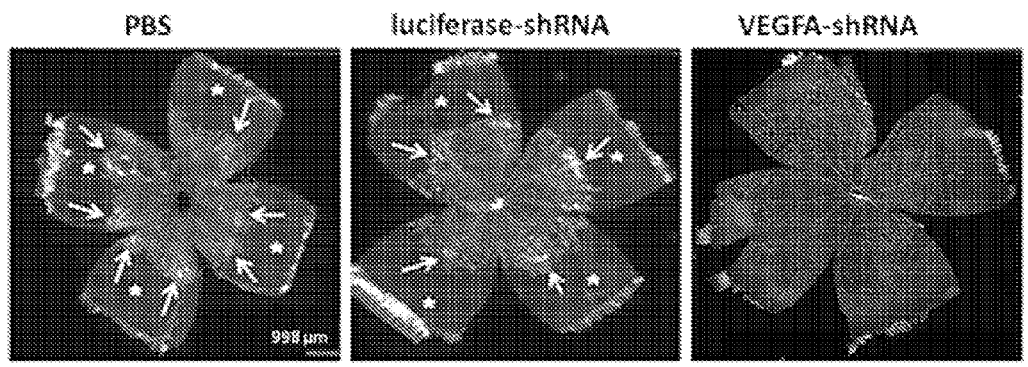
FIGS. 45A, 45B, and 45C show that lentivector-VEGFA-shRNA reduces IVNV without interfering with physiological retinal vascular development in the rat 50/10 OIR model. (A) Images of retinal flat mounts at p18 after subretinal injections in each group (PBS, control luciferase-shRNA, and VEGA-shRNA). (B and C) Quantification of IVNV (**P<0.01 versus PBS; †††P<0.001 versus luciferase-shRNA; B) and AVA (P=0.85, luciferase-shRNA versus PBS; P=0.15, VEGFA-shRNA versus PBS; C) in each group. Data shown in B and C are representative of at least 12 independent samples. Results are means±SEM. In panel A, asterisks indicate AVA; arrows, area with IVNV.
Figure 45B:
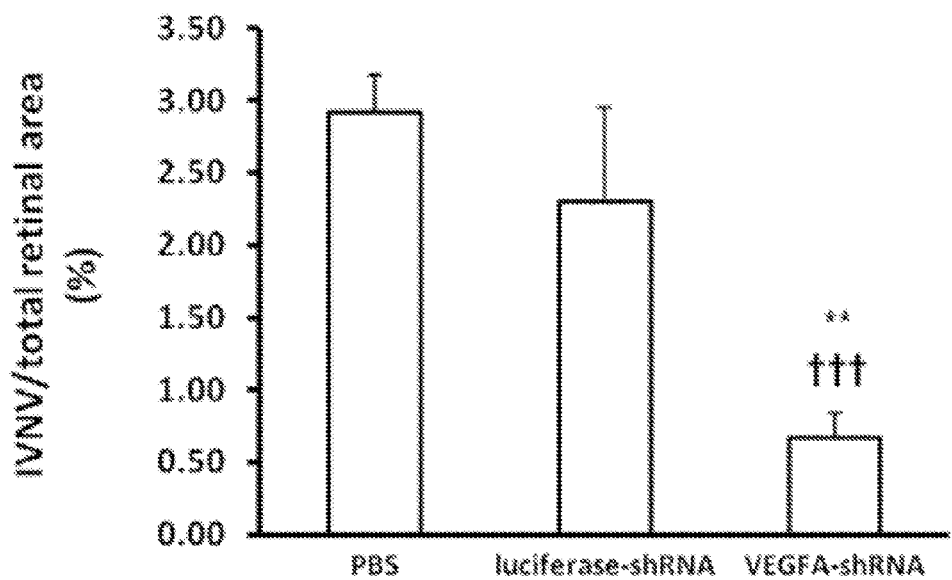
Figure 45C:
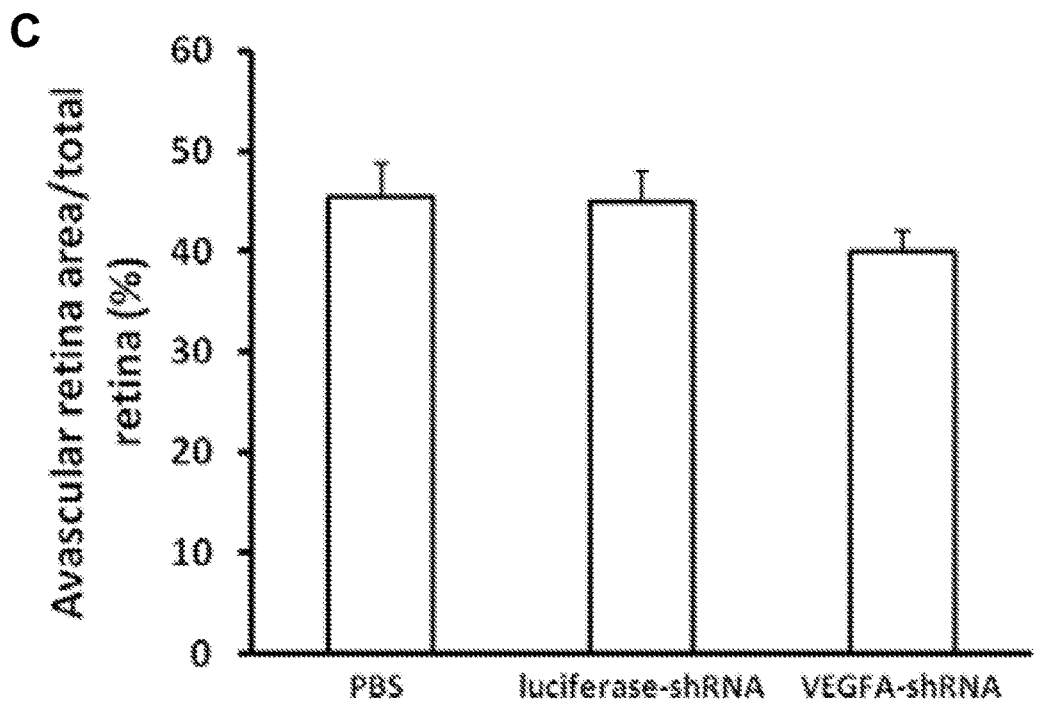

The effect of lentivector VEGFA-shRNA subretinal injections on IVNV and percentage AVA was then determined. For AVA, there was no difference in control or PBS-treated eyes with VEGFA-shRNA-treated eyes (FIG. 45A, 45C). However, there was a significant reduction in percentage IVNV in lentivector VEGFA-shRNA-treated eyes compared with the other groups (FIG. 45A, 45B). These findings indicate that Müller cell-derived VEGFA contributed to IVNV, and that knockdown of up-regulated VEGFA in Müller cells reduced pathological IVNV without interfering with physiological retinal vascular development or affecting retinal apoptosis in the 50/10 OIR model at p18.

Figure 46A:
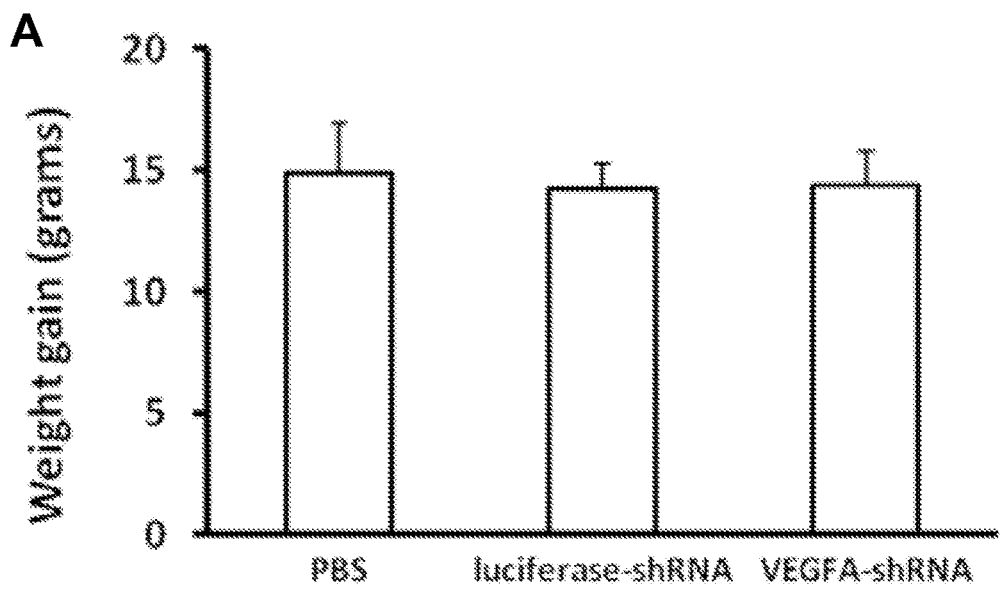
FIGS. 46A, 46B, 46C, and 46D show that the injection of lentivirus does not cause systemic effects or retinal morphological changes in the rat 50/10 OIR model. (A) Weight gain of pups from p8 to p18. (B) Rectal temperature at p18. (C) Retinal cross sections stained with DAPI at p18 show no difference in thickness of overall retina and inner nuclear layer. (D) Retinal-activated caspase 3 at p18. P>0.05 for VEGFA-shRNA versus either PBS or luciferase-shRNA. Results are means±SEM (n=5 to 15). GCL, ganglion cell layer; INL, inner nuclear layer; IPL, inner plexiform layer; ONL, outer nuclear layer; OPL, outer plexiform layer.
Figure 46B:
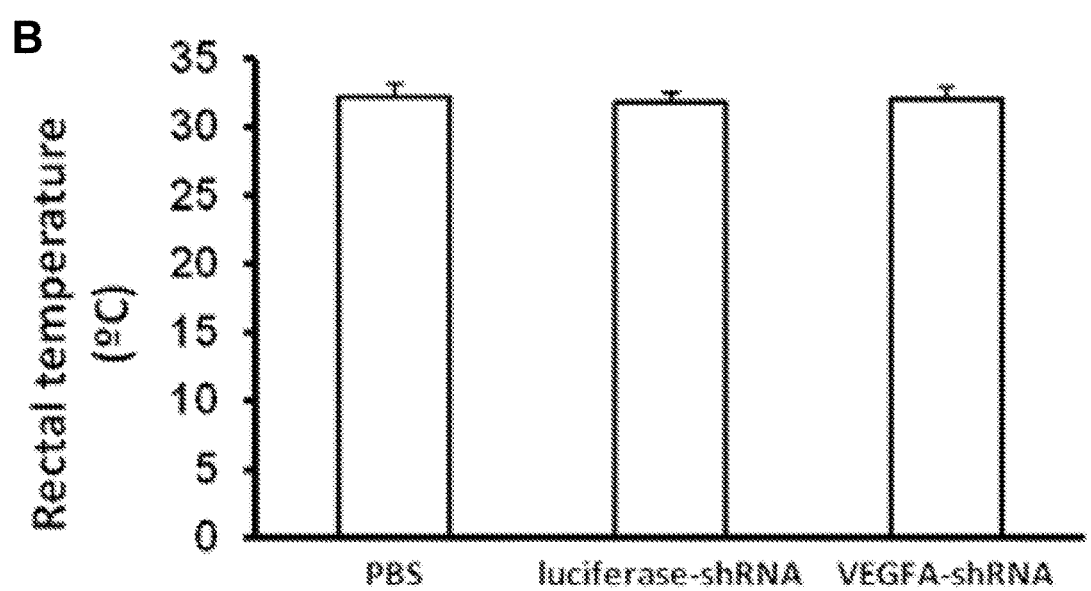
Figures 46C, 46D:
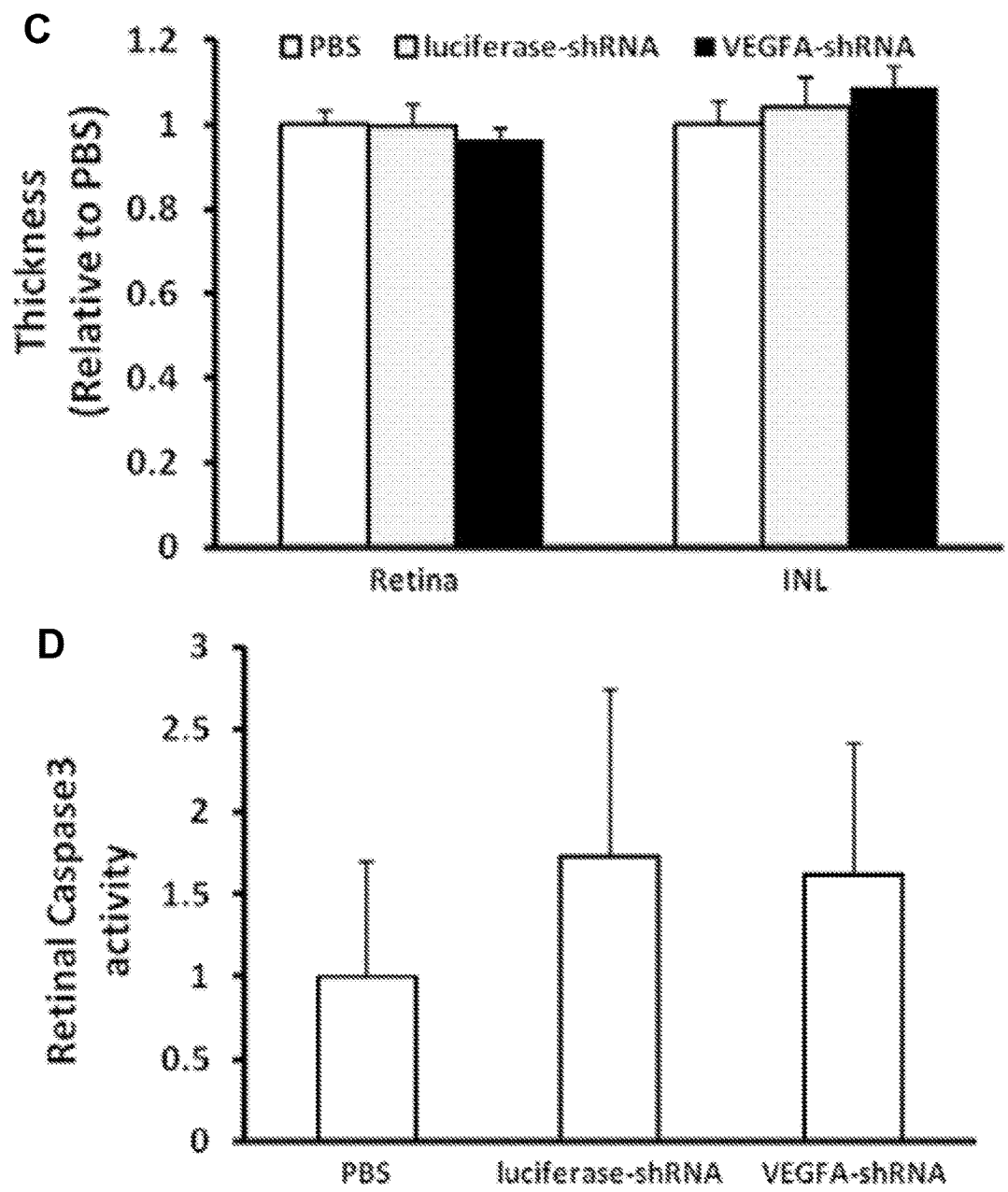

Reduced pup growth rate, or extrauterine growth restriction, is an associated risk factor for severe ROP in human infants. There were no significant differences in mean pup weights measured at p18 in all groups, as shown in FIG. 46A. Rectal temperature measured at p18 as an indicator of viral-induced systemic inflammation was also not different between the PBS, control, or VEGFA-shRNA lentivirus injected groups (FIG. 46B). In addition, lentivirus injection did not cause changes in retinal morphological characteristics, retinal thickness, or thickness of the inner nuclear (FIG. 46C), outer nuclear, inner plexiform, or outer plexiform layers. To determine whether lentivirus injection caused increased apoptosis, retinal caspase 3 activity was measured. The data showed no significant difference in retinas between PBS-treated eyes and either VEGFA-shRNAe or luciferase-shRNA-treated eyes (FIG. 46D).

Figures 47A, 47B:
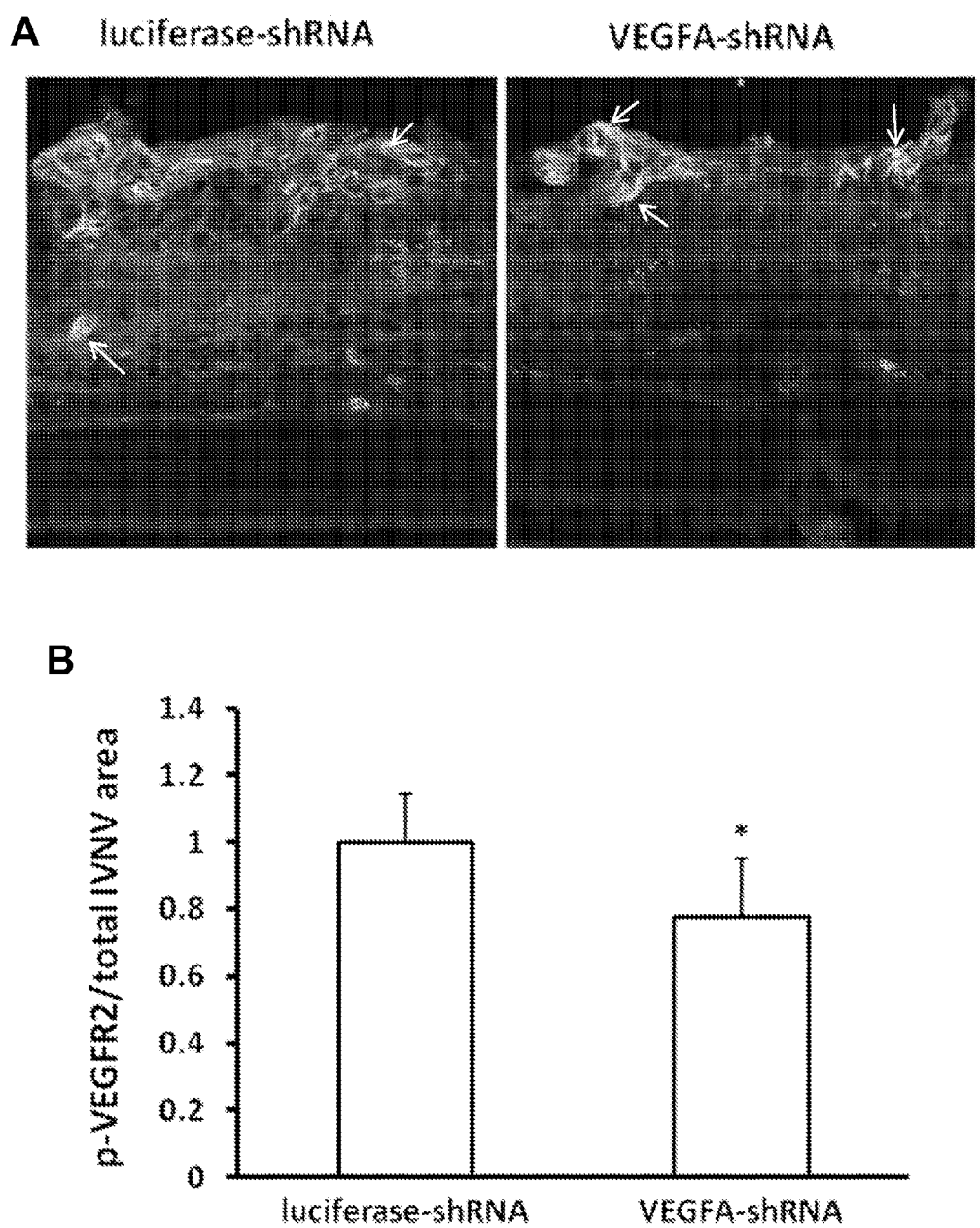
FIGS. 47A and 47B show that the knockdown of VEGFA in Müller cells by lentivector-VEGFA-shRNA reduces VEGFA signaling in vivo. (A) p-VEGFR2 labeling in a cross section through isolectin-stained IVNV or DAPI. (B) Quantification of p-VEGFR2 density in IVNV. *P<0.05 for VEGFA-shRNA versus luciferase-shRNA (n=3). Results are means±SEM.

Knockdown of VEGFA in Müller Cells Reduces VEGFA Signaling in Retinal Vascular Endothelial Cells Based on the data described herein, that the study examined whether the down-regulation of VEGFA in Müller cells reduced VEGF receptor signaling in retinal vascular endothelial cells. p-VEGFR2 was measured in retinal cryosections by IHC (FIG. 47). The data showed that, compared with luciferase-shRNA, the density of p-VEGFR2 (FIG. 47A, 47B) labeling normalized to the IVNV area, determined by lectin-positive staining, was qualitatively decreased in sections from pups that received lentivector VEGFA-shRNA in the 50/10 OIR model.

Discussion:

Elevated VEGFA has been found in the vitreous of infants with ROP. Evidence from animal studies indicates that hypoxia induces VEGFA expression and causes the pathological phases seen in ROP. Several types of retinal cells produce VEGFA either in pathological or physiological conditions, making broad and total inhibition of VEGFA signaling in the retina a concern, particularly in preterm infants in whom vasculature, neurons, and the neurovascular connections are developing. Therefore, targeting specific cells that overproduce VEGFA to knock down excessive expression without inhibiting physiological expression can reduce pathological features without interfering with development and maturation. By using the mouse model of OIR, investigators concluded that Müller cell or astrocyte-derived VEGFA was important in pathological angiogenesis. To address current-day ROP in countries that have resources to avoid high oxygen at birth, a rat model of variable OIR, the 50/10 OIR model, was used to assess overexpressed VEGFA that developed after birth from stresses relevant to those experienced by current-day human preterm infants.

The data herein indicates that repeated fluctuations in oxygen up-regulated VEGFA expression in the retina at several time points in the rat 50/10 OIR model, compared with room air-raised pups, that corresponded with persistent avascular retina and IVNV, which are features similar to those in human severe ROP. By using the same model, it was shown that inhibiting rat VEGFA with a neutralizing antibody significantly reduced IVNV area by approximately 3.5-fold, but caused adverse effects, including reduced pup growth between the time of intravitreal injection at postnatal day 12 and the time of sacrifice at p18. Therefore, to better target cells that overexpress VEGFA, VEGFA mRNA was localized in retinal sections using fluorescence in situ hybridization (FISH). Fourteen days after pups were exposed to repeated fluctuations in oxygen, mRNA signals of retinal VEGFA splice variants were detected in the inner nuclear layer and colocalized with CRALBP. Therefore, it was postulated that Müller cell-derived VEGFA can mediate pathological angiogenesis in the form of IVNV. To knock down Müller cell-derived VEGFA, shRNAs to VEGFA were designed and inserted into a lentiviral miR-30-based system driven by a CD44 promoter (as shown in FIGS. 42A, 43A), which was shown to exclusively target Müller cells in vivo in the rat. Usually, shRNA expression is under the control of polymerase III promoters, such as the U6 promoter, which drives shRNA expression in all cells. To express shRNA only in Müller cells driven by the CD44 promoter that is regulated by polymerase II, the shRNAs were embedded within a miR-30 context. The expression of the miR-30-based shRNAs is transcribed by the polymerase II-regulated CD44 promoter. The use of a polymerase II promoter to drive miR-30-based shRNAs has been shown to yield more efficient knockdown of the target gene than standard shRNA constructs.

The data indicate that the lentivector-driven miR-30-VEGFA-shRNA was specifically expressed in Müller cells. By using several cell models and molecular approaches, an optimal lentivector pFmCD44-driven VEGFA-shRNA that efficiently and specifically reduced Müller cell-derived VEGFA in vitro was determined, even though the knockdown efficiency was not high. That the CD44 promoter can have lower activity in vitro than in vivo explains the relatively low silencing of VEGFA by lentivector-VEGFA-shRNA. However, the VSV-G-CD44 promoter configuration was shown to yield high transduction efficiency and specificity for Müller cells in vivo.

The study then examined whether the lentivectors used would specifically target Müller cells in vivo and knock down VEGFA expression. The data indicate p18 to be the time for development of maximal IVNV in the rat 50/10 OIR model. For the lentivirus to transduce Müller cells, approximately a week is needed. Injections administered too early can adversely affect developing Müller cells. Based on these concerns and previous experiments, the time point, p8, was chosen to administer subretinal injections. The data described herein indicate that retinal VEGF expression increased in the 50/10 OIR model as early as postnatal day 8 and became maximal at p14. In this example, pups received lentivirus at p8, which provided 1 week for effective and safe shRNA transduction and knockdown of up-regulated VEGFA. Ten days after subretinal injections at p18, live imaging using the Micron III retinal imaging microscope showed GFP expression in retinas from pups injected with either lentivector luciferase-shRNA or VEGFA-shRNA, and this GFP expression was colocalized with CRALBP-labeled Müller cells in retinal cryosections. ELISA analysis showed that pups injected with VEGFA-shRNA had decreased VEGFA protein in retina compared with uninjected pups and pups injected with luciferase-shRNA-delivered virus, but there was no difference compared with pups raised in room air, indicating lentivector-VEGFA-shRNA reduced 50/10 OIR-induced VEGFA from pathological levels to the levels required to maintain physiological retinal development. It was then shown that transduction of Müller cells with VEGFA-shRNA in retinas of pups in the 50/10 OIR model caused almost complete inhibition of IVNV and some, albeit insignificant, inhibition of AVA compared with control (P=0.15). In addition, the vascular morphological characteristics of VEGFA-shRNA-treated retinas appeared more normal than those of control or PBS-injected eyes, indicating that reducing VEGF to physiological levels permits physiological-appearing retinal vascularization. In previous studies, comparing flat mounts from pups administered intravitreal anti-VEGF antibody injections with nonimmune IgG control injections, IVNV was reduced, but vascular morphological features still lacked physiological morphological features compared with eyes that had been treated with lentivector-VEGFA-shRNA. Although there can be associated damage with subretinal injections and subsequent retinal detachment, the data show that the bleb, or limited retinal detachment, associated with a successful subretinal injection was temporary and resolved within 24 hours, as determined using Micron III retinal imaging microscope. In addition, there was no increase in retinal apoptosis or changes in retinal morphological features with lentivector injections. Ocular injections of lentivirus also did not cause adverse effects on pup weight gain or systemic inflammation, as determined by rectal temperature.

Therefore, these results indicate that targeted partial silencing in cells that overexpress VEGFA (ie, Müller cells) can effectively inhibit pathological IVNV without interfering with physiological retinal vascular development or reducing weight gain during development using a model of OIR that is relevant to current-day ROP. Müller cells provide nutrition for retinal neurons, and ablation of Müller cells causes retinal vascular pathological features in a transgenic mouse model, indicating interactions can exist between Müller cells and retinal vascular endothelial cells. To identify whether knockdown of Müller cell-derived VEGFA, using these lentivector-delivered shRNAs, caused decreased VEGFA signaling in hRMVECs, p-VEGFR2 in IVNV labeled with isolectin in retinal cryosections was measured and significantly reduced p-VEGFR2 staining per area of IVNV in pups injected with lentivirus-delivered VEGFA-shRNA was found. For further examination, a co-culture of rMC-1s and hRMVECs was performed. There was no significant difference in the activation of VEGFR2 in hRM-VECs after growth with rMC-1s compared with that with human VEGFA stimulation, supporting the use of the rat/human co-culture to address this question. Then, it was determined that knockdown of VEGFA in rMC-1s by lentiviral-delivered VEGFA-shRNA reduced VEGFR2 signaling in hRMVECs in co-culture. The results together indicated that knockdown of Müller cell-derived VEGFA effectively inhibited VEGFA-regulated angiogenesis in retinal vascular endothelial cells.

In summary, VEGFA overexpression in Müller cells was localized and a lentiviral-delivered miR-30-embedded shRNA that targeted Müller cells was generated and efficiently reduced VEGFA from pathological levels to levels required for physiological retinal vascular development using a model relevant to ROP, the 50/10 OIR model. This study provides a concept to examine mechanisms involved in pathological IVNV and can be useful to determine pharmacological targets to safely reduce pathological features of ROP without interfering with the beneficial effect of major growth factors.

I claim:

1. A method of treating retinopathy of prematurity (ROP) comprising administering to a subject a composition comprising a vector, wherein the vector comprises a polymerase II (pol II) promoter and a first shRNA, wherein the first shRNA is embedded in microRNA, and wherein the first shRNA has a sense RNA strand and an antisense RNA strand, wherein the sense and the antisense RNA strands form an RNA duplex, wherein the sense RNA strand comprises a nucleotide sequence identical to a target sequence in STAT3, VEGFR2, or EPOR mRNA, and wherein the composition is administered via subretinal injection, wherein the first shRNA consists of SEQ ID NO:1, SEQ ID NO:2, SEQ ID NO:3, SEQ ID NO:13, SEQ ID NO:14, SEQ ID NO:15, SEQ ID NO:4, SEQ ID NO:5, SEQ ID NO:6, SEQ ID NO:19, SEQ ID NO:20, SEQ ID NO:21, SEQ ID NO:7, SEQ ID NO:8, SEQ ID NO:9, SEQ ID NO:25, SEQ ID NO:26, or SEQ ID NO:27.

2. The method of claim 1, wherein the vector is a viral vector.

3. The method of claim 1 further comprising administering a second shRNA.

4. The method of claim 3, wherein the second shRNA has a sense RNA strand and an antisense RNA strand, wherein the sense and the antisense RNA strands form an RNA duplex, and wherein the sense RNA strand comprises a nucleotide sequence identical to a target sequence in STAT3, VEGFR, or EPOR mRNA, and wherein the second shRNA is different than the first shRNA.

5. The method of claim 3, wherein the second shRNA is in the same vector as the first shRNA.

6. The method of claim 3, wherein the second shRNA is in a different vector than the first shRNA.

7. The method of claim 3, wherein the second shRNA is administered in a separate composition from the first shRNA.

8. The method of claim 1, wherein the pol II promoter is an endothelial cell-specific promoter.

9. The method of claim 8, wherein the endothelial cell-specific promoter is a VE-cad promoter.

10. The method of claim 1, wherein the intravitreal neovascularization (IVNV) phase of ROP in inhibited without interfering with physiologic retinal vascular development (PRVD).

* * * * *